(12) United States Patent
Kudithipudi et al.

(10) Patent No.: US 12,129,474 B2
(45) Date of Patent: Oct. 29, 2024

(54) COMPOSITION AND METHODS FOR PRODUCING TOBACCO PLANTS AND PRODUCTS HAVING REDUCED TOBACCO-SPECIFIC NITROSAMINES (TSNAS)

(71) Applicant: Altria Client Services LLC, Richmond, VA (US)

(72) Inventors: Chengalrayan Kudithipudi, Midlothian, VA (US); Dongmei Xu, Glen Allen, VA (US); James Strickland, Richmond, VA (US)

(73) Assignee: Altria Client Services LLC, Richmond, VA (US)

( * ) Notice: Subject to any disclaimer, the term of this patent is extended or adjusted under 35 U.S.C. 154(b) by 0 days.

(21) Appl. No.: 18/182,701

(22) Filed: Mar. 13, 2023

(65) Prior Publication Data

US 2023/0348925 A1    Nov. 2, 2023

Related U.S. Application Data

(63) Continuation of application No. 16/838,762, filed on Apr. 2, 2020, now Pat. No. 11,634,724, which is a continuation of application No. 15/727,523, filed on Oct. 6, 2017, now Pat. No. 10,647,989.

(60) Provisional application No. 62/503,103, filed on May 8, 2017, provisional application No. 62/405,607, filed on Oct. 7, 2016.

(51) Int. Cl.
| | |
|---|---|
| *C12N 15/82* | (2006.01) |
| *A01H 4/00* | (2006.01) |
| *A24B 13/00* | (2006.01) |
| *A24B 15/10* | (2006.01) |
| *A24B 15/24* | (2006.01) |
| *B01F 33/45* | (2022.01) |
| *B01F 33/452* | (2022.01) |
| *B01F 33/501* | (2022.01) |
| *B01F 35/75* | (2022.01) |
| *B01L 3/00* | (2006.01) |
| *C07K 14/415* | (2006.01) |
| *C12N 9/04* | (2006.01) |
| *G01N 1/38* | (2006.01) |
| *H02N 11/00* | (2006.01) |
| *G01N 35/00* | (2006.01) |
| *G01N 35/10* | (2006.01) |

(52) U.S. Cl.
CPC ......... *C12N 15/8243* (2013.01); *A01H 4/005* (2013.01); *A01H 4/008* (2013.01); *A24B 13/00* (2013.01); *A24B 15/10* (2013.01); *A24B 15/245* (2013.01); *B01F 33/45* (2022.01); *B01F 33/452* (2022.01); *B01F 33/50112* (2022.01); *B01F 35/754251* (2022.01); *B01L 3/502* (2013.01); *B01L 3/50825* (2013.01); *C07K 14/415* (2013.01); *C12N 9/0006* (2013.01); *C12N 15/8205* (2013.01); *C12N 15/8225* (2013.01); *C12N 15/825* (2013.01); *G01N 1/38* (2013.01); *H02N 11/006* (2013.01); *B01L 2200/0684* (2013.01); *B01L 2300/043* (2013.01); *B01L 2300/0672* (2013.01); *B01L 2300/0867* (2013.01); *B01L 2400/0403* (2013.01); *B01L 2400/043* (2013.01); *B01L 2400/0478* (2013.01); *B01L 2400/0683* (2013.01); *G01N 2035/00534* (2013.01); *G01N 35/1079* (2013.01)

(58) Field of Classification Search
None
See application file for complete search history.

(56) References Cited

U.S. PATENT DOCUMENTS

| | | | |
|---|---|---|---|
| 4,516,590 | A | 5/1985 | Teng |
| 4,528,993 | A | 7/1985 | Sensabaugh, Jr. et al. |
| 4,660,577 | A | 4/1987 | Sensabaugh, Jr. et al. |
| 4,732,856 | A | 3/1988 | Federoff |
| 4,762,785 | A | 8/1988 | Comai |
| 4,848,373 | A | 7/1989 | Lenkey |
| 4,945,050 | A | 7/1990 | Sanford et al. |
| 4,987,907 | A | 1/1991 | Townend |
| 5,004,863 | A | 4/1991 | Umbeck |
| 5,013,658 | A | 5/1991 | Dooner et al. |
| 5,104,310 | A | 4/1992 | Saltin |

(Continued)

FOREIGN PATENT DOCUMENTS

| | | |
|---|---|---|
| WO | WO 1998/049350 A1 | 5/1998 |
| WO | WO 1999/007865 A1 | 2/1999 |

(Continued)

OTHER PUBLICATIONS

Outchkourov, Nikolay S., et al. "Control of anthocyanin and non-flavonoid compounds by anthocyanin-regulating MYB and bHLH transcription factors in Nicotiana benthamiana leaves." Frontiers in Plant Science 5 (2014): 519. (Year: 2014).*

(Continued)

*Primary Examiner* — Weihua Fan
(74) *Attorney, Agent, or Firm* — Arnold & Porter Kaye Scholer LLP

(57) ABSTRACT

The present disclosure provides approaches for reducing tobacco-specific nitrosamines (TSNAs) in tobacco. Some of these approaches include genetically engineering tobacco plants to increase one or more antioxidants, increase oxygen radicle absorbance capacity (ORAC), or reduce nitrite. Also provided are methods and compositions for producing modified tobacco plants and tobacco products therefrom comprising reduced TSNAs.

19 Claims, 21 Drawing Sheets

Specification includes a Sequence Listing.

(56) References Cited

U.S. PATENT DOCUMENTS

| | | |
|---|---|---|
| 5,141,131 A | 8/1992 | Miller, Jr. et al. |
| 5,149,645 A | 9/1992 | Hoekema et al. |
| 5,159,135 A | 10/1992 | Umbeck |
| 5,177,010 A | 1/1993 | Goldman et al. |
| 5,231,019 A | 7/1993 | Paszkowski et al. |
| 5,316,931 A | 5/1994 | Donson et al. |
| 5,372,149 A | 12/1994 | Roth et al. |
| 5,463,174 A | 10/1995 | Moloney et al. |
| 5,464,763 A | 11/1995 | Schilperoort et al. |
| 5,469,976 A | 11/1995 | Burchell |
| 5,491,081 A | 2/1996 | Webb |
| 5,563,055 A | 10/1996 | Townsend et al. |
| 5,565,350 A | 10/1996 | Kmiec |
| 5,589,367 A | 12/1996 | Donson et al. |
| 5,659,026 A | 8/1997 | Baszczynski et al. |
| 5,689,035 A | 11/1997 | Webb |
| 5,731,181 A | 3/1998 | Kmiec |
| 5,756,325 A | 5/1998 | Kmiec |
| 5,760,012 A | 6/1998 | Kmiec et al. |
| 5,789,156 A | 8/1998 | Bujard et al. |
| 5,795,972 A | 8/1998 | Kmiec |
| 5,814,618 A | 9/1998 | Bujard et al. |
| 5,866,785 A | 2/1999 | Donson et al. |
| 5,871,984 A | 2/1999 | Kmiec |
| 5,879,918 A | 3/1999 | Tomes et al. |
| 5,886,244 A | 3/1999 | Tomes et al. |
| 5,889,190 A | 3/1999 | Donson et al. |
| 5,889,191 A | 3/1999 | Turpen |
| 5,932,782 A | 8/1999 | Bidney |
| 5,981,840 A | 11/1999 | Zhao et al. |
| 6,072,050 A | 6/2000 | Bowen et al. |
| 8,124,851 B2 | 2/2012 | Dewey et al. |
| 8,319,011 B2 | 11/2012 | Xu et al. |
| 9,187,759 B2 | 11/2015 | Dewey et al. |
| 9,228,194 B2 | 1/2016 | Dewey et al. |
| 9,228,195 B2 | 1/2016 | Dewey et al. |
| 9,247,706 B2 | 2/2016 | Dewey et al. |
| 9,913,451 B2 | 3/2018 | Dewey |
| 2004/0084056 A1* | 5/2004 | Lawson ............... A24B 15/18 131/299 |
| 2004/0118422 A1 | 6/2004 | Lundin et al. |
| 2005/0034635 A1 | 2/2005 | Lin et al. |
| 2005/0178398 A1 | 8/2005 | Breslin et al. |
| 2006/0191548 A1 | 8/2006 | Strickland et al. |
| 2006/0212960 A1 | 9/2006 | Nessler |
| 2006/0260014 A1 | 11/2006 | Li et al. |
| 2017/0233756 A1 | 8/2017 | Begemann et al. |

FOREIGN PATENT DOCUMENTS

| | | |
|---|---|---|
| WO | WO 99/25921 A1 | 5/1999 |
| WO | WO 2003/022081 A1 | 3/2003 |
| WO | WO 2004/041006 A1 | 5/2004 |
| WO | WO 2004/061098 A1 | 7/2004 |
| WO | WO 2010/069004 A1 | 6/2010 |
| WO | WO 2011/027315 A1 | 3/2011 |
| WO | WO 2013/064499 A1 | 5/2013 |
| WO | WO 2016/124932 A1 | 8/2016 |

OTHER PUBLICATIONS

Bai, Y., Pattanaik, S., Patra, B. et al. Flavonoid-related basic helix-loop-helix regulators, NtAn1a and NtAn1b, of tobacco have originated from two ancestors and are functionally active. Planta 234, 363-375 (2011). https://doi.org/10.1007/s00425-011-1407-y (Year: 2011).*

Beetham et al., "A Tool for Functional Plant Genomics: Chimeric Rna/Dna Oligonucleotides Cause in vitro Gene-specific Mutations," *Proc. Natl. Acad. Sci.*, 96:8774-8778 (1999).

Bowman et al., "Revised North Carolina Grade Index for Flue-Cured Tobacco," *Tobacco Science*, 32:39-40 (1988).

Canevascini et al., "Tissue-Specific Expression and Promoter Analysis of the Tobacco Itp1 Gene," *Plant Physiol.* 112(2):513-524 (1996).

Cermak et al., "Efficient Design and Assembly of Custom TALEN and Other TAL Effector-Based Constructs for DNA Targeting," *Nucleic Acids Research* 39(12):1-11 E82 (2011).

Chapters 4B and 4C of Tobacco, Production, Chemistry and Technology, Davis & Nielsen Editions, Blackwell Publishing, Oxford, pp. 70-103. (1999).

Christensen et al., "Maize polyubiquitin genes: structure, thermal perturbation of expression and transcript splicing, and promoter activity following transfer to protoplasts by electroporation" *Plant Mol. Biol.* 18:675-689) (1992).

Christensen et al., "Sequence Analysis and Transcriptional Regulation by Heat Shock of Polyubiquitin Transcripts from Maize," *Plant Mol. Biol.* 12:619-632 (1989).

Christou et al., "Stable Transformation of Soybean Callus by DNA-Coated Gold Particles," *Plant Physiol.* 87:671-674 (1988).

Crossway et al., "Micromanipulation Techniques in Plant Biotechnology," *Biotechniques*, 4:320-334 (1986).

De Wet et al., "Exogenous Gene Transfer in Maize" *The Experimental Manipulation of Ovule Tissues*, ed. pp. 197-209 (1985).

D'Halluin et al., "Transgenic Maize Plants by Tissue Electroporation," *Plant Cell*, 4:1495-1505 (1992).

Doyle et al., "TAL Effector-Nucleotide Targeter (TALE-NT) 2.0: tools for TAL Effector Design and Target Prediction," *Nucleic Acids Research*, 40:117-122 (2012).

Dubos et al. "MYB Transcription Factors in *Arabidopsis*," *Trends in Plant Science*, 15(10):573-581 (2010).

Estruch et al., "Transgenic Plants: An emerging approach to pest control," *Nat. Biotechnol.*15:137 (1997).

Fedoroff et al., "Cloning of the bronze locus in maize by a simple and generalizable procedure using the transposable controlling element Activator (Ac)," *Proc. Natl. Acad. Sci.*, 81:3825-3829 (1984).

Finer et al., "Transformation of soybean via particle bombardment of embryogenic suspension culture tissue," *In Vitro Cell Dev. Biol.*, 27P: 175-182 (1991).

Gates, et al., "Diversification of R2R2-MYB Transcription Factors in the Tomato Family Solanaceae," *Journal of Molecular Evolution*, 83(1-2):26-37 (2016).

Gatz et al., "Regulation of a modified CaMV 35S promoter by the Tn 10-enclosed Tet repressor in transgenic tobacco," *Mol. Gen. Genet.*, 227:229-237 (1991).

Goldman et al., "Female sterile tobacco plants are produced by stigma-specific cell ablation," *EMBO Journal*, 13:2976-2984 (1994).

Guevara-Garcia et al., "Tissue-specific and wound-inducible pattern of expression of the mannopine synthase promoter is determined by the interaction between positive and negative cis-regulatory elements," *Plant J.*, 4(3):495-505 (1993).

Hansen, et al., "Wound-inducible and organ-specific expression of ORF13 from *Agrobacterium rhizogenes* 8196 T-DNA in transgenic tobacco plants," *Mol Gen Genet*, 254, pp: 337-343 (1997 (Berlin, Germany).

Hildering et al., "Chimeric Structure of the Tomato Plant After Seed Treatment With EMS and X-Rays," THE Use of Induced Mutations in Plant Breeding (Supplement to Radiation Botany), vol. 5, Pergamon Press Ltd., pp: 317-320, with cover page (1965) (London, UK).

Hoekema et al., "A binary plant vector strategy based on separation of vir- and T-region of the *Agrobacterium tumefaciens* Ti-plasmid," *Nature*, 303(12):179-80 (1983).

Horsch et al., "A Simple and General Method for Transferring Genes into Plants," *Science*, 227(4691):1229-1231 (1985).

Huang et al., "Differential Activation of Anthocyanin Biosynthesis in *Arabidopsis* and Tobacco Over-Expressing an R2R3 MYB from Chinese Bayberry," *Plant Cell, Tissue and Organ Culture (PCTOC)*, 113(3):491-4899 (2013).

International Search Report and Written Opinion dated Feb. 2, 2018 in corresponding International Application No. PCT/US20017/055618.

Kaeppler et al., "Silicon carbide fiber-mediated DNA delivery into plant cells," *Plant Cell Reports* 9:415-418 (1990).

Kaeppler et al., "Silicon carbide fiber-mediated stable transformation of plant cells," *Theor. Appl. Genet.* 84:560-566 (1992).

(56) References Cited

OTHER PUBLICATIONS

Kawamata et al., "Temporal and spatial pattern of expression of the pea Phenylalanine ammonia-lyase gene1 promoter in transgenic tobacco," *Plant Cell Physiol.* 38(7):792-803(1997).

Lam, "8 Analysis of Tissue-Specific Elements in the CaMV 35S Promoter," Results and Problems in Cell Differentiation, 20, pp. 181-196 (1994) (Berlin, Germany).

Last et al., "pEmu: an improved promoter for gene expression in cereal cells," *Theor. Appl. Genet.* 81:581-588 (1991).

Matsuoka et al., "Tissue-specific light-regulated expression by the promoter of a $C_4$ gene, maize pyruvate, orthophosphate dikinases, in a $C_3$ plant, rice," *Proc Natl. Acad. Sci. USA* 90(20):9586-9590 (1993).

Mayo et al., "Genetic transformation of tobacco NT1 cells with Agrobacterium tumefaciens," *Nature Protocols*, 1(3):1105-1111 (2006).

McCabe et al., "Stable transformation of soybean (glycine max) by particle acceleration," *Biotechnology* 6:923-926 (1988).

McCallum et al., "Targeted Screening for Induced Mutations," *Nat. Biotechnol.*, 18:455-457 (2000).

McNellis et al., "Glucocorticoid-inducible Expression of a Bacterial Avirulence Gene in Transgenic *Arabidopsis* Induces Hypersensitive Cell Death," *Plant J.* 14(2):247-257) (1998).

Miller et al., "Exported Abstract Records, A Grade Index for Type 22 and 23 Fire-Cured Tobacco," *Tobacco Intern.*, 192(2):55-57 (1990).

Miller "Memorandum: Proposed Burley Tobacco Grade Index," Legacy Tobacco Document Library, The University of Tenessee Agricultural Experiment Station (Bates Document #523267826-523267833) (Jul. 1988).

Mitsunami et al., "Overexpression of the PAP1 Transcription Factor Reveals a Complex Regulation of Flavonoid and Phynylpropanoid Metabolism in Nicotiana tabacum Plants Attached by Spodoptera Litura," *PLoS One* 9(9):E108849 (2014).

Odell et al., "Identification of DNA sequences required for activity of the cauliflower mosaic virus 35S promoter," *Nature*, 313:810-812 (1985).

Official Standard Grades for Burley Tobacco (U.S. Type 31 and Foreign Type 93), effective Nov. 5, 1990 (55 F.R. 40645).

Official Standard Grades for Flue-Cured Tobacco (U.S. Types 11, 12, 13, 14 and Foreign Type 92), effective Mar. 27, 1989 (54 F.R. 7925).

Official Standard Grades for Pennsylvania Seedleaf Tobacco (U.S. Type 41), effective Jan. 8, 1965 (29 F.R. 16854).

Official Standard Grades for Ohio Cigar-Leaf Tobacco (U.S. Types 42, 43, and 44), effective Dec. 8, 1963 (28 F.R. 11719 and 28 F.R. 11926).

Official Standard Grades for Wisconsin Cigar-Binder Tobacco (U.S. Types 54 and 55), effective Nov. 20, 1969 (34 F.R. 17061).

Official Standard Grades for Georgia and Florida Shade-Grown Cigar-Wrapper Tobacco (U.S. Type 62), Effective Apr. 1971.

Orozco et al., "Localization of light-inducible and tissue-specific regions of the spinach ribulose bisphosphate carboxylase/oxygenase (rubisco) activase promoter in transgenic tobacco plants," *Plant Molecular Biology*, 23(6):1129-1138 (1993).

Paszkowski et al., "Direct Gene Transfer to Plants," *EMBO J.* 3:2717-2722) (1984).

Porta et al., "Use of Viral Replicons for the Expression of Genes in Plants" *Molecular Biotechnology*, 5:209-221 (1996).

Prouse et al., "Interactions between the R2R3-MYB Transcription Factor, AtMYB61, and Target DNA Binding Sites," *PLoS One* 2013, 8(5): e65132.

Riggs et al., "Stable Transformation of Tobacco by Electroporation: Evidence for Plasmid Concatenation," *Proc. Natl. Acad. Sci.*, 83:5602-5606) (1986).

Rinehart et al., "Tissue-Specific and Developmental Regulation of Cotton Gene FbL2A" *Plant Physiol.*, 112(3):1331-1341 (1996).

Russell et al., "Tissue-Specific Expression in Transgenic Maize of Four Endosperm Promoters from Maize and Rice," *Transgenic Res.* 6(2):157-168 (1997).

Schena et al., "A Steroid-inducible Gene Expression System for Plant Cells," *Proc. Natl. Acad. Sci.* 88:10421-10425 (1991).

Shillito et al., "Direct Gene Transfer to Protoplasts," *Meth. Enzymol.* 153:313-336 (1987).

Singh et al., "Cytological Characterization of Transgenic Soybean," *Theor. Appl. Genet.* 96:319-324 (1998).

Tanaka, et al., "Studies on Biological Effects of Ion Beams on Lethality, Molecular Nature of Mutation, Mutation Rate, and Spectrum of Mutation Phenotype for Mutation Breeding in Higher Plants," *Radiat. Res.* 51:223-233 (2010).

Tohge et al., "Functional genomics by integrated analysis of metabolome and transcriptome of *Arabidopsis* plants over-expressing an MYB transcription factor," *Plant Journal* 42(2):218-235 (2005).

Tomes et al., "Direct DNA Transfer into Intact Plant Cells Via Microprojectile Bombardment," *Plant Cell, Tissue, and Organ Culture*, Springer-Verlag ed. (1995).

Tso "Seed to Smoke," Chapter 1 in Davis and Nielsen (ed.), Tobacco: Production, Chemistry and Technology, Blackwell Science Publishing, pp. 1-31 with cover page (Oxford, UK).

Van Camp et al., "Tissue-Specific Activity of Two Manganese Superoxide Dismutase Promoters in Transgenic Tobacco," *Plant Physiol.* 112(2):525-535 (1996).

Velten et al., "Isolation of a Dual Plant Promoter Fragment from the Ti Plasmid of *Agrobacterium tumefaciens*" *EMBO J.* 3(12):2723-2730 (1984).

Verkerk, "Chimerism of the Tomato Plant After Seed Irradiation with Fast Neutrons," *Neth. J. Agric. Sci.* 19:197-203 (1971).

Weising et al., "Foreign Genes in Plants: Transfer, Structure, Expression, and Applications," *Ann. Rev. Genet.* 22:421-477 (1988).

Wernsman et al., "Tobacco," Chapter Seventeen: Principles of Cultivar Development, Crop Species, vol. 2, W. H. Fehr (ed.), MacMillan W. H. Fehr (ed.), pp. 669-698 (1987) (New York, NY).

Xie et al., "Metabolic Engineering of Proanthocyanidins Through Co-Expression of Anthocyanidin Reductase and the PAP1 MYB Transcription Factor," *The Plant Journal*, 45(6):895-907 (2006).

Yamamoto et al., "Light-responsive Elements of the Tobacco PSI-D Gene are Located Both Upstream and within the Transcribed Region," *Plant J.* 12(2):255-265 (1997).

Yamamoto et al., "The Promoter of a Pine Photosynthetic Gene Allows Expression of a jS-Glucuronidase Reporter Gene in Transgenic Rice Plants in a Light-Independent but Tissue-Specific Manner," *Plant Cell Physiol.* 35(5):773-778 (1994).

Search Report issued in European Patent Application No. 17787805, dated Sep. 22, 2020; 8 pages.

Wiernik et al., "Effect of Air-Curing on the Chemical Composition of Tobacco" *Recent Adv. Tab. Sci*, vol. 21 (Impact of Plant Manipulation and Post Harvest Phenomena on Leaf Composition), pp. 39-80 Symposium Proceedings 49th Meeting Tobacco Chemists' Research Conference, Sep. 24-27, 1995, Lexington, Kentucky, USA, available online: https://www.industrydocuments.ucsf.edu/docs/#id=xkvw0008.

Zhu et al., "Gain-of-function mutations: key tools for modifying or designing novel proteins in plant molecular engineering," *Journal of Experimental Botany*, 71(4), pp. 1203-1205, (Feb. 2020) (electronic publication), available online: https://doi.org/10.1093/jxb/erz519.

\* cited by examiner

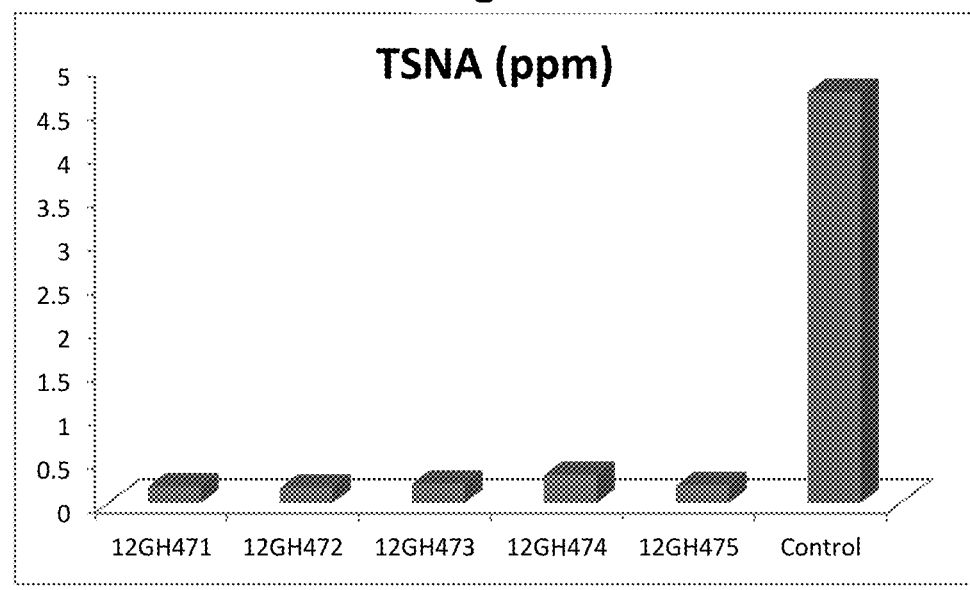

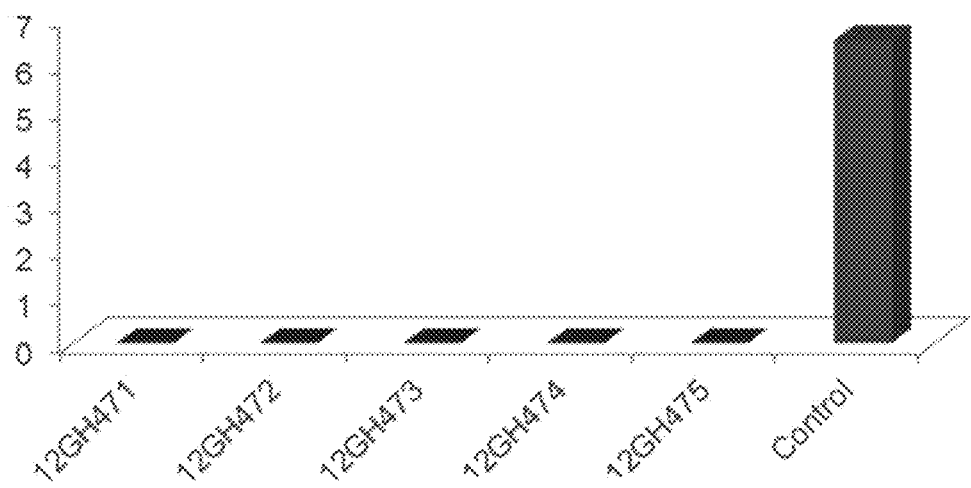
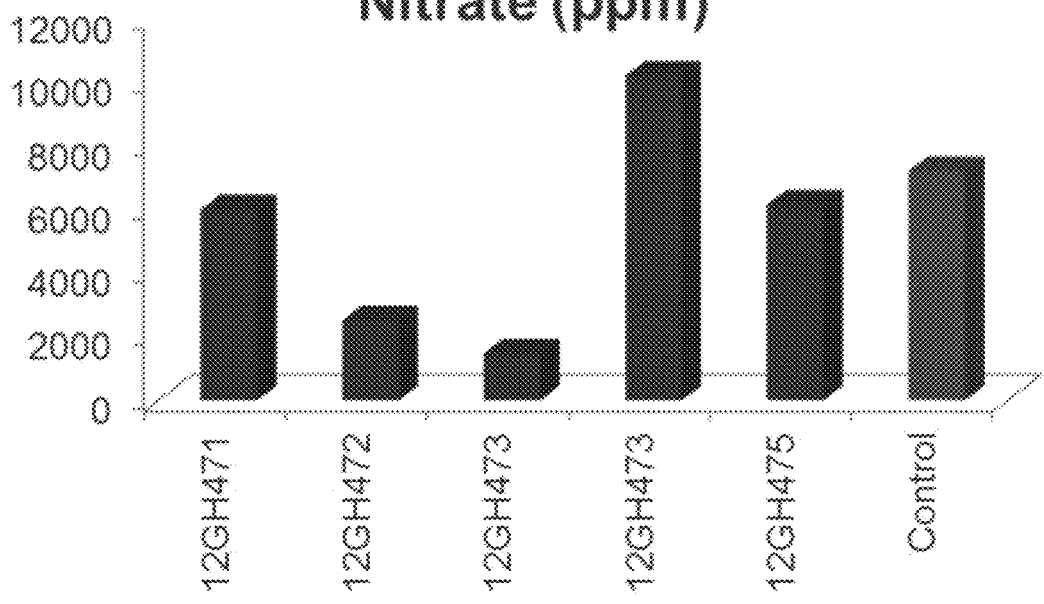

Figure 10
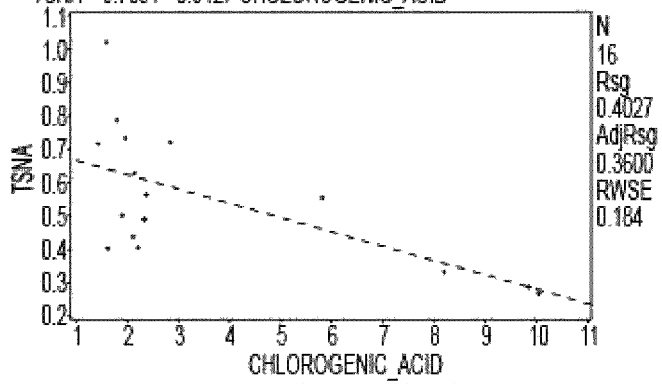
FIG. 10A
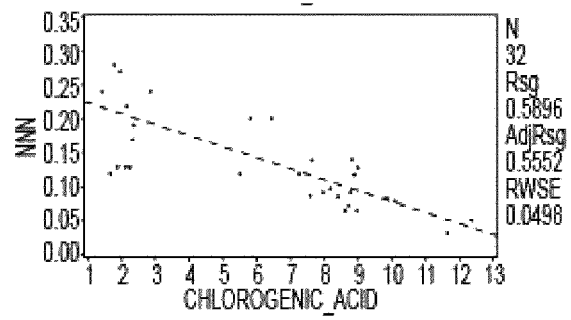
FIG. 10B
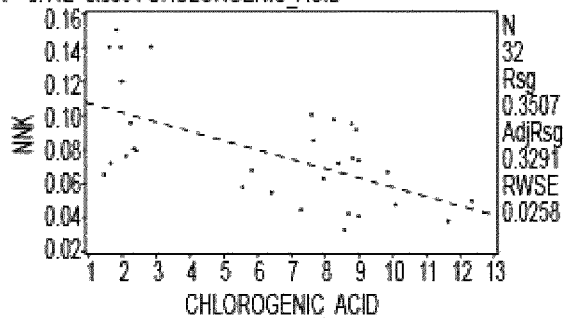
FIG. 10C

Figure 10
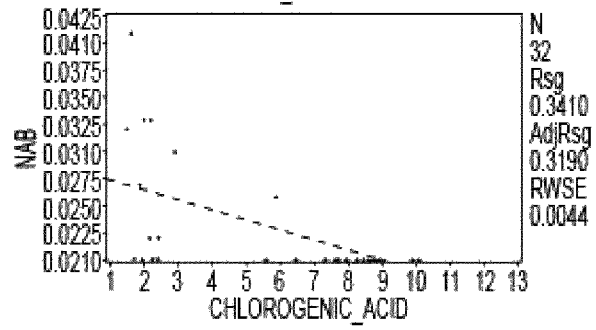
FIG. 10D
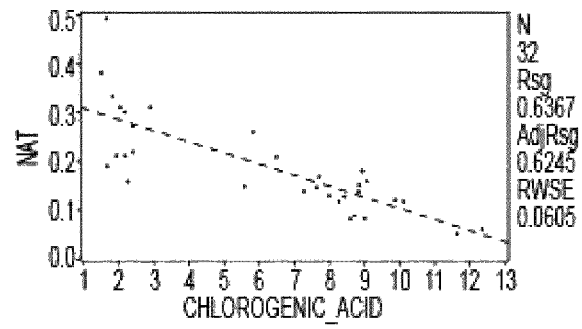
FIG. 10E

SEQUENCE LISTING

```
Sequence total quantity: 63
SEQ ID NO: 1                    moltype = AA   length = 330
FEATURE                         Location/Qualifiers
source                          1..330
                                mol_type = protein
                                organism = Nicotiana sp.
SEQUENCE: 1
MESKSSGGGE GKVVCVTGAS GFIASWLVKM LLQRGYTVNA TVRNLKDASK VDHLLGLDGA    60
KERLHLFKAE LLGEHSFDPA VDGCEGVFHT ASPVSLTAKS KEELVDPAVS GTLNVLRSCT   120
KSTSVRRVVI TSSTASVICN KNMSTPGAVA DETWYSDAEL CEERKEWYQL SKTLAEEAAW   180
KPAKENGLDL VTLHPGLVIG PLLQPTLNFS CEAIVNFIKE GKEAWSGGIY RFVDVRDVAN   240
AHILAFEVPS ANGRYCLVGV NGYSSLVLKI VQKLYPSITL PENFEDGLPL IPTFQVSSER   300
AKSLGVNFTS LELSVKDTVE SLIEKNFLKI                                    330

SEQ ID NO: 2                    moltype = AA   length = 416
FEATURE                         Location/Qualifiers
source                          1..416
                                mol_type = protein
                                organism = Nicotiana sp.
SEQUENCE: 2
MMCNIISLVS IINFFLLFYR VVVLPQHAAA SHSTVEFLPG FEGPLPFHLE TGYIGVGEYE    60
EVQLFYYFLK SESEPTKDPI LIWLSGGPGC SSFTALVYQI GPLYFEPNEY NGSLPKLTLN   120
PNSWTKVANI IFLDQPVNSG FSYATTSTTF KSTDLQACHH IYQFLRKWLI KHQEFIRNPM   180
YIGGDSYSGI TVPVITQLIS NGIEAGHKPS INLKGYILGN PSTFPLQYNY WVPYAHGMGL   240
ISDELYQATT LILYFKIYHI INAINLAYMV EVHRLSTYWA NDPRVQEALN VRKGAITRWT   300
RCRESIVNKT YTITFQDSIP YHVELSKKLY RSLIYSGDHD MGIPFQSTQF WIKSLNYSIV   360
DEWRPWSFDG QVAGYTRSYS NQMTFATVKG AGHVAPEYKP KECFTMFQRW LSHEPL       416

SEQ ID NO: 3                    moltype = AA   length = 569
FEATURE                         Location/Qualifiers
source                          1..569
                                mol_type = protein
                                organism = Nicotiana sp.
SEQUENCE: 3
MLSVASVEAQ KAELSSSVIP PSDQSTEEIH VFRSRLPDIQ ISNNVPLHVY LFERLSEFQD    60
RTCLIAGSSG QSYTFAETHL ICQKIAAGLT NIGIKKGDVI MTFLQNCAEF VFTFLSASMI   120
GAVITTANPF YTKAEAFKQL KASNAKLIVT QSQYVDKFRD SGENDPKIGE DFSVITIDDP   180
PENCLHFSVL SEANEEEMPK GIVIQPDDPV ALPFSSGTTG LPKGVILTHK SLITGVAQLV   240
DGDNPNLYLK QDDVVLCVLP LFHIFALNSV LLVSLRAGAS VLLMQKFEIG ALLELIQNHR   300
VSVAAVVPPL VLALAKNPMV DSFDLSSIRL VLSGAAPLGK ELEEALHQRV PQAIFGQYG   360
MTEAGPVVTM CPAFAKQPFS TKSGSCGSVV RNADLKVVDP ETGGSLGRNQ PGEICIRGSQ   420
IMKGYLNDDE ATARTIDVDG WLHTGDIGYV DDDDEIYIVD RVKELIKFKG FQVPPAELES   480
LLVSHPDIAD AAVVPQKDDA AGEVPVAFVV RSANGFEITE EAIKEFIAKQ VIFYKRLHKV   540
YFIHAIPKSP SGKILRKELR AKLAAPSTQ                                    569

SEQ ID NO: 4                    moltype = AA   length = 551
FEATURE                         Location/Qualifiers
source                          1..551
                                mol_type = protein
                                organism = Nicotiana sp.
SEQUENCE: 4
MGTRAVESSQ QQECEHIFRS RYPPVQVPDN VTLPDFVLHN VELYTDKMAF VDATTGKGYT    60
YGGVARDIRR FAKALRSLGL RKGRVVVVVL PNVPEYAIVA LGIMAAGGVF SGANPAAHSS   120
EIVKQVESAD GKLIVSDLPT YHKVKDCGLP VIILGEEHVE GTIHWDELLE AAERAGSRTD   180
HITNHEDEMV QQNDLCALPF SSGTTGLSKG VMLTHRNLVA NLCSTLFSVS PEMVGQVTTL   240
GLIPFFHIYG ITGICCATIR NKGKVVVLRR YELRAFLNAL ITHEVTFAPI VPPIILALVK   300
NPIVDEFDLS KLKLRSIMTA AAPLAPEILN EFEKKFPDVQ VQEAYGMTEH SCITLSHSDQ   360
HTAKRNSVGF ILPNLEVKFV DPDTGRSLPK NKPGEICVKS QCVMKGYYKN EFETCLTIDK   420
DGWLQTGDIG YIDDDGDIFL VDRIKELIKY KGFQVAPAEL EGILLTHPSV EDAAVVGLPD   480
EEAGEIPVAW VVLNSKAKES EEDIINYIAS TVAQYKRVRV VQFVDSIPKS PSGKILRRLI   540
KDKMLERLKN A                                                        551

SEQ ID NO: 5                    moltype = AA   length = 671
FEATURE                         Location/Qualifiers
source                          1..671
                                mol_type = protein
                                organism = Nicotiana sp.
SEQUENCE: 5
MTEIPPNSQM KTMLQKAVQS VQWTYTLFWQ LCPQQGALVW RDGYYNGAIK TRKTVQPMEV    60
SAEEASLHRS QQLRELYESL SAGESNQPAR RPSAALSPED LTESEWFYLM CVSFSFPPGI   120
GLPGKAYSKK HHIWIMGANE VDSKVFCRAI LAKSARIQTV VGIPLLDGVL ELGTTERVQE   180
EIGFINHVKS FFTEQQQPQL PKPALSEHST SNPTTFSEPH FYSGNTSPSA NVDIAHQDGG   240
AAGEEDEEEE EEEDDDEAEL DSDSIAIQSA ANPIAVEASE LMQLDVSEAI QLGSPDDDSQ   300
NMDSDFHLVG AGNTAHDYQR QADSFKAETA ISWPHFQDLQ QLPGGSSYDE LSQEDTHYSQ   360
TVSTILEHRS SKFSSTTMGC ISHDSAQSAF TLCPSTTVCS PNPAHCRHDD SLVDGGGASQ   420
WLLKSILFTV PFLHTKYQSE ASPKSRDVAT VDSSSTASRF RKGCSITSQE EPSGNHVLAE   480
RRRREKLNER FIILRSLVPF VTKMDKASIL GDTIEYVKQL RKKVQDLEAR ARDTEHSRDA   540
DKKGGTATVK VLQGRGKRRM NTVDGSVGGG QATITASPPS TTENEEVVQV QVSIIESDAL   600
```

```
VELRCPYKEG LLLNVMQMLR ELKVEVVAIQ SALNNGVFLA ELRAKVKENI CGRKASILEV    660
KRSIHQIIPR D                                                         671

SEQ ID NO: 6             moltype = AA  length = 683
FEATURE                  Location/Qualifiers
source                   1..683
                         mol_type = protein
                         organism = Nicotiana sp.
SEQUENCE: 6
MTEIPPNSQM QTMLQKAVQS VQWTYTLFWQ LCSQQGVLVW RDGYYNGAIK TRKTVQPMEV    60
SAEEEASLHRS QQLRELYESL SAGESNQPAR RPSAALSPED LTESEWFYLM CVSFSFPPGI   120
GLPGKAYSKK HHIWIMCANE VDSKVFCRAI LAKSARIQTV VCIPLLDGVL ELGTTERVQE    180
DIGFINHVKS FFTEQQQPQP PKPALSEHST SNSTTFSEPH FYSGNTPPSG NADIAQQDGG    240
AAGEEEDEEEE EEEDDEAELD SDSIAIQSEV GGAANPIAAE ASELMQLDMS EAIRLGSPDD   300
GSNNMDSDFH LVGAGNTADY QRQPDSFKAE TAISWAHFQD LQHLPGGSSY EELSQEDTHY    360
SQTVSTILEH FSNRSSKFSS TTMGCISHDS AQSAFTLCPS TTVDCSPNPA HCRRRHDDSL    420
LDGGGASPSS QWLLKSILFT VPFLHTKYQS EASPKSVDVA TVDSSSTASR FRKGCSITSQ    480
EEPSGNHVLA ERRRREKLNE RFIILRSLVP FVTKMDKASI LGDTIEYVKQ LHKKVQDLEA    540
RARHTEQSKD ADQKSGTATV KVLQGRGKRR MNTVEAGNIG GGAKMTAFP LSTTEDEEVV     600
QVEVSIIESD ALLELRCPYK EGLLLDVMQM LRELKVEVVA IQSSLNNGIF LAELRAKVKE    660
NIYGRKASIV EVKKSIHQII PRD                                            683

SEQ ID NO: 7             moltype = AA  length = 220
FEATURE                  Location/Qualifiers
source                   1..220
                         mol_type = protein
                         organism = Nicotiana sp.
SEQUENCE: 7
MNICTNKSSS GVKKGAWTEE EDVLLKKCIE KYGEGKWHQV PLRAGLNRCR KSCRLRWLNY    60
LRPHIKRGDF SFDEVDLILR LHKLLGNRWS LIAGRLPGRT ANDVKNYWNS HLRKKLIAPH    120
DQKESKQKAK KITITFRPRPR TFSKTNTCVK SNTNTVDKDI EGSSEIIRFN DNLKPTTEEL   180
TDDGIQWWAD LLANNYNNNG IEEADNSSPT LLHEEMPLLS                          220

SEQ ID NO: 8             moltype = AA  length = 419
FEATURE                  Location/Qualifiers
source                   1..419
                         mol_type = protein
                         organism = Nicotiana sp.
SEQUENCE: 8
MVVISAVVPT PSRVESLAKS GIQAIPKEYV RPQEELNGIG NIFEEEKKDE GPQVPTIDLK    60
EIDSEDKEIR EKCHKELKKA AMEWGVMYLV NHGISDQLID RVKVAGKTFF DQPVEEKEKY    120
ANDQPSGNVQ GYGSKLANSA CGQLEWEDYF FHCVFPEDKC DLSIWPKIPT DYIPATSEYA    180
KQIRNLATKI LAVLSIGLGL EEGRLEKEVG GKEDLLLQMK INYYPKCPQP ELALGVEAHT    240
DVSALTFILH NMVPGLQLFY EGQWVTAKCV PNSIIMHIGD TLEILSNGKY KSILHRGVVN    300
KEKVRISWAI FCEPPKEKII LKPLSETITE AEPPRFPPRT FAQHMAHKLF KKDDQDAAAE    360
HKVSKKDDPD SAAGHKPFKK DDQDAVVQQK VLKEDEQDAA AEHKVFKKDN QDAAAEESK     419

SEQ ID NO: 9             moltype = AA  length = 419
FEATURE                  Location/Qualifiers
source                   1..419
                         mol_type = protein
                         organism = Nicotiana sp.
SEQUENCE: 9
MVVISAVVPT PSRVESLAKS GIQAIPKEYV RPQEELNGIG NIFEEEKKDE GPQVPTIDLT    60
EIDSEDKEIR EKCHQELKKA AIEWGVMHLV NHGISDELID RVKVSGDTFF DQPVEEKEKY    120
ANDQPSGNVQ GYGSKLANSA CGQLEWEDYF FHCVFPEDKC NLSIWPKTPT DYIPATSEYA    180
KQIRNLATKI LAVLSIGLRL EEGRLEKEVG GMEDLLLQMK INYYPKCPQP ELALGVEAHT    240
DVSALTFILH NMVPGLQLFY EGQWVTAKCV PNSIIMHIGD TLEILSNGKY KSILHRGVVN    300
KEKIRISWAI FCEPPKEKII LKPLPETITE AEPPRFPPRT FAQHMAHKLF KKDDQDAAAE    360
HKVSKKDDPD SAAEHKPFKK DDQDAVAQQK VLKEDEQNAA AEHKVFKKDN QDAAAEESK     419

SEQ ID NO: 10            moltype = AA  length = 622
FEATURE                  Location/Qualifiers
source                   1..622
                         mol_type = protein
                         organism = Nicotiana sp.
SEQUENCE: 10
MAMGHQDQDG VPNNLRKQLA LAVRGIQWSY AIFWSTPVTQ PGVLEWSDGY YNGDIKTRKT    60
VQVGEVNEDQ LGLHRTEQLR ELYSSLLTGE GEEDLQPQAK RPSAALSPED LTDTEWYFLV    120
CMSFVFNVGQ GLPGKTSATN QTIWLCNAHQ AESRVFSRSL LAKSASIQTV VCFPYLGGVI    180
ELGVTELVLE DPNLIQQIKN SFEVDHSVIS KRPNYNSNDA KDDMNVASRK LDHNVLESDA    240
YPVEINNSSP HDSSNGFVAN QEAEDSLMVV GVIGETSQAQ SWKFVDDNMS NGVHNSLNSS    300
DCISQNYEKL SPLSNGEKET KPCPIDRQEH NQNKLHLLDH GDDAQYQAV ISTLLKSSDQ     360
LTLGPHFRNI NKKSSFAGWK NDTEAPRIGT AQKLLKKVLL EVPPRMHGGV T HKFSRENRKS  420
NGLWRPEVDD IDRSRVISER RRREKINERF MHLASMLPTG GKVDKISLLD ETIEYMKELE    480
RRVQELEARS GKKTNDTAEQ TSDNCGTSKF NDVNGSLKRK ACDMDEMEPE SCNELLKGSS    540
ADGIVISMID KEVSIKMRCL WSEGLLLKIM EALTDLQMDC HTVQSSKIDG ILSIAIESKS    600
NGLKTVSVGA IREVLQRVVW KS                                             622
```

```
SEQ ID NO: 11              moltype = AA  length = 364
FEATURE                    Location/Qualifiers
source                     1..364
                           mol_type = protein
                           organism = Nicotiana sp.
SEQUENCE: 11
MESSTKSQIP TQSEEERNCT YAMQLLSSSV LPFVLHSTIQ LEVFEILAKS NDTKLSASQI   60
VSQIPNCTKP EAPTMLNRML YVLASYSLFT CSIVEDEKNN GGQKRVYGLS QVGKFFVKNE  120
NGASMGPLLA LLQNKVFINS WFELKDAVLE GGVPFDRVHG VHAFEYPKSD PKFNDVFNKA  180
MINHTTVVMK KILENYKGFE NLKTLVDVGG GLGVNLKMIT SKYPTIKGTN FDLPHVVQHA  240
PSYPGVEHVG GDMFESVPEG DAIFMKWILH DWSDSHNLKL LKNCYKALPD NGKVIVVEAI  300
LPVKPDIDTA VVGVSQCDLI MMAQNPGGKE RSEEEFRALA TEAGFKGVNL ICCVCNFWVM  360
EFCK                                                              364

SEQ ID NO: 12              moltype = AA  length = 506
FEATURE                    Location/Qualifiers
source                     1..506
                           mol_type = protein
                           organism = Nicotiana sp.
SEQUENCE: 12
MDLLLLEKTL IGLFFAIIVA IVVSKLRSKN FKLPPGPIPV PVFGNWLQVG DDLNHRNLTE   60
YAKKFGDMFL LRMGQRNLVV VSSPELAKEV LHTQGVEFGS RTRNVVFDIF TGKGQDMVFT  120
VYGEHWRKMR RIMTVPFFTN KVVQQYRRGW EDEVAHVVED VKKNPESATN GIVLRKRLQL  180
MMYNNMYRIM FDRRFESEDD PLFNKLKALN GERSRLAQSF EYNYGDFIPI LRPFLRGYLN  240
ICKEIKQRRL QLFKDYFVDE RKKLANTTKS MDNNSLKCAI DHILEAEQKG EINEDNVLYI  300
VENINVAAIE TTLWSIEWGI AELVNHPEIQ KKLRDEIDSV LGVGVQITEP ELNKLPYLQA  360
VIKETLRLRM AIPLLVPHMN LHDAKLAGYD IPAESKILVN AWWLANNPAT WKKPEEFRPE  420
RFFEEEKHVE ANGNDPRYLP FGVGRRSCPG IILALPILGI TLGRLVQNFE LLPPPGQSKL  480
DTTEKGGQFS LHILKHSTIV MKPRSF                                      506

SEQ ID NO: 13              moltype = AA  length = 298
FEATURE                    Location/Qualifiers
source                     1..298
                           mol_type = protein
                           organism = Nicotiana sp.
SEQUENCE: 13
MGRKPCCVKE GLRKGPWSSK EDLLLTNYIK ENGEGQWRSL PKNAGLLRCG KSCRLRWMNY   60
LRPGIKRGNF SQDEEDLIVR LHSLLGNRWS LIAGRLPGRT DNEIKNYWNT HLIKKLKNAG  120
IEPKPHKNFS KCSKKESRKG PQQGKSRKIQ GKKSNNKNNK GQIVQVEKTK VFFPKPIRIS  180
CGISRNNSFE NVTLSTTCSS NSNSGEANLE NKENEVKLEE VSFFPRDLDF GKLLEGDAIY  240
DEFLMEESCH ISNKCSLPMN ESMLEKVYEE YLLLLSENCY LQDDHQNEQN FPVNVSDQ    298

SEQ ID NO: 14              moltype = AA  length = 381
FEATURE                    Location/Qualifiers
source                     1..381
                           mol_type = protein
                           organism = Nicotiana sp.
SEQUENCE: 14
MASEAHAAVH APPPVAPTVC VTGAAGFIGS WLVMRLLERG YNVHATVRDP ENKKKVKHLF   60
ELPKADTNLT LWKADLSVEG SFDEAIQGCQ GVFHVATPMD FESEDPENEV IKPTVRGMLS  120
IIESCAKANT VKRLVFTSSA GTLDAQEHQK LFYDETSWSD LDFIYAKKMT GWMYFVSKIL  180
AEKAAMEAAK KKNFDFISII PPLVVGPFLT PTFPPSLITA LSLITGNEAH YCIIKQGQYV  240
HLDDLCEAHI FLYEQPKAEG RFICASHHAI IYDVAKMVRE KWPEYYVPTE FKGIDKDLPV  300
VYFSPKKLTD MGFQFKYTLE DMYKGAIETC RQKQLLPFST QSTADNGRDK ETIPLSAENY  360
ASGKENSPVA NGTGKSTNGE I                                           381

SEQ ID NO: 15              moltype = AA  length = 382
FEATURE                    Location/Qualifiers
source                     1..382
                           mol_type = protein
                           organism = Nicotiana sp.
SEQUENCE: 15
MASEGHAAVH APSPPAAPTV CVTGAAGFIG SWLVMRLLER GYNVHATVRD PENKKKVKHL   60
LELPKADTNL TLWKADLSVE GSFDEAIQGC QGVFHVATPM DFESEDPENE VIKPTVRGML  120
SIIESCAKAN TVKRLVFTSS AGTVDVQEHQ KLLYDETSWS DLDFIYAKKM TGWMYFVSKI  180
LAEKAAMEAA KKKNIDFISI IPPLVVGPFL APTFPPSLIT ALSLITGNEA HYSIIKQGKY  240
VHLDDLCEAH IFLYEHPKAE GRFICASHHA IIYDVAKMVQ EKWPEYYVPT EFKGIDKDLS  300
VVYFSSKKLT DMGFQFKYTL EDMYKGAIET CRQKQLLPFS TRSTADNVRD KEAIPLSTEN  360
YASGKENSPV ANGTGKSTNG EI                                          382

SEQ ID NO: 16              moltype = AA  length = 213
FEATURE                    Location/Qualifiers
source                     1..213
                           mol_type = protein
                           organism = Nicotiana sp.
SEQUENCE: 16
MGRKPCCSKE GLRKGTWTAK EDMLLTNYIN EHGEGVWRSL PMKAGSRWSL IAGRIPGRTD   60
NEIKNYWNTH LLKKLKSEGL EPKIHKSLAK NTRRQKEKAN VSSQINQKGY KEKKKRNKKG  120
NIEENCNNIE EKEQVAKKIE EQWHTQDSVQ AMSGFSSTSE VASEKETNCN NVHCPSSGQS  180
```

```
LEENDNEIYE KLQASGDSKR CKLNFSAEVN KTP                                 213

SEQ ID NO: 17           moltype = AA  length = 435
FEATURE                 Location/Qualifiers
source                  1..435
                        mol_type = protein
                        organism = Nicotiana sp.
SEQUENCE: 17
MKIEVKESTM VKPAAETPQQ RLWNSNVDLV VPNFHTPSVY FYRPTGSPNF FDGKVLKEAL    60
SKALVPFYPM AGRLCRDEDG RIEIDCKGQG VLFVEAESDG VVDDFGDFAP TLELRQLIPA   120
VDYSQGIQSY ALLVLQITHF KCGGVSLGVG MQHHAADGAS GLHFINTWSD MARGLDLTIP   180
PFIDRTLLRA RDPPQPQFPH VEYQPPPTLK VTPENTPISE AVPETSVSIF KLTRDQINTL   240
KAKSKEDGNT VNYSSYEMLA GHVWRSTCMA RGLAHDQETK LYIATDGRSR LRPSLPPGYF   300
GNVIFTTTPI AVAGDIQSKP IWYAASKLHD ALARMDNDYL RSALDYLELQ PDLKALVRGA   360
HTFKCPNLGI TSWSRLPIHD ADFGWGRPIF MGPGGIAYEG LSFILPSPTN DGSQSVAISL   420
QAEHMKLFEK FLYDF                                                    435

SEQ ID NO: 18           moltype = AA  length = 436
FEATURE                 Location/Qualifiers
source                  1..436
                        mol_type = protein
                        organism = Nicotiana sp.
SEQUENCE: 18
MGSEKMMKIN IKESTLVKPS KPTPTKRLWS SNLDLIVGRI HLLTVYFYKP NGSSNFFDSK    60
IMKEALSNVL VSFYPMAGRL ARDEQGRIEI NCNGEGVLFV EAESDAFVDD FGDFTPSLEL   120
RKLIPTVDTS GDISTFPLII FQVTRFKCGG VSLGGGVPFH LSDGLSSIHF INTWSDIARG   180
LSVAIPPFID RTLLRARDPP TSSFEHVEYH PPPSLISSSK SLESTSPKPS TTTMLKFSSD   240
QLGLLKSKSK HDGSTYEILA AHIWRCTCKA RALSDDQLTK LHVATDGRSR LCPPLPPGYL   300
GNVVFTGTPM AKSSELLQEP LTNSAKRIHS ALSKMDDNYL RSALDYLELL PDLSALIRGP   360
TYFASPNLNI NSWTRLPVHD SDFGWGRPIH MGPACILYEG TVYILPSPNS KDRNLRLAVC   420
LDADHMPLFE KYLYEF                                                   436

SEQ ID NO: 19           moltype = AA  length = 715
FEATURE                 Location/Qualifiers
source                  1..715
                        mol_type = protein
                        organism = Nicotiana sp.
SEQUENCE: 19
MASNGHVNGG ENFELCKKSA DPLNWEMAAE SLRGSHLDEV KKMVSEFRKP MVKLGGESLT    60
VAQVAAIAVR DKSANGVKVE LSEEARAGVK ASSDWVMDSM NKGTDSYGVT TGFGATSHRR   120
TKNGGALQKE LIRFLNAGVF GNGTETSHTL PHSATRAAML VRINTLLQGY SGIRFEILEA   180
ITKLINSNIT PCLPLRGTIT ASGDLVPLSY IAGLLTGRPN SKAVGPNGET LNAEEAFRVA   240
GVNGGFFELQ PKEGLALVNG TAVGSGMASM VLFDSNILAV MSEVLSAIFA EVMNGKPEFT   300
DHLTHKLKHH PGQIEAAAIM EHILDGSSYV KAAQKLHEMD PLQKPKQDRY ALRTSPQWLG   360
PQIEVIRAAT KMIEREINSV NDNPLIDVSR NKALHGGNFQ GTPIGVSMDN ARLALASIGK   420
LMFAQFSELV NDYYNNGLPS NLTASRNPSL DYGFKGAEIA MASYCSELQF LANPVTNHVQ   480
SAEQHNGDVN SLGLISARKT AEAVDILKLM SSTYLVALCQ AIDLRHLEEN LKNAVKNTVS   540
QVAKRTLTMG ANGELHPARF CEKELLRIVD REYLFAYADD PCSCNYPLMQ KLRQVLVDHA   600
MNNGESEKNV NSSIFQKIGA FEDELKAVLP KEVESARAAL ESGNPAIPNR ITECRSYPLY   660
RFVRKELGTE LLTGEKVRSP GEECDKVFTA MCNGQIIDPM LECLKSWNGA PLPIC        715

SEQ ID NO: 20           moltype = AA  length = 341
FEATURE                 Location/Qualifiers
source                  1..341
                        mol_type = protein
                        organism = Nicotiana sp.
SEQUENCE: 20
MDNSAPDSLS RSETAVTYDS PYPLYAMAFS SLRSSSGHRI AVGSFLEDYN NRIDILSFDS    60
DSMTVKPLPN LSFEHPYPPT KLMFSPPSLR RPSSGDLLAS SGDFLRLWEI NEDSSTVEPI   120
SVLNNSKTSE FCAPLTSFDW NDVEPKRLGT CSIDTTCTIW DIEKSVVETQ LIAHDKEVHD   180
IAWGEARVFA SVSADGSVRI FDLRDKEHST IIYESPQPDT PLLRLAWNKQ DLRYMATILM   240
DSNKVVILDI RSPTMPVAEL ERHQASVNAI AWAPQSCKHI CSGGDDTQAL IWELPTVAGP   300
NGIDPMSVYS AGSEINQLQW SSSQPDWIGI AFANKMQLLR V                       341

SEQ ID NO: 21           moltype = AA  length = 440
FEATURE                 Location/Qualifiers
source                  1..440
                        mol_type = protein
                        organism = Nicotiana sp.
SEQUENCE: 21
MSMSVALLWV VSPTSEVSNG TGLLDSVREG NRVFVSSRFL ARDRNLMWNG RIKKGGRQRW    60
NFGSLIADPR YSCLGGSRTE KGSSFSVQSS LVASPAGEMT VSSEKKVYDV VLKQAALVKR   120
QLRSTDELEV KPDIVVPGNL GLLSEAYDRC GEVCAEYAKT FYLGTKLMTP ERRRAIWSIY   180
VWCRRTDELV DGPNASHITP QALDRWEARL EDIFSGRPFD MLDAALSDTV SRFPVDIQPF   240
RDMIEGMRMD LWKSRYNNFD ELYLYCYYVA GTVGLMSVPV MGIAPESKAT TESVYNAALA   300
LGLANQLTNI LRDVGEDARR GRVYLPQDEL AQAGLSDEDI FAGRVTDKWR NPMKKQIQRA   360
RKFFDESEKG VTELDSASRW PVSTALLLYR KILDEIEAND YNNFTRRAYV SKPKKLLTLP   420
IAYAKSLVPP NRTSSPLAKT                                               440
```

```
SEQ ID NO: 22             moltype = AA  length = 440
FEATURE                   Location/Qualifiers
source                    1..440
                          mol_type = protein
                          organism = Nicotiana sp.
SEQUENCE: 22
MSMSVALLWV VSPTSEVSNG TGLLDSVREG NRVFVSSRFL ARDRNLMWNG RIKKGGRQRW   60
NFGSLIADPR YSCLGGSRTE KGSSFSVQSS LVASPAGEMT VSSEKKVYDV VLKQAALVKR  120
QLRSTDELEV KPDIVVPGNL GLLSEAYDRC GEVCAEYAKT FYLGTKLMTP ERRRAIWAIY  180
VWCRRTDELV DGPNASHITP QALDRWEARL EDIFSGRPFD MLDAALSDTV SRFPVDIQPF  240
RDMIEGMRMD LWKSRYNNFD ELYLYCYYVA GTVGLMSVPV MGIAPESKAT TESVYNAALA  300
LGLANQLTNI LRDVGEDARR GRVYLPQDEL AQAGLSDEDI FAGRVTDKWR NFMKKQIQRA  360
RKFFDESEKG VTELDSASRW PVLAALLLYR KILDEIEAND YNNFTRRAYV SKPKKLLTLP  420
IAYAKSLVPP NRTSSPLAKT                                             440

SEQ ID NO: 23             moltype = AA  length = 248
FEATURE                   Location/Qualifiers
source                    1..248
                          mol_type = protein
                          organism = Nicotiana sp.
SEQUENCE: 23
MEGSSKGLRK GAWTTEEDSL LRQCINKYGE GKWHQVPVRA GLNRCRKSCR LRWLNYLKPS   60
IKRGKLSSDE VDLLLRLHRL LGNRWSLIAG RLPGRTANDV KNYWNTHLSK KHEPCCKIKM  120
KKRDITPIPT TPALKNNVYK PRPRSFTVNN DCNHLNAPPK VDVNPPCGLG NINNVCDNSI  180
IYNKDKKKDQ LVNNLIDGDN MWLEKFLEES QEVDILVPEA TTTEKGDTLA FDVDQLWSLF  240
DGETVKFD                                                          248

SEQ ID NO: 24             moltype = DNA  length = 992
FEATURE                   Location/Qualifiers
source                    1..992
                          mol_type = genomic DNA
                          organism = Nicotiana sp.
SEQUENCE: 24
atggaaagca agagttccgg aggcggagaa ggaaaggttg tatgtgtaac aggggcctct   60
ggtttcatag cttcatggct tgttaagatg ctacttcaac gtggttacac tgtcaatgcc  120
actgttcgca acctcaagga tgcgagtaaa gtggatcacc tgttaggcct tgacggagct  180
aaagagaggc tgcatctttt caaagctgag ttacttggtg agcattcgtt tgatcctgcc  240
gttgatggtt gtgaaggtgt cttcatacaa gcatccacctg tttctctcac agctaaatcc  300
aaggaggaac ttgtagaccc tgctgtgagc ggaacattaa acgtcccttag gtcatgtacc  360
aaatcaacat ctgttagaag agtggtcata acctcttcta ccgcttctgt tatttgcaat  420
aaaaacatgt caaccccctgg agctgtagct gatgagactt ggtattcaga tgcagaactc  480
tgtgaggaaa gaaggaatg gtatcaactc tccaaaacct tggctgagga agctgcttgg  540
aaattttgcaa aggagaatgg ggttggacttg gttacacttc atccaggtct agtcatcggt  600
ccacttctgc agcctacgct caatttctcg tgcgaggcta tagtgaactt cataaaagaa  660
ggaaagaag catggtctgg cggaatatat agatttgtcg atgttaggga tgttgctaat  720
gcacatatac tagcatttga ggtcccttca gcaaatggaa gatattgttt agttgggta  780
aatgatatt cttcttttggt ttttgaagatt gtacaaaagc tttaccttc catcactctc  840
cctgagaatt ttgaagatgg attacctctt atcccaacct tccaagtatc aagcgaaaga  900
gcaaaaaggt taggcgtcaa tttcacatct cttgagttga gcgtgaagga cactgttgaa  960
agcttgatag agaagaactt cctcaagatt tg                                992

SEQ ID NO: 25             moltype = DNA  length = 1251
FEATURE                   Location/Qualifiers
source                    1..1251
                          mol_type = genomic DNA
                          organism = Nicotiana sp.
SEQUENCE: 25
atgatgtgca atattatttc acttgtgtcc atcatcaact tcttttttgct gttttataga   60
gtttgtgtcc taccacaaca tgctgctgct tctcactcta ccgttgaatt tcttcctgga  120
tttgaaggtc cacttccttt ccatcttgag actgggtata ttggagtagg tgaatatgga  180
gaagtgcagc tcttttatta ttttcttaaa tcagaatcag aacccacaaa agatcctatt  240
ttgatttggc tctcaggagg acctggttgc tcttccttta ctgcacttgt ttatcaaata  300
gggccccttgt attttgagcc aaacgagtat aatgggagcc ttccaaagct aacattgaat  360
ccaaactcat ggaccaaggt agctaacata atattccttgg caacctgt gaatagtggc  420
ttctctctatg caacaacttc aacaacattc aagtctactg atctacaagc atgccaccat  480
atctaccagt ttttgcgaaa gtggttgatt aagcatcaag agttcattag gaatccaatg  540
tacattggtg gagattcata ttctggcatc actgttccag ttatcactca actaatatca  600
aatggaattg aagcagggca caagccatcg attaatctta agggatatat acttgggaat  660
cctagcacgt ttcctcttca atataactac tgggttcctt atgctcatgg aatgggactt  720
atctccgacg aactttatca ggctactact cttatccttt acttaaaat ttatcatatc  780
ataaatgcaa ttaatttagc ttacatggtt gaggtacaca ggttgtctac ttactgggca  840
aatgatccaa gagtacaaga agctcttaat gttcgtaagg gagctataac aagatggaca  900
agatgtaggg aaagtatcgt gaataaaact tacactatta ctttccaaga tagcataccct  960
tatcatgtgg aactcagcaa aaaacttttat cgatcactta tatacatgga cgatcatgat 1020
atggcattc cattccaatc aactcaattt tggataaaat ctctaaatta ttctattgtg 1080
gatgaatggc ggccatggag ttttgatggt caagttgcag gatatacaag atccttattcc 1140
aaccagatga catttgcaac tgtcaaggga gcaggacatg tagctcctga gtacaagcct 1200
aaagagtgct ttaccatgtt tcaaagatgg ttgtctcatg aaccactttg a           1251
```

```
SEQ ID NO: 26            moltype = DNA   length = 1710
FEATURE                  Location/Qualifiers
source                   1..1710
                         mol_type = genomic DNA
                         organism = Nicotiana sp.
SEQUENCE: 26
atgttgagtg tagctagtgt tgaagcccag aaagcagagt tatcttcttc tgtaattcct   60
ccttctgatc aatctactga agagatacac gtgtttagat caagattacc agatatacaa  120
atttccaaca atgttcctct tcatgtttac ttgtttgaga ggctctctga atttcaagat  180
aggacatgtc ttatagcagg cagcagtgga caatcctaca cttttgctga aactcatctc  240
atttgccaga aaatagctgc tggcttaaca aatataggaa tcaaaaaggg agatgtaatc  300
atgacttttc tccagaactg cgcggaattt gtgtttactt ttctctcggc ttctatgatt  360
ggcgccgtta taactacagc taatccattt tacacaaaag cagaggcgtt taagcaatta  420
aaagcgtcga atgcaaaact aatcgttact caatctcagt acgtggataa atttcgtgat  480
tctggagaga atgacccgaa aattggcgaa gattttttcag tcattacaat tgatgacccc  540
cctgaaaatt gcttacattt ctctgtactt tctgaagcta acgaaggaga aatgccaaag  600
ggaattgtaa tccaaccaga tgatccagta gctttaccat tttcttcagg aacaacaggg  660
ctaccaaaag gtgtgatttt aactcacaaa agtttaatca caggagtagc tcaattagtc  720
gacggagata atccaaattt gtacttaaaa caagacgacg tggtgctatg tgtgctacct  780
ttgtttcaca tatttgcgtt aaattcagtg cttttagtct cgttaagagc aggagctagt  840
gtttactaa tgcaaaaatt cgaaattggt gcattgctgg agctgataca aaaccaccgc  900
gtgtcagttg cagcagtagt tccgcccttg gttcttgctg tggcgaaaaa tccgatggtt  960
gattcgttcg atttgagttc gattaggctc gtgttgtccg gggcggcgcc gctggggaaa 1020
gagttggagg aagcgctaca tcaaagagtc ccgcaagcta tatttggtca ggggtatggt 1080
atgacagagg caggaccagt agtaacaatg tgcccagcat ttgcaaagca accattttca 1140
accaaatctg gctcatgtgg ttcagtagtt cgaaatgcaa acctcaaggt ggtcgacccc 1200
gaaactggtg gctccctcgg ccgcaaccaa cccggcgaaa tttgcatccg tggttcccaa 1260
atcatgaaag gttatctgaa tgatgatgag gccacggcac ggaccataga tgtcgatgga 1320
tggctccaca ctggtgatat aggatacgta gatgacgatg atgaaatata catcgtcgat 1380
agagtcaaag agcttatcaa gttcaaagga ttccaggtgc caccagctga gcttgagtcc 1440
cttctagtaa gccatccaga tattgcagat gctgctgttg taccgcaaaa agatgatgcc 1500
gcaggggaag tccagttgc atttgtggtc cgctccgcca atggttttga aattactgaa 1560
gaagctataa aggaatttat tgccaaacag gtgatattct ataaaagatt gcacaaggtg 1620
tatttttattc acgctattcc aaagtctccg tctggaaaga tactgaggaa agaactgaga 1680
gccaaactag ctgcgccctc cacccagtga                                   1710

SEQ ID NO: 27            moltype = DNA   length = 1656
FEATURE                  Location/Qualifiers
source                   1..1656
                         mol_type = genomic DNA
                         organism = Nicotiana sp.
SEQUENCE: 27
atgggaactc gtgcagtaga aagctcacag cagcaagaat gtgaacatat tttccggagt   60
agatatcctc cggttcaagt accggacaat gtgaccctcc cggattttgt gcttcacaat  120
gtagagttat acactgacaa aatgcatttt gtggatgcta ccactggcaa aggctacact  180
tatgccaagt tgcaagagaa cataaggagg ttcgccaagg ccttgagatc ccttggctta  240
aggaaaggac gggtggtggt ggtagttctt ccaaatgtac cagaatatgc tattgttgct  300
cttggaatca tggctgctgg tggcgtcttc tccggtgcaa atccagcagc tcattcatca  360
gaaatcgtga acaagttgaa atctgctgat ggcaagctta ttgtctctga tctaccaacc  420
tatcacaagg ttaagatttg gggctgcca gtaataatac taggtgaaga acatgtagaa  480
ggaacaattc attgggatga attgcttgaa gctgcagagc gtgccggttc cagaactgat  540
cacataacaa accatgaaga tgaaatggtg cagcaaaatg atttatgtgc actgcccttc  600
tcgtcaggca ctacggggct gtccaaggga gtgatgttaa cccacagaaa tctagtagca  660
aacctctgct ctacactctt cagtgttagc ccagaaatgg taggcaagt tacaacactg  720
ggtttgatac cattcttcca catttatggg ataactgtaa tctgttgtgc aaccattaga  780
aacaaaggga aagtggtagt cttgcgtgag tacgaactga gggcatttct aaatgcactc  840
attacacatg aagtgcacatt tgcaccaatt gtgccaccta tcatcttggc acttgttaag  900
aatcctattg tggatgaatt tgatctcagc aagcttaagc ttagatccat catgacagcg  960
gcagccccac ttgccctga gattcttaat gaatttgaaa agaaatttcc cgatgttcag 1020
gtccaagagg catatgggat gactgagcac agctgcatta ctctttctca tagtgaccag 1080
catactgcta aaagaaattc tgttggtttt attctaccta atttggaggt aaagttcgtt 1140
gatcctgata ccggtagatc tctccccaaa aacaaaccag cgagatatg tgtcaaaagc 1200
caatgtgtta tgaagggtta ctacaaaaat gaatttgaga cttgccttac cattgataag 1260
gatggatggc ttcagactgg tgacattggc tacattgacg tatgatggga tatcttccta 1320
gtcgatcgta tcaaagagct tatcaagtac aagggattcc aagttgctcc agctgagtta 1380
gaagggatcc ttctcacaca tccttcagta gaagatgctg cagtagttgg ctgccagat 1440
gaagaagcag gagagatacc agtggcatgg gtagtcttga actcaaaagc aaaagaaagc 1500
gaagaggaca ttatcaacta cattgcatcg actgttgcac agtataaacg agtgagagtg 1560
gtgcagttcg ttgatagtat tccaaaatct ccttctggaa aaatactgag aagacttatc 1620
aaggataaga tgctagagag acttaagaat gcatag                            1656

SEQ ID NO: 28            moltype = DNA   length = 2016
FEATURE                  Location/Qualifiers
source                   1..2016
                         mol_type = genomic DNA
                         organism = Nicotiana sp.
SEQUENCE: 28
atgacgagga taccgcctaa cagccagatg aaaaccatgt gcagaaggc agtgcaatcg   60
gttcaatgga catatactct tttctggcaa ttatgtcccc aacaagggc gttagtgtgg  120
```

```
agagatggat attacaatgg ggctataaag actagaaaga cagtgcagcc aatggaagtt    180
agcgctgagg aagcttctct tcacagaagc caacagctta gagaacttta cgaatcactt    240
tccgccggcg agtcaaatca gccagcgaga aggccgtcgg cagctttgtc accgaggac     300
ttgacggagt ccgagtggtt ttatctcatg tgtgtttctt tctcttttcc tcctggcatc    360
ggattacctg gcaaggctta ttcgaagaaa catcacatat ggatcatggg cgcaaacgag    420
gttgatagca aagtcttctg tagagctatt cttgccaaga gcgcccgcat acagacggtc    480
gttggtattc ctctcttgga tggtgtactg gaactgggaa ctacagaaag ggttcaagaa    540
gagattggat tcataaacca tgtaaagagc ttttcactg agcaacaaca acctcagcta     600
ccaaagccag ccttatctga gcactccact tccaatccca ccacctttc cgagccacat     660
ttttactccg gcaatacttc gccatctgct aatgttgata ttgcgcatca agatggcgga    720
gctgccggcg aagaagatga ggaggaggaa gaagaagaag atgatgatga agccgagttg    780
gactcggata gtatagcgat tcaaagcgcg gctaatccta ttgccgttga ggctagtgaa    840
ctcatgcagc ttgatgtgtc cgaggctata cagctcggct cgcccgatga tgactctgat    900
aatatgact ctgattttca tttggttggc gctggaaaca cggtccatga ctaccagtgc     960
caagctgact ctttcaaagc cgagaccgcc attagctggc cgcacttcca agaccttcaa   1020
caattaccag gtggctctag ttatgatgaa ttatacaag aagacacaca ctattctcaa    1080
acagtgtcaa ccattctcga cacccgaagc tccaaatttt cctctacaac aatgggctgt   1140
atttctcatg actcggccca atctgccttc acattgtgcc ctagcaccac cgtctgcagc   1200
ccgaatcccg cccactgccg ccacgacgac tcacttgtcg acggtggcgg cgcctcccag   1260
tggctgctca aaagcatact cttcactgtc ccatttcttc acactaaata ccaatctgaa   1320
gcttctccaa agtcacgtga cgtcgccact gttgattcct ccagtactgc ttctcgcttt   1380
cgcaaaggct gtagtataac gtcgcaagaa gagccaagtg gaaaccatgt acttgcaaa    1440
cgacgtcgta gagagaagct aaatgagcgt tttatcatat taaggtctct tgtaccttt    1500
gtaacgaaaa tggacaaagc ctccattttg ggtgacacca tagagtatgt caagcagtta   1560
cgtaagaaag ttcaggatct tgaagctcgt gctcgcgaca cggagcactc cagagatgca   1620
gataaaaaag gtgcacagc tacagtgaag gtgttgcaag gaagggtaa gaggagaatg    1680
aatacggtag atggaagtgt tggtggaggg caggcaacga taacggcgtc cccaccgtca   1740
acgacggaaa atgaggaggt tgtgcaagta caagtatcaa ttatcgaaag cgatgcattg   1800
gtggagctcc ggtgtccgta caaagagggg ttgctgttaa atgtaatgca gatgctaagg   1860
gaactcaaag tggaagttgt agccattcaa tcagctctta ataatggcgt cttcttggct   1920
gagttaagag ctaaggtaaa agagaatata tgtgaagaga aagcaagcat tttggaagta   1980
aaaaggtcaa tacatcagat aatccctaga gattaa                             2016

SEQ ID NO: 29         moltype = DNA   length = 2052
FEATURE               Location/Qualifiers
source                1..2052
                      mol_type = genomic DNA
                      organism = Nicotiana sp.
SEQUENCE: 29
atgacggaga taccgcctaa cagccagatg caaaccatgt tgcagaaggc tgtgcaatcg     60
gttcaatgga catatactct tttctggcaa ttatgttccc aacaagggt gttagtgtgg    120
agagatggat attacaatgg ggctataaag actagaaaga ctgtgcagcc aatggaagtt   180
agcgctgagg aagcttctct tcacagaagc caacagctta gagaacttta cgaatcactt   240
tccgccggcg agtcaaatca gccggcgaga aggccgtcgg cagctttgtc accgaggac    300
ttgacggaat ccgagtggtt ttatctcatg tgtgtttctt tctcttttcc tcctggcatc   360
ggattacctg gcaaggctta ttcaaagaaa catcacatat ggattatgtg cgcaaacgag   420
gttgatagca aagtcttctg tagagctatt cttgccaaga gtgcccgcat acagacggtc   480
gtctgtattc ctctcttgga tggtgtactg gaactgggaa ctacagaaag ggttcaagaa   540
gacattggat tcataaacca tgtaaagagc ttttcactg agcaacaaca acctcagcca    600
ccaaagccag ccttatctga gcactccact tccaattcca ccacctttc cgagccacac    660
ttttactccg gcaatactcc gccatctggc aatgctgata ttgcgcagca agatggcgga   720
gctgccggag aagaagatga ggaggaggaa gaagaagaag acgatgaagc cgagttggat   780
tcggatagta tagcaattca agtgaggtt ggtggcgcgg ctaatcctat agcggctgag    840
gctagtgaac tcatgcagct tgatatgtct gaggctatac ggcttggctc gcccgatgat   900
ggctctaata atatgactc tgattttcat ttggttggcg ctggaaatac ggctgactac    960
cagcgtcaac ctgactcttt caaagccgag actgccatta gctgggctca cttccaagac  1020
cttcaacatt taccaggtgg ctcagttat gaagaattat cacaagaaga cacacattat   1080
tctcaaacag tgtcaaccat tcttgaacac ttctcaaacc gaagctccaa attttcctct  1140
accacaatgg gctgtatttc tcatgactca gcccaatcgg ccttcacatt gtgcctagc   1200
accaccgtcg actgcagccc gaatcccgcc cactgccgcc gccacga cgattcactt     1260
ctcgacggtg gcggcgcctc cccctcctcc cagtggctgc tcaaaagcat actcttcact  1320
gtcccatttc ttcacactaa ataccaatct gaagcttctc cgaaatcagt tgacgtcgcc  1380
actgttgatt cctccagtac tgcttctcgc tttcgcaaag gctgtagtat aacgtcgcaa  1440
gaagagccca gtggaaacca tgtacttgca gaacgacgtc gtagagaaaa gctaaatgag  1500
cgttttatca tattaaggtc tcttgtacct tttgttacga aaatggataa agcctccatt  1560
ttgggtgaca ccatagagta tgtcaagcag ttacataaga agttcaggca tcttgaagct  1620
cgtgctcgtc acacggagca gtccaaagat gcagaccaaa aaagtggcac agctacagtg  1680
aaggtgttgc aagggagggg taagaggaga atgaatacgg tggaggccgg aaatattggt  1740
ggagggcagg caaagatgac ggcttttccg ctatcaacaa ccgaaggatga agaggttgtg  1800
caagtagaag tatcaattat tgaaagcgat gcattgttgg agctccgatg tccgtacaaa  1860
gaggggctgc tgttagatgt aatgcagatg ctaaggaac tcaaggtgga agttgtagcc   1920
attcaatcat ctcttaataa tggcatcttc ttggctgagt taagagctaa ggtaaaagag  1980
aatatatatg gaaggaaagc aagcattgtg gaagtaaaaa agtcaataca tcagataatc  2040
cctagagatt aa                                                       2052

SEQ ID NO: 30         moltype = DNA   length = 663
FEATURE               Location/Qualifiers
source                1..663
                      mol_type = genomic DNA
```

```
                       organism = Nicotiana sp.
SEQUENCE: 30
atgaatattt gtactaataa gtcgtcgtca ggagtgaaga aaggtgcatg gactgaagaa    60
gaagatgttc tattgaaaaa atgcatcgag aaatatggag aaggaaagtg gcatcaagtt   120
cctcttagag ctggtttgaa tagatgcaga aagagctgca gattaaggtg gctaaattat   180
ctaaggccac atataaagag aggagacttc tcttttgatg aagtagatct cattttgagg   240
cttcataagc tgttaggcaa cagatggtca cttattgctg gtagacttcc tggaaggacg   300
gcaaacgatg tcaaaaacta ctggaacagc atcttcgca agaagttaat tgctcctcat    360
gatcaaaagg agagcaagca aaaagcaaag aagatcacca tattcagacc tcggcctcga   420
accttctcaa agacaaatac ttgtgttaaa agtaacacaa atactgtaga taaggatatt   480
gaaggcagca gcgaaataat tagattcaac gataatttga agccaacaac tgaagaattg   540
acggatgatg gaattcaatg gtgggccgat ttactagcta acaattacaa caataatggg   600
attgaggaag ctgataattc atcaccaact ttgttgcatg aggaaatgcc acttctcagt   660
tga                                                                 663

SEQ ID NO: 31           moltype = DNA  length = 1260
FEATURE                 Location/Qualifiers
source                  1..1260
                        mol_type = genomic DNA
                        organism = Nicotiana sp.
SEQUENCE: 31
atggtggtga tcagtgcagt agttccaact ccttcaagag ttgaaagctt ggctaaaagt    60
ggaatccagg ctatccctaa agagtatgtg aggccacaag aagagttaaa tggaatagga   120
aacatatttg aggaagagaa gaaagatgaa ggacctcaag taccgacgat tgatctgaaa   180
gaaatcgact cagaggacaa ggaaattcgc gagaaatgcc acaaagagtt gaagaaagca   240
gctatggagt ggggtgttat gtaccttgtt aaccatggca tatcagatca gctaattgat   300
cgtgtcaagg ttgctggaaa gaccttcttt gatcaacctg ttgaagaaaa ggagaagtat   360
gctaatgacc aaccctctgg caatgtccaa ggctatggca gcaagttagc aaatagtgct   420
tgtggtcagc ttgaatggga ggattatttc ttccattgcg tttccccga ggacaagtgc    480
gacttatcca tctggcctaa aatccctact gactacattc cagcaacaag tgaatatgcc   540
aaacagatta ggaacctagc aacaaagatt ttggcagtgc tttctattgg gctgggacta   600
gaagaaggaa gactagagaa ggaagtcgga ggcaaggagg acctactgct tcaaatgaag   660
attaactact accccaaatg tccccaacca gaactagcac ttggcgttga agctcatact   720
gatgtgagtg cactgacttt tatcctccac aatatggtgc ctgggttaca acttttctat   780
gaaggacagt gggtaacggc aaagtgtgtg cctaattcca taatcatgca tattgggggac   840
acccttgaaa tcctaagcaa tggaaagtac aaaagcattc ttcacagagg ggttgtgaat   900
aaagagaaag taagaatctc atgggctatt ttctgtgagc cgccaaagga gaagatcatc   960
cttaagcccc tatctgagac tatcactgag gctgaaccac ctcgattccc acctcgcacc  1020
tttgcacagc atatggccca taagctcttc aagaaggatg atcaggatgc tgctgctgaa  1080
cacaaagtct ccaagaagga tgacccggat tctgctgctg acacaaaacc cttcaagaag  1140
gatgatcagg atgctgttgt tcagcaaaaa gtcctcaagg aggatgaaca ggatgccgct  1200
gctgagcaca aagtcttcaa gaaggataat caggatgctg ctgctgaaga atctaaatag  1260

SEQ ID NO: 32           moltype = DNA  length = 1260
FEATURE                 Location/Qualifiers
source                  1..1260
                        mol_type = genomic DNA
                        organism = Nicotiana sp.
SEQUENCE: 32
atggtggtga tcagtgcagt agttccaact ccttcaagag ttgaaagctt ggctaaaagt    60
ggaatccagg ctatccctaa agagtatgtg aggccacaag aagagttaaa tggaatagga   120
aacatatttg aggaagagaa gaaagatgaa ggacctcaag taccgacgat tgatctaaca   180
gaaatcgact cagaggacaa ggaaattcga gagaaatgcc accaagagtt gaagaaagca   240
gctatagaat ggggtgttat gcaccttgtt aaccatggca tatcagatga gctaattgat   300
cgtgtcaagg tttctggaga taccttcttt gatcaacctg ttgaagaaaa ggagaagtat   360
gctaatgacc aaccctctgg caatgtccaa ggctatggca gcaagctagc aaatagtgct   420
tgtggtcagc ttgagtggga ggattatttc ttccattgtg ttttcccctga ggacaagtgc   480
aacttatcca tctggccgaa aacccctaca gactacattc agcaacaag tgaatatgcc    540
aagcagatta ggaacctagc aacaaagatt ttggcagtgc tttctattgg gctgagacta   600
gaagaaggaa gactagagaa ggaagtcgga ggcatggagg acctgctgct tcaaatgaag   660
attaactact atcccaaatg cccccaacca gaactagcac ttggtgtcga agctcatact   720
gatgtcagtg cactgacttt tatcctccac aatatggtgc ctggcttgca acttttctac   780
gaaggacagt gggtaacggc aaagtgtgtg cctaattcca taatcatgca tattgggggac   840
acccttgaaa ttctaagcaa tggaaagtac aaagcattc ttcacagagg ggttgtgaat     900
aaagagaaaa taagaatctc atgggctatt ttctgtgagc cgccaaagga gaagatcatc   960
cttaagcccc tacctgagac tataactgag gctgagccac ctcgattccc acctcgcacc  1020
tttgcacagc atatggccca taagctcttc aagaaggatg atcaggatgc tgctgctgaa  1080
cacaaagtct ccaagaagga tgacccggat tctgctgctg aacacaaacc cttcaagaag  1140
gatgatcagg atgctgttgc tcagcaaaaa gtcctcaagg aggatgaaca gatgccgct    1200
gctgagcaca aagtcttcaa gaaggataat caggatgctg ctgctgaaga atctaaatag  1260

SEQ ID NO: 33           moltype = DNA  length = 1869
FEATURE                 Location/Qualifiers
source                  1..1869
                        mol_type = genomic DNA
                        organism = Nicotiana sp.
SEQUENCE: 33
atggctatgg gacaccaaga ccaagatgga gttccaaaca acttgagaaa gcaacttgct    60
cttgctgtta gaggtattca atggagctat gcaatcttct ggtcaactcc agttacacag   120
```

```
ccaggggtgt tggaatggag tgatgggtac tataatgggg atatcaagac taggaagaca    180
gttcaggtgg gggaagttaa tgaagaccaa cttgggttgc acagaactga gcaattgcga    240
gaactttata gttcactctt aacaggtgaa ggtgaagaag acttacaacc tcaggctaaa    300
aggccctcag ctgcattatc tcctgaagat ctcactgata cggagtggta tttcttagta    360
tgcatgtctt tcgtcttcaa tgttggacaa gggttgccaa ggaagacctc agcgacgaat    420
caaacaatct ggctatgcaa tgctcaccaa gcagagagta gagtattttc tcgctctctg    480
ctagcaaaga gtgcatctat ccagactgtc gtatgctttc catatttagg aggcgttatt    540
gagctgggag tcaccgagct tgtcttagaa gatcccaacc tcattcagca aataaaaaat    600
tcctttgagg ttgatcactc tgtttatttcg aagaggccta attacaactc caatgatgca    660
aaagatgaca tgaatgttgc tagccgaaag cttgatcata atgtacttga aagtgatgct    720
tatccagttg aaataaacaa cagttcaccg catgatagtt caaacggttt tgtgccaat    780
caagaggcag aagattcttt aatggtggta ggcgttatag gggaacttc acaagctcaa    840
agctggaagt tcgtggatga taatatgagt aacggtgtgc ataattcttt gaattccagt    900
gactgcatct ctcaaaatta tgaaaagttg tcccctcttt cgaatggaa aaaagaaact    960
aagccttgcc caatagaccg tcaagagcac aatcagaata aactgcatct tttagatcac   1020
caaggagatg acgctcaata tcaagctgtc atttctaccc ttttaaaaag ctctgaccaa   1080
ttaactttgg gaccacattt tagaaatatt aacaaaaagt caagctttgc tggttggaag   1140
aatgatactg aagcgccaag aatatgaact gcacaaaaac tattgaagaa ggtacttctt   1200
gaagttccta gaatgcatgt tggtgttaca cataaattca gcagagagaa tcgtaaaaag   1260
aacggccttt ggagaccgga ggttgatgac attgatagaa gccgtgttat tcagagagaa   1320
aggcgaagag aaaagataaa cgagagattt atgcatcttg catcaatgct gccgactggt   1380
ggcaaggttg acaaaatatc actacttgac gagacaataa aatacatgaa agagcttgag   1440
aggagagttc aagagctgga agctagatca ggaaaaaaaa caaatgatac tgcagagcag   1500
acatctgata attgtggcac tagtaaattc aatgacgtca atggatcgtt aaagaggaaa   1560
gcatgtgata tggatgaaat ggaacctgaa agctgtaatg aattactgaa aggcagttca   1620
gctgatggta ttgtcatcag tatgatcgat aaggaagtct cgatcaagat gaggtgtctt   1680
tggagcgagg gcttgttact taagattatg gaggcactaa ccgacctaca aatggattgc   1740
catacggttc aatcttccaa gattgatggg attttatcca ttgctattga atcaaagtca   1800
aatggattga aaactgtatc agttggagca attagagaag tacttcagcg agtagtctgg   1860
aaatcttga                                                           1869

SEQ ID NO: 34          moltype = DNA  length = 1095
FEATURE                Location/Qualifiers
source                 1..1095
                       mol_type = genomic DNA
                       organism = Nicotiana sp.
SEQUENCE: 34
atggaatcct caaccaaaag ccaaatacca acacaatcag aagaagagcg taactgcaca     60
tatgccatgc aactattgtc atcttcagtc ctcccctttg tgttgcattc aacaattcaa    120
ttggaagttt ttgagatatt agccaaatct aatgacacta aacttctgc ttctcaaatt    180
gtttctcaaa ttcctaactg cacaaaaacct gaagcaccta ctatgttaaa taggatgctt    240
tatgtcttgg ctagttactc cttgtttact tgttccattg ttgaagatga aaaaaataat    300
gggggccaaa aaagagtgta tggtttgtca caagtgggaa aattctttgt taaaaatgaa    360
aatggtgcat caatggggcc acttttggct ttgcttcaaa ataaagtatt cataaacagc    420
tggtttgaac taaagatgc agttcttgaa ggaggagttc catttgacag ggtacacggt    480
gtgcatgcat ttgaatatcc aaaatcggac ccaaaattca atgatgtttt caacaaggca    540
atgatcaaatc acacaactgt agtcatgaaa aaaatacttg aaaattacaa aggttttgag    600
aaccttaaaa ctttggttga tgttggaggt ggtcttggag ttaacctcaa gatgattaca    660
tctaaatacc ccacaattaa gggcactaat tttgatttgc cacatgttgt tcaacatgcc    720
ccttcctatc ctgggtgga acatgttggg ggagatatgt tgaaagtgt tccagaagga    780
gatgctattt ttatgaagtg gattcttcat gactggagta atagtcacaa cctcaagttg    840
ctaaagaact gctacaaggc tctaccagac aatggaaagg tgattgttgt tgaggccatt    900
ttaccagtga aaccagacat tgacaccgca gtggttggcg tttcgcaatg tgatttgatc    960
atgatggctc aaaatcctgg aggcaaagag cgatcggaag aggagtttcg agccttggct   1020
actgaagctg gattcaaagg cgttaactta atatgttgtg tctgtaattt ttgggtcatg   1080
gaattctgca agtag                                                    1095

SEQ ID NO: 35          moltype = DNA  length = 1521
FEATURE                Location/Qualifiers
source                 1..1521
                       mol_type = genomic DNA
                       organism = Nicotiana sp.
SEQUENCE: 35
atggatcttc tccttctaga gaagacccctt tagggttat tctttgctat cattgtagct     60
atagttgttt ctaagctacg tagcaagaat tttaagttgc ccccaggtcc gattcctgtg    120
ccagtttttg gcaattggct tcaagttggt gatgacttga atcacagaaa cctcactgaa    180
tatgccaaga aatttggtga catgttcttg ctaagaatgg acagaggaa tcttgtggta    240
gtgtcatccc ctgaactagc caaagaagtt tgcatacac aaggggttga atttggatca    300
agaacaaggaa atgtggtctt tgatattttc actgagaaag gccaagatat ggttttaca    360
gtatatggtg aacactggag gaaaatgagg aggattatga ctgttccatt ttttacaaac    420
aaagtggtgc agcagtatag gcgtgggtgg gaagatgaag tggcacatgt tgttgaggat    480
gtgaagaaaa atccagagtc agcaactaat gggattgtgt gaggaaaag gttgcagctt    540
atgatgtaca ataacatgta caggattatg tttgatagga gttttgagag tgaggatgat    600
ccttttgttta acaagcttaa ggcttttgaat gggggagagg atggattggc tcagagtttt    660
gagtacaatt atggtgattt tatcccctata ttgagacctt tcttgagagg ttacttgaac    720
atctgtaagg aaattaagca gaggaggttg cagcttttca agattacttt tgttgatgaa    780
agaaagaaac ttgcaaacac gacgaagagc atggacaata attcgctaaa gtgtgccatt    840
gatcacattc ttgaggctga acagaaggga gagatcaatg aggataatgt cctttacatt    900
gttgagaaca tcaatgttgc tgcaatagaa actacactgt ggtcaatcga gtggggtatt    960
```

```
gctgaactag tgaaccaccc tgaaatccag aagaaactcc gtgacgagat tgacagtgtt   1020
cttggagtag gagtgcaaat cactgagcca gaactcaaca agcttcctta ccttcaggct   1080
gtgatcaagg agaccttcg tctccgtatg caatccctc ttttagtccc acacatgaac    1140
cttcacgatg cgaagcttgc tggatatgac attcccgcgg agagcaagat cctggtaaac   1200
gcttggtggc tggctaacaa ccctgctacc tggaagaagc ccgaagagtt taggccagag   1260
aggttctttg aagaggagaa gcacgttgag gctaatggca atgacttcag atatcttcca   1320
tttggtgttg gtaggaggag ctgccctgga attatccttg cactgccaat tcttggcatt   1380
accttgggac gcttggtgca gaactttgag ttgttgcctc ctccaggaca gtcaaagctt   1440
gacacaacag agaaaggcgg gcaattcagt ctgcacattt tgaagcattc caccattgtg   1500
atgaaaccaa gatctttta a                                             1521

SEQ ID NO: 36          moltype = DNA   length = 897
FEATURE                Location/Qualifiers
source                 1..897
                       mol_type = genomic DNA
                       organism = Nicotiana sp.
SEQUENCE: 36
atgggaagaa aaccatgttg tgtaaaagag ggattgagaa aaggtccatg gtcttctaaa   60
gaagatttat tacttactaa tttatatcaag gaaaatggtg aaggacaatg gagatctttg  120
cctaagaatg ctgggttgct taggtgtgga aaaagttgta gactaagatg gatgaactat  180
ttaagaccag ggattaaaag aggaaatttc agtcaagatg aagaagatct tatagtgaga  240
ctacattctc ttttgggtaa tcgttggtca ctaattgctg gaagattacc aggtcgtaca  300
gacaatgaaa tcaagaatta ttggaacaca catttaatca agaagctcaa aaatgctgga  360
attgaaccaa aaccccacaa aaatttctcc aaatgttcca aaaaggaatc aagaaaagga  420
ccccaacaag ggaaatcaag aaaaatacaa ggcaaaaaga gcaacaacaa aaacaataag  480
ggtcaaattg tacaagttga gaagaccaaa gtattttttcc caaaacccat caggatttct  540
tgtggaattt caaggaacaa tagtttttgaa atgttacat tgagtactac ttgttcctca  600
aatagtaatt ctgagaagc taatcttgaa aacaaggaaa atgaggtgaa attagaagaa  660
gtttcattct ttccaaggga cttagatttt ggtaaattac ttgaagggga tgcaatttat  720
gatgaatttc taatgaaga aagttgccac atttcaaaca aatgttcaat gccaatgaat  780
gagagcatgt tggagaaagt atatgaagaa tatcttttac ttctttctga aaattgttac  840
cttcaagatg atcatcaaaa tgagcaaaat ttccctgtaa atgtttctga tcagtga     897

SEQ ID NO: 37          moltype = DNA   length = 1146
FEATURE                Location/Qualifiers
source                 1..1146
                       mol_type = genomic DNA
                       organism = Nicotiana sp.
SEQUENCE: 37
atggcaagtg aagctcatgc agctgttcat gctcctcctc cggtagcacc gacggtttgc   60
gtcactggag cagctggatt tattggctct tggcttgtca tgagactcct tgaacgtggt  120
tataatgttc acgctactgt tcgtgatcct gagaacaaga gaaggtaaa gcatctattc  180
gaattgccaa aagctgacac aaacttaacg ctgtggaaag cggacttgtc agtggaagga  240
agctttgatg aagccattca aggctgtcaa ggagtattcc atgtggcaac acctatggat  300
ttcgagtccg aggaccctga gaatgaagta attaaaccaa cagtcagggg aatgttaagc  360
atcatagaat catgtgctaa agcaaacaca gtgaagaggc tggttttcac ttcatcggct  420
ggaactctcg ggccaagaa acaccaaaag ttttcgatag acgagaccag ctggagcgac  480
ttggacttca tatatgctaa gaagatgaca ggatggatgt attttgtttc caagatactg  540
gcagagaagg ccgcaatgga agcagctaaa aagaagaact tgattttat tagcatcata  600
ccgccgctgg ttgttggtcc attcctcacg cctacattcc cacctagctt aatcactgca  660
cttcactaa ttactgggaa tgaagctcac tactgcatca ttaaacaagg tcaatatgtg  720
catttggatg atctttgtga ggctcatatt ttcctatatg agcagccaaa ggcagaggga  780
agattcatct cgcgctccca tcatgctatc atctatgatg tggcaaagat ggtccgagag  840
aaaatggcca agtactacgt ccctactgag tttaaaggca tcgataagga cttgcccgtg  900
gtgtattttt cgccaaagaa gctgacggat atggggtttc aattcaagta cacttttggag  960
gatatgtata aaggggccat tgaacttgt cgacagaagc agttgcttcc cttttctacc  1020
caaagcacag cagataatgg acgtgacaaa gaaaccattc cccttttctgc tgaaaactat  1080
gcaagtggca aagagaattc accagttgca aatggtacag gaaagtcaac caatggggaa  1140
atctag                                                             1146

SEQ ID NO: 38          moltype = DNA   length = 1149
FEATURE                Location/Qualifiers
source                 1..1149
                       mol_type = genomic DNA
                       organism = Nicotiana sp.
SEQUENCE: 38
atggcaagtg aaggtcatgc agctgttcat gccccttctc ctccggcagc gccgacagtt   60
tgcgtcactg gagcagctgg atttattggc tcttggcttg tcatgagact ccttgaacgt  120
ggttataatg ttcacgctac tgttcgtgat cctgagaaca agaagaaggt aaagcatcta  180
ttggaattgc caaagctga cacgaactta acgttgtgga agcagactt gtcagtggaa  240
ggaagctttg atgaagccat tcaaggctgt caaggagtat tccatgtggc aacgcctatg  300
gatttcgagt ccgaggatcc tgagaatgaa gtaattaaac caacagtcag gggaatgtta  360
agcatcatag aatcatgtgc taaagcaaac acagtgaaga ggctggttt cacttcatct  420
gctggaactc tcgatgtcca agagcaccaa aagctctat atgacgagac cagctggagt  480
gacttggact ttatatatgc taagaagatg acaggatgga tgtatttgt tccaagata   540
ctggcagaga aggccgcaat ggaagcagct aaaaagaaga acatcgattt cattagcatc  600
ataccgccac tggttgttgg tccattcctc gcgcctacat ccccacctag cttaatcact  660
gcccctttcac taattactgg gaatgaagct cactacagca tcattaaaca aggtaaatat  720
gtgcatttgg atgatctttg tgaggctcat attttccat atgagcaccc aaaggcagag  780
```

```
gggagattca tctgcgcgtc ccatcatgct atcatctatg atgtggcaaa gatggtccaa    840
gagaaatggc cggagtacta cgtccctact gagtttaaag gcatcgtaaa ggacttgtcc    900
gtggtgtatt tttcgtcaaa gaagctgacg gatatgggt ttcaattcaa gtacactttg    960
gaggatatgt ataaagggc cattgagact tgtcgacaga agcagttgct tcccttttct   1020
acccgaagca ctgcagataa tgtacgtgac aaagaagcca ttcctctttc tactgaaaac   1080
tatgcaagtg gcaagaaaa ttcaccagtt gcaaatggta cgggaaagtc aaccaatggt   1140
gaaatctag                                                           1149

SEQ ID NO: 39          moltype = DNA   length = 642
FEATURE                Location/Qualifiers
source                 1..642
                       mol_type = genomic DNA
                       organism = Nicotiana sp.
SEQUENCE: 39
atgggaagaa aaccctgttg ttctaaagaa ggtctgagga aaggtacatg gactgcaaaa     60
gaagatatgc tacttactaa ttatattaat gaacatggag aagttggatg gagatctctt    120
cctatgaaag ctggaagtcg ttggtctctc attgctggaa gaatacctgg tcgaacagac    180
aacgaaataa agaattattg gaacacacat ctctcaaga aactcaaatc cgaaggactt    240
gagccaaaaa tacacaaatc tcttgcaaaa aacactagaa gacaaaagga gaaagcaaat    300
gtttcttccc aaattaacca aaaaggttac aaggaaaaga agaagaggaa taaaaagggc    360
aatatcgaag aaaattgtaa caatattgaa gagaaagaac aagtagctaa gaagatagag    420
gagcagtggc atacgcagga ttccgtgcaa gcgatgtcag ggttttcaag tactagtgaa    480
gttgctagtg agaaggaaac taattgcaat aatgtccatt gtccttcttc tggtcaaagt    540
cttgaagaaa atgacaatga aatttatgag aagcttcagg ctagcggaga ttctaaacgt    600
tgcaaattga atttcagtgc agaggttaat aagacccctt aa                       642

SEQ ID NO: 40          moltype = DNA   length = 1308
FEATURE                Location/Qualifiers
source                 1..1308
                       mol_type = genomic DNA
                       organism = Nicotiana sp.
SEQUENCE: 40
atgaagatcg aggtgaaaga atcgacgatg gtaaagccgg cggcggagac gccacaacag     60
aggctgtgga actctaatgt ggatttggtg gtgccgaatt tccacacgcc aagtgtttat    120
ttttacaggc cgacgggatc cccaaatttc ttcgacgga aagtgctgaa agaagctcta    180
agcaaagcac ttgtgccgtt ttatcctatg gcggggaggc tgtgtaggga cgaagatggt    240
cgtattgaga ttgactgtaa aggtcagggg gtgcttttg tggaagctga gtcggatggt    300
gtggtggatg attttggtga ttttgccccg acgttagaac tccgtcaact catccccgcc    360
gttgattact cacaaggaat tcaatcgtat gctctcttag tgttgcagat aacacattt    420
aaatgtgggg gagtttccct tggtgtgggc atgcaacatc atgcagcaga tggagcttcc    480
ggtcttcact tcatcaacac atggtctgat atggctcgtg gtctgaccct caccatccca    540
cctttcattg accggaccct cctccgtgct cgtgatccac ctcagcctca gtttcccat    600
gtcgagtacc agccactcc cactctcaag gtaactccaa aaaacacccc tatatctgaa    660
gctgttcctg aaaccagcgt gtccatcttc aaattaaccc gtgatcaaat caataccctc    720
aaagcgaagt ccaaggaaga tggaaatacc gttaactaca gctcctacga gatgttggca    780
ggacatgtgt ggcgctccac gtgcatggca cgaggactcg ctcatgatca agaaaccaaa    840
ttgtacatag caacagatgg acgttccagg ctttcggcct ctctcccaca aggctatttc    900
ggtaatgtga tatttactac cactccttatt gcagtcgcag gtgatatcca atcgaagcct    960
atttggtatg ctgccagtaa attacatgat gcattggcta gaatggacaa cgattactta   1020
agatcagctc ttgattattt ggagttgcag cctgacttaa aggctcttgt tcgtggtgca   1080
catacgttta agtgcccgaa tttaggaata actagttggt ctaggctgcc aatccatgaa   1140
gctgatttg gctggggtag gcctatattt atgggacctg gtggtattgc ttatgaaggt   1200
ttaagcttta tattgccaag tcctacaaat gatggcagtc aatctgttgc aatctctcta   1260
caagcagaac acatgaaact tttcgagaag ttccttgtatg acttttga                 1308

SEQ ID NO: 41          moltype = DNA   length = 1311
FEATURE                Location/Qualifiers
source                 1..1311
                       mol_type = genomic DNA
                       organism = Nicotiana sp.
SEQUENCE: 41
atgggaagtg aaaaaatgat gaaaattaat atcaaggaat caacattagt aaaaccatca     60
aaaccaacac caacaaaaag actttggagt tctaacttag atttaatagt gggaagaatt    120
catctttaa cagtatattt ctataaacca aatggatctt caaatttctt tgattaaaa    180
ataatgaaag aagcattaag taatgttctt gtttcatttt acccaatggc tggaagatta    240
gctagagatg aacaaggaag aattgagata aattgtaatg gagaaggagt tttatttgtt    300
gaagctgaaa gtgatgcttt tgttgatgat tttggtgatt ttactccaag tttgaactt    360
aggaaacta ttcctactgt tgacacttct tggtgatattt ctactttcc cctcatcata    420
tttcaggtta ctcgtttcaa atgtggtgga gtttcacttg gtggaggatt attccacact    480
ttatcagatg gtctctcatc aattcacttc atcaacacat ggtccgatat agcccgaggc    540
ctctccgtcg ccatcccgcc gttcatcgac cggaccctcc tccgtgcacg gaccccacca    600
acatcgtctt tcgagcacgt cgagtatcat cctcctccat ctctaatttc atcatcaaaa    660
agcttagaat ccactagccc aaagcctagt accacaacca tgttaaaatt ctcctagtgac    720
caacttgggg cttctaaagtc caaacatgat ggtgcactta caacttacga aatcctcagtg    780
gcccatattt ggcgttgcac gtgcaagcga cgtgcactgt ccgacgatca attgaccaaa    840
ttacatgtgg ccactgatgg taggtctagg ctttgccctc ctttgccacc aggttactta    900
ggaaatgttg tgttcacagg cacacctatg gcaaaatcaa gtgaacttt acaagaacca    960
ttgacaaatt cagccaagag aattcatagt gcattatcaa aatgggatga caattccta   1020
agatcagctc tcgattacct cgaattactg cccgattat cggctttaat ccgtggaccg   1080
```

```
acgtactttg ctagccctaa tcttaatatt aatagttgga ctagattgcc tgttcatgat   1140
tcagattttg gatggggaag gccaattcat atgggaccag cttgcatttt atatgaaggg   1200
acagtttata tattgccaag tccaaatagt aaagatagga acttgcgttt ggctgtttgt   1260
ttagatgctg atcacatgcc actatttgag aagtatttgt atgaattttg a            1311

SEQ ID NO: 42          moltype = DNA   length = 2148
FEATURE                Location/Qualifiers
source                 1..2148
                       mol_type = genomic DNA
                       organism = Nicotiana sp.
SEQUENCE: 42
atggcatcaa atggtcatgt taatggagga gaaaactttg agttgtgcaa aaaatcagct   60
gatccattga attgggaaat ggcagctgaa tccttaagag ggagtcattt ggatgaagtg   120
aaaaaaatgg tgagtgaatt tagaaaacca atggtgagtg aagtttaaca                180
gtggcacaag tggctgctat tgctgttagg gacaaaagtg caaatggtgt taaagttgaa   240
ctttctgaag aggcaagagc tggtgttaaa gctagtagtg attgggttat ggacagtatg   300
aataaaggaa ctgatagtta tggtgttact actggttttg gtgctacatc tcataggaga   360
accaagaatg gtggtgctct tcaaaaagaa cttattaggt tcttgaatgc tggtgtttta   420
ggcaatggaa cagaaacaag ccacacattg ccacattcag caacaagggc agctatgctt   480
gttaggatca acacactcct acaaggctac tctggcatca gatttgaaat cttggaagct   540
attacaaaat tgattaacag caacatcact ccatgtttac ctctccgtgg aacgatcact   600
gcctcgggtg atcttgtccc tttatcctac attgctgatt tgtcactgg taggcctaat   660
tccaaggctg ttggtcccaa tggtgagaca cttaatgctg aagaagcgtt ccgcgttgct   720
ggtgttaacg gtggatttt cgagttgcag cctaaggaag gacttgcact tgtgaatggt   780
acagctgttg gttctggtat ggcatcaatg gtcctctttg attccaacat tcttgctgta   840
atgtctgaag ttttatcagc aattttcgct gaagtaatga acggaaagcc tgaattcact   900
gaccatttga cacacaagtt gaagcaccac cctggtcaaa ttgaggctgc tgctatatg   960
gaacatattt tggatggaag ctcttatgtg aaggcggctc aaaagctaca tgaaatggat   1020
cctctacaaa aaccaaagca agatcgttat gctctccgaa catctccaca atggcttggc   1080
cctcaaattg aagtcattcg cgctgcaact aagatgattg agagggagat taactcagtg   1140
aacgataacc ctttgatcga tgtttcaaga aacaaggcgt tacatggtgg caacttccaa   1200
ggcactccta tcggtgtttc catggataat gcaagattgg ctcttgcatc aattgggaaa   1260
ttgatgtttt ctcaattctc ggaacttgtc aacgactatt acaacaacgg tttgccctct   1320
aatctcactg catcaaggaa tccaagcttg gactatggtt tcaagggagc tgaaatccca   1380
atggcttctt actgctcaga acttcaattc ttggcaaatc cagtgacaaa ccatgtccaa   1440
agtgctgaac aacacaacca agatgtcaac tccttaggct taatctcagc aaggaaaaca   1500
gctgaagctg ttgatatctt aaagctcatg tcatcaactt atctcgtggc actttgccaa   1560
gctatagact tgaggcattt ggaagaaaac ttaaagaatg cagtcaagaa cacagttagc   1620
caagtagcta agagaactct tacaatgggt gctaatggta aacttcatcc agcaagattc   1680
tgtgaaaagg aattgcttcg aatcgttggat agggaatact tgttcgccta cgctgatgat   1740
ccttgcagtt gcaactaccc tttaatgcag aaactgagac aagtacttgt tgatcatgca   1800
atgaataatg gtgaaagtga gaagaatgtg aacagctcaa tctttcaaaa gattggagct   1860
ttcgaagtga aattgaaggc tgttttacca aaggaagttg agagtgcaag agctgcatta   1920
gaaagtggaa accctgctat tcctaacagg attacagaat gcagatctta tccattgtac   1980
aggtttgtga aaaggagct tggaacagaa ttattgacag gagaaaaagt ccgatcaccg   2040
ggcgaggagt gtgacaaagt gttcacagca atgtgcaatg acaaatcat tgatccaatg   2100
ttggagtgtc tcaagagctg gaatggtgct cctcttccta tctgttag                 2148

SEQ ID NO: 43          moltype = DNA   length = 1026
FEATURE                Location/Qualifiers
source                 1..1026
                       mol_type = genomic DNA
                       organism = Nicotiana sp.
SEQUENCE: 43
atggataatt cagctccaga ttcgttatcc agatcggaaa ccgccgtcac atacgactca   60
ccatatccac tctacgccat ggcttttctct tctctccgct catcctccgg tcacagaatc   120
gccgtcggaa gcttcctcga agattacaac aaccgcatcg acattctctc tttcgattcc   180
gattcaatga ccgttaagcc tctcccgaat ctctccttcg agcatcctta tcctccaaca   240
aagctaatgt tcagtcctcc ttctctccgt cgtccttcct ccggagatct cctcgcttcc   300
tccggcgatt tcctccgtct ttgggaaatt aacgaagatt catcaaccgt cgagccaatc   360
tcggttctca acaacagcaa aacgagcgag ttttgtgcgc cgttgacttc cttcgattgg   420
aacgatgtag agccgaaacg tctcggaact tgtagtattg atacgacgtg tacgatttgg   480
gatattgaga agtctgttgt tgagactcag cttatagctc atgataaaga ggttcatgac   540
attgcttggg gagaagctag ggttttcgca tcagtcgttg gagtcgttag gttaggatc   600
tttgatttac gtgataagga acattctaca atcatttacg agagtcctca gcctgatacg   660
cctttgttaa gacttgcttg gaacaaacaa gatcttagat atatggctac gattttgatg   720
gattctaata aggttgtgat tctcgatatt cgttcgccga ctatgcctgt tgctgagctt   780
gaaagacatc aggctagtgt gaatgctata gcttgggcgc ctcagagctg taaacatatt   840
tgttctggtg tgatgatac acaggctctt atttgggagc ttcctactgt tgctggaccc   900
aatgggattg atccgatgtc ggtttattcg gctggttcgg agattaatca gttgcagtgg   960
tcttcttcgc agcctgattg gattggtatt gcttttgcta acaaaatgca gctccttaga   1020
gtttga                                                              1026

SEQ ID NO: 44          moltype = DNA   length = 1323
FEATURE                Location/Qualifiers
source                 1..1323
                       mol_type = genomic DNA
                       organism = Nicotiana sp.
SEQUENCE: 44
```

```
atgagcatgt ctgttgcttt gttgtgggtt gtttctccca cttccgaggt ctcgaatggg    60
acaggattgt tggattcagt ccgagaagga aaccgcgtct ttgtatcatc caggttccta   120
gctcgagata ggaatttgat gtggaatggg agaatcaaga aaggtgggag acaaaggtgg   180
aattttggct ctttaattgc tgatccaaga tattcatgct tgggtggatc aagaactgaa   240
aagggaagca gtttctctgt acagtccagt ttggtggcta gcccagctgg agaaatgaca   300
gtgtcatcag agaaaaaggt ctatgatgtg gtattgaagc aagcagcttt agtgaagagg   360
cagctgagat ctaccgatga attagaagtg aaacctgata tagttgttcc agggaatttg   420
ggcttgttga gtgaagcata tgatcgttgt ggcgaagtat gtgcagagta tgcaaagaca   480
ttttacttag gaacaaagct aatgactcca gagagaagaa gagctatctg gtcaatatat   540
gtgtggtgca ggagaacgga tgagctagtc gatggcccta acgcatcaca cataactcca   600
caagctttag acaggtggga ggccaggctg gaagatattt tcagtgggcg gccatttgat   660
atgcttgatg ctgctttatc cgatactgtc tccagatttc ctgttgatat tcagccattc   720
agagatatga tagaaggaat gcgtatggac ttgtggaaat ccagatataa caacttcgat   780
gagctatatc tctattgtta ttatgttgct ggtacagtag gactgatgag tgttccagtt   840
atgggtattg cacctgaatc aaaggcaaca acagagagtg tatataatgc tgctttggct   900
ttagggcttg caaatcaact aaccaatata ctcagagatg taggagaaga tgccagaaga   960
ggacgagtat acttacctca agatgaatta gcacaggcag ggctttctga tgaagatata  1020
tttgctggaa gagtgaccga taagtggagg aactttatga gaaacaaat tcagagggcg  1080
aggaaattct ttgatgagtc agagaaaggt gtcacagaac tggactctgc tagtagatgg  1140
cctgtaagta cagcgctgct gttgtatcgc aagatattgg acgagattga agccaatgac  1200
tacaataact tcacaaggag ggcttatgtt agcaagccaa agaagcttct caccttgccc  1260
attgcttatg caaaatctct tgtgcccct aatagaactt cctctccact agcaaaaaca  1320
tga                                                                 1323

SEQ ID NO: 45          moltype = DNA   length = 1323
FEATURE                Location/Qualifiers
source                 1..1323
                       mol_type = genomic DNA
                       organism = Nicotiana sp.
SEQUENCE: 45
atgagcatgt ctgttgcttt gttgtgggtt gtttctccca cttccgaggt ctcgaatggg    60
acaggattgt tggattcagt ccgagaagga aaccgcgtct ttgtatcatc caggttccta   120
gctcgagata ggaatttgat gtggaatggg agaatcaaga aaggtgggag acaaaggtgg   180
aattttggct ctttaattgc tgatccaaga tattcatgct tgggtggatc aagaactgaa   240
aagggaagca gtttctctgt acagtccagt ttggtggcta gcccagctgg agaaatgaca   300
gtgtcatcag agaaaaaggt ctatgatgtg gtattgaagc aagcagcttt agtgaagagg   360
cagctgagat ctaccgatga attagaagtg aaacctgata ttgttgttcc agggaatttg   420
ggcttgttga gtgaagcata tgatcgttgt ggcgaagtat gtgcagagta tgcaaagaca   480
ttttacttag gaacaaagct aatgactcca gagagaagaa gagctatctg gcaatatat    540
gtgtggtgca ggagaacgga tgagctagtc gatggcccta acgcatcaca cataactcca   600
caagctttag acaggtggga ggccaggctg gaagatattt tcagtgggcg gccatttgat   660
atgcttgatg ctgctttatc cgatactgtc tccagatttc ctgttgatat tcagccattc   720
agagatatga tagaaggaat gcgtatggac ttgtggaaat ccagatataa caacttcgat   780
gagctatatc tctattgtta ttatgttgct ggtacagtag gactgatgag tgttccagtt   840
atgggtattg cacctgaatc aaaggcaaca acagagagtg tatataatgc tgctttggct   900
ttagggcttg caaatcaact aaccaatata ctcagagatg taggagaaga tgccagaaga   960
ggacgagtat acttacctca agatgaatta gcacaggcag ggctttctga tgaagatata  1020
tttgctggaa gagtgaccga taagtggagg aactttatga gaaacaaat tcagagggcg  1080
aggaaattct ttgatgagtc agagaaaggt gtcacagaac tggactctgc tagtagatgg  1140
cctgtgttag cagcgctgct gttgtatcgc aagatattgg acgagattga agccaatgac  1200
tacaataact tcacaaggag ggcttatgtt agcaagccaa agaagcttct caccttgccc  1260
attgcttatg caaaatctct tgtgcccct aatagaactt cctctccact agcaaaaaca  1320
tga                                                                 1323

SEQ ID NO: 46          moltype = DNA   length = 747
FEATURE                Location/Qualifiers
source                 1..747
                       mol_type = genomic DNA
                       organism = Nicotiana sp.
SEQUENCE: 46
atggagggtt cgtccaaagg gctgcgaaaa ggtgcttgga ctactgaaga agatagtctc    60
ttgagacagt gcattaataa gtatggagaa ggcaaatggc accaagttcc tgtaagagct   120
gggctaaacc ggtgcaggaa aagttgtaga ttaagatggt tgaactattt gaagccaagt   180
atcaagagag gaaaacttag ctctgatgaa gtcgatcttc ttcttcgcct tcataggctt   240
ctagggaata ggtggtcttt aattgctgga agattacctg gtcggaccgc aaatgacgtc   300
aagaattact ggaacactca tctgagtaag aaacatgaac cgtgttgtaa gataaagatg   360
aaaaagagag acattacgcc cattcctaca acaccggcac taaaaaacaa tgtttataag   420
cctcgacctc gatccttcac agttaacaac gactgcaacc atctcaatgc cccaccaaaa   480
gttgacgtta atcctccatg cctttggactt aacatcaata atgtttgtga caatagtatc   540
atatcaacaa aagataagaa gaaagaccaa ctagtgaata atttgattga tggagataat   600
atgtggttag agaaattcct agaggaaagc caagaggtag atattttggt tcctgaagcg   660
acgcaacag aaaaggggga caccttggct tttgacgttg atcaactttg gagtcttttc   720
gatggagaga ctgtgaaatt tgattag                                       747

SEQ ID NO: 47          moltype = AA   length = 717
FEATURE                Location/Qualifiers
source                 1..717
                       mol_type = protein
                       organism = Nicotiana sp.
```

```
SEQUENCE: 47
MASNGHVNGG ENFELCKKSS ATDPLNWEMA AESLRGSHLD EVKKMVSEFR KPMVKLGGET    60
LTVAQVAAIA VRDKSANGVK VELSEEARAG VKASSDWVMD SMNKGTDSYG VTTGFGATSH   120
RRTKNGGALQ KELIRFLNAG VFGNGTETSH TLPHSATRAA MLVRINTLLQ GYSGIRFEIL   180
EAIAKLINSN ITPCLPLRGT ITASGDLVPL SYIAGLLTGR PNSKAVSPNG ETLNAEEAFR   240
VAGVNGGFFE LQPKEGLALV NGTAVGSGMA SMVLFDSNIL AVMSEVLSAI FAEVMNGKPE   300
FTDHLTHKLK HHPGQIEAAA IMEHILDGSS YVKAAQKLHE MDPLQKPKQD RYALRTSPQW   360
LGPQIEVIRA ATKMIEREIN SVNDNPLIDV SRNKALHGGN FQGTPIGVSM DNARLALASI   420
GKLMFAQFSE LVNDYYNNGL PSNLTASRNP SLDYGFKGAE IAMASYCSEL QFLANPVTNH   480
VQSAEQHNQD VNSLGLISAR KTAEAVDILK LMSSTYLVAL CQAIDLRHLE ENLKNAVKNT   540
VSQVAKRTLT MGANGELHPA RFCEKELLRV VDREYLFAYA DDPCSCNYPL MQKLRQVLVD   600
HAMNNGESEK NVNSSIFQKI GAFEDELKAV LPKEVESARA ALECGNPAIA NRITECRSYP   660
LYRFVRKELG TELLTGERVR SPGEEECEKVF TAMCNGQIID PMLECLKSWN GAPLPIC    717

SEQ ID NO: 48            moltype = AA   length = 712
FEATURE                  Location/Qualifiers
source                   1..712
                         mol_type = protein
                         organism = Nicotiana sp.
SEQUENCE: 48
MAGVAQNGHQ EMDFCMKVDP LNWEMAADSL KGSHLDEVKK MVAEFRKPVV KLGGETLTVA    60
QVAAIAAKDN VKTVKVELSE GARAGVKASS DWVMDSMGKG TDSYGVTTGF GATSHRRTKN   120
GGALQKELIR FLNAGVFGNG TESCHTLPQS GTRAAMLVRI NTLLQGYSGI RFEILEAITK   180
LLNHNVTPCL PLRGTITASG DLVPLSYIAG LLTGRPNSKA VGPNGETLNA EEAFRVAGVN   240
GGFFELQPKE GLALVNGTAV GSGLASMVLF DANVLAVFSE VLSAIFAEVM NGKPEFTDHL   300
THKLKHHPGQ IEAAAIMEHI LDGSSYVKAA QKLHETDPLQ KPKQDRYALR TSPQWLGPQI   360
EVIRSATKMI EREINSVNDN PLIDVSRNKA LHGGNFQGTP IGVSMDNARL ALASIGKLMF   420
AQFSELVNDY YNNGLPSNLT AGRNPSLDYG FKGSEIAMAS YCSELQFLAN PVTNHVQSAE   480
QHNQDVNSLG LISARKTAEA VDILKLMSST YLVALCQAID LRHLEENLRN AVKNTVSQVA   540
KRTLTMGTNG ELHPSRFCEK DLLRVVDREY VFAYADDACS ANYPLMQKLR QVLVDHALQN   600
GENEKNANSS IFQKILAFED ELKAVLPKEV ESARAALESG NPAIANRIKE CRSYPLYRFV   660
RGELGAELLT GEKVRSPGEE CDKVFTAMCN GQIIDSLLEC LKEWNGAPLP IC          712

SEQ ID NO: 49            moltype = AA   length = 389
FEATURE                  Location/Qualifiers
source                   1..389
                         mol_type = protein
                         organism = Nicotiana sp.
SEQUENCE: 49
MVTVEEFRRA QRAEGPATVM AIGTATPSNC VDQSTYPDYY FRITNSEHKT ELKEKFKRMC    60
EKSMIKKRYM HLTEEILKEN PNICAYMAPS LDARQDIVVV EVPKLGKEAA QKAIKEWGQP   120
KSKISHLVFC TTSGVDMPGC DYQLTKLLGL RPSVKRFMMY QQGCFAGGTV LRMAKDLAEN   180
NKGARVLVVC SEITAVTFRG PNDTHLDSLV GQALFGDGAA AVIVGSDPIP DVERPLFELV   240
SAAQTLLPDS EGAIDGHLRE VGLTFHLLKD VPGLISKNIE KSLVEAFQPL GISDWNSLFW   300
IAHPGGPAIL DQVELKLGLK QEKLKATRNV LSNYGNMSSA CVLFILDEMR KASAKEGLGT   360
TGEGLEWGVL FGFGPGLTVE TVVLHSVAT                                   389

SEQ ID NO: 50            moltype = AA   length = 369
FEATURE                  Location/Qualifiers
source                   1..369
                         mol_type = protein
                         organism = Nicotiana sp.
SEQUENCE: 50
MAPSTLTALA EEKTLQTSFI RDEDERPKVA YNQFSDEIPI ISLKGIDDEG GINGRRGEIC    60
EKIVKACEDW GVFQVVDHGV DAQLISQMTT LAKQFFALPA EEKLRFDMSG GKKGGFIVSS   120
HLQGEVVQDW REIVTYFSYP IRARDYSRWP DKPEGWIDVT QKYSEKLMEL ACKLLEVLSE   180
AMGLEKEALT KACVDMDQKV VVNFYPKCPQ PDLTLGLKRH TDPGTITLLL QDQVGGLQAT   240
KDNGKTWITV QPVVGAFVVN LGDHGHFLSN GRFKNADHQA VVNSNSSRLS IATFQNPAPE   300
AIVYPLKIRE GEKAVMDEPV AFAEMYRRKM SKDLELARLK KLAKEQQIQA EEAAEKASE   360
TKPIDEILA                                                         369

SEQ ID NO: 51            moltype = AA   length = 145
FEATURE                  Location/Qualifiers
source                   1..145
                         mol_type = protein
                         organism = Nicotiana sp.
SEQUENCE: 51
MFGPQSGKDG WTDLTFMYDM IRIRDKSLCS SFLQIFSSEG CKMLEMTCEE HDKLAARSQF    60
LTHTIGRILS EMEVEPTPID TKGFQKLVQV KESSVRDSFD LFSGLFIHNR FARQQMKNLE   120
VAVEKTKQKL EERSKELQDP IISKF                                       145

SEQ ID NO: 52            moltype = AA   length = 376
FEATURE                  Location/Qualifiers
source                   1..376
                         mol_type = protein
                         organism = Nicotiana sp.
SEQUENCE: 52
MLSFTPLQSK PTPPTPTSNP TRWSWSHLTH HHPTTRRHFS ASSPSKVSYR RLSINAIDAA    60
QPYDYEALVS NQYAQSTRLK IAIVGFGNFG QFLAKAFVRQ GHVVFAHSRT DYSHIANSLG   120
```

```
VLFFQDPHDL CEQHPDVILL CTSIISTEPV LRSLPIQRLK RNTLFVDVLS VKEFPKNIFL    180
QVLPSHFDIL CTHPMFGPES GKDSWKDLAF VFDKVRIGEG ESRKGRVDRF LDIFEKEGCR    240
MVQMTCAEHD RYAAGSQFIT HTMGRVLEKL DLETTPINTK GYETLLNLVE NTSSDSFDLY    300
YGLFMYNKNA MEQLERLDLA FEALKKELFG HLHEVLRKQL FGKAEEAGQR RILTKLPKNG    360
YALPAPSSEA VKSENN                                                   376

SEQ ID NO: 53           moltype = DNA  length = 2154
FEATURE                 Location/Qualifiers
source                  1..2154
                        mol_type = genomic DNA
                        organism = Nicotiana sp.
SEQUENCE: 53
atggcatcaa atggtcatgt taatggagga gaaaactttg agttgtgcaa gaaatcatca    60
gccactgatc cattgaattg ggaaatggca gctgaatctt taagagggag tcatttggat   120
gaagtgaaaa aaatggtgag tgaatttaga aaaccaatgg taaaacttgg tggtgaaact   180
ttaacagtgg cacaagtggc tgctattgct gttaggdaca aaagtgcaaa tggtgttaaa   240
gttgaacttt ctgaagaggc aagagctggt gttaaagcta gtagtgattg ggttatggat   300
agtatgaata aaggaacaga tagttatggt gttactactg gttttggtgc tacatctcat   360
aggagaacca agaatggtgg tgctcttcaa aaagaactta ttaggttctt gaatgctggt   420
gttttggca atggaacaga aacaagccac acattgccac attcagcaac aagggcagct   480
atgcttgtta ggatcaacac actcctacaa ggctactctg catcagatt tgaaatcttg    540
gaagcaattg caaaattgat taacagcaac attactcatc gttacctct ccgtggcacg    600
atcactgcct cgggcgatct tgttcccttta tcctacattg ctggtttgct cactggtagg   660
cctaattcca aggctgttag tcccaatggt gagaccctta atgctgaaga agcgttccgc   720
gttgctggtg ttaacggtgg attttcgag ttgcagccta aggaaggact tgcacttgtg    780
aatggtacag cagttggttc tggtatggca tcaatggtcc tctttgattc caacattcat   840
gctgttatgt ctgaagtttt atcagcaatt ttcgctgaag ttatgaacgg aaagcccgaa   900
tttactgacc atttgacaca caagttgaag caccaccctg gtcaaattga ggctgctgct   960
attatgaac atatttgga tggaagctct tatgtgaagg cggctcaaaa agctacatgaa  1020
atggatcctc tccaaaaacc aaagcaagat cgttaatgtc tccgaacatc tccacaatgg  1080
cttggccctc aaattgaagt cattcgcgct gcaactaaga tgattgagag ggagattaac  1140
tcagtgaacg ataacccctt gatcgatgtt caagaaaca aggcattaca tggtggcaac  1200
ttccaaggca cccctatcgg tgtgtccatg gataatgcaa gattggctct tgcatcaatt  1260
gggaaattga tgttttgctca attctcggaa cttgtcaacg actattacaa caacggtttg  1320
ccatctaacc tcaccgcatc aaggaatcca agcttggact atggtttcaa gggagctgaa  1380
atcgccatgg catcttactg ctcagaactt caattcttgg caaatccagt gacaaaccat  1440
gtccaaagtg ctgagcaaca caaccaagat gtcaactcct tgggcttaat ctcagcaagg  1500
aaaacagctg aagctgtcga tatcttaaag ctcatgtcat caacttatct agtggcactt  1560
tgccaagcta tcgacttgag gcatttggag gaaaacttaa agaatgcagt caagaacaca  1620
gttagccaag tagctaagag aactcttaca atgggtgcta acggtgaact tcatccagca  1680
agattctgtg aaaaggaatt gctacgagtc gtggacaggg aatacttgtt cgcctacgct  1740
gatgatcctt gcagttgcaa ctacccttta atgcagaaac tgacacaagt acttgttgat  1800
catgcaatga ataatggtga aagtgagaag aatgtgaaaa gctcaatctt ccaaaagatt  1860
ggagctttcg aagacgaatt aaaggctgtt ttaccaaagg aagttgagag tgcaagagct  1920
gcattggaat gtgcaacccc tgctattgct aacaggatta cagaatgcag atcttatcca  1980
ttgtacaggt ttgtgagaaa ggagcttgga acagaactac taacaggaga aagagtccga  2040
tcaccgggcg aggagtgtga aaagtgttc acagcaatgt gcaatggaca gattattgat  2100
ccaatgttgg agtgtctcaa gagctggaat ggtgctcctc tacctatctg ttag         2154

SEQ ID NO: 54           moltype = DNA  length = 2139
FEATURE                 Location/Qualifiers
source                  1..2139
                        mol_type = genomic DNA
                        organism = Nicotiana sp.
SEQUENCE: 54
atggctggtg ttgcacaaaa tggtcaccaa gaaatggatt tttgcatgaa agtggatcca    60
ttaaactggg aaatggcagc tgattcattg aaaggaagcc atttagatga agtgaagaaa   120
atggtggctg agtttaggaa accagtagtg aaacttggag tgagactttt gacagtggct   180
caagttgcgg ctattgctgc aaaagataat gttaaaactg ttaaagtgga gcttttctgaa  240
ggggcaagag ctggtgttaa agctagcagt gattggtta tggacagtat gggtaaagga   300
actgatagtt atggtgttac aactggcttt ggtgctactt cacataggag gaccaagaat   360
ggtggtgctc ttcaaaagga acttattagg ttcttgaatg ctggagtttt tggcaatgga   420
acagagtcat gtcacacatt accacaatca gggacaaggg cagctatgtt agttaggatc   480
aacactctcc ttcaagggta ctctggcatc agatttgaaa tcttagaagc aatcactaaa   540
ttgcttaacc acaatgttac tccatgtttg cccctttcgcg gcaccatcac cgcctctggt   600
gatctcgtcc ccttgtccta cattgccggt ttactcactg gtcggcctaa ttctaaagca   660
gttggaccta atggcgaaac cctcaacgct gaagaagcgt ttcgtgttgc tggagttaac   720
ggtggatttt tcgagttgca gcctaaggaa ggcttgctc ttgtgaatgg tactgcagtt    780
ggttctggtt tggcctcaat ggttctcttt gatgctaatc ttctcgcgtg cttttctgaa   840
gttctctcag ctatttttgc tgaggtaatg aatggaaagc ccgagttcac tgaccacttg   900
acacacaagt tgaagcatca ccccggacaa attgaggctg ctctattat ggaacacatt    960
ttggatggta gctcttatgt gaaggcggct cagaagcttc acgaaacgga tcctctccaa  1020
aaaccaaagc aagatcgtta tgctcttaga acgtcgcccc aatggcttgg ccctcaaatt  1080
gaggtcatcc gttctgcaac caagatgatt gagagggaga ttaattcagt gaacgacaac  1140
cctttgatcg atgtttcaag aaacaaggca ttacacggtg gcaacttcca gggcactcca  1200
attggtgtct ctatggacaa tgctagatta gcccttgcat caataggaaa attgatgttt  1260
gcccaattct ccgagcttgt caacgattac tacaacaacg gattgccatc taatctgaca  1320
gcaggaagga atcctagctt ggactatggt ttcaaggat ctgagattgc catggcttca   1380
tactgttcag aacttcaatt cttggcaaat ccagtgacta accacgtaca aagcgccgag  1440
```

```
caacacaacc aagatgtgaa ctccttgggc ttaatctcag ctagaaaaac agctgaagcc   1500
gtggacatct taaagctaat gtcatccaca tatctagttg cactttgcca agcaatagac   1560
ttgaggcatt tggaagaaaa tctgaggaat gcagtcaaga acacggtgag ccaagtcgca   1620
aagagaactt taacaatggg taccaatgga gaacttcatc catcaagatt ctgtgaaaag   1680
gacttgcttc gagtcgttga cagggaatac gtcttcgcct atgctgacga cgcctgcagc   1740
gctaactacc cactgatgca gaaactaagg caagtcctcg tcgaccacgc cttgcaaaat   1800
ggcgaaaatg agaagaacgc aaacagctca atcttccaaa agatactagc ttttgaagac   1860
gagctaaagg ccgtgttgcc aaaagaagtc gagagtgcaa gagccgcgct ggaaagtggg   1920
aaccctgcaa ttgccaacag gataaaagaa tgcagatcct atccacttta caggtttgtt   1980
agaggagaac ttggagctga attattgacg ggagaaaaag tcaggtcacc aggtgaagaa   2040
tgtgacaaag tgttcacagc aatgtgcaat ggacaaatta ttgattcatt gttagaatgt   2100
ctcaaggaat ggaatggtgc acctcttcca atctgttag                          2139

SEQ ID NO: 55           moltype = DNA  length = 1170
FEATURE                 Location/Qualifiers
source                  1..1170
                        mol_type = genomic DNA
                        organism = Nicotiana sp.
SEQUENCE: 55
atggtgacgg tcgaggagtt tcgtagggca caacgtgccg agggtccggc cacggtcatg   60
gccatcggaa cagccacacc ttccaactgt gttgatcaaa gcacttaccc cgattactat   120
tttcgtatca ctaatagcga gcataagact gagcttaagg agaaatttaa gcgcatgtgt   180
gaaaaatcaa tgattaagaa aaggtacatg cacttaacag aggaaatctt gaaagagaat   240
cctaatattt gtgcatacat ggcaccttcc cttgatgcta gacaagacat agtggtggtt   300
gaagtgccaa aacttggcaa agaggcagcc caaaaggcca tcaaagaatg gggccagccc   360
aagtccaaaa ttagtcattt ggtctttttgt acaactaggta gtgtagacat gcccgggtgt   420
gactaccaac tcactaagct actcgggctc cgtccttcgg tcaagcggtt catgatgtac   480
caacaaggtt gctttgccgg tgggacggta ctccggatgg ctaaggactt ggccgaaaac   540
aacaagggcg ctcgagtcct tgttgtttgc tcagagatca ccgctgtcac gttccgtggg   600
cccaatgaca cccacttgga tagtttggtt gggcaagcct tttttggtga tggggcagcc   660
gcggtcattg taggttctga tccaattcca gatgtcgaga ggcctttgtt cgagcttgtt   720
tccgcagccc aaaccctact ccccgatagc gaaggcgcta tcgacggtca tctccgtgaa   780
gttgggctta cattccactt actcaaagat gttcctgggc ttatctcgaa aaacattgag   840
aaaagccttg tggaagcatt ccaaccttta ggaatttctc attggaactc tttattttgg   900
attgctcacc ctggtgggcc tgccattttg gaccaagttg aactaaaatt gggcctaaag   960
caagagaaac ttaaggctac aagaaatgta ttaagtaact atggcaatat gtcaagtgct   1020
tgtgtgttgt ttattttgga tgaaatgagg aaagcctctg caaagaagg tttaggaact   1080
actggtgaag ggcttgaatg gggtgtgctt tttggatttg ggcctgggct tacagttgag   1140
actgttgtcc ttcacagtgt tgctactag                                      1170

SEQ ID NO: 56           moltype = DNA  length = 1110
FEATURE                 Location/Qualifiers
source                  1..1110
                        mol_type = genomic DNA
                        organism = Nicotiana sp.
SEQUENCE: 56
atggcacctt cgacattgac agctctagca gaggaaaaga cacttcaaac aagtttcata   60
agagatgaag atgagcgacc aaaagtggcg tacaaccaat tcagcgatga gattccgatc   120
atatcgttga agggtattga tgatgagggt ggaattaatg gaagaagagg tgaaatatgt   180
gaaaagattg tcaaggcatg tgaagattgg ggcgttttcc aggtagttga tcatggtgtt   240
gatgctcaac ttatctcaca aatgacaact ctcgctcaac aattcttcgc ctttgcctgct   300
gaggaaaagc tacggtttga catgtcgggt ggcaagaaag gtggcttcat tgtctctagc   360
catctacagg gtgaagtggt ccaagattgg cgtgaaatag tgacctactt ctcatacca   420
attcgggcta gagactactc tagatggcca gacaaaccag agggatggat agatgtgact   480
caaaagtaca gtgaaaagtt aatggagttg gcttgcaaat tattggaagt actatcagag   540
gctatgggct tagagaagga ggccttaacc aaggcatgtg tggatatgga ccaaaaagtg   600
gttgtcaatt tttacccaaa gtgtccacag cctgacctta cccttgggct gaaacgacac   660
actgatccag gaaccatcac cctctgtta caagaccaag ttggtgggct tcaagccact   720
aaagataatg gcaaaacttg gattactgtt cagcccgttg ttggcgcttt tgttgtcaat   780
cttggtgacc atggtcattt tttgagcaat ggaaggttta agaacgctga tcatcaagca   840
gtggtgaact cgaatagcag cagattatcg atagctacgt tcagaatcc agcaccgagg   900
gcaatagtgt atcctttgaa aattagggaa ggagagaagg cagtgatgga cgagcccgta   960
gcatttgcag aaatgtatag gaggaaaatg agtaaggacc ttgagcttgc taggctcaag   1020
aaactagcca aggagcagca atacaagct gaagaagctg ctgagaaggc caagtcggaa   1080
accaagccta ttgatgaaat tcttgcttaa                                     1110

SEQ ID NO: 57           moltype = DNA  length = 438
FEATURE                 Location/Qualifiers
source                  1..438
                        mol_type = genomic DNA
                        organism = Nicotiana sp.
SEQUENCE: 57
atgtttggac cacaaagtgg aaaagatgga tggactgatt tgactttttat gtacgacatg   60
attcgaatta gataaaatc tctgtgttcc agttttctgc aaatattctc aagtgagggg   120
tgcaaaatgc tggaaatgac ttgtgaagag catgacaaat tggctgctcg aagtcaattt   180
ctgactcaca caattggcag gatcttatcc gaaatggagg ttgaacccac cccatagac   240
acgaagggat tcagaaaact tgttcaagtg aaggagagct cagttagaga tagttttgat   300
ctattcagcg ggctattcat acacaatagg tttgccaggc aacagatgaa aaatttagaa   360
gtagcagtgg agaaaactaa acagaagctt gaagagaggt cgaaggagct gcaggatcct   420
```

```
atcatatcta agttctag                                                      438

SEQ ID NO: 58           moltype = DNA  length = 1131
FEATURE                 Location/Qualifiers
source                  1..1131
                        mol_type = genomic DNA
                        organism = Nicotiana sp.
SEQUENCE: 58
atgttgtctt tcaccctct tcaatccaag ccaacaccac ccaccccac ctcaaacccc          60
acccgttggt cttggtctca tctcacccac caccacccca ctacccgccg ccacttctct       120
gcctcttcac cctccaaagt cagttaccgc cgccttagca ttaatgccat tgatgcagca       180
cagccatatg attatgaagc attagtttca aatcaatatg ctcagtcaac aagactcaag       240
attgctatag tgggttttgg caacttcggt cagtttcttg ctaaagcctt tgttcgtcaa       300
ggtcatgttg tttttgctca ttcaagaact gattactcac acattgcaaa ttctttaggt       360
gttttgtttt tcaagatcc acatgacctt tgtgagcaac atcctgatgt tattctactt        420
tgtacttcaa ttatatctac tgaacctgtc cttagatcac tccctattca aaggctaaaa       480
agaaacacat tatttgttga tgttttgtct gttaaagagt ttccaaagaa cattttcctt       540
caagttttgc cttcccattt tgatattttg tgtactcatc ctatgtttgg acctgaaagt       600
ggtaaggata gttggaaaga tttggccttt gtgtttgata aagttagaat tggtgaaggg       660
gaatcgagaa aaggaagggt tgataggttt cttgatatat ttgagaaaga agggtgtagg       720
atggtgcaga tgacgtgtgc ggagcatgat aggtatgctg caggttcgca gtttattaca       780
catacaatgg ggagagtatt ggagaagttg gatttggaa caactcctat taatacgaaa       840
gggtacgaga ctttgttgaa tttggttgag aatacttcta gtgatagctt tgacttgtac       900
tatgggttgt ttatgtacaa taagaatgcg atggagcagt tggaaagact tgatttggct       960
ttcgaggctt tgaagaagga gttatttggg catttgcatg aagtcttgag gaagcaattg      1020
ttcgggaagg cggaggaagc gggacagaga cgtatcttaa ccaagttgcc caagaatggg      1080
tatgcactac cagctccttc atcggaggct gttaaatctg agaacaattg a               1131

SEQ ID NO: 59           moltype = DNA  length = 2623
FEATURE                 Location/Qualifiers
misc_feature            1..2623
                        note = Chimera: comprises plant native sequences only
source                  1..2623
                        mol_type = other DNA
                        organism = synthetic construct
SEQUENCE: 59
cccgggttag tattcaaacc gaataaatca aagttaccaa accgaataaa tcgaaaccga         60
aaggagaaac cgcaccatac cgaatttaat taggtacgat attgatattg tattttaaaa       120
aatcgaatac caaaaatacc gaattaaaat atctaaatat cgtacagtac cgaccgataa       180
atactctata agcatcatca tgtcaccatt cctgcttgga aatagatgta ataatgtaat       240
tcaaggtgaa gatcattgaa aatgagatat ttggactctt agataattgt gcaactgata       300
tttttattta ctttttttct ttcatccaat aattgcgtta cattaaaaat gagatatttg       360
gattaatatt cttctccttg accacaaagc aaggaaagcc taaggaccga tagtaaagtt       420
gtattcgtgt ggttgcgtgt tagttttgag cggcaaaata aattatgtta aggtaaaatta      480
tttttggaac aataataaaa ttatttctgt ataatatata aatcatatat ttgaaccgta       540
gaattatcag ttaatacttg tatatgagga ggctaactac gttagagcgc taacgagaat       600
acttcatata ccgtattttt tacgataata ataatgtaat gtgaaattgc tatccaaaag       660
gcacctaatt ttgtccaccg ttcaaaggaa aggacaagga agtagtagcg tgtaggtttg       720
gtgctgtaca aaataagcaa gacacgtgtt gcctattat aggataatcc ataaggcaat        780
ttcgtcttaa gtcggccatt gcacctttaa aaggagcctc tttgttccca aaatcttcat       840
cctttgattt ctctattctc aatatctcct caatttttct ctagtcttca aacacttcta       900
aaggtacatt aacttcttct ttcttttttgt tcctcttatt ttatgctact tttatttaat      960
ttcgatctat atttttagga tctaaatact cattttgat ttgtttaatc gctctgtata       1020
tatgcaccaa gttgaaattt tgtaagttt attttgttcg gtctatattt taagatctga      1080
aataccettt actgagaaaa aaaaaactca accttgttct tgttgtaacct ggtgaattt      1140
gttattgttg tgtatacagt taaaaaactc aagtcttgat tttattgttt ccctttttgta     1200
gtttgtatat acatagagct gaattggtgt tctaattttg gttgattttt atgtatacag      1260
tataaaatcg atcttagttt tgttcattga tttgtatttg cacaaagttg gaattttgcg      1320
tttgttattt tgatgattga aacctttct gtatatacag ctcgagatgg agggttcgtc       1380
caaagggctg cgaaaaggtg cttggactac tgaagaagat agtctcttga gacagtgcat      1440
taataagtat ggagaaggca aatggcacca agttcctgta agagctgggc taaaccggtg      1500
caggaaaagt tgtagattaa gatggttgaa ctatttgaag ccaagtatca agagaggaaa      1560
acttagctct gatgaagtcg atcttcttct tcgccttcat aggcttctag ggaataggtg      1620
gtctttaatt gctggaagat tacctggtcg gaccgcaagt gaccgcaaga attactggaa      1680
cactcatctg agtaagaaac atgaaccgtg ttgtaagata aagatgaaaa agagagacat      1740
tacgcccatt cctacaacac cggcactaaa aaacaatgtt tataagcctc gacctcgatc      1800
cttcacagtt aacaacgact gcaaccatct caatgccca ccaaaagttg acgttaatcc       1860
tccatgcctt ggacttaaca tcaataatgt ttgtgacaat agtatcatat acaacaaaga      1920
taagaagaaa gaccaactag tgaataattt gattgatgaa gataatatgt ggttagaagaa     1980
attcctagag gaaagccaag aggtagatat tttggttcct gaagcgacga acagaaaa        2040
gggggacacc ttggcttttg acgttgatca actttggagt cttttcgatg gagagactgt     2100
gaaatttgat tagtctagaa ataacagagg gcgcgcgagc ggtggctact gatcgcctat     2160
gagttctgtg attctacttg taattcaga agtgtttca gtgtcttgtt ttctggaagt        2220
ccgttcggtt ttagtaact tttagctcaa aaatgtgatct gtacgatggt atttgtatgt     2280
ttgtgggtct tttacatata cgcttgtaat cgatcaatgt agaatgctgt gtgcctttc      2340
cgtcaacagc ttatttagtg tttactctgt atacgtatat ctaatatata gtactgattc     2400
tttcatctgg tgatttgttt tcctaaagag attattatca tagcttaat tgaatgatac      2460
aaagaggtgt tgcctggctt caccagagca gaaattttca ttgatatagg gtacaaatgt     2520
cattcacata atgttaagag ataagttttt caatgtcctc aagagcccac caagagtttc    2580
```

```
ttccgggaat tgcttaaatt atcttaaatt taaattgtaa aac                  2623

SEQ ID NO: 60           moltype = DNA   length = 2539
FEATURE                 Location/Qualifiers
misc_feature            1..2539
                        note = Chimera: comprises plant native sequences only
source                  1..2539
                        mol_type = other DNA
                        organism = synthetic construct
SEQUENCE: 60
cccgggttag tattcaaacc gaataaatca aagttaccaa accgaataaa tcgaaaccga   60
aaggagaaac cgcaccatac cgaatttaat taggtacgat attgatattg tattttaaaa  120
aatcgaatac caaaaatacc gaattaaaat atctaaatat cgtacagtac cgaccgataa  180
atactctata agcatcatca tgtcaccatt cctgcttgga aatagatgta ataatgtaat  240
tcaaggtgaa gatcattgaa aatgagatat ttggactctt agataattgt gcaactgata  300
tttttattta cttttttttct ttcatccaat aattgcgtta cattaaaaat gagatatttg  360
gattaatatt cttctccttg accacaaagc aaggaaagcc taaggaccga tagtaaagtt  420
gtattcgtgt ggttgcgtgt tagttttgag cggcaaaata aattatgtta aggtaaatta  480
tttttggaac aataataaaa ttatttctgt ataatatata aatcatatat ttgaaccgta  540
gaattatcag ttaatacttg tatatgagga ggctaactac gttagagcgc taacgagaat  600
acttcatata ccgtatttt tacgataata ataatgtaat gtgaaattgc tatccaaaag   660
gcacctaatt ttgtccaccg ttcaaaggaa aggacaagga agtagtagg tgtaggtttg   720
gtgctgtaca aaataagcaa gacacgtgtt gccttattat aggataatcc ataaggcaat   780
ttcgtcttaa gtcggccatt gcacctttaa aaggagcctc tttgttccca aaatcttcat   840
cctttgattt ctctattctc aatatctcct caattttct ctagtcttca aacacttctc    900
aaggtacatt aacttcttct ttcttttttgt tcctcttatt ttatgctact tttatttaat   960
ttcgatctat attttagga tctaaatact cattttgat ttgtttaatc gctctgtata    1020
tatgcaccaa gttgaaattt ttgtaagttt attttgttcg gtctatattt taagatctga  1080
aatacccttt actgagaaaa aaaaaactca accttgattt tgttgtacct ggttgaattt  1140
gttattgttg tgtatacagt taaaaaactc aagtcttgat tttattgttt cccttttgta  1200
gtttgtatat acatagagct gaattggtgt tctaatttg gttgattttt atgtatacag   1260
tataaaatcg atcttagttt tgttcattga tttgtatttg cacaaagttg gaattttgcg   1320
tttgttattt tgatgattga aaccttttct gtatatacag ctcgagatga atatttgtac   1380
taataagtcg tcgtcaggag tgaagaaagg tgcatggact gaagaagaag atgttctatt   1440
gaaaaaatgc atcgagaaat atggagaagg aaagtggcat caagttcctc ttagagctgg   1500
tttgaataga tgcagaaaga gctgcagatt aaggtggcta aattatctaa ggccacatat   1560
aaagagagga gacttctctt ttgatgaagt agatctcatt ttgaggcttc ataagctgtt   1620
aggcaacaga tggtcactta ttgctggtag acttcctgga aggacggcaa acgatgtcaa   1680
aaactactgg aacagccatc ttcgcaagaa gttaattgct cctcatgatc aaaaggaagg   1740
caagcaaaaa gcaaagaaga tcaccatatt cagacctcgg cctcgaacct tctcaaagac   1800
aaatacttgt gttaaaagta acacaaatac tgtagataag gatattgaag gcagcagcga   1860
aataattaga ttcaacgata atttgaagcc aacaactgaa gaattgacgg atgatggaat   1920
tcaatggtgg gccgatttac tagctaacaa ttacaacaat aatgggattg aggaagctga   1980
taattcatca ccaactttgt tgcatgagga aatgccactt ctcagttgat ctagaaataa   2040
cagagggcgc gcgagcggtg gctactgatc gcctatgagt tctgtgattc tacttgtaat   2100
ttcagaagtg ttttcagtgt cttgttttct ggaagtccgt ctggttttta gtaacttta    2160
gctcaaaaat gtgtctgtac gatggtattt gtatgtttgt gggtcttttta catatacgct   2220
tgtaatcgat caatgtagaa tgctgtgtgc cttttccgtc aacagcttat ttagtgttta   2280
ctctgtatac gtatatctaa tatatagtac tgattcttc atctggtgat ttgttttcct    2340
aaagagatta ttatcatagc tttaattgaa tgatacaaag aggtgttgcc tggcttcacc   2400
agagcagaaa ttttcattga tatagggtac aaatgtcatt cacataatgt taagagataa   2460
gttttcaat gtcctcaaga gcccaccaag agtttcttcc gggaattgct taaattatct   2520
taaatttaaa ttgtaaaac                                             2539

SEQ ID NO: 61           moltype = DNA   length = 3701
FEATURE                 Location/Qualifiers
misc_feature            1..3701
                        note = Chimera: comprises plant native sequences only
source                  1..3701
                        mol_type = other DNA
                        organism = synthetic construct
SEQUENCE: 61
cccgggaaac taataagaac aagcaatata agagaattcg taaaaaactt tctagttctt   60
gaacatctac ccatgtgaat tctcttttat ttttgtacac tataattaaa ttaacatggc   120
taaaccaatt atgccaactg aataaattat caatattgat aaacttcagg tttacaccat   180
gacgtgtgca attatgaata aactccaagt ttattatgat atgagttttt atatcaataa   240
acttctactt tactgtgaca ttcttttgtt tgtgtagtac aaattggaga ataaagcgtg   300
taacttttca catacatatt accccgctat aagttgtagt aagaaagaat attaaatctt   360
tccttttctt atagtctcaa tataaccaat cgcttttgcg aatactttag aaactaaata   420
agtttctttg agacttacta caacataatg ccttattgat aatcaatttt gttccttcaa   480
aatagtaata attggctctt ccagagctct caattaattt tgtactacca catattcatc   540
aacatccata tggtgaatat ctctttaaa gagaaagtta taccattatg gttatggtca    600
aaattatatg caatatttgt ttcttgcatt accgttgcct tttagtaatc acattgccaa   660
aatattttgg cctacaataa gtacgtgacc aatgaccatt tatgccataa tgacattatt   720
ttcttatttt ctctcaaacc tccttcaaga gatgagtgtg gtatatacta ctagcacgct   780
catattcttc caaaaatgaa tatgtattca taaatcacat attgtcacat tcacatcatg   840
aatgaccata aatcatctat atgtgcttta caaaatctca tgtcaaatcg atgataaata   900
ttactttcac atagtgaatg attatttga gaatacttat tattctcatt accacaatga    960
aaatgattat aatttcgtct attgtcacat ccacatccat tgatacattc atggtaataa  1020
```

```
ttttatcttc tttcagacgt atcatatatt gctatcacat tctcgtaagg gaatgagaat    1080
aaagcaaatt caatgggacg agtttccact ttttgtgctc acaatcatac atgaatttga    1140
tcatggcaat acatagaaat tttatcactt ttggtggtta taatttctta caaactctat    1200
tagagttata ataaaaattt attgtctttg cttgtattta aaatcaaatt ataaaatttt    1260
aaaaattcaa aagagaaaaa taaagtaaaa tacttacttt aaatccagaa tttaatcacg    1320
aaggaagttc atggaataat tgacgatcat tatgctcaat cccaaagctt ctactcaatt    1380
ggttacagtc tcgtgccgat aacgtgttat aaaacaataa aagaagaaca atattgcaga    1440
gaaagagaga gagggaattc ttattgaatt ttaggatgaa ttacaatgga ataggacccc    1500
tctatttata gggaaagagt gacttagcca ccaagtaaga tccctaaaat ctctctaaaa    1560
tatagacatt caccttaaat aaaactctat ttataacaaa aacaaaattg ttctagacga    1620
gaatcatttt cacttttttaa tgttttctt ctactccttt agttttttcct taaaccaaaa    1680
taaaaaaaaa gtctatattt ttctatcctt tttcttctct agttttaata cattccataa    1740
aatttgtggt gaaattgtac tttctccttt ttttcctct ttagtttcat agaaatttaaa    1800
caataaaacg aaaacatcaa aatatatcaa caaatagtaa atttcattac atttattttt    1860
ttgctcaaag tgctctttg ttgaatactc aaagtatata gtatattaca gttctaatca    1920
ggaattattc actgaaatat tgactgattt taggttcgtg tgatcgatta aatacctctt    1980
gaaccactac aaatttaacg aattaataac ttttacctaa cattttgtta cccatgtatt    2040
aatttgaatt tatactatta cttcctattt atgagtaata taacataatt tctgtgtaaa    2100
ggacagaaaa tacagaattt gattaattca aaattaatta tacttcaaaa aatatccacaa    2160
ggatatcaaa atttatcaaa taaggagca acgtcatttt cggctctccc acacaattca    2220
aaataattca aaacagaacc ggctagacct aacctaacca aaccatggtt aatacaaatc    2280
taaatcaccg aaaaacaatc ttaaccatag ttaataaccc gtattaatta acccgatatc    2340
catttcgcct tgcccttatt cattctccta taaaacagag gccctcagt atagcgaaga    2400
ctcacaattc gaatttcgaa aactcatctc tttctgtttt aacggcgtct tgataaacgc    2460
cgctccttct ctcctcctct ttgaaatttg aattttagg gtttcgtgaa actcgagaac    2520
aatgaatatt tgtactaata agtcgtcgtc aggagtgaaa aaagtcgcat ggactgaaga    2580
agaagatgtt ctattgaaaa aatgcatcga gaaatatgaa gaaggaaagt ggcatcaagt    2640
tcctcttaga gctggtttga atagatgcag aaagagctgc agattaaggt ggctaaatta    2700
tctaaggcca catataaaga gaggagactt ctctttttgat gaagtagatc tcattttgag    2760
gcttcataag ctgttaggca acagatggtc acttattgct ggtagacttc ctggaaggac    2820
ggcaaacgat gtcaaaaact actgaacag ccatcttcgc aagaagttaa ttgctcctca    2880
tgatcaaaag gagagcaagc aaaaagcaaa aagatcacc atattcagac ctcggcctcg    2940
aaccttctca aagacaaata cttgtgttaa aagtaacaca aatactgtag ataaggatat    3000
tgaaggcagc agcgaaataa ttagattcaa cgataatttg aagcaacaa ctgaagaatt    3060
gacggatgat ggaattcaat ggtgggccga tttactagct aacaattaca acaataatgc    3120
gattgaggaa gctgataatt catcaccaac tttgttgcat gaggaaatgc cacttctcag    3180
ttgatctaga aataacagag ggcgcgcgag cggtggctac tgatcgccta tgagttctgt    3240
gattctactt gtaatttcag aagtgttttc agtgtcttgt tttctggaag tccgtctggt    3300
ttttagtaac ttttagctca aaaatgtgtc tgtacgatga tatttgtatg tttgtgggtc    3360
ttttacatat acgcttgtaa tcgatcaatg tagaatgctg tgtgccttttt ccgtcaacag    3420
cttatttagt gtttactctg tatacgtata tctaatatat agtactgatt ctttcatctg    3480
gtgatttgtt ttcctaaaga gattattatc atagctttaa ttgaatgata caagaggtg    3540
ttgcctggct tcaccagagc agaaattttc attgatatag ggtacaaatg tcattcacat    3600
aatgttaaga gataagtttt tcaatgtcct caagagccca ccaagagttt cttccgggaa    3660
ttgcttaaat tatcttaaat ttaaattgta cccgtttaaa c                       3701

SEQ ID NO: 62           moltype = DNA   length = 6230
FEATURE                 Location/Qualifiers
misc_feature            1..6230
                        note = Chimera: comprises plant native sequences only
source                  1..6230
                        mol_type = other DNA
                        organism = synthetic construct
SEQUENCE: 62
cccgggttag tattcaaacc gaataaatca aagttaccaa accgaataaa tcgaaaccga     60
aaggagaaac cgcaccatac cgaatttaat taggtacgat attgatattg tattttaaaa    120
aatcgaatac caaaaatacc gaattaaaat atctaaatat cgtacagtac cgaccgataa    180
atactctata agcatcatca tgtcaccatt cctgcttgga aatagatgta ataatgtaat    240
tcaaggtgaa gatcattgaa aatgatgatat ttggactctt agataattgt gcaactgata    300
tttttattta cttttttct ttcatccaat aattgcgtta cattaaaaat gagatatttg    360
gattaatatt cttctccttg accacaaagc aaggaaagcc taaggaccga tagtaaagtt    420
gtattcgtgt ggttgcgtgt tagttttgag cggcaaaata aattatgtta aggtaaatta    480
ttttttggaac aataataaaa ttatttctgt ataatatata aatcatatat ttgaaccgta    540
gaattatcag ttaatacttg tatatgagga ggctaactac gttagagcgc taacgaaat    600
acttcatata ccgtattttt tacgataata ataatgtaat gtgaaattgc tatccaaaag    660
gcacctaatt ttgtccaccg ttcaaaggaa aggacaagga agtagtagcg tgtaggtttg    720
gtgctgtaca aaataagcaa gacacgtgtt gccttattat aggataatcc ataaggcaat    780
ttcgtcttaa gtcggccatt gcaccttttaa aaggagcctc tttgttccca aatcttcat    840
ccttttgattt ctctattctc aatatctcct caattttctc ctagtcttca aacacttctc    900
aaggtacatt aacttcttct ttcttttttgt tcctcttatt ttatgctact ttatttaat    960
ttcgatctat attttttagga tctaaatact cattttgat ttgttaatc gctctgtata    1020
tatgcaccaa gttgaaattt tgtaagttt attttgttcg gtctatattt taagatctga    1080
aatcccttt actgagaaaa aaaaaactca accttgattt tgttgtacct ggttgaattt    1140
gttattgtg tatacagt taaaaactc aagtcttgat tttattgtt ccctttgta    1200
gtttgtatat acatagagct gaattggtgt tctaatttg gttgattttt atgtatacag    1260
tataaaatcg atcttagttt tgttcattga tttgtatttg cacaaagttg gaattttgcg    1320
tttgttattt tgatgattga aacctttttct gtatatacag ctcgagatga atatttgtac    1380
taataagtcg tcgtcaggag tgaagaaagg tgcatggact gaagaagaag atgttctatt    1440
gaaaaaatgc atcgagaaat atggagaagg aaagtggcat caagttcctc ttagagctgg    1500
```

```
tttgaataga tgcagaaaga gctgcagatt aaggtggcta aattatctaa ggccacatat    1560
aaagagagga gacttctctt ttgatgaagt agatctcatt ttgaggcttc ataagctgtt    1620
aggcaacaga tggtcactta ttgctggtag acttcctgga aggacggcaa acgatgtcaa    1680
aaaactactgg aacagccatc ttcgcaagaa gttaattgct cctcatgatc aaaaggagag    1740
caagcaaaaa gcaaagaaga tcaccatatt cagacctcgg cctcgaacct tctcaaagac    1800
aaatacttgt gttaaaagta acacaaatac tgtagataag gatattgaag gcagcagcga    1860
aataattaga ttcaacgata atttgaagcc aacaactgaa gaattgacgg atgatggaat    1920
tcaatggtgg gccgatttac tagctaacaa ttacaacaat aatgggattg aggaagctga    1980
taattcatca ccaactttgt tgcatgagga aatgccactt ctcagttgat ctagaaataa    2040
cagagggcgc gcgagcggtg gctactgatc gcctatgagt tctgtgattc tacttgtaat    2100
ttcagaagtg ttttcagtgt cttgtttct ggaagtccgt ctggttttta gtaacttta     2160
gctcaaaaat gtgtctgtac gatggtattt gtatgtttgt gggtctttta catatacgct    2220
tgtaatcgat caatgtagaa tgctgtgtgc cttttccgtc aacagcttat ttagtgttta    2280
ctctgtatac gtatatctaa tatatagtac tgattcttc atctggtgat ttgtttcct     2340
aaagagatta ttatcatagc tttaattgaa tgatacaaag aggtgttgcc tggcttcacc    2400
agagcagaaa ttttcattga tatagggtac aaatgtcatt cacataatgt taagagataa    2460
gttttttcaat gtcctcaaga gcccaccaag agtttcttcc gggaattgct taaattatct    2520
taaatttaaa ttgtaaaact aataagaaca agcaatataa gagaattcgt aaaaaacttt    2580
ctagttcttg aacatctacc catgtgaatt ctctttttatt tttgtacact ataattaaat    2640
taacatggct aaaccaatta tgccaactga ataaattatc aatattgata aacttcaggt    2700
ttacaccatg acgtgtgcaa ttatgaataa actccaagtt tattatgata tgagttttta    2760
tatcaataaa cttctactt actgtgacat tcttttgttt gtgtagtaca aattggagaa    2820
taaagcgtgt aacttttcac atacatatta ccccgctata agttgtagta atagaagata    2880
ttaaatcttt cctttcttta tagtctcaat ataaccaatc gcttttgcga atactttaga    2940
aactaaaataa gtttctttga gacttactac aacataatgc cttattgata atcaattttg    3000
ttccttcaaa atagtaataa ttggctcttc cagagctcat aattaatttt gtactaccac    3060
atattcatca acatccatat ggtgaatatc tctttttaaag agaaagttat accattatgg    3120
ttatggtcaa aattatatgc aatatttgtt tcttgcatta ccgttgcctt ttagtaatca    3180
cattgccaaa atatttggc ctacaataag tacgtgacca atgaccattt atgccataat    3240
gacattattt tcttattttc tctcaaacct ccttcaagag agtagtgtgg tatatactac    3300
tagcacgctc atattcttcc aaaaatgaat atgtattcat aaatcacata ttgtcacatt    3360
cacatcatga atggaccata atcatctata tgtgctttac aaaatctcat gtcaaatcga    3420
tgataaatat tactttcaca tagtgaatga ttattttgag aatacttatt attctcatta    3480
ccacaatgaa aatgattata atttcgtcta ttgtcacatc cacatccatt gatacattca    3540
tggtaataat tttatcttct ttcagacgta tcatatattg ctatcacatt ctcgtaaggg    3600
aatgagaata aagcaaattc aatgggacga gtttccactt tttgtgctca caatcataca    3660
tgaatttgat catggcaata catagaaatt ttatcacttt tggtggttat aatttcttac    3720
aaactctatt agagttataa taaaatttta ttgtctttgc ttgtatttaa aatcaaatta    3780
taaaattta aaaaattcaaa agagaaaaat aaagtaacttta acttacttta aatccagaat    3840
ttaatcacga aggaagttca tggaataatt gacgatcatt atgctcaatc ccaaagcttc    3900
tactcaattg gttacagtct cgtgccgata acgtgttata aaacaataaa agaagaacaa    3960
tattgcagag aaagagagag agggaattct tattgaattt taggatgaat tacaatgaaa    4020
taggaccccct ctatttatag ggaaagagtg acttagccac caagtaaaat ccctaaaatc    4080
tctctaaaat atagacattc accttaaata aaactctatt tataacaaaa acaaaattgt    4140
tctagacgag aatcatttc acttttaat gtttttcttc tactccttta gttttcctt       4200
aaaccaaaat aaaaaaaaag tctatatttt tctatccttt tcttctcta gttttaatac      4260
attccataaa atttgtgggtg aaattgtact ttctccttt tttctcctt tagtttcata     4320
gaaattaaac aataaaacga aaacatcaaa atatatcaac aaaatagtaaa tttcattaca    4380
tttatttttt tgctcaaagt gctctttgt tgaatactca aagtatatag tatattcag     4440
ttctaatcag gaattattca ctgaaatatt gactgatttt aggttcgtgt gatcgattaa    4500
atacctcttg aaccactaca aatttaacga attaataact tttacctaac attttgttac    4560
ccatgtatta atttgaattt atactattac ttcctattta tgagtaatat aacataattt    4620
ctgtgtaaag gacagaaat acagaatttg attaattcaa aattaattat acttcaaaaa     4680
atatcacaag gatatcaaaa tttatcaaat aaaggagcaa cgtcattttc ggctctccca    4740
cacaattcaa aataattcaa aacagaaccg gctagaccta acctaaccaa accatggtta    4800
atacaaatct aaatcaccga aaaacaatct taaccatagt taataaccg tattaattaa     4860
cccgatatcc atttcgcctt gcccttattc atttctccta aaaacagagg cccttcagta    4920
tagcgaagac tcacaattcg aatttcgaaa actcatctct ttctgtttta acggcgtctt    4980
gataaacgcc gctccttctc tcctcctctt tgaaatttga atttttaggg ttcgtgaaa     5040
ctcgagaaca atgaattt gtactaataa gtcgtcgtca ggagtgaaga aaggtgcatg     5100
gactgaagaa gaagatgttc tattgaaaaa atgcatcgag aaatatggag aaggaaagtg    5160
gcatcaagtt cctcttagag ctggttaa tagatgcaga aagagctgca gattaaggtg      5220
gctaaattat ctaaggccac atataaagag aggagacttc tcttttgatg aagtagatct    5280
catttgagg cttcataagc tgttaggcaa cagatggtca cttattgctg gtagacttct      5340
tggaaggacg gcaaacgatg tcaaaaacta ctggaacagc catcttcgca agaagttaat    5400
tgctcctcat gatcaaaagg agagcaagca aaaagcaaag aagatcacca tattcagacc    5460
tcggcctcga accttctcaa agacaaatac ttgtgttaaa agtaacacaa atactgtaga    5520
taaggatatt gaaggcagca gcgaaataat tgattaattta agccaacaac    5580
tgaagaattg acggatgatg gaattcaatg gtgggccgat ttactagcta acaattacaa    5640
caataatggg attgaggaag ctgataattc atcaccaact ttgttgcatg aggaaatgcc    5700
acttctcagt tgatctagaa ataacagagg gcgcgcgagc ggtggctact gatcgcctat    5760
gagttctgtg attctacttg taatttcaga agtgttttca gtgtcttgtt ttctggaagt    5820
ccgtctggtt tttagtaact tttagctcaa aatgtgtctg tacgatggt atttgtatgt     5880
ttgtgggtct tttacatata cgcttgtaat gatcaatgt agaatgctgt gtgccttttc    5940
cgtcaacagc ttatttagtg tttactctgt atacgtatat ctaatatata tgactgattc    6000
tttcatctgg tgatttgttt tcctaaagag attattatca tagctttaat tgaatgatac    6060
aaagaggtgt tgcctggctt caccagagca gaaattttca ttgatatagg gtacaaatgt    6120
cattcacata atgttaagag ataagttttt caatgtcctc aagagcccac caagagtttc    6180
ttccgggaat tgcttaaatt atcttaaatt taaattgtac ccgtttaaac                6230
```

| SEQ ID NO: 63 | moltype = DNA length = 7583 |
|---|---|
| FEATURE | Location/Qualifiers |
| misc_feature | 1..7583 |
| | note = Chimera: comprises plant native sequences only |
| source | 1..7583 |
| | mol_type = other DNA |
| | organism = synthetic construct |

SEQUENCE: 63

```
cccgggttag tattcaaacc gaataaatca aagttaccaa accgaataaa tcgaaaccga   60
aaggagaaac cgcaccatac cgaatttaat taggtacgat attgatattg tattttaaaa  120
aatcgaatac caaaaatacc gaattaaaat atctaaatat cgtacagtac cgaccgataa  180
atactctata agcatcatca tgtcaccatt cctgcttgga aatagatgta ataatgtaat  240
tcaaggtgaa gatcattgaa aatgagatat ttggactctt agataattgt gcaactgata  300
ttttttattta ctttttttct ttcatccaat aattgcgtta cattaaaaat gagatatttg  360
gattaatatt cttctccttg accacaaagc aaggaaagcc taaggaccga tagtaaagtt  420
gtattcgtgt ggttgcgtgt tagttttgag cggcaaaata aattatgtta aggtaaatta  480
tttttggaac aataataaaa ttatttctgt ataatatata aatcatatat ttgaaccgta  540
gaattatcag ttaatacttg tatatgagga ggctaactac gttagagcgc taacgagaat  600
acttcatata ccgtattttt tacgataata ataatgtaat gtgaaattgc tatccaaaag  660
gcacctaatt ttgtccaccg ttcaaaggaa aggacaagga agtagtagcg tgtaggtttg  720
gtgctgtaca aaataagcaa gacacgtgtt gcctattaa aggataatcc ataaggcaat  780
ttcgtcttaa gtcggccatt gcacctttaa aaggagcctc tttgttccca aaatcttcat  840
cctttgattt ctctattctc aatatctcct caattttttct ctagtcttca aacacttctc  900
aaggtacatt aacttcttct ttcttttgt tcctcttatt ttatgctact tttatttaat  960
ttcgatctat attttttagga tctaaatact cattttttgt tgtttaatc gctctgtata 1020
tatgcaccaa gttgaaattt ttgtaagttt atttttgttcg gtctatattt taagatctga 1080
aatacccttt actgagaaaa aaaaaactca accttgattt tgttgtacct ggttgaattt 1140
gttattgttg tgtatacagt taaaaaactc aagtcttgat tttattgttt cccttttgta 1200
gtttgtatat acatagagct gaattggtgt tctaattttg gttgattttt atgtatacag 1260
tataaaatcg atcttagttt tgttcattga tttgtatttg cacaaagttg gaattttgcg 1320
tttgttattt tgatgattga aacctttttct gtatatacag ctcgagatga cggagatacc 1380
gcctaacagc cagatgaaaa ccatgttgca gaaggcagtg caatcggttc aatggacata 1440
tactcttttc tggcaattat gtccccaaca aggggcgtta gtgtgagag atggatatta 1500
caatggggct ataaagacta gaaagacagt gcagccaatg gaagttagcg ctgaggaagc 1560
ttctcttcac agaagccaac agcttagaga actttacgaa tcactttccg ccggcgagtc 1620
aaatcagcca gcgagaaggc cgtcggcagc tttgtcaccg gaggacttga cggagtccga 1680
gtggttttat ctcatgtgtg tttctttctc ttttcctcct ggcatcggat tacctggcaa 1740
ggcttattcg aagaaacatc acatatggat catgggcgca aacgaggttg atagcaaagt 1800
cttctgtaga gctattcttg ccaagagcgc ccgcatacag acggtcgttg gtattcctct 1860
cttggatggt gtactggaac tgggaactac agaaagggtt caagaagaga ttggattcat 1920
aaaccatgta aagagctttt tcactgagca acaacaacct cagctaccaa agccagcctt 1980
atctgagcac tccacttcca atcccaccac cttttccgag ccacattttt actccggcaa 2040
tacttcgcca tctgctaatg ttgatattgc gcatcaagat ggcggagctg ccggcgaaga 2100
agatgaggag gaggaagaag aagaagatga tgatgaagcc gagttggact cggatagtat 2160
agcgattcaa agcgcggcta atcctattgc cgttgaggct agtgaactca tgcagcttga 2220
tgtgtccgag gctatacagc tcggctcgcc cgatgatgac tctgataata tggactctga 2280
ttttcatttg gttggcgctg gaaacacggc tcatgactac cagcgccaag ctgactcttt 2340
caaagccgag accgccatta gctggccgca cttccaagac cttaacaat taccaggtgg 2400
ctctagttat gatgaattat cacaagaaga cacacactat tctcaaacag tgtcaaccat 2460
tctcgaacac cgaagctcca aattttcctc tacaacaatg ggctgtattt ctcatgactc 2520
ggcccaatct gccttcacat tgtgccctag caccaccgtc tgcagcccga atcccgccca 2580
ctgccgccac gacgactcac ttgtcgacgg tggcggcgcc tccagtggc tgctcaaaag 2640
catactcttc actgtcccat ttcttcacac taaataccaa tctgaagctt ctccaaagtc 2700
acgtgacgtc gccactgttg attcctccag tactgcttct cgctttcgca aaggctgtag 2760
tataacgtcg caagaagagc caagtggaaa ccatgtactt gcagaacgac gtcgtagaga 2820
gaagctaaat gagcgttta tcatattaag gtctcttgta cctttgtaa cgaaaatgga 2880
caaagcctcc attttgggtg acaccataga gtatgtcaag cagttacgta agaaagttca 2940
ggatcttgaa gctcgtgctc gcgacacgga gcactccaga gatgcagata aaaaaggtgg 3000
cacagctaca gtgaaggtgt tgcaaggaag gggtaagagg agaatgaata cggtagatgg 3060
aagtgttggt ggagggcagg caacgataac ggcgtcccca ccgtcaacga cggaaaatga 3120
ggaggttgtg caagtacaag tatcaattat cgaaagcgat gcattggtgg agctccggtg 3180
tccgtacaaa gaggggttgc tgttaaatgt aatgcagatg ctaagggaac tcaaagtgga 3240
agttgtagcc attcaatcag ctcttaataa tggcgtcttc ttggctgagt taagagctaa 3300
ggtaaaagag aatatatgtg gaaggaaagc aagcattttg gaagtaaaaa ggtcaataca 3360
tcagataatc cctagagatt aatctagaaa taacagaggg cgcgagcg tggctactg 3420
atcgcctatg agttctgtga ttctacttgt aatttcagaa gtgttttcag tgtcttgttt 3480
tctggaagtc cgtctggttt ttagtaactt ttagctcaaa aatgtgtctg tacgatggta 3540
tttgtatgtt tgtgggtctt ttacatatac gcttgtaatc gatcaatgta gaatgctgta 3600
tgcctttttcc gtcaacagct tatttagtgt ttactctgta tacgtatatc taatatatag 3660
tactgattct ttcatctggt gatttgtttt cctaaagaga ttattatcat agctttaatt 3720
gaatgataca aagaggtgtt gcctggcttc accagagcag aaattttcat tgatataggg 3780
tacaaatgtc attcacataa tgttaagaga taagttttcc aatgtcctca agagcccacc 3840
aaagagtttc tccgggaatt gcttaaatta tcttaaattt aaattgtaaa actaataaga 3900
acaagcaata taagagaatt cgtaaaaaac tttctagttc ttgaacatct acccatgtga 3960
attctctttt atttttgtac actataatta aattaacatg gctaaccaa ttatgccaac 4020
tgaataaatt atcaatattg ataaacttca ggttacacc atgacgtgtg caattatgaa 4080
taaactccaa gttattatg atatgagttt ttatatcaat aaacttctac tttactgtga 4140
cattcttttg tttgtgtagt acaaattgga gaataaagcg tgtaacttt cacatacata 4200
```

```
ttacccgct ataagttgta gtaatagaag atattaaatc tttcctttct ttatagtctc  4260
aatataacca atcgcttttg cgaatactttt agaaactaaa taagtttctt tgagacttac  4320
tacaacataa tgccttattg ataatcaatt ttgttccttc aaaatagtaa taattggctc  4380
ttccagagct ctcaattaat tttgtactac cacatattca tcaacatcca tatggtgaat  4440
atctcttttta aagagaaagt tataccatta tggttatggt caaaattata tgcaatattt  4500
gtttcttgca ttaccgttgc cttttagtaa tcacattgcc aaaatatttt ggcctacaat  4560
aagtacgtga ccaatgacca tttatgccat aatgacatta ttttcttatt ttctctcaaa  4620
cctccttcaa gagatgagtg tggtatatac tactagcacg ctcatattct tccaaaaatg  4680
aatatgtatt cataaatcac atattgtcac attcacatca tgaatggacc ataatcatct  4740
atatgtgctt tacaaaatct catgtcaaat cgatgataaa tattactttc acatagtgaa  4800
tgattatttt gagaatactt attattctca ttaccacaat gaaaatgatt ataatttcgt  4860
ctattgtcac atccacatcc attgatacat tcatggtaat aattttatct tctttcagac  4920
gtatcatata ttgctatcac attctcgtaa gggaatgaga ataaagcaaa ttcaatggga  4980
cgagtttcca cttttttgtgc tcacaatcat acatgaattt gatcatggca atacatagaa  5040
attttatcac ttttggtggt tataatttct tacaaactct attagagtta taataaaaat  5100
ttattgtctt tgcttgtatt taaaatcaaa ttataaaatt ttaaaaattc aaaagagaaa  5160
aataaagtaa aatacttact ttaaatccag aatttaatca cgaaggaagt tcatggaata  5220
attgacgatc attatgctca atcccaaagc ttctactcaa ttggttacag tctcgtgccg  5280
ataacgtgtt ataaaacaat aaaagaagaa caatattgca gagaaagaga gagagggaat  5340
tcttattgaa ttttaggatg aattacaatg gaataggacc cctctattta tagggaaaga  5400
gtgacttagc caccaagtaa aatccctaaa atctctctaa aatatagaca ttcaccttaa  5460
ataaaactct atttataaca aaaacaaaat tgttctagac ggaatcatt ttcactttt  5520
aatgtttttc ttctactcct ttagttttc cttaaaccaa aataaaaaaa aagtctatat  5580
tttctatcc tttttcttct ctagttttaa tacattccat aaaatttgtg gtgaaattgt  5640
actttctcct tttttttcct ctttagtttc atagaaatta aacaataaaa cgaaaacatc  5700
aaaatatatc aacaaatagt aaatttcatt acatttattt ttttgctcaa agtgctcttt  5760
tgttgaatac tcaaagtata tagtatatta cagttctaat caggaattat tcactgaaat  5820
attgactgat tttaggttcg tgtgatcgat taaatacctc ttgaaccact acaaatttaa  5880
cgaattaata acttttacct aacatttgt tacccatgta ttaatttgaa tttatactat  5940
tacttcctat ttatgagtaa tataacataa tttctgtgta aaggacagaa aatacagaat  6000
ttgattaatt caaaattaat tatacttcaa aaaatatcac aaggatatca aaatttatca  6060
aataaaggag caacgtcatt ttcggctctc ccacacaatt caaaataatt caaaacagaa  6120
ccggctagac ctaacctaac caaaccatgg ttaatacaaa tctaaatcac cgaaaaacaa  6180
tcttaaccat agttaataac ccgtattaat taacccgata tccatttcgc cttgcccta   6240
ttcattctcc tataaaacag aggcccttca gtatagcgaa gactcacaat tcgaatttcg  6300
aaaactcatc tcttttctgtt ttaacggcgt cttgataaac gccgctcctt ctctcctcct  6360
ctttgaaatt tgaatttta gggtttcgtg aaactcgaga acaatgaata tttgtactaa  6420
taagtcgtcg tcaggagtga agaaaggtgc atggactgaa gaagaagatg ttctattgaa  6480
aaaatgcatc gagaaatatg gagaaggaaa gtggcatcaa gttcctctta gagctggttt  6540
gaatagatgc agaaagagct gcagattaag gtggctaaat tatctaaggc cacatataaa  6600
gagaggagac ttctctttg atgaagtaga tctcattttg aggcttcata agctgttagg  6660
caacagatgg tcacttattg ctggtagact tcctggaagg acggcaaacg atgtcaaaaa  6720
ctactggaac agccatcttc gcaagaagtt aattgctcct catgatcaaa aggagagcaa  6780
gcaaaaagca aagaagatca ccatattcag acctcggcct cgaaccttct caaagacaaa  6840
tacttgtgtt aaaagtaaca caaatactgt agataaggat attgaaggca gcagcgaaat  6900
aattagattc aacgataatt tgaagccaac aactgaagaa ttgacggatg atggaattca  6960
atggtgggcc gatttactag ctaacaatta caacaataat gggattgagg aagctgataa  7020
ttcatcacca actttgttgc atgaggaaat gccacttctc agttgatcta gaaataacag  7080
agggcgcgcg agcggtggct actgatcgcc tatgagttct gtgattctac ttgtaatttc  7140
agaagtgttt tcagtgtctt gttttctgga agtccgtctg gttttagta acttttagct  7200
caaaaatgtg tctgtacgat ggtatttgta tgtttgtggg tcttttacat atacgcttgt  7260
aatcgatcaa tgtagaatgc tgtgtgcctt ttccgtcaac agcttattta gtgtttactc  7320
tgtatacgta tatctaatat atagtactga ttctttcatc tggtgatttg ttttcctaaa  7380
gagattatta tcatagcttt aattgaatga tacaaagagg tgttgcctgg cttcaccaga  7440
gcagaaattt tcattgatat agggtacaaa tgtcattcac ataatgttaa gagataagtt  7500
tttcaatgtc ctcaagagcc caccaagagt ttcttccggg aattgcttaa attatcttaa  7560
atttaaattg tacccgttta aac                                         7583
```

COMPOSITION AND METHODS FOR PRODUCING TOBACCO PLANTS AND PRODUCTS HAVING REDUCED TOBACCO-SPECIFIC NITROSAMINES (TSNAS)

CROSS-REFERENCE TO RELATED APPLICATIONS

This application is a Continuation of U.S. patent application Ser. No. 16/838,762, filed Apr. 2, 2020, which is a Continuation of U.S. patent application Ser. No. 15/727,523, filed Oct. 6, 2017 (now U.S. Pat. No. 10,647,989, Issued: May 12, 2020), which claims priority to U.S. Provisional Application No. 62/405,607, filed Oct. 7, 2016, and U.S. Provisional Application No. 62/503,103, filed May 8, 2017. Each of these applications are incorporated by reference herein in their entireties.

INCORPORATION OF SEQUENCE LISTING

A sequence listing contained in the file named "P34473US04_ST26.xml" which is 131,184 bytes (measured in MS-Windows®) and created on Mar. 31, 2023, comprises 63 sequences, is filed electronically herewith and incorporated by reference in its entirety.

FIELD

The present disclosure relates generally to methods for reducing tobacco specific nitrosamines (TSNAs) comprising modulating the levels of antioxidants, nitrite, or oxygen radical absorbance capacity (ORAC). Also provided are methods and compositions related to reducing or eliminating TSNAs in cured leaf from tobacco plants and products, their development via breeding or transgenic approaches, and production of tobacco products from those tobacco plants.

BACKGROUND

Tobacco-specific nitrosamines (TSNAs), such as N-nitrosonornicotine (NNN) and 4-(methylnitrosamino)-1-(3-pyridyl)-1-butanone (NNK), can be found in smokeless tobacco; mainstream smoke; and side stream smoke of cigarettes. It has been reported that air-cured and flue-cured tobacco contain tobacco-specific nitrosamines. See, "Effect of Air-Curing on the Chemical Composition of Tobacco", Wiernik et al., *Recent Adv. Tob. Sci*, (1995), 21, pp. 39-80. According to Wiernik et al., TSNAs are not present in significant quantities in growing tobacco plants or fresh cut tobacco (green tobacco), but are formed during the curing process. Bacterial populations which reside on the tobacco leaf are stated to largely cause the formation of nitrites from nitrate during curing and possibly affect the direct catalysis of the nitrosation of secondary amines at physiological pH values. The affected secondary amines include tobacco alkaloids, which form TSNAs when nitrosated.

Prior reports suggest several approaches to reduce TSNA levels. For example, WO2003/022081 proposed methods for reducing tobacco-specific nitrosamine (TSNA) content in cured tobacco by increasing the levels of antioxidants in the tobacco prior to harvesting. Specifically, WO2003/022081 proposed root pruning of the tobacco plant prior to harvesting; severing the xylem tissue of the tobacco plant prior to harvesting; and administering antioxidants and/or chemicals which increase antioxidants to the tobacco plant after harvesting. Despite previous attempts and proposals, simpler, more uniform, more economical and non-labor-intensive methods are desirable for reducing TSNA levels in cured tobacco leaf. Here, the inventors address this need by providing methods and compositions for reducing TSNAs by manipulating antioxidant levels via, inter alia, modification of genes involved in antioxidant biosynthesis or regulation thereof.

SUMMARY

In one aspect, the present disclosure provides cured tobacco leaf from a modified tobacco plant described here, where the cured tobacco leaf comprises a reduced level of one or more tobacco-specific nitrosamines (TSNAs) and further comprises an increased level of one or more antioxidants, wherein said reduced and increased levels are compared to cured tobacco leaf from a control tobacco plant of the same variety when grown and cured under comparable conditions.

In another aspect, the present disclosure provides a tobacco product comprising or made from cured leaf from a modified tobacco plant described here.

In one aspect, the present disclosure provides cured tobacco leaf from a modified tobacco plant comprising a reduced level of one or more tobacco-specific nitrosamines (TSNAs) and further comprising an increased level of one or more antioxidants, wherein said reduced and increased levels are compared to cured tobacco leaf from a control tobacco plant of the same variety when grown and cured under comparable conditions.

In another aspect, the present disclosure provides cured tobacco leaf from a modified tobacco plant comprising a reduced level of one or more tobacco-specific nitrosamines (TSNAs) and further comprising a reduced level of nitrite, wherein said reduced levels are compared to cured tobacco leaf from a control tobacco plant of the same variety when grown and cured under comparable conditions.

In one aspect, the present disclosure provides a modified tobacco plant or cured tobacco leaf from a modified tobacco plant comprising a reduced level of one or more tobacco-specific nitrosamines (TSNAs) and further comprising an increased level of oxygen radical absorbance capacity (ORAC), and wherein said reduced and increased levels are compared to a control tobacco plant or cured tobacco leaf from a control tobacco plant of the same variety when grown and cured under comparable conditions.

In another aspect, the present disclosure provides a seed giving rise to a modified tobacco plant described here.

In one aspect, the present disclosure provides a method comprising: planting a seed; and growing from the seed a modified tobacco plant described here.

In another aspect, the present disclosure provides a method comprising preparing a tobacco product using cured tobacco leaf from a modified tobacco plant described here.

In one aspect, the present disclosure provides a method of reducing the level of one or more TSNAs in cured tobacco leaf from a tobacco plant, said method comprising increasing the level of one or more antioxidants in said tobacco plant by expressing a biosynthetic enzyme, a regulatory transcription factor, a transporter, a catabolic enzyme, or a combination thereof, for said one or more antioxidants.

In another aspect, the present disclosure provides a method for producing a tobacco plant comprising: crossing at least one tobacco plant of a first tobacco variety with at least one tobacco plant of a second tobacco variety, wherein said at least one tobacco plant of said first tobacco variety is a modified tobacco plant described here; and selecting for a progeny tobacco plant capable of producing cured tobacco leaf comprising reduced levels of one or more tobacco-specific nitrosamines (TSNAs) and further comprising one or more traits selected from the group consisting of: a reduced level of nitrite, an increased level of oxygen radical absorbance capacity (ORAC), and an increased level of one or more antioxidants; wherein said reduced or increased level is compared to a control tobacco plant or cured tobacco leaf from a control tobacco plant of the same cross grown and cured under comparable conditions.

In one aspect, the present disclosure provides a method for reducing the level of one or more TSNAs in cured tobacco leaf or a tobacco product made therefrom, the method comprising increasing the level of one or more antioxidants in a tobacco plant via a transgene encoding or directly modulating an antioxidant biosynthetic enzyme, a regulatory transcription factor of an antioxidant, an antioxidant transporter, an antioxidant metabolic enzyme, or a combination thereof; and reducing the level of one or more TSNAs in cured tobacco leaf from the tobacco plant or a tobacco product made from the cured tobacco leaf.

In one aspect, the present disclosure provides a method for reducing the level of one or more TSNAs in cured tobacco leaf or a tobacco product made therefrom, the method comprising increasing the level of one or more antioxidants in a tobacco plant via a genetic modification in an endogenous gene, wherein the endogenous gene encodes an antioxidant biosynthetic enzyme, a regulatory transcription factor of an antioxidant, an antioxidant transporter, an antioxidant metabolic enzyme, or a combination thereof; and reducing the level of one or more TSNAs in cured tobacco leaf from the tobacco plant or a tobacco product made from the cured tobacco leaf.

In one aspect, the present disclosure provides a method for manufacturing a tobacco product, the method comprising obtaining cured tobacco leaf comprising a transgene or comprising a genetic modification in an endogenous gene, and further comprising an increased level of one or more antioxidants compared to a control cured tobacco leaf lacking the transgene or the genetic modification, wherein an endogenous gene encodes an antioxidant biosynthetic enzyme, a regulatory transcription factor of an antioxidant, an antioxidant transporter, an antioxidant metabolic enzyme, or a combination thereof, wherein the transgene encodes or directly modulates an antioxidant biosynthetic enzyme, a regulatory transcription factor of an antioxidant, an antioxidant transporter, an antioxidant metabolic enzyme, or a combination thereof; and producing a tobacco product from cured tobacco leaf, wherein the tobacco product comprises a reduced level of one or more TSNAs relative to a control tobacco product prepared from a control cured tobacco leaf.

In one aspect, the present disclosure provides a method for preparing cured tobacco leaf, the method comprising growing a tobacco plant comprising a transgene or a genetic modification in an endogenous gene, and further comprising an increased level of one or more antioxidants compared to a control tobacco plant lacking the transgene or the genetic modification, wherein an endogenous gene encodes an antioxidant biosynthetic enzyme, a regulatory transcription factor of an antioxidant, an antioxidant transporter, an antioxidant metabolic enzyme, or a combination thereof, wherein the transgene encodes or directly modulates an antioxidant biosynthetic enzyme, a regulatory transcription factor of an antioxidant, an antioxidant transporter, an antioxidant metabolic enzyme, or a combination thereof; and preparing cured leaf from a tobacco plant, wherein cured leaf comprises a reduced level of one or more TSNAs relative to a control cured leaf from a control tobacco plant not comprising the transgene or the genetic modification.

In one aspect, the present disclosure provides cured leaf of a modified tobacco plant, wherein cured leaf comprises a reduced level of one or more tobacco-specific nitrosamines (TSNAs) and further comprises an increased level of one or more antioxidants and a reduced nitrite level, wherein reduced and increased levels are compared to a control cured leaf of an unmodified tobacco plant of the same variety when grown and cured under comparable conditions, wherein the modification comprises a transgene or a genetic modification in an endogenous gene, wherein a transgene or an endogenous gene encodes an antioxidant biosynthetic enzyme, a regulatory transcription factor of an antioxidant, an antioxidant transporter, an antioxidant metabolic enzyme, or a combination thereof; wherein the modified tobacco plant does not comprise a transgene overexpressing an *Arabidopsis* PAP1 protein.

BRIEF DESCRIPTION OF THE SEQUENCES

SEQ ID NOs: 1 to 23 and 47 to 52 are amino acid sequences of selected genes that are involved in antioxidant production. SEQ ID NOs: 24 to 46 and 53 to 58 are corresponding nucleic acid sequences that encode SEQ ID NOs: 1 to 23, and 47 to 52. SEQ ID NOs:59 to 63 are polynucleotides encoding recombinant DNA molecules comprising cisgenic promoters, coding regions, and terminators.

BRIEF DESCRIPTION OF THE DRAWINGS

FIGS. 4A-4E: TSNA reduction in five AtPAP1 overexpression lines. FIG. 4A: total TSNAs are reduced in AtPAP1 overexpression lines. FIG. 4B: NNN levels are reduced in AtPAP1 overexpression lines compared to controls. FIG. 4C: NNK levels are reduced in AtPAP1 overexpression lines compared to controls. FIG. 4D: NAB levels are reduced in AtPAP1 overexpression lines compared to controls. FIG. 4E: NAT levels are reduced in AtPAP1 overexpression lines compared to controls.

FIGS. 6A-6B: Nitrite and Nitrate levels in AtPAP1 overexpression plants. FIG. 6A: Nitrite levels in AtPAP1 overexpression plants are reduced compared to controls. FIG. 6B: Nitrate levels in AtPAP1 overexpression plants are not consistently different from controls.

FIG. 10: Accumulation of Chlorogenic Acid is inversely correlated with TSNA levels. A negative correlation is observed between CGA levels and total TSNA levels as shown in Table 4 and FIG. 10A. This correlation is also observed between CGA levels and individual TSNAs NNN (FIG. 10B), NNK (FIG. 10C), NAB (FIG. 10D), and NAA (FIG. 10E).

DETAILED DESCRIPTION

Figure 1:
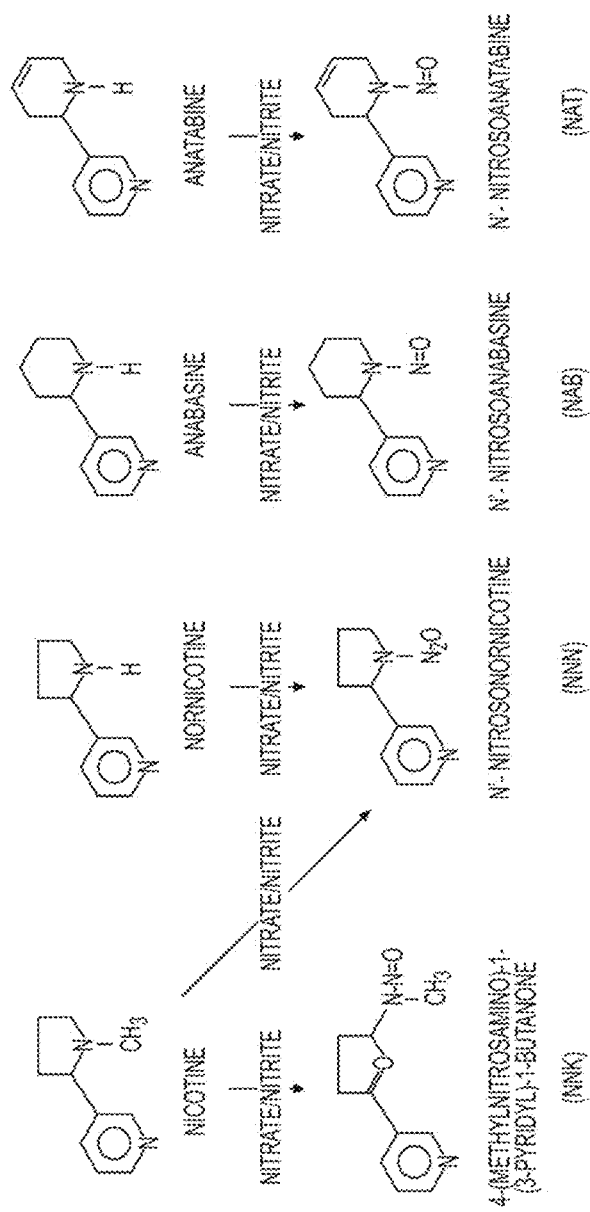
FIG. 1: TSNAs are formed when alkaloids nitrosinate in the presence of nitrite.

Unless defined otherwise, technical and scientific terms used herein have the same meaning as commonly understood by one of ordinary skill in the art. One skilled in the art will recognize many methods can be used in the practice of the present disclosure. Indeed, the present disclosure is in no way limited to the methods and materials described. For purposes of the present disclosure, the following terms are defined below.

Any references cited herein, including, e.g., all patents, published patent applications, and non-patent publications, are incorporated by reference in their entirety.

As used herein, the singular form "a," "an," and "the" include plural references unless the context clearly dictates otherwise. For example, the term "a compound" or "at least one compound" may include a plurality of compounds, including mixtures thereof.

The term "about" is used herein to mean approximately, roughly, around, or in the region of. When the term "about" is used in conjunction with a numerical range, it modifies that range by extending the boundaries above and below the numerical values set forth by 10%.

As used herein, a tobacco plant can be from any plant from the *Nicotiana tabacum* genus including, but not limited to *Nicotiana tabacum tabacum*; *Nicotiana tabacum amplexicaulis* PI 271989; *Nicotiana tabacum benthamiana* PI 555478; *Nicotiana tabacum bigelovii* PI 555485; *Nicotiana tabacum debneyi*; *Nicotiana tabacum excelsior* PI 224063; *Nicotiana tabacum glutinosa* PI 555507; *Nicotiana tabacum goodspeedii* PI 241012; *Nicotiana tabacum gossei* PI 230953; *Nicotiana tabacum hesperis* PI 271991; *Nicotiana tabacum knightiana* PI 555527; *Nicotiana tabacum maritima* PI 555535; *Nicotiana tabacum megalosiphon* PI 555536; *Nicotiana tabacum nudicaulis* PI 555540; *Nicotiana tabacum paniculata* PI 555545; *Nicotiana tabacum plumbaginifolia* PI 555548; *Nicotiana tabacum repanda* PI 555552; *Nicotiana tabacum rustica*; *Nicotiana tabacum suaveolens* PI 230960; *Nicotiana tabacum sylvestris* PI 555569; *Nicotiana tabacum tomentosa* PI 266379; *Nicotiana tabacum tomentosiformis*; and *Nicotiana tabacum trigonophylla* PI 555572.

In one aspect, this disclosure provides methods and compositions related to modified tobacco plants, seeds, plant components, plant cells, and products made from modified tobacco plants, seeds, plant parts, and plant cells. In one aspect, a modified seed provided herein gives rise to a modified plant provided herein. In one aspect, a modified plant, seed, plant component, plant cell, or plant genome provided herein comprises a recombinant DNA construct provided herein. In another aspect, cured tobacco material or tobacco products provided herein comprise modified tobacco plants, plant components, plant cells, or plant genomes provided herein.

As used herein, "modified" refers to plants, seeds, plant components, plant cells, and plant genomes that have been subjected to mutagenesis, genome editing, genetic transformation, or a combination thereof.

In one aspect, the present disclosure provides a modified tobacco plant capable of producing cured tobacco leaf comprising a reduced level of one or more tobacco-specific nitrosamines (TSNAs) and further comprising an increased level of one or more antioxidants, wherein the reduced and increased levels are compared to a control tobacco plant or cured leaf from a control tobacco plant of the same variety when grown and cured under comparable conditions. In one aspect, a reduced level of one or more TSNAs is less than 50% of the level of the one or more TSNAs in cured leaf from a control plant. In another aspect, a modified tobacco plant further comprises an increased level of oxygen radical absorbance capacity (ORAC) compared to a control tobacco plant when grown and cured under comparable conditions. In a further aspect, cured leaf from a modified tobacco plant comprises a reduced level of nitrite compared to cured leaf from a control tobacco plant when grown and cured under comparable conditions.

In another aspect, cured leaf from a modified tobacco plant comprises a reduced level of total TSNAs compared to the cured leaf from a control tobacco plant when grown and cured under comparable conditions. In one aspect, reduced one or more TSNAs are selected from the group consisting of N'-nitrosonornicotine (NNN), 4-methylnitrosoamino-1-(3-pyridyl)-1-butanone (NNK), N'-nitrosoanatabine (NAT) N'-nitrosoanabasine (NAB), and any combination thereof. In one aspect, the level of total TSNAs or an individual TSNA is measured based on a freeze-dried cured leaf sample using liquid chromatograph with tandem mass spectrometry (LC/MS/MS).

In one aspect, the present disclosure provides cured leaf from a modified tobacco plant comprising a reduced level of 4-methylnitrosoamino-1-(3-pyridyl)-1-butanone (NNK) compared to cured leaf from a control tobacco plant of the same variety when grown and cured under comparable conditions. In one aspect, a reduced level of NNK is less than 50% of the level of the NNK in cured leaf from a control plant. In one aspect, a modified tobacco plant or cured leaf from a modified tobacco plant further comprises an increased level of one or more antioxidants compared to a control tobacco plant or cured tobacco leaf from a control plant of the same variety when grown and cured under comparable conditions. In another aspect, a modified tobacco plant or cured leaf from a modified tobacco plant further comprises an increased level of oxygen radical absorbance capacity (ORAC) compared to a control tobacco or cured tobacco leaf from a control plant when grown and cured under comparable conditions. In a further aspect, cured leaf from a modified tobacco plant comprises a reduced level of nitrite compared to cured leaf from a control tobacco plant when grown and cured under comparable conditions. The role of nitrite in the formation is nitrosamines and TSNAs is linked to the reduction of nitrate by the activity of bacteria during the curing process. Nitrite is believed to generate nitrosating compounds which then react with secondary amines such as the tobacco alkaloids nicotine, nornicotine, anabasine, and anatabine to form TSNAs. Reducing the amount of nitrite and therefore the nitrosation of tobacco alkaloids, the production of TSNAs can be prevented during the curing process.

In one aspect, a modified tobacco plant or cured leaf from a modified tobacco plant comprises an increased level of one or more antioxidants selected from the group consisting of anthocyanidin, flavanone, flavanol, flavone, flavonol, isoflavone, hydroxybenzoic acid, hydroxycinnamic acid, ellagitannin, stibene, lignan, carotenoids, and glycyrrhzin.

In another aspect, a modified tobacco plant or cured leaf from a modified tobacco plant comprises an increased level of one or more antioxidants selected from the group consisting of Delphnidin, Cyanidin, Procyanidin, Prodelphinidin, Hesperetin, Naringenin, Catechin, Epicatechin, Apigenin, Luteonin, Quercetin, Myricetin, Rutin, Genistein, Daidzein, Gallic acid, Vanillic acid, Protocatechuic acid, Ferunic acid, Cinnamic acid, Coumeric acid, Chlorogenic acid, Coffeic acid, ferulic acid, Sanguiin, Resveratrol, Sesamin, Caretonoids, and Vitamin C.

In one aspect, a modified tobacco plant or cured leaf from a modified tobacco plant comprises an antioxidant that is undetectable in the control plant or leaf. In another aspect, a modified tobacco plant or cured leaf from a modified tobacco plant comprises an antioxidant that does not exist in the control plant.

In another aspect, the present disclosure provides cured leaf from a modified tobacco plant comprising a reduced level of one or more tobacco-specific nitrosamines (TSNAs) and further comprising a reduced level of nitrite, wherein the reduced levels are compared to cured leaf from a control tobacco plant of the same variety when grown and cured under comparable conditions. In another aspect, a modified tobacco plant or cured leaf from a modified tobacco plant further comprises an increased level of oxygen radical absorbance capacity (ORAC) compared to the control tobacco plant or cured leaf from the control tobacco plant when grown and cured under comparable conditions.

In a further aspect, the present disclosure provides a modified tobacco plant capable of producing cured leaf comprising a reduced level of one or more tobacco-specific nitrosamines (TSNAs) and further comprising an increased level of oxygen radical absorbance capacity (ORAC), and wherein the reduced and increased levels are compared to a control tobacco plant or cured leaf from a control tobacco plant of the same variety when grown and cured under comparable conditions.

In one aspect, a reduced or increased level is within about 10%, within about 20%, within about 30%, within about 40%, within about 50%, within about 60%, within about 70%, within about 80%, within about 90%, within about 92%, within about 94%, within about 95%, within about 96%, within about 97%, within about 98%, or within about 99% lower or higher than the level in a control tobacco plant or cured leaf from a control tobacco plant when grown and cured under comparable conditions.

In another aspect, a reduced or increased level is within about 1 fold, within about 2 folds, within about 3 folds, within about 4 folds, within about 5 folds, within about 6 folds, within about 7 folds, within about 8 folds, within about 9 folds, within about 10 folds, within about 15 folds, within about 20 folds, within about 25 folds, or within about 30 folds lower or higher than the level in a control tobacco plant or cured leaf from a control tobacco plant when grown and cured under comparable conditions.

In one aspect, a reduced or increased level is at least about 10%, at least about 20%, at least about 30%, at least about 40%, at least about 50%, at least about 60%, at least about 70%, at least about 80%, at least about 90%, at least about 92%, at least about 94%, at least about 95%, at least about 96%, at least about 97%, at least about 98%, or at least about 99% lower or higher than the level in a control tobacco plant or cured leaf from a control tobacco plant when grown and cured under comparable conditions.

In another aspect, a reduced or increased level is at least about 1 fold, at least about 2 folds, at least about 3 folds, at least about 4 folds, at least about 5 folds, at least about 6 folds, at least about 7 folds, at least about 8 folds, at least about 9 folds, at least about 10 folds, at least about 15 folds, at least about 20 folds, at least about 25 folds, or at least about 30 folds lower or higher than the level in a control tobacco plant or cured leaf from a control tobacco plant when grown and cured under comparable conditions.

In one aspect, a reduced or increased level is about 10%, about 20%, about 30%, about 40%, about 50%, about 60%, about 70%, about 80%, about 90%, about 92%, about 94%, about 95%, about 96%, about 97%, about 98%, or about 99% lower or higher than the level in a control tobacco plant or cured leaf from a control tobacco plant when grown and cured under comparable conditions.

In another aspect, a reduced or increased level is about 1 fold, about 2 folds, about 3 folds, about 4 folds, about 5 folds, about 6 folds, about 7 folds, about 8 folds, about 9 folds, about 10 folds, about 15 folds, about 20 folds, about 25 folds, or about 30 folds lower or higher than the level in a control tobacco plant or cured leaf from a control tobacco plant when grown and cured under comparable conditions.

In one aspect, a reduced or increased level is about 1-2 folds, about 2-3 folds, about 3-4 folds, about 4-5 folds, about 5-6 folds, about 6-7 folds, about 7-8 folds, about 8-9 folds, about 9-10 folds, about 10-15 folds, about 15-20 folds, about 20-25 folds, about 25-30 folds, or about 30-50 folds lower or higher than the level in a control tobacco plant or cured leaf from a control tobacco plant when grown and cured under comparable conditions.

In another aspect, a reduced or increased level is about 1-10 folds, about 2-10 folds, about 3-10 folds, about 4-10 folds, about 5-10 folds, about 6-10 folds, about 7-10 folds, about 8-10 folds, about 9-10 folds, about 10-50 folds, about 15-50 folds, about 20-50 folds, about 25-50 folds, or about 30-50 folds lower or higher than the level in a control tobacco plant or cured leaf from a control tobacco plant when grown and cured under comparable conditions.

In one aspect, cured leaf from a modified tobacco plant produces or comprises less than 2, less than 1.8, less than 1.5, less than 1.2, less than 1.0, less than 0.8, less than 0.6, less than 0.4, less than 0.3, less than 0.2, less than 0.15, less than 0.1, or less than 0.05 ppm total TSNAs. In one aspect, cured leaf from a modified tobacco plant comprises between 2 and 0.05, between 1.8 and 0.05, between 1.5 and 0.05, between 1.2 and 0.05, between 1.0 and 0.05, between 0.8 and 0.05, between 0.6 and 0.05, between 0.4 and 0.05, between 0.3 and 0.05, between 0.2 and 0.05, between 0.15 and 0.05, or between 0.1 and 0.05 ppm total TSNAs. In one aspect, cured leaf from a modified tobacco plant comprises between 2 and 0.05, between 1.8 and 0.1, between 1.5 and 0.15, between 1.2 and 0.2, between 1.0 and 0.3, between 0.8 and 0.4, or between 0.6 and 0.5 ppm total TSNAs.

In one aspect, cured leaf from a modified tobacco plant comprises or produces less than 0.08 ppm NNK, wherein the level of the NNK level is measured based on a freeze-dried cured leaf sample using liquid chromatograph with tandem mass spectrometry (LC/MS/MS).

As used herein, "comparable conditions" refers to similar environmental conditions, agronomic practices, and/or curing process for growing or curing tobacco and making meaningful comparisons between two or more plant genotypes so that neither environmental conditions nor agronomic practices (including curing process) would contribute to, or explain, any differences observed between the two or more plant genotypes. Environmental conditions include, for example, light, temperature, water, humidity, and nutrition (e.g., nitrogen and phosphorus). Agronomic practices include, for example, seeding, clipping, undercutting, transplanting, topping, suckering, and curing. See Chapters 4B and 4C of Tobacco, Production, Chemistry and Technology, Davis & Nielsen, eds., Blackwell Publishing, Oxford (1999), pp. 70-103.

As used herein, a "reduced" or "increased" level refers to a statistically significant change (reduction or increase) from a reference point. As used herein, "statistically significant" refers to a p-value of less than 0.05, a p-value of less than 0.025, a p-value of less than 0.01, or a p-value of less than 0.001 when using an appropriate measure of statistical significance (e.g., a one-tailed two sample t-test).

As used herein, a "control plant" refers to a comparator plant that is an unmodified tobacco plant of the same variety or a tobacco plant having no transgene of interest, depending on the context or the purpose of the control plant. Control tobacco plants and plants of interest are grown and cured under comparable conditions.

In one aspect, a modified tobacco plant provided herein has similar or higher leaf yield compared to a control tobacco plant when grown and cured under comparable conditions. In an aspect, leaf yield is selected from the group consisting of fresh yield, dry yield, and cured yield. In one aspect, a modified tobacco plant provided herein produces a leaf yield mass within about 50%, within about 45%, within about 40%, within about 35%, within about 30%, within about 25%, within about 20%, within about 15%, within about 10%, within about 5%, within about 4%, within about 3%, within about 2%, within about 1%, or within about 0.5% compared to a control tobacco plant when grown and cured under comparable conditions. In another aspect, a modified tobacco plant provided herein produces a leaf yield mass at least 0.25%, 0.5%, 1%, 2.5%, 5%, 10%, 15%, 20%, 25%, 30%, 40%, 50%, 60%, 70%, 80%, 90%, 100%, or more than 100% higher compared to a control tobacco plant when grown and cured under comparable conditions. In another aspect, a modified tobacco plant provided herein produces a leaf yield mass 0.25%-100%, 0.5%-100%, 1%-100%, 2.5%-100%, 5%-100%, 10%-100%, 15%-100%, 20%-100%, 25%-100%, 30%-100%, 40%-100%, 50%-100%, 60%-100%, 70%-100%, 80%-100%, 90%-100%, 100%-200%, 100%-175%, 100%-150%, 100%-125%, 0.25%-50%, 0.5%-50%, 1%-50%, 2.5%-50%, 5%-50%, 10%-50%, 15%-50%, 20%-50%, 25%-50%, 30%-50%, 40%-50%, 50%-200%, 50%-175%, 50%-150%, 50%-125%, 0.25%-25%, 0.5%-25%, 1%-25%, 2.5%-25%, 5%-25%, 10%-25%, 15%-25%, 20%-25%, 25%-200%, 25%-175%, 25%-150%, or 25%-125% higher compared to a control tobacco plant when grown and cured under comparable conditions.

In one aspect, a modified tobacco plant provided herein has a similar or comparable plant height compared to a control tobacco plant when grown and cured under comparable conditions. In one aspect, a modified tobacco plant provided herein comprises a height within about 50%, within about 45%, within about 40%, within about 35%, within about 30%, within about 25%, within about 20%, within about 15%, within about 10%, within about 5%, within about 4%, within about 3%, within about 2%, within about 1%, or within about 0.5% compared to a control tobacco plants when grown and cured under comparable conditions. In another aspect, a modified tobacco plant provided herein comprises a height 0.25%, 0.5%, 1%, 2.5%, 5%, 10%, 15%, 20%, 25%, 30%, 40%, 50%, 60%, 70%, 80%, 90%, 100%, or more than 100% taller compared to a control tobacco plant when grown and cured under comparable conditions. In another aspect, a modified tobacco plant comprises a height 0.25%-100%, 0.5%-100%, 1%-100%, 2.5%-100%, 5%-100%, 10%-100%, 15%-100%, 20%-100%, 25%-100%, 30%-100%, 40%-100%, 50%-100%, 60%-100%, 70%-100%, 80%-100%, 90%-100%, 100%-200%, 100%-175%, 100%-150%, 100%-125%, 0.25%-50%, 0.5%-50%, 1%-50%, 2.5%-50%, 5%-50%, 10%-50%, 15%-50%, 20%-50%, 25%-50%, 30%-50%, 40%-50%, 50%-200%, 50%-175%, 50%-150%, 50%-125%, 0.25%-25%, 0.5%-25%, 1%-25%, 2.5%-25%, 5%-25%, 10%-25%, 15%-25%, 20%-25%, 25%-200%, 25%-175%, 25%-150%, or 25%-125% taller compared to a control tobacco plant when grown and cured under comparable conditions.

In one aspect, a modified tobacco plant provided herein produces leaf that has a similar or higher USDA grade index value compared to a control tobacco plant when grown and cured under comparable conditions. In one aspect, a modified tobacco plant provided herein produces leaf with a USDA grade index value within about 50%, within about 45%, within about 40%, within about 35%, within about 30%, within about 25%, within about 20%, within about 15%, within about 10%, within about 5%, within about 4%, within about 3%, within about 2%, within about 1%, or within about 0.5% compared to a control tobacco plant when grown and cured under comparable conditions. In one aspect, a modified tobacco plant provided herein is capable of producing leaf having a USDA grade index value of 55 or more, 60 or more, 65 or more, 70 or more, 75 or more, 80 or more, 85 or more, 90 or more, or 95 or more. In one aspect, a modified tobacco plant provided herein produces leaf with a USDA grade index value at least 1, 2, 3, 4, 5, 6, 7, 8, 9, 10, 12, 13, 14, 15, 16, 17, 18, 19, 20, 21, 22, 23, 24, 25, 26, 27, 28, 29, 30, 35, 40, 45, 50, or more than 50 units higher compared to a control tobacco plant when grown and cured under comparable conditions. In one aspect, a modified tobacco plant provided herein produces leaf with a USDA grade index value 1-50, 1-45, 1-40, 1-35, 1-30, 1-29, 1-28, 1-27, 1-26, 1-25, 1-24, 1-23, 1-22, 1-21, 1-20, 1-19, 1-18, 1-17, 1-16, 1-15, 1-14, 1-13, 1-12, 1-11, 1-10, 1-9, 1-8, 1-7, 1-6, 1-5, 1-4, 1-3, 1-2, 2-50, 2-45, 2-40, 2-35, 2-30, 2-29, 2-28, 2-27, 2-26, 2-25, 2-24, 2-23, 2-22, 2-21, 2-20, 2-19, 2-18, 2-17, 2-16, 2-15, 2-14, 2-13, 2-12, 2-11, 2-10, 2-9, 2-8, 2-7, 2-6, 2-5, 2-4, 2-3, 3-50, 3-45, 3-40, 3-35, 3-30, 3-29, 3-28, 3-27, 3-26, 3-25, 3-24, 3-23, 3-22, 3-21, 3-20, 3-19, 3-18, 3-17, 3-16, 3-15, 3-14, 3-13, 3-12, 3-11, 3-10, 3-9, 3-8, 3-7, 3-6, 3-5, 3-4, 4-50, 4-45, 4-40, 4-35, 4-30, 4-29, 4-28, 4-27, 4-26, 4-25, 4-24, 4-23, 4-22, 4-21, 4-20, 4-19, 4-18, 4-17, 4-16, 4-15, 4-14, 4-13, 4-12, 4-11, 4-10, 4-9, 4-8, 4-7, 4-6, 4-5, 5-50, 5-45, 5-40, 5-35, 5-30, 5-29, 5-28, 5-27, 5-26, 5-25, 5-24, 5-23, 5-22, 5-21, 5-20, 5-19, 5-18, 5-17, 5-16, 5-15, 5-14, 5-13, 5-12, 5-11, 5-10, 5-9, 5-8, 5-7, 5-6, 10-50, 10-40, 10-30, 10-20, 20-50, 20-30, 20-40, or 20-30 units higher compared to a control tobacco plant when grown and cured under comparable conditions.

Tobacco grades are evaluated based on factors including, but not limited to, the leaf stalk position, leaf size, leaf color, leaf uniformity and integrity, ripeness, texture, elasticity, sheen (related with the intensity and the depth of coloration of the leaf as well as the shine), hygroscopicity (the faculty of the tobacco leaf to absorb and to retain the ambient moisture), and green nuance or cast. Leaf grade can be determined, for example, using an Official Standard Grade published by the Agricultural Marketing Service of the US Department of Agriculture (7 U.S.C. § 511). See, e.g., Official Standard Grades for Burley Tobacco (U.S. Type 31 and Foreign Type 93), effective Nov. 5, 1990 (55 F.R. 40645); Official Standard Grades for Flue-Cured Tobacco (U.S. Types 11, 12, 13, 14 and Foreign Type 92), effective Mar. 27, 1989 (54 F.R. 7925); Official Standard Grades for Pennsylvania Seedleaf Tobacco (U.S. Type 41), effective Jan. 8, 1965 (29 F.R. 16854); Official Standard Grades for Ohio Cigar-Leaf Tobacco (U.S. Types 42, 43, and 44), effective Dec. 8, 1963 (28 F.R. 11719 and 28 F.R. 11926); Official Standard Grades for Wisconsin Cigar-Binder Tobacco (U.S. Types 54 and 55), effective Nov. 20, 1969 (34 F.R. 17061); Official Standard Grades for Wisconsin Cigar-Binder Tobacco (U.S. Types 54 and 55), effective Nov. 20, 1969 (34 F.R. 17061); Official Standard Grades for Georgia and Florida Shade-Grown Cigar-Wrapper Tobacco (U.S. Type 62), Effective April 1971. A USDA grade index value can be determined according to an industry accepted grade index. See, e.g., Bowman et al, *Tobacco Science,* 32:39-40 (1988); Legacy Tobacco Document Library (Bates Document #523267826-523267833, Jul. 1, 1988, Memorandum on the Proposed Burley Tobacco Grade Index); and Miller et al., 1990, *Tobacco Intern.,* 192:55-57 (all foregoing references are incorporated by inference in their entirety). Alternatively, leaf grade can be determined via hyper-spectral imaging. See e.g., WO 2011/027315 (published on Mar. 10, 2011, and incorporated by inference in its entirety).

In one aspect, a modified tobacco plant provided herein comprises tobacco leaf with reduced total TSNAs and further comprises one or more desirable or enhanced properties, e.g., inhibited or reduced sucker growth prior to or after topping. In one aspect, a modified plant provided herein comprises fewer total suckers, smaller suckers, or both compared to a control plant lacking such modification when grown and cured under comparable conditions. In one aspect, smaller suckers of a modified plant provided herein comprise reduced mass, reduced length, reduced diameter, or a combination thereof compared to suckers of a control plant grown and cured under comparable conditions.

Unless specified otherwise, measurements of the level of total TSNAs, individual TSNA, total or individual alkaloid, total or individual antioxidant, leaf yield, or leaf grade index values mentioned herein for cured leaf from a tobacco plant, variety, cultivar, or line refer to average measurements, including, for example, an average of multiple leaves (e.g., 2, 3, 4, 5, 6, 7, 8, 9, 10, 11, 12, 13, 14, 15, 16, 17, 18, 19, or 20 or more leaves) of a single plant or an average measurement from a population of tobacco plants from a single variety, cultivar, or line. A population of tobacco plants or a collection of tobacco leaf for determining an average measurement (e.g., fresh weight or leaf grading) can be of any size, for example, 5, 10, 15, 20, 25, 30, 35, 40, or 50. Industry-accepted standard protocols are followed for determining average measurements or grade index values.

In one aspect, a modified tobacco plant or leaf provided here has a similar leaf chemistry profile compared to a control plant when grown and cured under comparable conditions. Without being limiting, a leaf chemistry profile can comprise the amount of alkaloids (e.g., nicotine, nornicotine, anabasine, anatabine), malic acid, and reducing sugars (e.g., dextrose), or a combination thereof in a tobacco plant or tobacco leaf. In one aspect, a modified plant or leaf provided herein comprises a total alkaloids level within about 90%, within about 80%, within about 70%, within about 60%, within about 50%, within about 45%, within about 40%, within about 35%, within about 30%, within about 25%, within about 20%, within about 15%, within about 10%, within about 5%, within about 4%, within about 3%, within about 2%, within about 1%, or within about 0.5% of the total alkaloids level of a control plant when grown and cured under comparable conditions. In one aspect, a modified plant or leaf provided herein comprises a nicotine level within about 90%, within about 80%, within about 70%, within about 60%, within about 50%, within about 45%, within about 40%, within about 35%, within about 30%, within about 25%, within about 20%, within about 15%, within about 10%, within about 5%, within about 4%, within about 3%, within about 2%, within about 1%, or within about 0.5% of the nicotine level of a control plant when grown and cured under comparable conditions. In one aspect, a modified plant or leaf provided herein comprises a nornicotine level within about 50%, within about 45%, within about 40%, within about 35%, within about 30%, within about 25%, within about 20%, within about 15%, within about 10%, within about 5%, within about 4%, within about 3%, within about 2%, within about 1%, or within about 0.5% of the nornicotine level of a control plant when grown and cured under comparable conditions. In one aspect, a modified plant or leaf provided herein comprises an anabasine level within about 50%, within about 45%, within about 40%, within about 35%, within about 30%, within about 25%, within about 20%, within about 15%, within about 10%, within about 5%, within about 4%, within about 3%, within about 2%, within about 1%, or within about 0.5% of the anabasine level of a control plant when grown and cured under comparable conditions. In one aspect, a modified plant or leaf provided herein comprises an anatabine level within about 50%, within about 45%, within about 40%, within about 35%, within about 30%, within about 25%, within about 20%, within about 15%, within about 10%, within about 5%, within about 4%, within about 3%, within about 2%, within about 1%, or within about 0.5% of the anatabine level of a control plant when grown and cured under comparable conditions. In one aspect, a modified plant or leaf provided herein comprises a malic acid level within about 50%, within about 45%, within about 40%, within about 35%, within about 30%, within about 25%, within about 20%, within about 15%, within about 10%, within about 5%, within about 4%, within about 3%, within about 2%, within about 1%, or within about 0.5% of the malic acid level of a control plant when grown and cured under comparable conditions. In one aspect, a modified plant or leaf provided herein comprises a reducing sugars level within about 50%, within about 45%, within about 40%, within about 35%, within about 30%, within about 25%, within about 20%, within about 15%, within about 10%, within about 5%, within about 4%, within about 3%, within about 2%, within about 1%, or within about 0.5% of the reducing sugars level of a control plant when grown and cured under comparable conditions. In one aspect, a modified plant or leaf provided herein comprises a dextrose level within about 50%, within about 45%, within about 40%, within about 35%, within about 30%, within about 25%, within about 20%, within about 15%, within about 10%, within about 5%, within about 4%, within about 3%, within about 2%, within about 1%, or within about 0.5% of the dextrose level of a control plant when grown and cured under comparable conditions.

In one aspect, a plant component provided herein includes, but is not limited to, a leaf, a stem, a root, a seed, a flower, pollen, an anther, an ovule, a pedicel, a fruit, a meristem, a cotyledon, a hypocotyl, a pod, an embryo, endosperm, an explant, a callus, a tissue culture, a shoot, a cell, and a protoplast. In further aspects, this disclosure provides tobacco plant cells, tissues, and organs that are not reproductive material and do not mediate the natural reproduction of the plant. In another aspect, this disclosure also provides tobacco plant cells, tissues, and organs that are reproductive material and mediate the natural reproduction of the plant. In another aspect, this disclosure provides tobacco plant cells, tissues, and organs that cannot maintain themselves via photosynthesis. In another aspect, this disclosure provides somatic tobacco plant cells. Somatic cells, contrary to germline cells, do not mediate plant reproduction.

Provided cells, tissues and organs can be from seed, fruit, leaf, cotyledon, hypocotyl, meristem, embryos, endosperm, root, shoot, stem, pod, flower, inflorescence, stalk, pedicel, style, stigma, receptacle, petal, sepal, pollen, anther, filament, ovary, ovule, pericarp, phloem, and vascular tissue. In another aspect, this disclosure provides a tobacco plant chloroplast. In a further aspect, this disclosure provides an epidermal cell, a stomata cell, a leaf hair (trichome), a root hair, or a storage root. In another aspect, this disclosure provides a tobacco protoplast.

Skilled artisans understand that tobacco plants naturally reproduce via seeds, not via asexual reproduction or vegetative propagation. In one aspect, this disclosure provides tobacco endosperm. In another aspect, this disclosure provides a tobacco endosperm cell. In a further aspect, this disclosure provides a male or female sterile tobacco plant, which cannot reproduce without human intervention.

In one aspect, a modified plant, seed, plant part, or plant cell provided herein comprises one or more non-naturally occurring mutations. In one aspect, a mutation provided herein suppresses TSNA levels in cured leaf from a tobacco plant. Types of mutations provided herein include, for example, substitutions (point mutations), deletions, insertions, duplications, and inversions. Such mutations are desirably present in the coding region of a gene; however, mutations in a promoter or other regulatory region, an intron, an intron-exon boundary, or an untranslated region of a gene may also be desirable.

In one aspect, a modified tobacco plant comprises one or more mutations or modifications capable of providing the reduced level of one or more TSNAs. In another aspect, one or more mutations are further capable of providing one or more traits selected from the group consisting of: i. a reduced level of nitrite, ii. an increased level of oxygen radicle absorbance capacity (ORAC), and iii. an increased level of one or more antioxidants; wherein the reduced or increased level is compared to a control tobacco plant or cured leaf from a control tobacco plant when grown and cured under comparable. In one aspect, a mutation comprises a mutation type selected from the group consisting of an insertion, a deletion, an inversion, a duplication, a substitution, and a combination thereof.

In one aspect, a modified tobacco plant comprises one or more mutations or modifications capable of activating one or more genes encoding a biosynthetic enzyme, a regulatory transcription factor, a transporter, a catabolic enzyme, or a combination thereof, for one or more antioxidants. In another aspect, one or more mutations or modifications are in one or more genes encoding a biosynthetic enzyme, a regulatory transcription factor, a transporter, a catabolic enzyme, or a combination thereof, for one or more antioxidants selected from the group consisting of anthocyanidin, flavanone, flavanol, flavone, flavonol, isoflavone, hydroxybenzoic acid, hydroxycinnamic acid, ellagitannin, stibene, lignan, carotenoids, and glycyrrhzin. In a further aspect, one or more mutations or modifications are in one or more genes encoding a biosynthetic enzyme, a regulatory transcription factor, a transporter, a catabolic enzyme, or a combination thereof, for one or more antioxidants selected from the group consisting of Delphnidin, Cyanidin, Procyanidin, Prodelphinidin, Hesperetin, Naringenin, Catechin, Epicatechin, Apigenin, Luteonin, Quercetin, Myricetin, Rutin, Genistein, Daidzein, Gallic acid, Vanillic acid, Protocatechuic acid, Ferunic acid, Cinnamic acid, Coumeric acid, Chlorogenic acid, Coffeic acid, ferulic acid, Sanguiin, Resveratrol, Sesamin, Caretonoids, and Vitamin C.

In one aspect, a modified tobacco plant of the present specification comprises tobacco leaves with increased levels of anthocyanins. In a further aspect, a modified tobacco plant with increased levels of anthocyanins further comprises leaves that have a purple or crimson visual appearance. In one aspect, a modified tobacco plant of the present specification comprises tobacco leaves with increased levels of antioxidants and without increased levels of anthocyanins. In a further aspect, a modified tobacco plant comprising increased levels of antioxidants and without increased levels of anthocyanins further comprises leaves with a visual appearance similar to an unmodified tobacco plant.

As used herein, a "biosynthetic enzyme" refers to a protein that functions in the synthesis of antioxidants, alkaloids, TSNAs, nitrite, nitrate, Chlorogenic Acid or other proteins affecting the activity or stability of antioxidants, alkaloids, TSNAs, nitrite, nitrate or Chlorogenic Acid. These proteins catalyze reactions that result in the transformation of one molecular structure into another structure as part of a biosynthesis pathway. Exemplary biosynthetic enzymes include but are limited to Anthocyanidin synthase2 (NtANS2), Dihyfroflavonol-4-reductase (NtDFR2), Shikimate O-hydroxycinnamoyl transferase (HCT) and Hydroxycinnamoyl CoA quinate Transferase (HQT). The activity of a biosynthetic enzyme effects the total concentration of different molecule species that compose a biosynthetic pathway.

As used herein, a "regulatory transcription factor" is a protein that binds a promoter element of a target gene to modulate the transcription of one or more genes involved in antioxidant biosynthesis, transport, catabolism, or other processes affecting the level of one or more antioxidants. Exemplary regulatory transcription factors include AtPAP1, NtPAP1, NtMYB3-like, NtJAF13, and AtTTG1. A regulatory transcription factor can bind DNA as part of a protein complex or individually. A regulatory transcription factor can have a single target or multiple targets and can bind different targets with varying affinities. The activity of a regulatory transcription factor can be to activate, repress, or attenuate transcription from a target loci.

As used herein, a "transport protein" can be a transmembrane protein that actively or passively moves molecules across a biological membrane. A transport protein can aid in the movement of ions, small molecules or macromolecules. A transport protein can be referred to as a transmembrane transporter, a transmembrane pump, an anion transport protein, a cation transport protein, or an escort protein. Transport proteins can also facilitate the movement of molecules or proteins in vesicles composed of biological membrane. A transport protein can be integrated into a biological membrane. A Transport protein can be anchored to a biological membrane via different modifications such as but not limited to myristolation, prenylation or palmitoylation.

In one aspect, a modified tobacco plant comprises one or more mutations in a gene encoding a polypeptide having at least 50%, 55%, 60%, 65%, 70%, 75%, 80%, 85%, 90%, 95%, 97%, 98%, 99%, or 100% identity to a sequence selected from the group consisting of SEQ ID No. 1 to 23 and 47 to 52. In another aspect, a modified tobacco plant comprises one or more mutations in a gene comprise a coding sequence having at least 50%, 55%, 60%, 65%, 70%, 75%, 80%, 85%, 90%, 95%, 97%, 98%, 99%, or 100% identity to a sequence selected from the group consisting of SEQ ID No. 24 to 46 and 53 to 58.

In one aspect, a modified plant, seed, plant component, plant cell, or plant genome provided herein comprises one or more transgenes. As used herein, a "transgene" refers to a polynucleotide that has been transferred into a genome by any method known in the art. In one aspect, a transgene is an exogenous polynucleotide. In one aspect, a transgene is an endogenous polynucleotide that is integrated into a new genomic locus where it is not normally found.

As used herein, "modified", in the context of plants, seeds, plant components, plant cells, and plant genomes, refers to a state containing changes or variations from their natural or native state. For instance, a "native transcript" of a gene refers to an RNA transcript that is generated from an unmodified gene. Typically, a native transcript is a sense transcript. Modified plants or seeds contain molecular changes in their genetic materials, including either genetic or epigenetic modifications. Typically, modified plants or seeds, or a parental or progenitor line thereof, have been subjected to mutagenesis, genome editing (e.g., without being limiting, via methods using site-specific nucleases), genetic transformation (e.g., without being limiting, via methods of *Agrobacterium* transformation or microprojectile bombardment), or a combination thereof. In one aspect, a modified plant provided herein comprises no non-plant genetic material or sequences. In yet another aspect, a modified plant provided herein comprises no interspecies genetic material or sequences. In one aspect, this disclosure provides methods and compositions related to modified plants, seeds, plant components, plant cells, and products made from modified plants, seeds, plant parts, and plant cells. In one aspect, a modified seed provided herein gives rise to a modified plant provided herein. In one aspect, a modified plant, seed, plant component, plant cell, or plant genome provided herein comprises a recombinant DNA construct or vector provided herein. In another aspect, a product provided herein comprises a modified plant, plant component, plant cell, or plant chromosome or genome provided herein. The present disclosure provides modified plants with desirable or enhanced properties, e.g., without being limiting, disease, insect, or pest tolerance (for example, virus tolerance, bacteria tolerance, fungus tolerance, nematode tolerance, arthropod tolerance, gastropod tolerance); herbicide tolerance; environmental stress resistance; quality improvements such as yield, nutritional enhancements, environmental or stress tolerances; any desirable changes in plant physiology, growth, development, morphology or plant product(s) including starch production, modified oils production, high oil production, modified fatty acid content, high protein production, fruit ripening, enhanced animal and human nutrition, biopolymer production, pharmaceutical peptides and secretable peptides production; improved processing traits; improved digestibility; low raffinose; industrial enzyme production; improved flavor; nitrogen fixation; hybrid seed production; and fiber production.

As used herein, "genome editing" or editing refers to targeted mutagenesis, insertion, deletion, inversion, substitution, or translocation of a nucleotide sequence of interest in a genome using a targeted editing technique. A nucleotide sequence of interest can be of any length, e.g., at least 1, at least 2, at least 3, at least 4, at least 5, at least 6, at least 7, at least 8, at least 9, at least 10, at least 15, at least 20, at least 25, at least 30, at least 35, at least 40, at least 45, at least 50, at least 75, at least 100, at least 250, at least 500, at least 1000, at least 2500, at least 5000, at least 10,000, or at least 25,000 nucleotides. As used herein, a "targeted editing technique" refers to any method, protocol, or technique that allows the precise and/or targeted editing of a specific location in a genome (e.g., the editing is not random). Without being limiting, use of a site-specific nuclease is one example of a targeted editing technique. Another non-limiting example of a targeted editing technique is the use of one or more tether guide Oligos (tgOligos). As used herein, a "targeted edit" refers to a targeted mutagenesis, insertion, deletion, inversion, or substitution caused by a targeted editing technique. A nucleotide sequence of interest can be an endogenous genomic sequence or a transgenic sequence.

In one aspect, a "targeted editing technique" refers to any method, protocol, or technique that allows the precise and/or targeted editing of a specific location in a genome (e.g., the editing is not random). Without being limiting, use of a site-specific nuclease is one example of a targeted editing technique.

In one aspect, a targeted editing technique is used to edit an endogenous locus or an endogenous gene. In another aspect, a targeted editing technique is used to edit a transgene. As used herein, an "endogenous gene" or a "native copy" of a gene refers to a gene that originates from within a given organism, cell, tissue, genome, or chromosome. An "endogenous gene" or a "native copy" of a gene is a gene that was not previously modified by human action.

In one aspect, a modified tobacco plant described here comprises one or more mutations are introduced via a system selected from the group consisting of chemical mutagenesis, irradiation mutagenesis, transposon mutagenesis, Agrobacterium-mediated transformation, a meganuclease, a zinc-finger nuclease (ZFN), a transcription activator-like effector nuclease (TALEN), a clustered regularly-interspaced short palindromic repeats (CRISPR)/Cas9 system, a CRISPR/Cpf1 system, a CRISPR/Csm1 system, and a combination thereof (see, for example, U.S. Patent Application publication 2017/0233756).

In one aspect, methods provided herein are capable of producing a tobacco plant comprising a reduced level of one or more TSNAs using mutagenesis. Mutagenesis methods include, without limitation, chemical mutagenesis, for example treatment of seeds with ethyl methylsulfate (EMS) (Hildering and Verkerk, In, The use of induced mutations in plant breeding. Pergamon Press, pp. 317-320, 1965); or UV-irradiation, X-rays, electron beams, ion beams (e.g., carbon ion beam, helium ion beam, neon ion beam), and fast neutron irradiation (see, for example, Verkerk, *Neth. J. Agric. Sci.* 19:197-203, 1971; Poehlman, Breeding Field Crops, Van Nostrand Reinhold, New York (3.sup.rd ed.), 1987; and Tanaka, *J. Radiat. Res.* 51:223-233, 2010); transposon tagging (Fedoroff et al., 1984; U.S. Pat. Nos. 4,732,856 and 5,013,658); and T-DNA insertion methodologies (Hoekema et al., 1983; U.S. Pat. No. 5,149,645). EMS-induced mutagenesis consists of chemically inducing random point mutations over the length of a genome. Fast neutron mutagenesis consists of exposing seeds to neutron bombardment which causes large deletions through double stranded DNA breakage. Transposon tagging comprises inserting a transposon within an endogenous gene to reduce or eliminate expression of the gene.

In addition, a fast and automatable method for screening for chemically induced mutations, TILLING (Targeting Induced Local Lesions In Genomes), using denaturing HPLC or selective endonuclease digestion of selected PCR products is also applicable to the present disclosure. See, McCallum et al. (2000) *Nat. Biotechnol.* 18:455-457. Mutations that impact gene expression or that interfere with the function of genes provided herein can be determined using methods that are well known in the art. Insertional mutations in gene exons usually result in null-mutants. Mutations in conserved residues can be particularly effective in inhibiting the function of a protein.

The screening and selection of mutagenized tobacco plants can be through any methodologies known to those having ordinary skill in the art. Examples of screening and selection methodologies include, but are not limited to, Southern analysis, PCR amplification for detection of a polynucleotide, Northern blots, RNase protection, primer-extension, RT-PCR amplification for detecting RNA transcripts, Sanger sequencing, Next Generation sequencing technologies (e.g., Illumina, PacBio, Ion Torrent, 454) enzymatic assays for detecting enzyme or ribozyme activity of polypeptides and polynucleotides, and protein gel electrophoresis, Western blots, immunoprecipitation, and enzyme-linked immunoassays to detect polypeptides. Other techniques such as in situ hybridization, enzyme staining, and immunostaining also can be used to detect the presence or expression of polypeptides and/or polynucleotides. Methods for performing all of the referenced techniques are known.

In one aspect, a modified plant or plant genome provided herein is mutated or edited by a nuclease selected from the group consisting of a meganuclease, a zinc-finger nuclease (ZFN), a transcription activator-like effector nuclease (TALEN), a CRISPR/Cas9 nuclease, a CRISPR/Cpf1 nuclease, or a CRISPR/Csm1 nuclease. As used herein, "editing" or "genome editing" refers to targeted mutagenesis of at least 1, at least 2, at least 3, at least 4, at least 5, at least 6, at least 7, at least 8, at least 9, or at least 10 nucleotides of an endogenous plant genome nucleic acid sequence, or removal or replacement of an endogenous plant genome nucleic acid sequence. In one aspect, an edited nucleic acid sequence provided herein has at least 99.9%, at least 99.5%, at least 99%, at least 98%, at least 97%, at least 96%, at least 95%, at least 94%, at least 93%, at least 92%, at least 91%, at least 90%, at least 85%, at least 80%, or at least 75% sequence identity with an endogenous nucleic acid sequence. In one aspect, an edited nucleic acid sequence provided herein has at least 99.9%, at least 99.5%, at least 99%, at least 98%, at least 97%, at least 96%, at least 95%, at least 94%, at least 93%, at least 92%, at least 91%, at least 90%, at least 85%, at least 80%, or at least 75% sequence identity with a polynucleotide selected from the group consisting of SEQ ID NOs: 24 to 46 and 53 to 58, and fragments thereof. In another aspect, an edited nucleic acid sequence provided herein has at least 99.9%, at least 99.5%, at least 99%, at least 98%, at least 97%, at least 96%, at least 95%, at least 94%, at least 93%, at least 92%, at least 91%, at least 90%, at least 85%, at least 80%, or at least 75% sequence identity with a polynucleotide encoding a polypeptide selected from the group consisting of SEQ ID NOs: 1 to 23 and 47 to 52.

Meganucleases, ZFNs, TALENs, CRISPR/Cas9, CRISPR/Csm1, and CRISPR/Cpf1 induce a double-strand DNA break at a target site of a genomic sequence that is then repaired by the natural processes of homologous recombination (HR) or non-homologous end-joining (NHEJ). Sequence modifications then occur at the cleaved sites, which can include deletions or insertions that result in gene disruption in the case of NHEJ, or integration of donor nucleic acid sequences by HR. In one aspect, a method provided herein comprises editing a plant genome with a nuclease provided herein to mutate at least 1, at least 2, at least 3, at least 4, at least 5, at least 6, at least 7, at least 8, at least 9, at least 10, or more than 10 nucleotides in the plant genome via HR with a donor polynucleotide. In one aspect, a mutation provided herein is caused by genome editing using a nuclease. In another aspect, a mutation provided herein is caused by non-homologous end-joining or homologous recombination.

In one aspect, a mutation provided herein provides a dominant mutant that activates the expression or activity of a gene of interest, e.g., a gene selected from the group consisting of a biosynthetic enzyme, a regulatory transcription factor, a transporter, a catabolic enzyme, or a combination thereof, for one or more antioxidants.

Meganucleases, which are commonly identified in microbes, are unique enzymes with high activity and long recognition sequences (>14 bp) resulting in site-specific digestion of target DNA. Engineered versions of naturally occurring meganucleases typically have extended DNA recognition sequences (for example, 14 to 40 bp). The engineering of meganucleases can be more challenging than that of ZFNs and TALENs because the DNA recognition and cleavage functions of meganucleases are intertwined in a single domain. Specialized methods of mutagenesis and high-throughput screening have been used to create novel meganuclease variants that recognize unique sequences and possess improved nuclease activity.

ZFNs are synthetic proteins consisting of an engineered zinc finger DNA-binding domain fused to the cleavage domain of the FokI restriction endonuclease. ZFNs can be designed to cleave almost any long stretch of double-stranded DNA for modification of the zinc finger DNA-binding domain. ZFNs form dimers from monomers composed of a non-specific DNA cleavage domain of FokI endonuclease fused to a zinc finger array engineered to bind a target DNA sequence.

The DNA-binding domain of a ZFN is typically composed of 3-4 zinc-finger arrays. The amino acids at positions −1, +2, +3, and +6 relative to the start of the zinc finger ∞-helix, which contribute to site-specific binding to the target DNA, can be changed and customized to fit specific target sequences. The other amino acids form the consensus backbone to generate ZFNs with different sequence specificities. Rules for selecting target sequences for ZFNs are known in the art.

The FokI nuclease domain requires dimerization to cleave DNA and therefore two ZFNs with their C-terminal regions are needed to bind opposite DNA strands of the cleavage site (separated by 5-7 bp). The ZFN monomer can cute the target site if the two-ZF-binding sites are palindromic. The term ZFN, as used herein, is broad and includes a monomeric ZFN that can cleave double stranded DNA without assistance from another ZFN. The term ZFN is also used to refer to one or both members of a pair of ZFNs that are engineered to work together to cleave DNA at the same site.

Without being limited by any scientific theory, because the DNA-binding specificities of zinc finger domains can in principle be re-engineered using one of various methods, customized ZFNs can theoretically be constructed to target nearly any gene sequence. Publicly available methods for engineering zinc finger domains include Context-dependent Assembly (CoDA), Oligomerized Pool Engineering (OPEN), and Modular Assembly.

TALENs are artificial restriction enzymes generated by fusing the transcription activator-like effector (TALE) DNA binding domain to a FokI nuclease domain. When each member of a TALEN pair binds to the DNA sites flanking a target site, the FokI monomers dimerize and cause a double-stranded DNA break at the target site. The term TALEN, as used herein, is broad and includes a monomeric TALEN that can cleave double stranded DNA without assistance from another TALEN. The term TALEN is also used to refer to one or both members of a pair of TALENs that work together to cleave DNA at the same site.

Transcription activator-like effectors (TALEs) can be engineered to bind practically any DNA sequence. TALE proteins are DNA-binding domains derived from various plant bacterial pathogens of the genus *Xanthomonas*. The X pathogens secrete TALEs into the host plant cell during infection. The TALE moves to the nucleus, where it recognizes and binds to a specific DNA sequence in the promoter region of a specific DNA sequence in the promoter region of a specific gene in the host genome. TALE has a central DNA-binding domain composed of 13-28 repeat monomers of 33-34 amino acids. The amino acids of each monomer are highly conserved, except for hypervariable amino acid residues at positions 12 and 13. The two variable amino acids are called repeat-variable diresidues (RVDs). The amino acid pairs NI, NG, HD, and NN of RVDs preferentially recognize adenine, thymine, cytosine, and guanine/adenine, respectively, and modulation of RVDs can recognize consecutive DNA bases. This simple relationship between amino acid sequence and DNA recognition has allowed for the engineering of specific DNA binding domains by selecting a combination of repeat segments containing the appropriate RVDs.

Besides the wild-type FokI cleavage domain, variants of the FokI cleavage domain with mutations have been designed to improve cleavage specificity and cleavage activity. The FokI domain functions as a dimer, requiring two constructs with unique DNA binding domains for sites in the target genome with proper orientation and spacing. Both the number of amino acid residues between the TALEN DNA binding domain and the FokI cleavage domain and the number of bases between the two individual TALEN binding sites are parameters for achieving high levels of activity.

The relationship between amino acid sequence and DNA recognition of the TALE binding domain allows for designable proteins. Software programs such as DNA Works can be used to design TALE constructs. Other methods of designing TALE constructs are known to those of skill in the art. See Doyle et al,. *Nucleic Acids Research* (2012) 40: W117-122.; Cermak et al., *Nucleic Acids Research* (2011). 39:e82; and tale-nt.cac.cornell.edu/about.

A CRISPR/Cas9 system, CRISPR/Csm1, or a CRISPR/Cpf1 system are alternatives to the FokI-based methods ZFN and TALEN. The CRISPR systems are based on RNA-guided engineered nucleases that use complementary base pairing to recognize DNA sequences at target sites.

CRISPR/Cas9, CRISPR/Csm1, and a CRISPR/Cpf1 systems are part of the adaptive immune system of bacteria and archaea, protecting them against invading nucleic acids such as viruses by cleaving the foreign DNA in a sequence-dependent manner. The immunity is acquired by the integration of short fragments of the invading DNA known as spacers between two adjacent repeats at the proximal end of a CRISPR locus. The CRISPR arrays, including the spacers, are transcribed during subsequent encounters with invasive DNA and are processed into small interfering CRISPR RNAs (crRNAs) approximately 40 nt in length, which combine with the trans-activating CRISPR RNA (tracrRNA) to activate and guide the Cas9 nuclease. This cleaves homologous double-stranded DNA sequences known as protospacers in the invading DNA. A prerequisite for cleavage is the presence of a conserved protospacer-adjacent motif (PAM) downstream of the target DNA, which usually has the sequence 5-NGG-3 but less frequently NAG. Specificity is provided by the so-called "seed sequence" approximately 12 bases upstream of the PAM, which must match between the RNA and target DNA. Cpf1 acts in a similar manner to Cas9, but Cpf1 does not require a tracrRNA.

In still another aspect, a modified tobacco plant provided herein further comprises one or more mutations in one or more loci encoding a nicotine demethylase (e.g., CYP82E4, CYP82E5, CYP82E10) that confer reduced amounts of nornicotine (See U.S. Pat. Nos. 8,319,011; 8,124,851; 9,187,759; 9,228,194; 9,228,195; 9,247,706) compared to control plant lacking one or more mutations in one or more loci encoding a nicotine demethylase. In one aspect, a modified tobacco plant described herein further comprises reduced nicotine demethylase activity compared to a control plant when grown and cured under comparable conditions. In another aspect, a modified tobacco plant described herein further comprises a reduced level of total alkaloids compared to the control plant when grown and cured under comparable conditions. In another aspect, a tobacco plant provided herein further comprises one or more mutations in a Nic1 locus, a Nic2 locus, or both, which confer reduced amounts of nicotine compared to a control plant lacking one or more mutations in a Nic1 locus, a Nic2 locus, or both. In another aspect, a modified tobacco plant described herein further comprises a reduced level of nicotine compared to the control plant when grown and cured under comparable conditions. In a further aspect, a modified tobacco plant described herein comprises a substantially similar level of nicotine compared to the control plant when grown and cured under comparable conditions.

In one aspect, a modified tobacco plant described herein is a cisgenic plant. As used herein, "cisgenesis" or "cisgenic" refers to genetic modification of a plant, plant cell, or plant genome in which all components (e.g., promoter, donor nucleic acid, selection gene) have only plant origins (i.e., no non-plant origin components are used). In one aspect, a modified plant, plant cell, or plant genome provided herein is cisgenic. Cisgenic plants, plant cells, and plant genomes provided herein can lead to ready-to-use tobacco lines. In another aspect, a modified tobacco plant provided herein comprises no non-tobacco genetic material or sequences. In one aspect, a cisgenic construct of the present specification encodes a polynucleotide selected from the group consisting of Ubi4-P:PAP1-HSP-T (SEQ ID NO:59), Ubi4-P:NtAN2-HSP-T(SEQ ID NO:60), Tub-P: NtAN2-HSP-T(SEQ ID NO:61), Ubi4-P:NtAN2-HSP-T: Tub-P:NtAN2-HSP-T(SEQ ID NO:62), and Ubi4-P: NtAN1a-HSP-T:Tub-P:NtAN2-HSP-T (SEQ ID NO:63).

In one aspect, a modified tobacco plant described herein comprises one or more transgenes or recombinant DNA constructs capable of providing a reduced level of one or more TSNAs compared to a control plant without the one or more transgenes.. In another aspect, a modified tobacco plant comprises one or more transgenes or recombinant DNA constructs further providing the one or more traits selected from the group consisting of: i. a reduced level of nitrite, ii. an increased level of oxygen radicle absorbance capacity (ORAC), and iii. an increased level of one or more antioxidants; wherein the reduced or increased level is compared to a control tobacco plant when grown and cured under comparable.

In another aspect, a modified tobacco plant comprises one or more transgenes or recombinant DNA constructs encoding a biosynthetic enzyme, a regulatory transcription factor, a transporter, a catabolic enzyme, or a combination thereof, for one or more antioxidants selected from the group consisting of anthocyanidin, flavanone, flavanol, flavone, flavonol, isoflavone, hydroxybenzoic acid, hydroxycinnamic acid, ellagitannin, stibene, lignan, carotenoids, and glycyrrhzin. In another aspect, a modified tobacco plant comprises one or more transgenes or recombinant DNA constructs encoding a biosynthetic enzyme, a regulatory transcription factor, a transporter, a catabolic enzyme, or a combination thereof, for one or more antioxidants selected from the group consisting of Delphnidin, Cyanidin, Procyanidin, Prodelphinidin, Hesperetin, Naringenin, Catechin, Epicatechin, Apigenin, Luteonin, Quercetin, Myricetin, Rutin, Genistein, Daidzein, Gallic acid, Vanillic acid, Protocatechuic acid, Ferunic acid, Cinnamic acid, Coumeric acid, Chlorogenic acid, Coffeic acid, ferulic acid, Sanguiin, Resveratrol, Sesamin, Caretonoids, and Vitamin C. In one aspect, one or more transgenes or recombinant DNA constructs encode a polypeptide having at least 50%, 55%, 60%, 65%, 70%, 75%, 80%, 85%, 90%, 95%, 97%, 98%, 99%, or 100% identity to a sequence selected from the group consisting of SEQ ID No. 1 to 23 and 47 to 52. In another aspect, one or more transgenes or recombinant DNA constructs encode a gene comprise a coding sequence having at least 50%, 55%, 60%, 65%, 70%, 75%, 80%, 85%, 90%, 95%, 97%, 98%, 99%, or 100% identity to a sequence selected from the group consisting of SEQ ID No. 24 to 46 and 53 to 58.

In one aspect, a recombinant DNA construct of the present disclosure comprises a promoter capable of driving gene transcription in a plant, operably linked to a polynucleotide encoding a polypeptide having at least 70%, at least 75%, at least 80%, at least 85%, at least 90%, at least 95%, at least 96%, at least 97%, at least 98%, at least 99% or 100% sequence identity to a polypeptide selected from the group consisting of SEQ ID NOs: 1 to 23 and 47 to 52. In one aspect, a recombinant DNA construct or expression cassette in a transgene provided herein comprises a promoter selected from the group consisting of a constitutive promoter, an inducible promoter, and a tissue-preferred promoter (for example, without being limiting, a leaf-specific promoter, a shoot-specific promoter, a root-specific promoter, or a meristem-specific promoter).

Exemplary constitutive promoters include the core promoter of the Rsyn7 promoter and other constitutive promoters disclosed in U.S. Pat. No. 6,072,050; the core CaMV 35S promoter (Odell et al. (1985) Nature 313:810-812); ubiquitin (Christensen et al. (1989) Plant Mol. Biol. 12:619-632 and Christensen et al. (1992) Plant Mol. Biol. 18:675-689); pEMU (Last et al. (1991) Theor. Appl. Genet. 81:581-588); MAS (Velten et al. (1984) EMBO J 3:2723-2730); ALS promoter (U.S. Pat. No. 5,659,026), and the like.

Exemplary chemical-inducible promoters include the tobacco PR-1a promoter, which is activated by salicylic acid. Other chemical-inducible promoters of interest include steroid-responsive promoters (see, for example, the glucocorticoid-inducible promoter in Schena et al. (1991) Proc. Natl. Acad. Sci. USA 88:10421-10425 and McNellis et al. (1998) Plant J. 14(2):247-257) and tetracycline-inducible promoters (see, for example, Gatz et al. (1991) Mol. Gen. Genet. 227:229-237, and U.S. Pat. Nos. 5,814,618 and 5,789,156). Additional exemplary promoters that can be used herein are those responsible for heat-regulated gene expression, light-regulated gene expression (for example, the pea rbcS-3A; the maize rbcS promoter; the chlorophyll alb-binding protein gene found in pea; or the Arabssu promoter), hormone-regulated gene expression (for example, the abscisic acid (ABA) responsive sequences from the Em gene of wheat; the ABA-inducible HVA1 and HVA22, and rd29A promoters of barley and *Arabidopsis*; and wound-induced gene expression (for example, of wunl), organ specific gene expression (for example, of the tuberspecific storage protein gene; the 23-kDa zein gene from maize described by; or the French bean (β-phaseolin gene), or pathogen-inducible promoters (for example, the PR-1, prp-1, or (β-1,3 glucanase promoters, the fungal-inducible wirla promoter of wheat, and the nematode-inducible promoters, TobRB7-5A and Hmg-1, of tobacco arid parsley, respectively).

Additional exemplary tissue-preferred promoters include those disclosed in Yamamoto et al. (1997) Plant J. 12(2): 255-265; Kawamata et al. (1997) Plant Cell Physiol. 38(7): 792-803; Hansen et al. (1997) Mol. Gen. Genet. 254(3):337-343; Russell et al. (1997) Transgenic Res. 6(2):157-168; Rinehart et al. (1996) Plant Physiol. 112(3):1331-1341; Van Camp et al. (1996) Plant Physiol. 112(2):525-535; Canevascini et al. (1996) Plant Physiol. 112(2):513-524; Yamamoto et al. (1994) Plant Cell Physiol. 35(5):773-778; Lam (1994) Results Probl. Cell Differ. 20:181-196; Orozco et al. (1993)

Plant Mol. Biol. 23(6):1129-1138; Matsuoka et al. (1993) Proc Natl. Acad. Sci. USA 90(20):9586-9590; and Guevara-Garcia et al. (1993) Plant J. 4(3):495-505.

As used herein, "operably linked" refers to a functional linkage between two or more elements. For example, an operable linkage between a polynucleotide of interest and a regulatory sequence (e.g., a promoter) is a functional link that allows for expression of the polynucleotide of interest. Operably linked elements may be contiguous or non-contiguous.

In one aspect, a transgene provided herein comprises a heterologous or non-tobacco promoter or coding sequence. In another aspect, a transgene provided herein comprises a endogenous or tobacco-origin promoter or coding sequence. As used herein, "heterologous" refers to a sequence that originates from a foreign species, or, if from the same species, is substantially modified from its native form in composition and/or genomic locus by deliberate human intervention. The term also is applicable to nucleic acid constructs, also referred to herein as "polynucleotide constructs" or "nucleotide constructs." In this manner, a "heterologous" nucleic acid construct is intended to mean a construct that originates from a foreign species, or, if from the same species, is substantially modified from its native form in composition and/or genomic locus by deliberate human intervention. Heterologous nucleic acid constructs include, but are not limited to, recombinant nucleotide constructs that have been introduced into a plant or plant part thereof, for example, via transformation methods or subsequent breeding of a transgenic plant with another plant of interest.

In one aspect, a recombinant DNA construct, modified plant, seed, plant component, plant cell, or plant genome provided herein comprises a heterologous promoter operably linked to a polynucleotide encoding a polypeptide having at least 40%, at least 50%, at least 60%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to a polypeptide selected from the group consisting of SEQ ID NOs: 24 to 46 and 53 to 58.

Enhancer elements are regions of DNA that can be bound by proteins to activate RNA transcription. In one aspect, a promoter sequence used herein is operably linked to an enhancer element. In one aspect, an enhancer element provided herein is a CsVMV promoter.

Also provided herein are the transformation of tobacco plants with recombinant constructs or expression cassettes described herein using any suitable transformation methods known in the art. Methods for introducing polynucleotide sequences into tobacco plants are known in the art and include, but are not limited to, stable transformation methods, transient transformation methods, and virus-mediated methods. "Stable transformation" refers to transformation where the nucleotide construct of interest introduced into a plant integrates into a genome of the plant and is capable of being inherited by the progeny thereof "Transient transformation" is intended to mean that a sequence is introduced into the plant and is only temporally expressed or is only transiently present in the plant.

In one aspect, methods and compositions provided herein comprise the introduction of one or more polynucleotides into one or more plant cells. In one aspect, a plant genome provided herein is modified to include an introduced polynucleotide or recombinant DNA construct. As used herein, "plant genome" refers to a nuclear genome, a mitochondrial genome, or a plastid (e.g., chloroplast) genome of a plant cell. In another aspect, a polynucleotide provided herein is integrated into an artificial chromosome. In one aspect, an artificial chromosome comprising a polynucleotide provided herein is integrated into a plant cell.

In one aspect, transgenes provided herein comprise a recombinant DNA construct. In one aspect, recombinant DNA constructs or expression cassettes provided herein can comprise a selectable marker gene for the selection of transgenic cells. Selectable marker genes include, but are not limited to, genes encoding antibiotic resistance, such as those encoding neomycin phosphotransferase II (NEO) and hygromycin phosphotransferase (HPT), as well as genes conferring resistance to herbicidal compounds, such as glufosinate ammonium, bromoxynil, imidazolinones, triazolopyrimidines, sulfonylurea (e.g., chlorsulfuron and sulfometuron methyl), and 2,4-dichlorophenoxyacetate (2,4-D). Additional selectable markers include phenotypic markers such as β-galactosidase and fluorescent proteins such as green fluorescent protein (GFP).

In one aspect, methods and compositions provided herein comprise a vector. As used herein, the terms "vector" or "plasmid" are used interchangeably and refer to a circular, double-stranded DNA molecule that is physically separate from chromosomal DNA. In one aspect, a plasmid or vector used herein is capable of replication in vivo. A "transformation vector," as used herein, is a plasmid that is capable of transforming a plant cell. In an aspect, a plasmid provided herein is a bacterial plasmid. In another aspect, a plasmid provided herein is an *Agrobacterium* Ti plasmid or derived from an *Agrobacterium* Ti plasmid.

In one aspect, a plasmid or vector provided herein is a recombinant vector. As used herein, the term "recombinant vector" refers to a vector formed by laboratory methods of genetic recombination, such as molecular cloning. In another aspect, a plasmid provided herein is a synthetic plasmid. As used herein, a "synthetic plasmid" is an artificially created plasmid that is capable of the same functions (e.g., replication) as a natural plasmid (e.g., Ti plasmid). Without being limited, one skilled in the art can create a synthetic plasmid de novo via synthesizing a plasmid by individual nucleotides, or by splicing together nucleic acid molecules from different pre-existing plasmids.

Vectors are commercially available or can be produced by recombinant DNA techniques routine in the art. A vector containing a nucleic acid can have expression elements operably linked to such a nucleic acid, and further can include sequences such as those encoding a selectable marker (e.g., an antibiotic resistance gene). A vector containing a nucleic acid can encode a chimeric or fusion polypeptide (i.e., a polypeptide operatively linked to a heterologous polypeptide, which can be at either the N-terminus or C-terminus of the polypeptide). Representative heterologous polypeptides are those that can be used in purification of the encoded polypeptide (e.g., 6×His tag, glutathione S-transferase (GST)).

Suitable methods of introducing polynucleotides (e.g., transgenes, recombinant vectors, recombinant DNA constructs, expression constructs) into plant cells of the present disclosure include microinjection (Crossway et al. (1986) *Biotechniques* 4:320-334), electroporation (Shillito et al. (1987) *Meth. Enzymol.* 153:313-336; Riggs et al. (1986) *Proc. Natl. Acad. Sci. USA* 83:5602-5606), *Agrobacterium*-mediated transformation (U.S. Pat. Nos. 5,104,310, 5,149, 645, 5,177,010, 5,231,019, 5,463,174, 5,464,763, 5,469,976, 4,762,785, 5,004,863, 5,159,135, 5,563,055, and 5,981, 840), direct gene transfer (Paszkowski et al. (1984) *EMBO J.* 3:2717-2722), and ballistic particle acceleration (see, for example, U.S. Pat. Nos. 4,945,050, 5,141,131, 5,886,244, 5,879,918, and 5,932,782; Tomes et al. (1995) in *Plant Cell, Tissue, and Organ Culture Fundamental Methods*, ed. Gamborg and Phillips (Springer-Verlag, Berlin); McCabe et al. (1988) *Biotechnology* 6:923-926). Also see Weissinger et al. (1988) *Ann. Rev. Genet.* 22:421-477; Christou et al. (1988) *Plant Physiol.* 87:671-674 (soybean); McCabe et al. (1988) *Bio/Technology* 6:923-926 (soybean); Finer and McMullen (1991) *In Vitro Cell Dev. Biol.* 27P: 175-182 (soybean); Singh et al. (1998) *Theor. Appl. Genet.* 96:319-324 (soybean); De Wet et al. (1985) in *The Experimental Manipulation of Ovule Tissues*, ed. Chapman et al. (Longman, N.Y.), pp. 197-209 (pollen); Kaeppler et al. (1990) *Plant Cell Reports* 9:415-418 and Kaeppler et al. (1992) *Theor. Appl. Genet.* 84:560-566 (whisker-mediated transformation); D'Halluin et al. (1992) *Plant Cell* 4:1495-1505 (electroporation). In one aspect, a bacterial cell provided herein comprises a recombinant DNA construct or recombinant vector provided herein.

In another aspect, recombinant constructs or expression cassettes provided herein may be introduced into plants by contacting plants with a virus or viral nucleic acids. Generally, such methods involve incorporating an expression cassette of the present disclosure within a viral DNA or RNA molecule. It is recognized that promoters for use in the expression cassettes provided herein also encompass promoters utilized for transcription by viral RNA polymerases. Methods for introducing polynucleotides into plants and expressing a protein encoded therein, involving viral DNA or RNA molecules, are known in the art. See, for example, U.S. Pat. Nos. 5,889,191, 5,889,190, 5,866,785, 5,589,367, 5,316,931, and Porta et al. (1996) *Molecular Biotechnology* 5:209-221.

Any plant tissue that can be subsequently propagated using clonal methods, whether by organogenesis or embryogenesis, may be transformed with a recombinant construct or an expression cassette provided herein. By "organogenesis" in intended the process by which shoots and roots are developed sequentially from meristematic centers. By "embryogenesis" is intended the process by which shoots and roots develop together in a concerted fashion (not sequentially), whether from somatic cells or gametes. Exemplary tissues that are suitable for various transformation protocols described herein include, but are not limited to, callus tissue, existing meristematic tissue (e.g., apical meristems, axillary buds, and root meristems) and induced meristem tissue (e.g., cotyledon meristem and hypocotyl meristem), hypocotyls, cotyledons, leaf disks, pollen, embryos, and the like.

It is understood that any modified tobacco plant of the present disclosure can further comprise additional agronomically desirable traits, for example, by transformation with a genetic construct or transgene using a technique known in the art. Without limitation, an example of a desired trait is herbicide resistance, pest resistance, disease resistance, high yield, high grade index value, curability, curing quality, mechanical harvestability, holding ability, leaf quality, height, plant maturation (e.g., early maturing, early to medium maturing, medium maturing, medium to late maturing, or late maturing), stalk size (e.g., a small, medium, or a large stalk), or leaf number per plant (e.g., a small (e.g., 5-10 leaves), medium (e.g., 11-15 leaves), or large (e.g., 16-21) number of leaves), or any combination. In one aspect, tobacco plants capable of producing cured leaf with reduced TSNA or seeds provided herein comprise one or more transgenes expressing one or more insecticidal proteins, such as, for example, a crystal protein of *Bacillus thuringiensis* or a vegetative insecticidal protein from *Bacillus cereus*, such as VIP3 (see, for example, Estruch et al. (1997) *Nat. Biotechnol.* 15:137). In another aspect, tobacco plants provided herein further comprise an introgressed trait conferring resistance to brown stem rot (U.S. Pat. No. 5,689,035) or resistance to cyst nematodes (U.S. Pat. No. 5,491,081).

The level and/or activity of polypeptides provided herein may be modulated by employing a polynucleotide that is not capable of directing, in a transformed plant, the expression of a protein or an RNA. For example, the polynucleotides of the invention may be used to design polynucleotide constructs that can be employed in methods for altering or mutating a genomic nucleotide sequence in an organism. Such polynucleotide constructs include, but are not limited to, RNA:DNA vectors, RNA:DNA mutational vectors, RNA:DNA repair vectors, mixed-duplex oligonucleotides, self-complementary RNA:DNA oligonucleotides and recombinogenic oligonucleobases. Such nucleotide constructs and methods of use are known in the art. See, U.S. Pat. Nos. 5,565,350; 5,731,181; 5,756,325; 5,760,012; 5,795,972 and 5,871,984; each of which is incorporated herein by reference as if set forth in its entirety. See also, International Patent Application Publication Nos. WO 98/149350, WO 99/107865 and WO 99/125921; and Beetham et al. (1999) *Proc. Natl. Acad. Sci. USA* 96:8774-8778; each of which is incorporated herein by reference as if set forth in its entirety.

The present disclosure also provides compositions and methods for inhibiting the expression or function of one or more polypeptides that suppress, directly or indirectly, the production or accumulation of one or more antioxidants in a plant, particularly plants of the *Nicotiana tabacum* genus, including tobacco plants of various commercial varieties.

In one aspect, inhibition of the expression of one or more polypeptides provided herein may be obtained by RNA interference (RNAi) by expression of a transgene capable of producing an inhibitory sequence provided herein. In one aspect, RNAi comprises expressing a non-coding RNA. As used herein, a "non-coding RNA" is selected from the group consisting of a microRNA (miRNA), a small interfering RNA (siRNA), a trans-acting siRNA (ta-siRNA), a transfer RNA (tRNA), a ribosomal RNA (rRNA), an intron, a hairpin RNA (hpRNA), and an intron-containing hairpin RNA (ih-pRNA). In one aspect, a single non-coding RNA provided herein inhibits the expression of at least 1, at least 2, at least 3, at least 4, at least 5, at least 6, at least 7, at least 8, at least 9, at least 10, or more than 10 polypeptides. In one aspect, a non-coding RNA provided herein is stably transformed into a plant genome. In another aspect, a non-coding RNA provided herein is transiently transformed into a plant genome.

As used herein, the terms "suppress," "inhibit," "inhibition," "inhibiting", and "downregulation" are defined as any method known in the art or described herein that decreases the expression or function of a gene product (e.g., an mRNA, a protein, a non-coding RNA). "Inhibition" can be in the context of a comparison between two cells, for example, a modified cell versus a control cell. Inhibition of expression or function of a gene product can also be in the context of a comparison between plant cells, organelles, organs, tissues, or plant components within the same plant or between different plants, and includes comparisons between developmental or temporal stages within the same plant or plant component or between plants or plant components. "Inhibition" includes any relative decrement of function or production of a gene product of interest, up to and including complete elimination of function or production of that gene product. The term "inhibition" encompasses any method or composition that down-regulates translation and/or transcription of the target gene product or functional activity of the target gene product. "Inhibition" need not comprise complete elimination of expression of a gene product. In an aspect, a gene product in a modified cell provided herein comprises expression that is at least 1%, at least 2%, at least 3%, at least 4%, at least 5%, at least 10%, at least 20%, at least 25%, at least 30%, at least 40%, at least 50%, at least 60%, at least 70%, at least 80%, at least 90%, at least 95%, or 100% lower than the expression of the gene product in a control cell. In another aspect, a gene product in a modified cell provided herein comprises expression that is between 1% and 100%, between 1% and 95%, between 1% and 90%, between 1% and 80%, between 1% and 70%, between 1% and 60%, between 1% and 50%, between 1% and 40%, between 1% and 30%, between 1% and 25%, between 1% and 20%, between 1% and 15%, between 1% and 10%, between 1% and 5%, between 5% and 25%, between 5% and 50%, between 5% and 75%, between 5% and 100%, between 10% and 25%, between 10% and 50%, between 10% and 75%, between 10% and 100%, between 25% and 50%, between 25% and 75%, between 25% and 100%, or between 50% and 100% lower than the expression of the gene product in a control cell.

As used herein, a "target site" refers to a location of a polynucleotide sequence that is bound to and cleaved by a site-specific nuclease introducing a double stranded break into the nucleic acid backbone. In another aspect a target site comprises at least 10, at least 11, at least 12, at least 13, at least 14, at least 15, at least 16, at least 17, at least 18, at least 19, at least 20, at least 21, at least 22, at least 23, at least 24, at least 25, at least 26, at least 27, at least 29, or at least 30 consecutive nucleotides. In another aspect, a target site provided herein is at least 10, at least 20, at least 30, at least 40, at least 50, at least 75, at least 100, at least 125, at least 150, at least 200, at least 250, at least 300, at least 400, or at least 500 nucleotides. In one aspect a site-specific nuclease binds to a target site. In another aspect a site-specific nuclease binds to a target site via a guiding non-coding RNA (i.e., such as, without being limiting, a CRISPR RNA or single-guide RNA (both described in detail below)). In one aspect, a non-coding RNA provided herein is complementary to a target site. It will be appreciated that perfect complementarity is not required for a non-coding RNA to bind to a target site; at least 1, at least 2, at least 3, at least 4, or at least 5, at least 6, at least 7 or at least 8 mismatches between a target site and a non-coding RNA can be tolerated. As used herein, a "target region" or a "targeted region" refers to a polynucleotide sequence that is desired to be modified. In one aspect, a "target region," "targeted region," or a "target gene" is flanked by two or more, three or more, four or more, five or more, six or more, seven or more, eight or more, nine or more, or ten or more target sites. A "target gene" refers to a polynucleotide sequence encoding a gene that is desired to be modified or from which transcript expression is desired to be modulated. In one aspect, a polynucleotide sequence comprising a target gene further comprises one or more target sites. In another aspect, a transgene is said to be targeting a target site or a target gene. In another aspect, a target region comprises one or more, two or more, three or more, four or more, five or more, six or more, seven or more, eight or more, nine or more, or ten or more target genes. Without being limiting, in one aspect a target region can be subject to deletion or inversion. As used herein, "flanked" when used to describe a target region, refers to two or more target sites physically surrounding the target region, with one target site on each side of the target region.

As used herein, in the context of a transgene "directly modulating" or "directly modulates" refers to inducing a change in the transcript or protein level of a target gene by an agent produced by the transgene and sharing sufficient homology with at least a portion of the target gene. Direct modulation can result in a change in transcriptional activity, transcript stability, transcript constitution, or transcript expression level which can either increase or decrease the number of transcripts available for translation and can either increase or decrease the number of protein molecules.

A target site can be positioned in a polynucleotide sequence encoding a leader, an enhancer, a transcriptional start site, a promoter, a 5'-UTR, an exon, an intron, a 3'-UTR, a polyadenylation site, or a termination sequence. It will be appreciated that a target site can be also be positioned upstream or downstream of a sequence encoding a leader, an enhancer, a transcriptional start site, a promoter, a 5'-UTR, an exon, an intron, a 3'-UTR, a polyadenylation site, or a termination sequence. In one aspect, a target site is positioned within 10, within 20, within 30, within 40, within 50, within 75, within 100, within 125, within 150, within 200, within 250, within 300, within 400, within 500, within 600, within 700, within 800, within 900, within 1000, within 1250, within 1500, within 2000, within 2500, within 5000, within 10,000, or within 25,000 nucleotides of a polynucleotide encoding a leader, an enhancer, a transcriptional start site, a promoter, a 5'-UTR, an exon, an intron, a 3'-UTR, a polyadenylation site, a gene, or a termination sequence.

As used herein, "upstream" refers to a nucleic acid sequence that is positioned before the 5' end of a linked nucleic acid sequence. As used herein, "downstream" refers to a nucleic acid sequence is positioned after the 3' end of a linked nucleic acid sequence. As used herein, "5'" refers to the start of a coding DNA sequence or the beginning of an RNA molecule. As used herein, "3'" refers to the end of a coding DNA sequence or the end of an RNA molecule. It will be appreciated that an "inversion" refers to reversing the orientation of a given polynucleotide sequence. For example, if the sample sequence 5'-ATGATC-3' is inverted it will read 5'-CTAGTA-3' in reverse orientation. Additionally, the sample sequence 5'-ATGATC-3' is considered to be in "opposite orientation" to the sample sequence 5'-CTAGTA-3'.

The term "inhibitory sequence" encompasses any polynucleotide or polypeptide sequence capable of inhibiting the expression or function of a gene in a plant, such as full-length polynucleotide or polypeptide sequences, truncated polynucleotide or polypeptide sequences, fragments of polynucleotide or polypeptide sequences, variants of polynucleotide or polypeptide sequences, sense-oriented nucleotide sequences, antisense-oriented nucleotide sequences, the complement of a sense- or antisense-oriented nucleotide sequence, inverted regions of nucleotide sequences, hairpins of nucleotide sequences, double-stranded nucleotide sequences, single-stranded nucleotide sequences, combinations thereof, and the like. The term "polynucleotide sequence" includes sequences of RNA, DNA, chemically modified nucleic acids, nucleic acid analogs, combinations thereof, and the like.

Inhibitory sequences are designated herein by the name of the target gene product. Thus, as a non-limiting example, an "gene X inhibitory sequence" refers to an inhibitory sequence that is capable of inhibiting the expression of a gene X locus in a plant, for example, at the level of transcription and/or translation, or which is capable of inhibiting the function of a gene product. When the phrase "capable of inhibiting" is used in the context of a transgene containing polynucleotide inhibitory sequence, it is intended to mean that the inhibitory sequence itself exerts the inhibitory effect; or, where the inhibitory sequence encodes an inhibitory nucleotide molecule (for example, hairpin RNA, miRNA, or double-stranded RNA polynucleotides), or encodes an inhibitory polypeptide (e.g., a polypeptide that inhibits expression or function of the target gene product), following its transcription (for example, in the case of an inhibitory sequence encoding a hairpin RNA, miRNA, or double-stranded RNA polynucleotide) or its transcription and translation (in the case of an inhibitory sequence encoding an inhibitory polypeptide), the transcribed or translated product, respectively, exerts the inhibitory effect on the target gene product (e.g., inhibits expression or function of the target gene product).

An inhibitory sequence provided herein can be a sequence triggering gene silencing via any silencing pathway or mechanism known in the art, including, but not limited to, sense suppression/co-suppression, antisense suppression, double-stranded RNA (dsRNA) interference, hairpin RNA interference and intron-containing hairpin RNA interference, amplicon-mediated interference, ribozymes, small interfering RNA, artificial or synthetic microRNA, and artificial trans-acting siRNA.

One aspect of the present application relates to methods of screening and selecting cells for targeted edits and methods of selecting cells comprising targeted edits. Nucleic acids can be isolated using various techniques. For example, nucleic acids can be isolated using any method including, without limitation, recombinant nucleic acid technology, and/or the polymerase chain reaction (PCR). General PCR techniques are described, for example in PCR Primer: A Laboratory Manual, Dieffenbach & Dveksler, Eds., Cold Spring Harbor Laboratory Press, 1995. Recombinant nucleic acid techniques include, for example, restriction enzyme digestion and ligation, which can be used to isolate a nucleic acid. Isolated nucleic acids also can be chemically synthesized, either as a single nucleic acid molecule or as a series of oligonucleotides. Polypeptides can be purified from natural sources (e.g., a biological sample) by known methods such as DEAE ion exchange, gel filtration, and hydroxyapatite chromatography. A polypeptide also can be purified, for example, by expressing a nucleic acid in an expression vector. In addition, a purified polypeptide can be obtained by chemical synthesis. The extent of purity of a polypeptide can be measured using any appropriate method, e.g., column chromatography, polyacrylamide gel electrophoresis, or HPLC analysis.

Also provided herein is cured tobacco material made from tobacco leaf, tobacco plants, or plant components provided herein. "Curing" is the aging process that reduces moisture and brings about the destruction of chlorophyll giving tobacco leaf a golden color and by which starch is converted to sugar. Cured tobacco therefore has a higher reducing sugar content and a lower starch content compared to harvested green leaf. In one aspect, tobacco plants or plant components provided herein can be cured using conventional means, e.g., flue-cured, barn-cured, fire-cured, air-cured or sun-cured. See, for example, Tso (1999, Chapter 1 in Tobacco, Production, Chemistry and Technology, Davis & Nielsen, eds., Blackwell Publishing, Oxford) for a description of different types of curing methods. Cured tobacco is usually aged in a wooden drum (e.g., a hogshead) or cardboard cartons in compressed conditions for several years (e.g., two to five years), at a moisture content ranging from 10% to about 25%. See, U.S. Pat. Nos. 4,516,590 and 5,372,149. Cured and aged tobacco then can be further processed. Further processing includes conditioning the tobacco under vacuum with or without the introduction of steam at various temperatures, pasteurization, and fermentation. Fermentation typically is characterized by high initial moisture content, heat generation, and a 10 to 20% loss of dry weight. See, for example, U.S. Pat. Nos. 4,528,993, 4,660,577, 4,848,373, 5,372,149; U.S. Publication No. 2005/0178398; and Tso (1999, Chapter 1 in Tobacco, Production, Chemistry and Technology, Davis & Nielsen, eds., Blackwell Publishing, Oxford). Cured, aged, and fermented tobacco can be further processed (e.g., cut, shredded, expanded, or blended). See, for example, U.S. Pat. Nos. 4,528,993; 4,660,577; and 4,987,907. In one aspect, the cured tobacco material of the present disclosure is flue-cured, sun-cured, air-cured, or fire-cured.

Tobacco material obtained from modified tobacco lines, varieties or hybrids of the present disclosure can be used to make tobacco products. As used herein, "tobacco product" is defined as any product made or derived from tobacco that is intended for human use or consumption. In an aspect, a tobacco product provided herein comprises cured components from a modified tobacco plant provided herein. In another aspect, a tobacco product provided herein comprises cured tobacco leaf from a modified tobacco plant provided herein.

Tobacco products provided herein include, without limitation, cigarette products (e.g., cigarettes, bidi cigarettes, kreteks), cigar products (e.g., cigars, cigar wrapping tobacco, cigarillos), pipe tobacco products, products derived from tobacco, tobacco-derived nicotine products, smokeless tobacco products (e.g., moist snuff, dry snuff, snus, chewing tobacco, moist smokeless tobacco, fine cut chewing tobacco, long cut chewing tobacco, pouched chewing tobacco), films, chewables (e.g., gum), lozenges, dissolving strips, tabs, tablets, shaped parts, gels, consumable units, insoluble matrices, hollow shapes, reconstituted tobacco, expanded tobacco, and the like. See, for example, U.S. Patent Publication No. US 2006/0191548.

As used herein, "cigarette" refers a tobacco product having a "rod" and "filler". The cigarette "rod" includes the cigarette paper, filter, plug wrap (used to contain filtration materials), tipping paper that holds the cigarette paper (including the filler) to the filter, and all glues that hold these components together. The "filler" includes (1) all tobaccos, including but not limited to reconstituted and expanded tobacco, (2) non-tobacco substitutes (including but not limited to herbs, non-tobacco plant materials and other spices that may accompany tobaccos rolled within the cigarette paper), (3) casings, (4) flavorings, and (5) all other additives (that are mixed into tobaccos and substitutes and rolled into the cigarette).

In one aspect, this disclosure provides nicotine derived from and a method of producing nicotine from a modified tobacco plant provided herein for use in a product.

In one aspect, a method provided herein comprises preparing a tobacco product using cured tobacco leaf from a modified tobacco plant provided herein.

As used herein, "reconstituted tobacco" refers to a part of tobacco filler made from tobacco dust and other tobacco scrap material, processed into sheet form and cut into strips to resemble tobacco. In addition to the cost savings, reconstituted tobacco is very important for its contribution to cigarette taste from processing flavor development using reactions between ammonia and sugars.

As used herein, "expanded tobacco" refers to a part of tobacco filler which is processed through expansion of suitable gases so that the tobacco is "puffed" resulting in reduced density and greater filling capacity. It reduces the weight of tobacco used in cigarettes.

Tobacco products derived from plants of the present disclosure also include cigarettes and other smoking articles, particularly those smoking articles including filter elements, where the rod of smokeable material includes cured tobacco within a tobacco blend. In an aspect, a tobacco product of the present disclosure is selected from the group consisting of a cigarillo, a non-ventilated recess filter cigarette, a vented recess filter cigarette, a bidi cigarette, a cigar, snuff, pipe tobacco, cigar tobacco, cigarette tobacco, chewing tobacco, leaf tobacco, hookah tobacco, shredded tobacco, and cut tobacco. In another aspect, a tobacco product of the present disclosure is a smokeless tobacco product. Smokeless tobacco products are not combusted and include, but not limited to, chewing tobacco, moist smokeless tobacco, snus, and dry snuff. Chewing tobacco is coarsely divided tobacco leaf that is typically packaged in a large pouch-like package and used in a plug or twist. Moist smokeless tobacco is a moist, more finely divided tobacco that is provided in loose form or in pouch form and is typically packaged in round cans and used as a pinch or in a pouch placed between an adult tobacco consumer's cheek and gum. Snus is a heat treated smokeless tobacco. Dry snuff is finely ground tobacco that is placed in the mouth or used nasally. In a further aspect, a tobacco product of the present disclosure is selected from the group consisting of loose leaf chewing tobacco, plug chewing tobacco, moist snuff, and nasal snuff. In yet another aspect, a tobacco product of the present disclosure is selected from the group consisting of an electronically heated cigarette, an e-cigarette, an electronic vaporing device.

The present disclosure further provides a method for manufacturing a tobacco product comprising tobacco material from tobacco plants provided herein. In one aspect, methods provided herein comprise conditioning aged tobacco material made from tobacco plants provided herein to increase its moisture content from between about 12.5% and about 13.5% to about 21%, blending the conditioned tobacco material to produce a desirable blend. In one aspect, the method of manufacturing a tobacco product provided herein further comprises casing or flavoring the blend. Generally, during the casing process, casing or sauce materials are added to blends to enhance their quality by balancing the chemical composition and to develop certain desired flavor characteristics. Further details for the casing process can be found in *Tobacco Production, Chemistry and Technology*, Edited by L. Davis and M. Nielsen, Blackwell Science, 1999.

Tobacco material provided herein can be also processed using methods including, but not limited to, heat treatment (e.g., cooking, toasting), flavoring, enzyme treatment, expansion and/or curing. Both fermented and non-fermented tobaccos can be processed using these techniques. Examples of suitable processed tobaccos include dark air-cured, dark fire cured, burley, flue cured, and cigar filler or wrapper, as well as the products from the whole leaf stemming operation. In one aspect, tobacco fibers include up to 70% dark tobacco on a fresh weight basis. For example, tobacco can be conditioned by heating, sweating and/or pasteurizing steps as described in U.S. Publication Nos. 2004/0118422 or 2005/0178398.

Tobacco material provided herein can be subject to fermentation. Fermenting typically is characterized by high initial moisture content, heat generation, and a 10 to 20% loss of dry weight. See, e.g., U.S. Pat. Nos. 4,528,993; 4,660,577; 4,848,373; and 5,372,149. In addition to modifying the aroma of the leaf, fermentation can change either or both the color and texture of a leaf. Also during the fermentation process, evolution gases can be produced, oxygen can be taken up, the pH can change, and the amount of water retained can change. See, for example, U.S. Publication No. 2005/0178398 and Tso (1999, Chapter 1 in Tobacco, Production, Chemistry and Technology, Davis & Nielsen, eds., Blackwell Publishing, Oxford). Cured, or cured and fermented tobacco can be further processed (e.g., cut, expanded, blended, milled or comminuted) prior to incorporation into the oral product. The tobacco, in some cases, is long cut fermented cured moist tobacco having an oven volatiles content of between 48 and 50 weight percent prior to mixing with a copolymer and, optionally, flavorants and other additives.

In one aspect, tobacco material provided herein can be processed to a desired size. In certain aspects, tobacco fibers can be processed to have an average fiber size of less than 200 micrometers. In one aspect, tobacco fibers are between 75 and 125 micrometers. In another aspect, tobacco fibers are processed to have a size of 75 micrometers or less. In one aspect, tobacco fibers include long cut tobacco, which can be cut or shredded into widths of about 10 cuts/inch up to about 110 cuts/inch and lengths of about 0.1 inches up to about 1 inch. Double cut tobacco fibers can have a range of particle sizes such that about 70% of the double cut tobacco fibers falls between the mesh sizes of −20 mesh and 80 mesh.

Tobacco material provided herein can be processed to have a total oven volatiles content of about 10% by weight or greater; about 20% by weight or greater; about 40% by weight or greater; about 15% by weight to about 25% by weight; about 20% by weight to about 30% by weight; about 30% by weight to about 50% by weight; about 45% by weight to about 65% by weight; or about 50% by weight to about 60% by weight. Those of skill in the art will appreciate that "moist" tobacco typically refers to tobacco that has an oven volatiles content of between about 40% by weight and about 60% by weight (e.g., about 45% by weight to about 55% by weight, or about 50% by weight). As used herein, "oven volatiles" are determined by calculating the percentage of weight loss for a sample after drying the sample in a pre-warmed forced draft oven at 110° C. for 3.25 hours. An oral product can have a different overall oven volatiles content than the oven volatiles content of the tobacco fibers used to make the oral product. The processing steps described herein can reduce or increase the oven volatiles content.

In one aspect, tobacco plants, seeds, plant components, plant cells, and plant genomes provided herein are from a tobacco type selected from the group consisting of flue-cured tobacco, sun-cured tobacco, air-cured tobacco, dark air-cured tobacco, and dark fire-cured tobacco. In another aspect, tobacco plants, seeds, plant components, plant cells, and plant genomes provided herein are from a tobacco type selected from the group consisting of Burley tobacco, Maryland tobacco, bright tobacco, Virginia tobacco, Oriental tobacco, Turkish tobacco, dark tobacco, and Galpão tobacco. In one aspect, a tobacco plant or seed provided herein is a hybrid plant or seed. As used herein, a "hybrid" is created by crossing two plants from different varieties or species, such that the progeny comprises genetic material from each parent. Skilled artisans recognize that higher order hybrids can be generated as well. For example, a first hybrid can be made by crossing Variety C with Variety D to create a C×D hybrid, and a second hybrid can be made by crossing Variety E with Variety F to create an E×F hybrid. The first and second hybrids can be further crossed to create the higher order hybrid (C×D)×(E×F) comprising genetic information from all four parent varieties.

Flue-cured tobaccos (also called Virginia or bright tobaccos) amount to approximately 40% of world tobacco production. Flue-cured tobaccos are often also referred to as "bright tobacco" because of the golden-yellow to deep-orange color it reaches during curing. Flue-cured tobaccos have a light, bright aroma and taste. Flue-cured tobaccos are generally high in sugar and low in oils. Major flue-cured tobacco growing countries are Argentina, Brazil, China, India, Tanzania and the U.S. In one aspect, modified tobacco plants or seeds provided herein are in a flue-cured tobacco background selected from the group consisting of CC 13, CC 27, CC 33, CC35, CC 37, CC 65, CC 67, CC 700, GF 318, GL 338, GL 368, GL 939, K 346, K 399, K326, NC 102, NC 196, NC 291, NC 297, NC 299, NC 471, NC 55, NC 606, NC 71, NC 72, NC 92, PVH 1118, PVH 1452, PVH 2110, SPEIGHT 168, SPEIGHT 220, SPEIGHT 225, SPEIGHT 227, SPEIGHT 236, and any variety essentially derived from any one of the foregoing varieties. In another aspect, modified tobacco plants or seeds provided herein are in a flue-cured tobacco background selected from the group consisting of Coker 48, Coker 176, Coker 371-Gold, Coker 319, Coker 347, GL 939, K 149, K326, K 340, K 346, K 358, K 394, K 399, K 730, NC 27NF, NC 37NF, NC 55, NC 60, NC 71, NC 72, NC 82, NC 95, NC 297, NC 606, NC 729, NC 2326, McNair 373, McNair 944, Ox 207, Ox 414 NF, Reams 126, Reams 713, Reams 744, RG 8, RG 11, RG 13, RG 17, RG 22, RG 81, RG H4, RG H51, Speight H-20, Speight G-28, Speight G-58, Speight G-70, Speight G-108, Speight G-111, Speight G-117, Speight 168, Speight 179, Speight NF-3, Va 116, Va 182, and any variety essentially derived from any one of the foregoing varieties. See WO 2004/041006 A1. In further aspects, modified tobacco plants, seeds, hybrids, varieties, or lines provided herein are in any flue cured background selected from the group consisting of K326, K346, and NC196.

Air-cured tobaccos include Burley, Maryland, and dark tobaccos. The common factor is that curing is primarily without artificial sources of heat and humidity. Burley tobaccos are light to dark brown in color, high in oil, and low in sugar. Burley tobaccos are air-cured in barns. Major Burley growing countries are Argentina, Brazil, Italy, Malawi, and the U.S. Maryland tobaccos are extremely fluffy, have good burning properties, low nicotine and a neutral aroma. Major Maryland growing countries include the U.S. and Italy. In one aspect, modified tobacco plants or seeds provided herein are in a Burley tobacco background selected from the group consisting of Clay 402, Clay 403, Clay 502, Ky 14, Ky 907, Ky 910, Ky 8959, NC 2, NC 3, NC 4, NC 5, NC 2000, TN 86, TN 90, TN 97, R 610, R 630, R 711, R 712, NCBH 129, HB4488PLC, PD 7319LC, Bu 21×Ky 10, HB04P, Ky 14×L 8, Kt 200, Newton 98, Pedigo 561, Pf561 and Va 509. In further aspects, modified tobacco plants, seeds, hybrids, varieties, or lines provided herein are in any Burley background selected from the group consisting of TN 90, KT 209, KT 206, KT212, and HB 4488. In another aspect, modified tobacco plants or seeds provided herein are in a Maryland tobacco background selected from the group consisting of Md 10, Md 40, Md 201, Md 609, Md 872 and Md 341.

Dark air-cured tobaccos are distinguished from other types primarily by its curing process which gives dark air-cured tobacco its medium- to dark-brown color and distinct aroma. Dark air-cured tobaccos are mainly used in the production of smokeless tobacco products including chewing tobacco and snuff. In one aspect, modified tobacco plants or seeds provided herein are in a dark air-cured tobacco background selected from the group consisting of Sumatra, Jatim, Dominican Cubano, Besuki, One sucker, Green River, Virginia sun-cured, and Paraguan Passado.

Dark fire-cured tobaccos are generally cured with low-burning wood fires on the floors of closed curing barns. Dark fire-cured tobaccos are used for making pipe blends, cigarettes, chewing tobacco, snuff and strong-tasting cigars. Major growing regions for dark fire-cured tobaccos are Tennessee, Kentucky, and Virginia, USA. In one aspect, modified tobacco plants or seeds provided herein are in a dark fire-cured tobacco background selected from the group consisting of Narrow Leaf Madole, Improved Madole, Tom Rosson Madole, Newton's VH Madole, Little Crittenden, Green Wood, Little Wood, Small Stalk Black Mammoth, DT 508, DT 518, DT 592, KY 171, DF 911, DF 485, TN D94, TN D950, VA 309, and VA 359.

Oriental tobaccos are also referred to as Greek, aroma and Turkish tobaccos due to the fact that they are typically grown in eastern Mediterranean regions such as Turkey, Greece, Bulgaria, Macedonia, Syria, Lebanon, Italy, and Romania. The small plant and leaf size, characteristic of today's Oriental varieties, as well as its unique aroma properties are a result of the plant's adaptation to the poor soil and stressful climatic conditions in which it develop over many past centuries. In one aspect, modified tobacco plants or seeds provided herein are in an Oriental tobacco background selected from the group consisting of Izmir, Katerini, Samsun, Basma and Krumovgrad, Trabzon, Thesalian, Tasova, Sinop, Izmit, Hendek, Edirne, Semdinli, Adiyanman, Yayladag, Iskenderun, Duzce, Macedonian, Mavra, Prilep, Bafra, Bursa, Bucak, Bitlis, Balikesir, and any variety essentially derived from any one of the foregoing varieties.

In one aspect, modified tobacco plants, seeds, hybrids, varieties, or lines provided herein are essentially derived from or in the genetic background of BU 64, CC 101, CC 200, CC 13, CC 27, CC 33, CC 35, CC 37, CC 65, CC 67, CC 301, CC 400, CC 500, CC 600, CC 700, CC 800, CC 900, CC 1063, Coker 176, Coker 319, Coker 371 Gold, Coker 48, CU 263, DF911, Galpão, GL 26H, GL 338, GL 350, GL 395, GL 600, GL 737, GL 939, GL 973, GF 157, GF 318, RJR 901, HB 04P, K 149, K 326, K 346, K 358, K394, K 399, K 730, NC 196, NC 37NF, NC 471, NC 55, NC 92, NC2326, NC 95, NC 925, PVH 1118, PVH 1452, PVH 2110, PVH 2254, PVH 2275, VA 116, VA 119, KDH 959, KT 200, KT204LC, KY 10, KY 14, KY 160, KY 17, KY 171, KY 907, KY 907LC, KTY14×L8 LC, Little Crittenden, McNair 373, McNair 944, male sterile KY 14×L8, Narrow Leaf Madole, MS KY171, Narrow Leaf Madole (phph), MS Narrow Leaf Madole, MS TND950, PD 7302LC, PD 7305LC, PD 7309LC, PD 7312LC, PD 7318LC, PD 7319LC, MSTKS 2002, TKF 2002, TKF 6400, TKF 4028, TKF 4024, KT206LC, KT209LC, KT210LC, KT212LC, NC 100, NC 102, NC 2000, NC 291, NC 297, NC 299, NC 3, NC 4, NC 5, NC 6, NC7, NC 606, NC 71, NC 72, NC 810, NC BH 129, NC 2002, Neal Smith Madole, OXFORD 207, 'Perique', PVH03, PVH09, PVH19, PVH50, PVH51, R 610, R 630, R 7-11, R 7-12, RG 17, RG 81, RG H51, RGH 4, RGH 51, RS 1410, Speight 168, Speight 172, Speight 179, Speight 210, Speight 220, Speight 225, Speight 227, Speight 234, Speight G-28, Speight G-70, Speight H-6, Speight H20, Speight NF3, TI 1406, TI 1269, TN 86, TN86LC, TN 90, TN90LC, TN 97, TN97LC, TN D94, TN D950, a TR (Tom Rosson) Madole, VA 309, VA 359, or any commercial tobacco variety according to standard tobacco breeding techniques known in the art.

All foregoing mentioned specific varieties of dark air-cured, Burley, Maryland, dark fire-cured, or Oriental type are only listed for exemplary purposes. Any additional dark air-cured, Burley, Maryland, dark fire-cured, or Oriental varieties are also contemplated in the present application.

Also provided herein are populations of tobacco plants described herein. In one aspect, a population of tobacco plants provided herein has a planting density of between about 5,000 and about 8000, between about 5,000 and about 7,600, between about 5,000 and about 7,200, between about 5,000 and about 6,800, between about 5,000 and about 6,400, between about 5,000 and about 6,000, between about 5,000 and about 5,600, between about 5,000 and about 5,200, between about 5,200 and about 8,000, between about 5,600 and about 8,000, between about 6,000 and about 8,000, between about 6,400 and about 8,000, between about 6,800 and about 8,000, between about 7,200 and about 8,000, or between about 7,600 and about 8,000 plants per acre. In another aspect, a population of tobacco plants provided herein is in a soil type with low to medium fertility.

Also provided herein are containers of seeds from tobacco plants described herein. A container of tobacco seeds of the present disclosure may contain any number, weight, or volume of seeds. For example, a container can contain at least, or greater than, about 100, at least, or greater than, about 200, at least, or greater than, about 300, at least, or greater than, about 400, at least, or greater than, about 500, at least, or greater than, about 600, at least, or greater than, about 700, at least, or greater than, about 800, at least, or greater than, about 900, at least, or greater than, about 1000, at least, or greater than, about 1500, at least, or greater than, about 2000, at least, or greater than, about 2500, at least, or greater than, about 3000, at least, or greater than, about 3500, at least, or greater than, or about 4000 or more seeds. Alternatively, the container can contain at least, or greater than, about 1 ounce, at least, or greater than, about 5 ounces, at least, or greater than, about 10 ounces, at least, or greater than, about 1 pound, at least, or greater than, about 2 pounds, at least, or greater than, about 3 pounds, at least, or greater than, about 4 pounds, at least, or greater than, about 5 pounds or more seeds. Containers of tobacco seeds may be any container available in the art. By way of non-limiting example, a container may be a box, a bag, a packet, a pouch, a tape roll, a tube, or a bottle.

The present disclosure also provides methods for breeding tobacco lines, cultivars, or varieties comprising cured leaf with reduced or eliminated TSNAs (and, optionally, also comprising increased antioxidants or decreased nitrite). Breeding can be carried out via any known procedures. DNA fingerprinting, SNP mapping, haplotype mapping or similar technologies may be used in a marker-assisted selection (MAS) breeding program to transfer or breed a desirable trait or allele into a tobacco plant. For example, a breeder can create segregating populations in an $F_2$ or backcross generation using $F_1$ hybrid plants provided herein or further crossing the $F_1$ hybrid plants with other donor plants with an agronomically desirable genotype. Plants in the $F_2$ or backcross generations can be screened for a desired agronomic trait or a desirable chemical profile using one of the techniques known in the art or listed herein. Depending on the expected inheritance pattern or the MAS technology used, self-pollination of selected plants before each cycle of backcrossing to aid identification of the desired individual plants can be performed. Backcrossing or other breeding procedure can be repeated until the desired phenotype of the recurrent parent is recovered. In one aspect, a recurrent parent in the present disclosure can be a flue-cured variety, a Burley variety, a dark air-cured variety, a dark fire-cured variety, or an Oriental variety. In another aspect, a recurrent parent can be a modified tobacco plant, line, or variety. Other breeding techniques can be found, for example, in Wernsman, E. A., and Rufty, R. C. 1987. Chapter Seventeen. Tobacco. Pages 669-698 In: Cultivar Development. Crop Species. W. H. Fehr (ed.), MacMillan Publishing Go., Inc., New York, N.Y., incorporated herein by reference in their entirety.

Results of a plant breeding program using modified tobacco plants described herein includes useful lines, cultivars, varieties, progeny, inbreds, and hybrids of the present disclosure. As used herein, the term "variety" refers to a population of plants that share constant characteristics which separate them from other plants of the same species. A variety is often, although not always, sold commercially. While possessing one or more distinctive traits, a variety is further characterized by a very small overall variation between individuals within that variety. A "pure line" variety may be created by several generations of self-pollination and selection, or vegetative propagation from a single parent using tissue or cell culture techniques. A variety can be essentially derived from another line or variety. As defined by the International Convention for the Protection of New Varieties of Plants (Dec. 2, 1961, as revised at Geneva on Nov. 10, 1972; on Oct. 23, 1978; and on Mar. 19, 1991), a variety is "essentially derived" from an initial variety if: a) it is predominantly derived from the initial variety, or from a variety that is predominantly derived from the initial variety, while retaining the expression of the essential characteristics that result from the genotype or combination of genotypes of the initial variety; b) it is clearly distinguishable from the initial variety; and c) except for the differences which result from the act of derivation, it conforms to the initial variety in the expression of the essential characteristics that result from the genotype or combination of genotypes of the initial variety. Essentially derived varieties can be obtained, for example, by the selection of a natural or induced mutant, a somaclonal variant, a variant individual from plants of the initial variety, backcrossing, or transformation. A first tobacco variety and a second tobacco variety from which the first variety is essentially derived, are considered as having essentially identical genetic background. A "line" as distinguished from a variety most often denotes a group of plants used non-commercially, for example in plant research. A line typically displays little overall variation between individuals for one or more traits of interest, although there may be some variation between individuals for other traits.

In one aspect, the present disclosure provides a method of producing a tobacco plant comprising crossing at least one tobacco plant of a first tobacco variety with at least one tobacco plant of a second tobacco variety, where the at least one tobacco plant of the first tobacco variety comprising one or more desired traits, e.g., comprising a reduced level of one or more tobacco-specific nitrosamines (TSNAs) in cured leaf and further comprising one or more traits selected from the group consisting of: a reduced level of nitrite, an increased level of oxygen radical absorbance capacity (ORAC), and an increased level of one or more antioxidants, wherein said reduced or increased level is compared to a control tobacco plant of the same cross grown and cured under comparable conditions; and selecting for progeny tobacco plants that exhibit the one or more desired traits. In one aspect, a first tobacco variety provided herein comprises modified tobacco plants. In another aspect, a second tobacco variety provided herein comprises modified tobacco plants. In one aspect, a first or second tobacco variety is male sterile. In another aspect, a first or second tobacco variety is cytoplasmically male sterile. In another aspect, a first or second tobacco variety is female sterile. In one aspect, a first or second tobacco variety is an elite variety. In another aspect, a first or second tobacco variety is a hybrid.

In one aspect, the present disclosure provides a method of introgressing one or more transgenes or mutations into a tobacco variety, the method comprising: (a) crossing a first tobacco variety comprising one or more transgenes or mutations provided herein with a second tobacco variety without the one or more transgenes or mutations to produce one or more progeny tobacco plants; (b) genotyping the one or more progeny tobacco plants for the one or more transgenes or mutations; and (c) selecting a progeny tobacco plant comprising the one or more transgenes or mutations. In another aspect, these methods further comprise backcrossing the selected progeny tobacco plant with the second tobacco variety. In further aspects, these methods further comprise: (d) crossing the selected progeny plant with itself or with the second tobacco variety to produce one or more further progeny tobacco plants; and (e) selecting a further progeny tobacco plant comprising the one or more transgenes or mutations. In one aspect, the second tobacco variety is an elite variety.

In one aspect, the present disclosure provides a method of growing a population of modified tobacco plants disclosed herein, where the method comprises planting a population of tobacco seeds comprising one or more mutations, one or more transgenes, or both as described herein, where the one or more modified tobacco plants or cured leaf of one or more modified tobacco plants comprise a reduced level of one or more TSNAs and further comprises one or more traits selected from the group consisting of an increased level of one or more antioxidants, an increased level of oxygen radical absorbance capacity (ORAC), and a reduced level of nitrite, wherein said reduced or increased level is compared to control tobacco plants or cured leaf of a control tobacco plant of the same variety when grown and cured under comparable conditions.

In one aspect, the present disclosure provides a method of growing a modified tobacco plant described herein comprising planting a modified tobacco seed described herein; and growing the modified tobacco plant from the seed. In an aspect, growing comprises germinating a seed. In another aspect, growing comprises placing a seedling in soil, agar, agar-based media, or a hydroponics system. In another aspect, growing comprises providing a seed or plant with water, light (e.g., artificial light, sunlight), fertilizer, a rooting media, or a combination thereof. In an aspect, growing can take place indoors (e.g., a greenhouse) or outdoors (e.g., a field). In one aspect, growing comprises placing a seed or a plant in a container.

In one aspect, this disclosure provides a method for manufacturing a modified seed, comprising introducing a recombinant DNA construct provided herein into a plant cell; screening a population of plant cells for the recombinant DNA construct; selecting one or more plant cells from the population; generating one or more modified plants from the one or more plant cells; and collecting one or more modified seeds from the one or more modified plants.

As used herein, "locus" is a chromosome region where a polymorphic nucleic acid, trait determinant, gene, or marker is located. The loci of this disclosure comprise one or more polymorphisms in a population; e.g., alternative alleles are present in some individuals. As used herein, "allele" refers to an alternative nucleic acid sequence at a particular locus. The length of an allele can be as small as 1 nucleotide base, but is typically larger. For example, a first allele can occur on one chromosome, while a second allele occurs on a second homologous chromosome, e.g., as occurs for different chromosomes of a heterozygous individual, or between different homozygous or heterozygous individuals in a population. As used herein, a chromosome in a diploid plant is "hemizygous" when only one copy of a locus is present. For example, an inserted transgene is hemizygous when it only inserts into one sister chromosome (i.e., the second sister chromosome does not contain the inserted transgene).

In one aspect, a modified plant, seed, plant component, plant cell, or plant genome is homozygous for a transgene provided herein. In another aspect, a modified plant, seed, plant component, plant cell, or plant genome is heterozygous for a transgene provided herein. In one aspect, a modified plant, seed, plant component, plant cell, or plant genome is hemizygous for a transgene provided herein. In one aspect, a modified plant, seed, plant component, plant cell, or plant genome is homozygous for a mutation provided herein. In another aspect, a modified plant, seed, plant component, plant cell, or plant genome is heterozygous for a mutation provided herein. In one aspect, a modified plant, seed, plant component, plant cell, or plant genome is hemizygous for a mutation provided herein.

As used herein, "introgression" or "introgress" refers to the transmission of a desired allele of a genetic locus from one genetic background to another.

As used herein, "crossed" or "cross" means to produce progeny via fertilization (e.g. cells, seeds or plants) and includes crosses between different plants (sexual) and self-fertilization (selfing).

As used herein, "backcross" and "backcrossing" refer to the process whereby a progeny plant is repeatedly crossed back to one of its parents. In a backcrossing scheme, the "donor" parent refers to the parental plant with the desired gene or locus to be introgressed. The "recipient" parent (used one or more times) or "recurrent" parent (used two or more times) refers to the parental plant into which the gene or locus is being introgressed. The initial cross gives rise to the $F_1$ generation. The term "$BC_1$" refers to the second use of the recurrent parent, "$BC_2$" refers to the third use of the recurrent parent, and so on. In one aspect, a backcross is performed repeatedly, with a progeny individual of each successive backcross generation being itself backcrossed to the same parental genotype.

As used herein, "elite variety" means any variety that has resulted from breeding and selection for superior agronomic performance.

As used herein, "selecting" or "selection" in the context of breeding refer to the act of picking or choosing desired individuals, normally from a population, based on certain pre-determined criteria.

In one aspect, tobacco plants provided herein are hybrid plants. Hybrids can be produced by preventing self-pollination of female parent plants (e.g., seed parents) of a first variety, permitting pollen from male parent plants of a second variety to fertilize the female parent plants, and allowing $F_1$ hybrid seeds to form on the female plants. Self-pollination of female plants can be prevented by emasculating the flowers at an early stage of flower development. Alternatively, pollen formation can be prevented on the female parent plants using a form of male sterility. For example, male sterility can be produced by male sterility (MS), or transgenic male sterility where a transgene inhibits microsporogenesis and/or pollen formation, or self-incompatibility. Female parent plants containing MS are particularly useful. In aspects in which the female parent plants are MS, pollen may be harvested from male fertile plants and applied manually to the stigmas of MS female parent plants, and the resulting $F_1$ seed is harvested. Additionally, female sterile plants can also be used to prevent self-fertilization.

Plants can be used to form single-cross tobacco $F_1$ hybrids. Pollen from a male parent plant is manually transferred to an emasculated female parent plant or a female parent plant that is male sterile to form $F_1$ seed. Alternatively, three-way crosses can be carried out where a single-cross $F_1$ hybrid is used as a female parent and is crossed with a different male parent. As another alternative, double-cross hybrids can be created where the $F_1$ progeny of two different single-crosses are themselves crossed. Self-incompatibility can be used to particular advantage to prevent self-pollination of female parents when forming a double-cross hybrid.

In one aspect, a tobacco variety provided herein is male sterile. In another aspect, a tobacco variety provided herein is cytoplasmic male sterile (CMS). Male sterile tobacco plants may be produced by any method known in the art. Methods of producing male sterile tobacco are described in Wernsman, E. A., and Rufty, R. C. 1987. Chapter Seventeen. Tobacco. Pages 669-698 In: Cultivar Development. Crop Species. W. H. Fehr (ed.), MacMillan Publishing Go., Inc., New York, N.Y. 761 pp. In another aspect, a tobacco variety provided herein is female sterile. As a non-limiting example, female sterile plants can be made by mutating the STIG1 gene. See, for example, Goldman et al. 1994, *EMBO Journal* 13:2976-2984.

As used herein, the term "sequence identity" or "identity" in the context of two polynucleotide or polypeptide sequences makes reference to the residues in the two sequences that are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity."

The use of the term "polynucleotide" is not intended to limit the present disclosure to polynucleotides comprising DNA. Those of ordinary skill in the art will recognize that polynucleotides and nucleic acid molecules can comprise ribonucleotides and combinations of ribonucleotides and deoxyribonucleotides. Such deoxyribonucleotides and ribonucleotides include both naturally occurring molecules and synthetic analogues. The polynucleotides of the present disclosure also encompass all forms of sequences including, but not limited to, single-stranded forms, double-stranded forms, hairpins, stem-and-loop structures, and the like.

As used herein, the term "polypeptide" refers to a chain of at least two covalently linked amino acids.

Nucleic acid molecules, polypeptides, or proteins provided herein can be isolated or substantially purified. An "isolated" or "purified" nucleic acid molecule, polypeptide, protein, or biologically active portion thereof, is substantially or essentially free from components that normally accompany or interact with the polynucleotide or protein as found in its naturally occurring environment. For example, an isolated or purified polynucleotide or protein is substantially free of other cellular material, or culture medium when produced by recombinant techniques, or substantially free of chemical precursors or other chemicals when chemically synthesized. In another aspect, an isolated polypeptide provided herein is substantially free of cellular material in preparations having less than about 30%, less than about 20%, less than about 10%, less than about 5%, or less than about 1% (by dry weight) of chemical precursors or non-protein-of-interest chemicals. Fragments of the disclosed polynucleotides and polypeptides encoded thereby are also encompassed by the present invention. Fragments of a polynucleotide may encode polypeptide fragments that retain the biological activity of the native polypeptide. Alternatively, fragments of a polynucleotide that are useful as hybridization probes or PCR primers using methods known in the art generally do not encode fragment polypeptides retaining biological activity. Fragments of a polynucleotide provided herein can range from at least about 20 nucleotides, about 50 nucleotides, about 70 nucleotides, about 100 nucleotides, about 150 nucleotides, about 200 nucleotides, about 250 nucleotides, about 300 nucleotides, and up to the full-length polynucleotide encoding the polypeptides of the invention, depending on the desired outcome.

Nucleic acids can be isolated using techniques routine in the art. For example, nucleic acids can be isolated using any method including, without limitation, recombinant nucleic acid technology, and/or the polymerase chain reaction (PCR). General PCR techniques are described, for example in PCR Primer: A Laboratory Manual, Dieffenbach & Dveksler, Eds., Cold Spring Harbor Laboratory Press, 1995. Recombinant nucleic acid techniques include, for example, restriction enzyme digestion and ligation, which can be used to isolate a nucleic acid. Isolated nucleic acids also can be chemically synthesized, either as a single nucleic acid molecule or as a series of oligonucleotides. Polypeptides can be purified from natural sources (e.g., a biological sample) by known methods such as DEAE ion exchange, gel filtration, and hydroxyapatite chromatography. A polypeptide also can be purified, for example, by expressing a nucleic acid in an expression vector. In addition, a purified polypeptide can be obtained by chemical synthesis. The extent of purity of a polypeptide can be measured using any appropriate method, e.g., column chromatography, polyacrylamide gel electrophoresis, or HPLC analysis.

In one aspect, this disclosure provides methods of detecting in plant cells one or more recombinant nucleic acids and polypeptides described here. Without being limiting, nucleic acids also can be detected using hybridization. Hybridization between nucleic acids is discussed in detail in Sambrook et al. (1989, Molecular Cloning: A Laboratory Manual, 2nd Ed., Cold Spring Harbor Laboratory Press, Cold Spring Harbor, NY).

Polypeptides can be detected using antibodies. Techniques for detecting polypeptides using antibodies include enzyme linked immunosorbent assays (ELISAs), Western blots, immunoprecipitations and immunofluorescence. An antibody provided herein can be a polyclonal antibody or a monoclonal antibody. An antibody having specific binding affinity for a polypeptide provided herein can be generated using methods well known in the art. An antibody provided herein can be attached to a solid support such as a microtiter plate using methods known in the art.

Detection (e.g., of an amplification product, of a hybridization complex, of a polypeptide) can be accomplished using detectable labels. The term "label" is intended to encompass the use of direct labels as well as indirect labels. Detectable labels include enzymes, prosthetic groups, fluorescent materials, luminescent materials, bioluminescent materials, and radioactive materials.

In one aspect, the present disclosure also provides a method of reducing the level of one or more TSNAs in cured leaf from a tobacco plant, the method comprising increasing the level of one or more antioxidants in the tobacco plant by expressing a biosynthetic enzyme, a regulatory transcription factor, a transporter, a catabolic enzyme, or a combination thereof, for the one or more antioxidants. In another aspect, a method comprises expressing a gene promoting the production or accumulation of one or more antioxidants are selected from the group consisting of anthocyanidin, flavanone, flavanol, flavone, flavonol, isoflavone, hydroxybenzoic acid, hydroxycinnamic acid, ellagitannin, stibene, lignan, carotenoids, and glycyrrhzin. In a further aspect, a method comprises expressing a gene promoting the production or accumulation of one or more antioxidants are selected from the group consisting of Delphnidin, Cyanidin, Procyanidin, Prodelphinidin, Hesperetin, Naringenin, Catechin, Epicatechin, Apigenin, Luteonin, Quercetin, Myricetin, Rutin, Genistein, Daidzein, Gallic acid, Vanillic acid, Protocatechuic acid, Ferunic acid, Cinnamic acid, Coumeric acid, Chlorogenic acid, Coffeic acid, ferulic acid, Sanguiin, Resveratrol, Sesamin, Caretonoids, and Vitamin C. In one aspect, a method does not substantially reduce the level of total alkaloids in the tobacco plant. In another aspect, a method does not substantially reduce the level of nicotine in the tobacco plant.

In one aspect, the present disclosure provides a method for reducing the level of one or more TSNAs in cured tobacco leaf or a tobacco product made therefrom, the method comprising increasing the level of one or more antioxidants in a tobacco plant via a transgene encoding or directly modulating an antioxidant biosynthetic enzyme, a regulatory transcription factor of an antioxidant, an antioxidant transporter, an antioxidant metabolic enzyme, or a combination thereof; and reducing the level of one or more TSNAs in cured tobacco leaf from the tobacco plant or a tobacco product made from the cured tobacco leaf. In another aspect of a method described herein, the level of one or more TSNAs reduces by at least 50%, by at least 45%, by at least 40%, by at least 35%, by at least 30%, by at least 25%, by at least 20%, by at least 15%, by at least 10%, or by at least 5%, compared to cured leaf from a control tobacco plant not comprising a transgene. In a further aspect of a method described herein, cured leaf of the modified tobacco plant produces or comprises less than 2, less than 1.9, less than 1.8, less than 1.7, less than 1.6, less than 1.5, less than 1.4, less than 1.3, less than 1.2, less than 1.1, less than 1.0, less than 0.9, less than 0.8, less than 0.7, less than 0.6, less than 0.5, less than 0.4, less than 0.3, less than 0.2, less than 0.15, less than 0.1, or less than 0.05 ppm total TSNAs. In a further aspect of a method described herein, cured leaf of the modified tobacco plant comprises between 2 and 0.05, between 1.9 and 0.05, between 1.8 and 0.05, between 1.7 and 0.05, between 1.6 and 0.05, between 1.5 and 0.05, between 1.4 and 0.05, between 1.3 and 0.05, between 1.2 and 0.05, between 1.1 and 0.05, between 1.0 and 0.05, between 0.9 and 0.05, between 0.8 and 0.05, between 0.7 and 0.05, between 0.6 and 0.05, between 0.5 and 0.05, between 0.4 and 0.05, between 0.3 and 0.05, between 0.2 and 0.05, between 0.15 and 0.05, or between 0.1 and 0.05 ppm total TSNAs. In a further aspect of a method described herein, cured leaf of the modified tobacco plant comprises between 2 and 0.05, between 1.8 and 0.1, between 1.5 and 0.15, between 1.2 and 0.2, between 1.0 and 0.3, between 0.8 and 0.4, or between 0.6 and 0.5 ppm total TSNAs. In a further aspect of a method described herein, one or more TSNAs are selected from the group consisting of N'-nitrosonornicotine (NNN), 4-methylnitrosoamino-1-(3-pyridyl)-1-butanone (NNK), N'-nitrosoanatabine (NAT), N'-nitrosoanabasine (NAB), and any combination thereof. In a further aspect of a method described herein, the TSNA reduction comprises a reduction of NNK. In a further aspect of a method described herein, the TSNA reduction consists of a reduction of NNK. In a further aspect of a method described herein, NNK is reduced below 0.08 parts per million, below 0.07 parts per million, below 0.06 parts per million, or below 0.05 parts per million, as measured in freeze-dried cured leaf samples using liquid chromatography with tandem mass spectrometry.

In another aspect of a method described herein, the tobacco plant comprises reduced nicotine demethylase activity compared to a control plant. In a further aspect of a method described herein, the tobacco plant comprises at least one mutation in a nicotine demethylase gene selected from the group consisting of CYP82E4, CYP82E5, CYP82E10, and a combination thereof. In another aspect of a method described herein, a method reduces nitrite levels in cured tobacco leaf comprising the transgene. In another aspect of a method described herein, a method increases the oxygen radical absorbance capacity level in cured tobacco leaf comprising the transgene. In another aspect of a method described herein, the one or more antioxidants that are increased in cured tobacco leaf comprising the transgene are selected from the group consisting of anthocyanidin, flavanone, flavanol, flavone, flavonol, isoflavone, hydroxybenzoic acid, hydroxycinnamic acid, ellagitannin, stibene, lignan, carotenoids, and glycyrrhzin. In a further aspect of a method described herein, the one or more antioxidants that are increased in cured tobacco leaf comprising the transgene are selected from the group consisting of Delphnidin, Cyanidin, Procyanidin, Prodelphinidin, Hesperetin, Naringenin, Catechin, Epicatechin, Apigenin, Luteonin, Quercetin, Myricetin, Rutin, Genistein, Daidzein, Gallic acid, Vanillic acid, Protocatechuic acid, Ferunic acid, Cinnamic acid, Coumeric acid, Chlorogenic acid, Coffeic acid, ferulic acid, Sanguiin, Resveratrol, Sesamin, Caretonoids, and Vitamin C In a further aspect of a method described herein, a method does not substantially reduce the level of total alkaloids in a tobacco plant. In a further aspect of a method described herein, a method does not substantially reduce the level of nicotine in a tobacco plant. In an aspect of a method described herein, a transgene encodes or directly modulates a biosynthetic enzyme, a regulatory transcription factor, a transporter, a metabolic enzyme, or a combination thereof, for one or more antioxidants selected from the group consisting of anthocyanidin, flavanone, flavanol, flavone, flavonol, isoflavone, hydroxybenzoic acid, hydroxycinnamic acid, ellagitannin, stibene, lignan, carotenoids, and glycyrrhzin. In a further aspect of a method described herein, a transgene encodes or directly modulates a biosynthetic enzyme, a regulatory transcription factor, a transporter, a metabolic enzyme, or a combination thereof, for one or more antioxidants selected from the group consisting of Delphnidin, Cyanidin, Procyanidin, Prodelphinidin, Hesperetin, Naringenin, Catechin, Epicatechin, Apigenin, Luteonin, Quercetin, Myricetin, Rutin, Genistein, Daidzein, Gallic acid, Vanillic acid, Protocatechuic acid, Ferunic acid, Cinnamic acid, Coumeric acid, Chlorogenic acid, Coffeic acid, ferulic acid, Sanguiin, Resveratrol, Sesamin, Caretonoids, and Vitamin C In another aspect of a method described herein, the transgene encodes a protein comprising a sequence having at least 50%, 55%, 60%, 65%, 70%, 75%, 80%, 85%, 90%, 95%, 97%, 98%, 99%, or 100% identity to a sequence selected from the group consisting of SEQ ID No. 1 to 23 and 47 to 52.

In one aspect, the present disclosure provides a method for reducing the level of one or more TSNAs in cured tobacco leaf or a tobacco product made therefrom, a method comprising increasing the level of one or more antioxidants in a tobacco plant via a genetic modification in an endogenous gene, wherein the endogenous gene encodes an antioxidant biosynthetic enzyme, a regulatory transcription factor of an antioxidant, an antioxidant transporter, an antioxidant metabolic enzyme, or a combination thereof; and reducing the level of one or more TSNAs in cured tobacco leaf from the tobacco plant or a tobacco product made from the cured tobacco leaf. In another aspect of a method described herein, the level of one or more TSNAs is reduced by at least 50%, by at least 45%, by at least 40%, by at least 35%, by at least 30%, by at least 25%, by at least 20%, by at least 15%, by at least 10%, or by at least 5%, compared to cured leaf from a control tobacco plant not comprising a transgene. In a further aspect of a method described herein, one or more TSNAs are selected from the group consisting of N'-nitrosonornicotine (NNN), 4-methylnitrosoamino-1-(3-pyridyl)-1-butanone (NNK), N'-nitrosoanatabine (NAT) N'-nitrosoanabasine (NAB), and any combination thereof. In further aspect of a method described herein, the TSNA reduction comprises a reduction of NNK. In a further aspect of a method described herein, the TSNA reduction consists of a reduction of NNK. In a further aspect of a method described herein, NNK is reduced below 0.08 parts per million as measured in freeze-dried cured leaf samples using liquid chromatography with tandem mass spectrometry.

In another aspect of a method described herein, a tobacco plant comprises reduced nicotine demethylase activity compared to a control plant. In a further aspect of a method described herein, a tobacco plant comprises at least one mutation in a nicotine demethylase gene selected from the group consisting of CYP82E4, CYP82E5, CYP82E10, and a combination thereof. In another aspect of a method described herein, a method reduces nitrite levels in cured tobacco leaf comprising a transgene. In another aspect of a method described herein, a method increases the oxygen radical absorbance capacity level in cured tobacco leaf comprising a transgene. In another aspect of a method described herein, a method increases the oxygen radical absorbance capacity level in cured tobacco leaf comprising a transgene. In another aspect of a method described herein, one or more increased antioxidants are tobacco native antioxidants. In another aspect of a method described herein, the one or more antioxidants that are increased in cured tobacco leaf comprising a transgene are selected from the group consisting of anthocyanidin, flavanone, flavanol, flavone, flavonol, isoflavone, hydroxybenzoic acid, hydroxycinnamic acid, ellagitannin, stibene, lignan, carotenoids, and glycyrrhzin. In a further aspect of the method, the one or more antioxidants that are increased in cured tobacco leaf comprising the transgene are selected from the group consisting of Delphnidin, Cyanidin, Procyanidin, Prodelphinidin, Hesperetin, Naringenin, Catechin, Epicatechin, Apigenin, Luteonin, Quercetin, Myricetin, Rutin, Genistein, Daidzein, Gallic acid, Vanillic acid, Protocatechuic acid, Ferunic acid, Cinnamic acid, Coumeric acid, Chlorogenic acid, Coffeic acid, ferulic acid, Sanguiin, Resveratrol, Sesamin, Caretonoids, and Vitamin C.

In a further aspect of a method described herein, a method does not substantially reduce the level of total alkaloids in a tobacco plant. In a further aspect of a method described herein, a method does not substantially reduce the level of nicotine in a tobacco plant. In another aspect of a method described herein, an endogenous gene encodes a protein comprising a sequence having at least 50%, 55%, 60%, 65%, 70%, 75%, 80%, 85%, 90%, 95%, 97%, 98%, 99%, or 100% identity to a sequence selected from the group consisting of SEQ ID No. 1 to 23 and 47 to 52.

In one aspect, the present disclosure provides a method for manufacturing a tobacco product, the method comprising obtaining cured tobacco leaf comprising a transgene or comprising a genetic modification in an endogenous gene, and further comprising an increased level of one or more antioxidants compared to cured tobacco leaf control lacking a transgene or a genetic modification, wherein an endogenous gene encodes an antioxidant biosynthetic enzyme, a regulatory transcription factor of an antioxidant, an antioxidant transporter, an antioxidant metabolic enzyme, or a combination thereof, wherein a transgene encodes or directly modulates an antioxidant biosynthetic enzyme, a regulatory transcription factor of an antioxidant, an antioxidant transporter, an antioxidant metabolic enzyme, or a combination thereof; and producing a tobacco product from cured tobacco leaf, wherein a tobacco product comprises a reduced level of one or more TSNAs relative to a control tobacco product prepared from a control cured tobacco leaf. In another aspect of a method described herein, cured tobacco leaf comprises a transgene encoding or directly modulating an antioxidant biosynthetic enzyme, a regulatory transcription factor of an antioxidant, an antioxidant transporter, an antioxidant metabolic enzyme, or a combination thereof. In another aspect of a method described herein, cured tobacco leaf comprises a genetic modification in an antioxidant biosynthetic enzyme, a regulatory transcription factor of an antioxidant, an antioxidant transporter, an antioxidant metabolic enzyme, or a combination thereof.

In another aspect of a method described herein, the level of one or more TSNAs is reduced by at least 50%, by at least 45%, by at least 40%, by at least 35%, by at least 30%, by at least 25%, by at least 20%, by at least 15%, by at least 10%, or by at least 5%, compared to cured leaf from a control tobacco plant not comprising a transgene. In another aspect of a method described herein, the level of one or more TSNAs is reduced by at least 50%, by at least 45%, by at least 40%, by at least 35%, by at least 30%, by at least 25%, by at least 20%, by at least 15%, by at least 10%, or by at least 5%, compared to cured leaf from a control tobacco plant not comprising a genetic modification in an endogenous gene. In another aspect of a method described herein, cured tobacco leaf comprises a reduced nitrite level compared to a control plant without a transgene. In another aspect of a method described herein, the cured tobacco leaf comprises a reduced nitrite level compared to a control plant without a genetic modification in an endogenous gene.

In one aspect, the present disclosure provides a method for preparing cured tobacco leaf, the method comprising growing a tobacco plant comprising a transgene or a genetic modification in an endogenous gene, and further comprising an increased level of one or more antioxidants compared to a control cured tobacco leaf lacking a transgene or a genetic modification, wherein an endogenous gene encodes an antioxidant biosynthetic enzyme, a regulatory transcription factor of an antioxidant, an antioxidant transporter, an antioxidant metabolic enzyme, or a combination thereof, wherein a transgene encodes or directly modulates an antioxidant biosynthetic enzyme, a regulatory transcription factor of an antioxidant, an antioxidant transporter, an antioxidant metabolic enzyme, or a combination thereof; and preparing cured leaf from a tobacco plant, wherein cured leaf comprises a reduced level of one or more TSNAs relative to a control cured leaf from a control tobacco plant not comprising a transgene or a genetic modification. In another aspect of a method described herein, cured tobacco leaf comprises a transgene encoding or directly modulating an antioxidant biosynthetic enzyme, a regulatory transcription factor of an antioxidant, an antioxidant transporter, an antioxidant metabolic enzyme, or a combination thereof. In another aspect of a method described herein, cured tobacco leaf comprises a genetic modification in an antioxidant biosynthetic enzyme, a regulatory transcription factor of an antioxidant, an antioxidant transporter, an antioxidant metabolic enzyme, or a combination thereof.

In another aspect of a method described herein, the level of one or more TSNAs is reduced by at least 50%, by at least 45%, by at least 40%, by at least 35%, by at least 30%, by at least 25%, by at least 20%, by at least 15%, by at least 10%, or by at least 5%, compared to cured leaf from a control tobacco plant not comprising a transgene. In another aspect of a method described herein, the level of one or more TSNAs is reduced by at least 50%, by at least 45%, by at least 40%, by at least 35%, by at least 30%, by at least 25%, by at least 20%, by at least 15%, by at least 10%, or by at least 5%, compared to cured leaf from a control tobacco plant not comprising a genetic modification in an endogenous gene. In another aspect of a method described herein, cured tobacco leaf comprises a reduced nitrite level compared to a control plant without a transgene. In another aspect of a method described herein, cured tobacco leaf comprises a reduced nitrite level compared to a control plant without a genetic modification in an endogenous gene.

In one aspect, the present disclosure provides cured leaf of a modified tobacco plant, wherein cured leaf comprises a reduced level of one or more tobacco-specific nitrosamines (TSNAs) and further comprises an increased level of one or more antioxidants and a reduced nitrite level, wherein reduced and increased levels are compared to a control cured leaf of an unmodified tobacco plant of the same variety when grown and cured under comparable conditions, wherein a modification comprises a transgene or a genetic modification in an endogenous gene, wherein a transgene or an endogenous gene encodes an antioxidant biosynthetic enzyme, a regulatory transcription factor of an antioxidant, an antioxidant transporter, an antioxidant metabolic enzyme, or a combination thereof; wherein a modified tobacco plant does not comprise a transgene overexpressing an *Arabidopsis* PAP1 protein. In a further aspect of a method described herein, cured leaf of the modified tobacco plant produces or comprises less than 2, less than 1.9, less than 1.8, less than 1.7, less than 1.6, less than 1.5, less than 1.4, less than 1.3, less than 1.2, less than 1.1, less than 1.0, less than 0.9, less than 0.8, less than 0.7, less than 0.6, less than 0.5, less than 0.4, less than 0.3, less than 0.2, less than 0.15, less than 0.1, or less than 0.05 ppm total TSNAs. In a further aspect of a method described herein, cured leaf of the modified tobacco plant comprises between 2 and 0.05, between 1.9 and 0.05, between 1.8 and 0.05, between 1.7 and 0.05, between 1.6 and 0.05, between 1.5 and 0.05, between 1.4 and 0.05, between 1.3 and 0.05, between 1.2 and 0.05, between 1.1 and 0.05, between 1.0 and 0.05, between 0.9 and 0.05, between 0.8 and 0.05, between 0.7 and 0.05, between 0.6 and 0.05, between 0.5 and 0.05, between 0.4 and 0.05, between 0.3 and 0.05, between 0.2 and 0.05, between 0.15 and 0.05, or between 0.1 and 0.05 ppm total TSNAs. In a further aspect of a method described herein, cured leaf of the modified tobacco plant comprises between 2 and 0.05, between 1.8 and 0.1, between 1.5 and 0.15, between 1.2 and 0.2, between 1.0 and 0.3, between 0.8 and 0.4, or between 0.6 and 0.5 ppm total TSNAs. In a further aspect of a method described herein, one or more TSNAs are selected from the group consisting of N'-nitrosonornicotine (NNN), 4-methylnitrosoamino-1-(3-pyridyl)-1-butanone (NNK), N'-nitrosoanatabine (NAT) N'-nitrosoanabasine (NAB), and any combination thereof. In a further aspect of a method described herein, the TSNA reduction comprises a reduction of NNK. In a further aspect of a method described herein, the TSNA reduction consists of a reduction of NNK. In a further aspect of a method described herein, NNK is reduced below 0.08 parts per million, below 0.07 parts per million, below 0.06 parts per million, or below 0.05 parts per million, as measured in freeze-dried cured leaf samples using liquid chromatography with tandem mass spectrometry. In another aspect of a method described herein, a tobacco plant comprises reduced nicotine demethylase activity compared to a control plant. In a further aspect of a method described herein, a tobacco plant comprises at least one mutation in a nicotine demethylase gene selected from the group consisting of CYP82E4, CYP82E5, CYP82E10, and a combination thereof. In a further aspect of a method described herein, a method provides a tobacco product comprising cured leaf of a modified tobacco plant.

Having now generally described the disclosure, the same will be more readily understood through reference to the following examples that are provided by way of illustration, and are not intended to be limiting of the present disclosure, unless specified.

The following are exemplary embodiments of the present disclosure.

Embodiment 1. Cured leaf of a modified tobacco plant, wherein said cured leaf comprises a reduced level of one or more tobacco-specific nitrosamines (TSNAs) and further comprises an increased level of one or more antioxidants, wherein said reduced and increased levels are compared to a control cured leaf of an unmodified tobacco plant of the same variety when grown and cured under comparable conditions.

Embodiment 2. A tobacco product comprising the cured leaf of embodiment 1.

Embodiment 3. A tobacco product made from the cured leaf of any one of embodiments 1 or 2.

Embodiment 4. The cured leaf of any one of embodiments 1 to 3, wherein said one or more antioxidants are endogenous antioxidants.

Embodiment 5. The cured leaf of any one of embodiments 1 to 4, wherein said one or more antioxidants are not exogenous antioxidants administered, added, or introduced to said cured leaf or modified tobacco plant.

Embodiment 6. The cured leaf of any one of embodiments 1 to 5, wherein said one or more antioxidants are produced by said modified tobacco plant.

Embodiment 7. The cured leaf of any one of embodiments 1 to 6, wherein said one or more antioxidants are produced in vivo in said cured leaf.

Embodiment 8. The cured leaf of any one of embodiments 1 to 7, wherein said cured leaf comprises an increased level of oxygen radical absorbance capacity (ORAC) compared to said control cured leaf.

Embodiment 9. The cured leaf of any one of embodiments 1 to 8, wherein said modified tobacco plant comprises in a green leaf an increased level of oxygen radical absorbance capacity (ORAC) compared to said unmodified tobacco plant of the same variety when grown under comparable conditions.

Embodiment 10. The cured leaf of any one of embodiments 1 and 4 to 9, wherein said reduced or increased level is within about 10%, within about 20%, within about 30%, within about 40%, within about 50%, within about 60%, within about 70%, within about 80%, within about 90%, within about 92%, within about 94%, within about 95%, within about 96%, within about 97%, within about 98%, or within about 99% lower or higher than the level in said control cured leaf.

Embodiment 11. The cured leaf of any one of embodiments 1 and 4 to 10, wherein said reduced or increased level is within about 1 fold, within about 2 folds, within about 3 folds, within about 4 folds, within about 5 folds, within about 6 folds, within about 7 folds, within about 8 folds, within about 9 folds, within about 10 folds, within about 15 folds, within about 20 folds, within about 25 folds, or within about 30 folds lower or higher than the level in said control cured leaf.

Embodiment 12. The cured leaf of any one of embodiments 1 and 4 to 11, wherein said reduced or increased level is at least about 10%, at least about 20%, at least about 30%, at least about 40%, at least about 50%, at least about 60%, at least about 70%, at least about 80%, at least about 90%, at least about 92%, at least about 94%, at least about 95%, at least about 96%, at least about 97%, at least about 98%, or at least about 99% lower or higher than the level in said control cured leaf.

Embodiment 13. The cured leaf of any one of embodiments 1 and 4 to 12, wherein said reduced or increased level is at least about 1 fold, at least about 2 folds, at least about 3 folds, at least about 4 folds, at least about 5 folds, at least about 6 folds, at least about 7 folds, at least about 8 folds, at least about 9 folds, at least about 10 folds, at least about 15 folds, at least about 20 folds, at least about 25 folds, or at least about 30 folds lower or higher than the level in said control cured leaf.

Embodiment 14. The cured leaf of any one of embodiments 1 and 4 to 13, wherein said reduced or increased level is about 10%, about 20%, about 30%, about 40%, about 50%, about 60%, about 70%, about 80%, about 90%, about 92%, about 94%, about 95%, about 96%, about 97%, about 98%, or about 99% lower or higher than the level in said control cured leaf.

Embodiment 15. The cured leaf of any one of embodiments 1 and 4 to 14, wherein said reduced or increased level is about 1 fold, about 2 folds, about 3 folds, about 4 folds, about 5 folds, about 6 folds, about 7 folds, about 8 folds, about 9 folds, about 10 folds, about 15 folds, about 20 folds, about 25 folds, or about 30 folds lower or higher than the level in said control cured leaf.

Embodiment 16. The cured leaf of any one of embodiments 1 and 4 to 15, wherein said reduced or increased level is about 1-2 folds, about 2-3 folds, about 3-4 folds, about 4-5 folds, about 5-6 folds, about 6-7 folds, about 7-8 folds, about 8-9 folds, about 9-10 folds, about 10-15 folds, about 15-20 folds, about 20-25 folds, about 25-30 folds, or about 30-50 folds lower or higher than the level in said control cured leaf.

Embodiment 17. The cured leaf of any one of embodiments 1 and 4 to 16, wherein said reduced or increased level is about 1-10 folds, about 2-10 folds, about 3-10 folds, about 4-10 folds, about 5-10 folds, about 6-10 folds, about 7-10 folds, about 8-10 folds, about 9-10 folds, about 10-50 folds, about 15-50 folds, about 20-50 folds, about 25-50 folds, or about 30-50 folds lower or higher than the level in said control cured leaf.

Embodiment 18. The cured leaf of any one of embodiments 1 to 9, wherein said increased level of one or more antioxidants is from the modification in said modified tobacco plant.

Embodiment 19. The cured leaf of embodiment 18, wherein said modification in said modified tobacco plant comprises a tobacco genome mutation or a transgene.

Embodiment 20. The cured leaf of any one of embodiments 18 or 19, wherein said modification in said modified tobacco plant comprises a tobacco genome mutation in a gene encoding a biosynthetic enzyme, a regulatory transcription factor, a transporter, a catabolic enzyme, or a combination thereof, for one or more antioxidants selected from the group consisting of anthocyanidin, flavanone, flavanol, flavone, flavonol, isoflavone, hydroxybenzoic acid, hydroxycinnamic acid, ellagitannin, stibene, lignan, carotenoids, and glycyrrhzin.

Embodiment 21. The cured leaf of any one of embodiments 18 to 20, wherein said modification in said modified tobacco plant comprises a tobacco genome mutation in a gene encoding a biosynthetic enzyme, a regulatory transcription factor, a transporter, a catabolic enzyme, or a combination thereof, for one or more antioxidants selected from the group consisting of Delphnidin, Cyanidin, Procyanidin, Prodelphinidin, Hesperetin, Naringenin, Catechin, Epicatechin, Apigenin, Luteonin, Quercetin, Myricetin, Rutin, Genistein, Daidzein, Gallic acid, Vanillic acid, Protocatechuic acid, Ferunic acid, Cinnamic acid, Coumeric acid, Chlorogenic acid, Coffeic acid, ferulic acid, Sanguiin, Resveratrol, Sesamin, Caretonoids, and Vitamin C.

Embodiment 22. The cured leaf of any one of embodiments 18 to 21, wherein said modification in said modified tobacco plant comprises a tobacco genome mutation in a gene encoding a protein comprising a sequence having at least 50%, 55%, 60%, 65%, 70%, 75%, 80%, 85%, 90%, 95%, 97%, 98%, 99%, or 100% identity to a sequence selected from the group consisting of SEQ ID No. 1 to 23 and 47 to 52.

Embodiment 23. The cured leaf of any one of embodiments 18 to 22, wherein said modification in said modified tobacco plant comprises a transgene encoding or directly modulating a biosynthetic enzyme, a regulatory transcription factor, a transporter, a catabolic enzyme, or a combination thereof, for one or more antioxidants selected from the group consisting of anthocyanidin, flavanone, flavanol, flavone, flavonol, isoflavone, hydroxybenzoic acid, hydroxycinnamic acid, ellagitannin, stibene, lignan, carotenoids, and glycyrrhzin.

Embodiment 24. The cured leaf of any one of embodiments 18 to 23, wherein said modification in said modified tobacco plant comprises a transgene encoding or directly modulating a biosynthetic enzyme, a regulatory transcription factor, a transporter, a catabolic enzyme, or a combination thereof, for one or more antioxidants selected from the group consisting of Delphnidin, Cyanidin, Procyanidin, Prodelphinidin, Hesperetin, Naringenin, Catechin, Epicatechin, Apigenin, Luteonin, Quercetin, Myricetin, Rutin, Genistein, Daidzein, Gallic acid, Vanillic acid, Protocatechuic acid, Ferunic acid, Cinnamic acid, Coumeric acid, Chlorogenic acid, Coffeic acid, ferulic acid, Sanguiin, Resveratrol, Sesamin, Caretonoids, and Vitamin C.

Embodiment 25. The cured leaf of any one of embodiments 18 to 24, wherein said modification in said modified tobacco plant comprises a transgene encoding a protein comprising a sequence having at least 50%, 55%, 60%, 65%, 70%, 75%, 80%, 85%, 90%, 95%, 97%, 98%, 99%, or 100% identity to a sequence selected from the group consisting of SEQ ID No. 1 to 23 and 47 to 52.

Embodiment 26. The cured leaf of any one of embodiments 18 to 25, wherein said modification in said modified tobacco plant comprises a transgene that targets a gene comprising a sequence having at least 50%, 55%, 60%, 65%, 70%, 75%, 80%, 85%, 90%, 95%, 97%, 98%, 99%, or 100% identity to a sequence selected from the group consisting of SEQ ID No. 24 to 46 and 53 to 58.

Embodiment 27. The cured leaf of any one of embodiments 1 to 26, wherein said cured leaf comprises a reduced level of nitrite compared to said control cured leaf.

Embodiment 28. The cured leaf of any one of embodiments 1 to 27, wherein said cured leaf is flue-cured tobacco, air-cured burley tobacco, air-cured dark tobacco, fire-cured dark tobacco, or oriental tobacco.

Embodiment 29. Cured leaf from a modified tobacco plant comprising a reduced level of one or more tobacco-specific nitrosamines (TSNAs) and further comprising an increased level of one or more antioxidants, wherein said reduced and increased levels are compared to a control tobacco plant of the same variety when grown and cured under comparable conditions.

Embodiment 30. The cured leaf from a modified tobacco plant of embodiment 29, wherein said cured leaf from a modified tobacco plant comprises an increased level of oxygen radical absorbance capacity (ORAC) compared to said control tobacco plant when grown and cured under-grown and cured under comparable conditions.

Embodiment 31. The cured leaf from a modified tobacco plant of any one of embodiments 29 or 30, wherein said cured leaf from a modified tobacco plant comprises a reduced level of nitrite compared to said control tobacco plant when grown and cured under comparable conditions.

Embodiment 32. The cured leaf from a modified tobacco plant of any one of embodiments 29 to 31, wherein said cured leaf from a modified tobacco plant comprises a reduced level of total TSNAs compared to said control tobacco plant when grown and cured under comparable conditions.

Embodiment 33. The cured leaf from a modified tobacco plant of any one of embodiments 29 to 32, wherein said one or more antioxidants are tobacco endogenous antioxidants.

Embodiment 34. Cured leaf from a modified tobacco plant comprising a reduced level of one or more tobacco-specific nitrosamines (TSNAs) and further comprising a reduced level of nitrite, wherein said reduced levels are compared to cured leaf from a control tobacco plant of the same variety when grown and cured under comparable conditions.

Embodiment 35. The cured leaf from a modified tobacco plant of embodiment 34, wherein said cured leaf from a modified tobacco plant comprises an increased level of oxygen radical absorbance capacity (ORAC) compared to said control tobacco plant when grown and cured under comparable conditions.

Embodiment 36. Cured leaf from a modified tobacco plant comprising a reduced level of one or more tobacco-specific nitrosamines (TSNAs) and further comprising an increased level of oxygen radical absorbance capacity (ORAC), and wherein said reduced and increased levels are compared to cured leaf from a control tobacco plant of the same variety when grown and cured under comparable conditions.

Embodiment 37. The cured leaf from a modified tobacco plant of any one of embodiments 30, 35, or 36, wherein said increased level of oxygen radical absorbance capacity (ORAC) is based on a green leaf sample or cured leaf sample.

Embodiment 38. The cured leaf from a modified tobacco plant of any one of embodiments 29 to 37, wherein said one or more tobacco-specific nitrosamines (TSNAs) are selected from the group consisting of N'-nitrosonornicotine (NNN), 4-methylnitrosoamino-1-(3-pyridyl)-1-butanone (NNK), N'-nitrosoanatabine (NAT) N'-nitrosoanabasine (NAB), and any combination thereof.

Embodiment 39. The cured leaf from a modified tobacco plant of any one of embodiments 29 to 38, wherein said increased level of said one or more TSNAs is based on cured leaf sample.

Embodiment 40. The cured leaf from a modified tobacco plant of any one of embodiments 29 to 39, wherein the level of said one or more TSNAs is measured based on a freeze-dried cured leaf sample using liquid chromatograph with tandem mass spectrometry (LC/MS/MS).

Embodiment 41. The cured leaf from a modified tobacco plant of any one of embodiments 29 to 33, wherein said one or more antioxidants are selected from the group consisting of anthocyanidin, flavanone, flavanol, flavone, flavonol, isoflavone, hydroxybenzoic acid, hydroxycinnamic acid, ellagitannin, stibene, lignan, carotenoids, and glycyrrhzin.

Embodiment 42. The cured leaf from a modified tobacco plant of any one of embodiments 29 to 33, wherein said one or more antioxidants are selected from the group consisting of Delphnidin, Cyanidin, Procyanidin, Prodelphinidin, Hesperetin, Naringenin, Catechin, Epicatechin, Apigenin, Luteonin, Quercetin, Myricetin, Rutin, Genistein, Daidzein, Gallic acid, Vanillic acid, Protocatechuic acid, Ferunic acid, Cinnamic acid, Coumeric acid, Chlorogenic acid, Coffeic acid, ferulic acid, Sanguiin, Resveratrol, Sesamin, Caretonoids, and Vitamin C.

Embodiment 43. The cured leaf from a modified tobacco plant of any one of embodiments 29 to 42, wherein said modified tobacco plant comprises an antioxidant that is undetectable in said cured leaf from a control plant.

Embodiment 44. The cured leaf of a modified tobacco plant of any one of embodiments 29 to 43, wherein said modified tobacco plant comprises an antioxidant that does not exist in said cured leaf from a control plant.

Embodiment 45. The cured leaf from a modified tobacco plant of any one of embodiments 29 to 44, wherein said cured leaf from a modified tobacco plant comprises one or more mutations capable of providing said reduced level of one or more TSNAs.

Embodiment 46. The cured leaf from a modified tobacco plant of embodiment 45, wherein said one or more mutations are further capable of providing one or more traits selected from the group consisting of:
  A. a reduced level of nitrite,
  B. an increased level of oxygen radicle absorbance capacity (ORAC), and
  C. an increased level of one or more antioxidants;
  D. wherein said reduced or increased level is compared to said cured leaf of a control tobacco plant when grown and cured under comparable.

Embodiment 47. The cured leaf from a modified tobacco plant of any one of embodiments 45 or 46, wherein said one or more mutations comprise a mutation type selected from the group consisting of an insertion, a deletion, an inversion, a duplication, a substitution, and a combination thereof.

Embodiment 48. The cured leaf from a modified tobacco plant of any one of embodiments 45 to 47, wherein said one or more mutations are capable of activating one or more genes encoding a biosynthetic enzyme, a regulatory transcription factor, a transporter, a catabolic enzyme, or a combination thereof, for one or more antioxidants.

Embodiment 49. The cured leaf from a modified tobacco plant of any one of embodiments 45 to 48, wherein said one or more mutations are in one or more genes encoding a biosynthetic enzyme, a regulatory transcription factor, a transporter, a catabolic enzyme, or a combination thereof, for one or more antioxidants selected from the group consisting of anthocyanidin, flavanone, flavanol, flavone, flavonol, isoflavone, hydroxybenzoic acid, hydroxycinnamic acid, ellagitannin, stibene, lignan, carotenoids, and glycyrrhzin.

Embodiment 50. The cured leaf from a modified tobacco plant of any one of embodiments 45 to 49, wherein said one or more mutations are in one or more genes encoding a biosynthetic enzyme, a regulatory transcription factor, a transporter, a catabolic enzyme, or a combination thereof, for one or more antioxidants selected from the group consisting of Delphnidin, Cyanidin, Procyanidin, Prodelphinidin, Hesperetin, Naringenin, Catechin, Epicatechin, Apigenin, Luteonin, Quercetin, Myricetin, Rutin, Genistein, Daidzein, Gallic acid, Vanillic acid, Protocatechuic acid, Ferunic acid, Cinnamic acid, Coumeric acid, Chlorogenic acid, Coffeic acid, ferulic acid, Sanguiin, Resveratrol, Sesamin, Caretonoids, and Vitamin C.

Embodiment 51. The cured leaf from a modified tobacco plant of any one of embodiments 45 to 50, wherein said one or more mutations are introduced via a system selected from the group consisting of chemical mutagenesis, irradiation mutagenesis, transposon mutagenesis, *Agrobacterium*-mediated transformation, protoplast transformation, electroporation, ballistic transformation, a meganuclease, a zinc-finger nuclease (ZFN), a transcription activator-like effector nuclease (TALEN), a clustered regularly-interspaced short palindromic repeats (CRISPR)/Cas9 system, a CRISPR/Cpf1 system, a CRISPR/Csm1 system, and a combination thereof.

Embodiment 52. The modified tobacco plant of any one of embodiments 45 to 51, one or more mutations are in a gene encoding a polypeptide having at least 50%, 55%, 60%, 65%, 70%, 75%, 80%, 85%, 90%, 95%, 97%, 98%, 99%, or 100% identity to a sequence selected from the group consisting of SEQ ID No. 1 to 23 and 47 to 52.

Embodiment 53. The modified tobacco plant of any one of embodiments 45 to 52, one or more mutations are in a gene comprise a coding sequence having at least 50%, 55%, 60%, 65%, 70%, 75%, 80%, 85%, 90%, 95%, 97%, 98%, 99%, or 100% identity to a sequence selected from the group consisting of SEQ ID No. 24 to 46 and 53 to 58.

Embodiment 54. The modified tobacco plant of any one of embodiments 29 to 44, wherein said modified tobacco plant comprises one or more transgenes capable of providing said reduced level of one or more TSNAs in cured leaf.

Embodiment 55. The cured leaf from a modified tobacco plant of embodiment 54, wherein said one or more transgenes further cause said one or more traits selected from the group consisting of:
A. a reduced level of nitrite,
B. an increased level of oxygen radicle absorbance capacity (ORAC), and
C. an increased level of one or more antioxidants;
D. wherein said reduced or increased level is compared to said cured leaf from a control tobacco plant when grown and cured under comparable.

Embodiment 56. The modified tobacco plant of any one of embodiments 54 or 55, wherein said one or more transgenes comprises a promoter selected from the group consisting of a constitutive promoter, an inducible promoter, and a tissue-preferred promoter.

Embodiment 57. The modified tobacco plant of any one of embodiments 54 to 56, wherein said one or more transgenes comprises a leaf-specific promoter, a shoot-specific promoter, or a root-specific promoter.

Embodiment 58. The modified tobacco plant of any one of embodiments 54 to 57, wherein said one or more transgenes encode a biosynthetic enzyme, a regulatory transcription factor, a transporter, a catabolic enzyme, or a combination thereof, for one or more antioxidants selected from the group consisting of anthocyanidin, flavanone, flavanol, flavone, flavonol, isoflavone, hydroxybenzoic acid, hydroxycinnamic acid, ellagitannin, stibene, lignan, carotenoids, and glycyrrhzin.

Embodiment 59. The modified tobacco plant of any one of embodiments 54 to 58, wherein said one or more transgenes encode a biosynthetic enzyme, a regulatory transcription factor, a transporter, a catabolic enzyme, or a combination thereof, for one or more antioxidants selected from the group consisting of Delphnidin, Cyanidin, Procyanidin, Prodelphinidin, Hesperetin, Naringenin, Catechin, Epicatechin, Apigenin, Luteonin, Quercetin, Myricetin, Rutin, Genistein, Daidzein, Gallic acid, Vanillic acid, Protocatechuic acid, Ferunic acid, Cinnamic acid, Coumeric acid, Chlorogenic acid, Coffeic acid, ferulic acid, Sanguiin, Resveratrol, Sesamin, Caretonoids, and Vitamin C.

Embodiment 60. The modified tobacco plant of any one of embodiments 54 to 59, wherein said one or more transgenes encodes one or more polypeptides having at least 50%, 55%, 60%, 65%, 70%, 75%, 80%, 85%, 90%, 95%, 97%, 98%, 99%, or 100% identity to a sequence selected from the group consisting of SEQ ID No. 1 to 23 and 47 to 52.

Embodiment 61. The modified tobacco plant of any one of embodiments 54 to 60, wherein said one or more transgenes targets one or more endogenous genes having at least 50%, 55%, 60%, 65%, 70%, 75%, 80%, 85%, 90%, 95%, 97%, 98%, 99%, or 100% identity to a sequence selected from the group consisting of SEQ ID No. 24 to 46 and 53 to 58.

Embodiment 62. The modified tobacco plant of any one of embodiments 54 to 61, wherein said one or more transgenes comprises one or more polynucleotide sequences encoding one or more polypeptides having at least 50%, 55%, 60%, 65%, 70%, 75%, 80%, 85%, 90%, 95%, 97%, 98%, 99%, or 100% identity to a sequence selected from the group consisting of SEQ ID No. 1 to 23 and 47 to 52.

Embodiment 63. The modified tobacco plant of any one of embodiments 54 to 62, wherein said one or more transgenes comprise a sequence having at least 50%, 55%, 60%, 65%, 70%, 75%, 80%, 85%, 90%, 95%, 97%, 98%, 99%, or 100% identity to a sequence selected from the group consisting of SEQ ID No. 24 to 46 and 53 to 58.

Embodiment 64. The modified tobacco plant of any one of embodiments 54 to 63, wherein said one or more transgenes comprise a sequence having at least 50%, 55%, 60%, 65%, 70%, 75%, 80%, 85%, 90%, 95%, 97%, 98%, 99%, or 100% identity to a sequence selected from the group consisting of SEQ ID No. 24 to 46 and 53 to 58.

Embodiment 65. The modified tobacco plant of any one of embodiments 54 to 64, wherein said modified tobacco plant is a cis-genic plant.

Embodiment 66. The modified tobacco plant of any one of embodiments 29 to 65, wherein said modified tobacco plant has a similar or higher leaf yield compared to said control tobacco plant when grown and cured under comparable conditions.

Embodiment 67. The modified tobacco plant of embodiment 66, wherein said higher leaf yield is at least 0.5%, 1%, 2.5%, 5%, 10%, 15%, or at least 20% higher.

Embodiment 68. The modified tobacco plant of any one of embodiments 29 to 66, wherein said modified tobacco plant has a similar plant height compared to said control tobacco plant when grown and cured under comparable conditions.

Embodiment 69. The modified tobacco plant of embodiment 68, wherein said similar plant height is within 1%, 5%, 10%, 20%, or 25%.

Embodiment 70. The modified tobacco plant of any one of embodiments 29 to 68, wherein said modified tobacco plant has a similar cured leaf chemistry profile compared to said control tobacco plant when grown and cured under comparable conditions.

Embodiment 71. The modified tobacco plant of any one of embodiments 29 to 68, wherein said modified tobacco plant produces cured leaf that has a similar or higher USDA grade index value compared to cured leaf from said control tobacco plant when grown and cured under comparable conditions.

Embodiment 72. The modified tobacco plant of embodiment 45 or 54, wherein said modified tobacco plant is homozygous for said one or more transgenes or said one or more mutations.

Embodiment 73. The modified tobacco plant of any one of embodiments 45, 54, or 72, wherein said modified tobacco plant is hemizygous for said one or more transgenes or said one or more mutations.

Embodiment 74. The modified tobacco plant of any one of embodiments 45, 54, 72, or 73, wherein said modified tobacco plant is heterozygous for said one or more transgenes or said one or more mutations.

Embodiment 75. The modified tobacco plant of any one of embodiments 29 to 74, wherein said modified tobacco plant further comprises reduced nicotine demethylase activity compared to said control plant when grown and cured under comparable conditions.

Embodiment 76. The modified tobacco plant of embodiment 75, wherein said tobacco plant comprises at least one mutation in a nicotine demethylase gene selected from the group consisting of CYP82E4, CYP82E5, CYP82E10, and a combination thereof.

Embodiment 77. The cured leaf from a modified tobacco plant of any one of embodiments 29 to 75, wherein said modified tobacco plant further comprises a reduced level of total alkaloids compared to said cured leaf from a control plant when grown and cured under comparable conditions.

Embodiment 78. The cured leaf from a modified tobacco plant of any one of embodiments 29 to 77, wherein said modified tobacco plant further comprises a substantially similar level of total alkaloids compared to said cured leaf from a control plant when grown and cured under comparable conditions.

Embodiment 79. The cured leaf from a modified tobacco plant of any one of embodiments 29 to 78, wherein said modified tobacco plant further comprises a reduced level of nicotine compared to said cured leaf from a control plant when grown and cured under comparable conditions.

Embodiment 80. The cured leaf from a modified tobacco plant of any one of embodiments 29 to 79, wherein said modified tobacco plant further comprises a substantially similar level of nicotine compared to said cured leaf from a control plant when grown and cured under comparable conditions.

Embodiment 81. The modified tobacco plant of embodiment any one of embodiments 29 to 80, wherein said modified plant is selected from the group consisting of a flue-cured variety, a Burley variety, a Maryland variety, a dark variety, and an Oriental variety.

Embodiment 82. The modified tobacco plant of any one of embodiments 29 to 81, wherein said modified tobacco plant is selected from the group consisting a BU 64 plant, a CC 101 plant, a CC 200 plant, a CC 13 plant, a CC 27 plant, a CC 33 plant, a CC 35 plant, a CC 37 plant, a CC 65 plant, a CC 67 plant, a CC 301 plant, a CC 400 plant, a CC 500 plant, CC 600 plant, a CC 700 plant, a CC 800 plant, a CC 900 plant, a CC 1063 plant, a Coker 176 plant, a Coker 319 plant, a Coker 371 Gold plant, a Coker 48 plant, a CU 263 plant, a DF911 plant, a *Galpao* plant, a GL 26H plant, a GL 338 plant, a GL 350 plant, a GL 395 plant, a GL 600 plant, a GL 737 plant, a GL 939 plant, a GL 973 plant, a GF 157 plant, a GF 318 plant, an RJR 901 plant, an HB 04P plant, a K 149 plant, a K 326 plant, a K 346 plant, a K 358 plant, a K394 plant, a K 399 plant, a K 730 plant, an NC 196 plant, an NC 37NF plant, an NC 471 plant, an NC 55 plant, an NC 92 plant, an NC2326 plant, an NC 95 plant, an NC 925 plant, a PVH 1118 plant, a PVH 1452 plant, a PVH 2110 plant, a PVH 2254 plant, a PVH 2275 plant, a VA 116 plant, a VA 119 plant, a KDH 959 plant, a KT 200 plant, a KT204LC plant, a KY 10 plant, a KY 14 plant, a KY 160 plant, a KY 17 plant, a KY 171 plant, a KY 907 plant, a KY 907LC plant, a KTY14×L8 LC plant, a Little Crittenden plant, a McNair 373 plant, a McNair 944 plant, a male sterile KY 14×L8 plant, a Narrow Leaf Madole plant, a MS KY171 plant, a Narrow Leaf Madole (phph) plant, a MS Narrow Leaf Madole plant, a MS TND950 plant, a PD 7302LC plant, a PD 7305LC plant, a PD 7309LC plant, a PD 7312LC plant, a PD 7318LC plant, a PD 7319LC plant, a MSTKS 2002 plant, a TKF 2002 plant, a TKF 6400 plant, a TKF 4028 plant, a TKF 4024 plant, a KT206LC plant, a KT209LC plant, a KT210LC plant, a KT212LC plant, an NC 100 plant, an NC 102 plant, an NC 2000 plant, an NC 291 plant, an NC 297 plant, an NC 299 plant, an NC 3 plant, an NC 4 plant, an NC 5 plant, an NC 6 plant, an NC7 plant, an NC 606 plant, an NC 71 plant, an NC 72 plant, an NC 810 plant, an NC BH 129 plant, an NC 2002 plant, a Neal Smith Madole plant, an OXFORD 207 plant, a 'Perique' plant, a PVH03 plant, a PVH09 plant, a PVH19 plant, a PVH50 plant, a PVH51 plant, an R 610 plant, an R 630 plant, an R 7-11 plant, an R 7-12 plant, an RG 17 plant, an RG 81 plant, an RG H51 plant, an RGH 4 plant, an RGH 51 plant, an RS 1410 plant, a Speight 168 plant, a Speight 172 plant, a Speight 179 plant, a Speight 210 plant, a Speight 220 plant, a Speight 225 plant, a Speight 227 plant, a Speight 234 plant, a Speight G-28 plant, a Speight G-70 plant, a Speight H-6 plant, a Speight H20 plant, a Speight NF3 plant, a TI 1406 plant, a TI 1269 plant, a TN 86 plant, a TN86LC plant, a TN 90 plant, a TN90LC plant, a TN 97 plant, a TN97LC plant, a TN D94 plant, a TN D950 plant, a TR (Tom Rosson) Madole plant, a VA 309 plant, and a VA 359 plant.

Embodiment 83. The modified tobacco plant of any one of embodiments 29 to 82, wherein said modified tobacco plant is a hybrid.

Embodiment 84. The modified tobacco plant of any one of embodiments 29 to 83, wherein said modified tobacco plant is male sterile or cytoplasmically male sterile (CMS).

Embodiment 85. The modified tobacco plant of any one of embodiments 29 to 84, wherein said modified tobacco plant is female sterile.

Embodiment 86. The cured tobacco leaf or modified tobacco plant of any one of embodiments 29 to 85, wherein said reduced or increased level is within about 10%, within about 20%, within about 30%, within about 40%, within about 50%, within about 60%, within about 70%, within about 80%, within about 90%, within about 92%, within about 94%, within about 95%, within about 96%, within about 97%, within about 98%, or within about 99% lower or higher than the level in said control cured tobacco leaf or tobacco plant when grown and cured under comparable conditions.

Embodiment 87. The cured tobacco leaf or modified tobacco plant of any one of embodiments 29 to 86, wherein said reduced or increased level is within about 1 fold, within about 2 folds, within about 3 folds, within about 4 folds, within about 5 folds, within about 6 folds, within about 7 folds, within about 8 folds, within about 9 folds, within about 10 folds, within about 15 folds, within about 20 folds, within about 25 folds, or within about 30 folds lower or higher than the level in said control cured tobacco leaf or tobacco plant when grown and cured under comparable conditions.

Embodiment 88. The cured tobacco leaf or modified tobacco plant of any one of embodiments 29 to 87, wherein said reduced or increased level is at least about 10%, at least about 20%, at least about 30%, at least about 40%, at least about 50%, at least about 60%, at least about 70%, at least about 80%, at least about 90%, at least about 92%, at least about 94%, at least about 95%, at least about 96%, at least about 97%, at least about 98%, or at least about 99% lower or higher than the level in said control cured tobacco leaf or tobacco plant when grown and cured under comparable conditions.

Embodiment 89. The cured tobacco leaf or modified tobacco plant of any one of embodiments 29 to 88, wherein said reduced or increased level is at least about 1 fold, at least about 2 folds, at least about 3 folds, at least about 4 folds, at least about 5 folds, at least about 6 folds, at least about 7 folds, at least about 8 folds, at least about 9 folds, at least about 10 folds, at least about 15 folds, at least about 20 folds, at least about 25 folds, or at least about 30 folds lower or higher than the level in said control cured tobacco leaf or tobacco plant when grown and cured under comparable conditions.

Embodiment 90. The cured tobacco leaf or modified tobacco plant of any one of embodiments 29 to 89, wherein said reduced or increased level is about 10%, about 20%, about 30%, about 40%, about 50%, about 60%, about 70%, about 80%, about 90%, about 92%, about 94%, about 95%, about 96%, about 97%, about 98%, or about 99% lower or higher than the level in said control cured tobacco leaf or tobacco plant when grown and cured under comparable conditions.

Embodiment 91. The cured tobacco leaf or modified tobacco plant of any one of embodiments 29 to 90, wherein said reduced or increased level is about 1 fold, about 2 folds, about 3 folds, about 4 folds, about 5 folds, about 6 folds, about 7 folds, about 8 folds, about 9 folds, about 10 folds, about 15 folds, about 20 folds, about 25 folds, or about 30 folds lower or higher than the level in said control cured tobacco leaf or tobacco plant when grown and cured under comparable conditions.

Embodiment 92. The cured tobacco leaf or modified tobacco plant of any one of embodiments 29 to 91, wherein said reduced or increased level is about 1-2 folds, about 2-3 folds, about 3-4 folds, about 4-5 folds, about 5-6 folds, about 6-7 folds, about 7-8 folds, about 8-9 folds, about 9-10 folds, about 10-15 folds, about 15-20 folds, about 20-25 folds, about 25-30 folds, or about 30-50 folds lower or higher than the level in said control cured tobacco leaf or tobacco plant when grown and cured under comparable conditions.

Embodiment 93. The cured tobacco leaf or modified tobacco plant of any one of embodiments 29 to 92, wherein said reduced or increased level is about 1-10 folds, about 2-10 folds, about 3-10 folds, about 4-10 folds, about 5-10 folds, about 6-10 folds, about 7-10 folds, about 8-10 folds, about 9-10 folds, about 10-50 folds, about 15-50 folds, about 20-50 folds, about 25-50 folds, or about 30-50 folds lower or higher than the level in said cured tobacco leaf or control tobacco plant when grown and cured under comparable conditions.

Embodiment 94. A tobacco leaf of the modified tobacco plant of any one of embodiments 29 to 93.

Embodiment 95. The tobacco leaf of embodiment 94, wherein said tobacco leaf is cured tobacco leaf.

Embodiment 96. The tobacco leaf of any one of embodiments 94 or 95, wherein said cured tobacco leaf is air-cured, fire-cured, sun-cured, or flue-cured.

Embodiment 97. The cured tobacco leaf of any one of embodiments 94 to 96 comprising less than 2 ppm total TSNAs, wherein the level of said total TSNAs is measured based on a freeze-dried cured leaf sample using liquid chromatograph with tandem mass spectrometry (LC/MS/MS).

Embodiment 98. The cured tobacco leaf of any one of embodiments 94 to 97, wherein said cured tobacco leaf comprises less than 2, less than 1.8, less than 1.5, less than 1.2, less than 1.0, less than 0.8, less than 0.6, less than 0.4, less than 0.3, less than 0.2, less than 0.15, less than 0.1, or less than 0.05 ppm total TSNAs.

Embodiment 99. The cured tobacco leaf of any one of embodiments 94 to 98, wherein said cured tobacco leaf comprises between 2 and 0.05, between 1.8 and 0.05, between 1.5 and 0.05, between 1.2 and 0.05, between 1.0 and 0.05, between 0.8 and 0.05, between 0.6 and 0.05, between 0.4 and 0.05, between 0.3 and 0.05, between 0.2 and 0.05, between 0.15 and 0.05, or between 0.1 and 0.05 ppm total TSNAs.

Embodiment 100. The cured tobacco leaf of any one of embodiments 94 to 99, wherein said cured tobacco leaf comprises between 2 and 0.05, between 1.8 and 0.1, between 1.5 and 0.15, between 1.2 and 0.2, between 1.0 and 0.3, between 0.8 and 0.4, or between 0.6 and 0.5 ppm total TSNAs.

Embodiment 101. The cured tobacco leaf of any one of embodiments 94 to 100, comprising less than 0.08 ppm 4-methylnitrosoamino-1-(3-pyridyl)-1-butanone (NNK), wherein the level of said total TSNAs is measured based on a freeze-dried cured leaf sample using liquid chromatograph with tandem mass spectrometry (LC/MS/MS).

Embodiment 102. A tobacco product comprising cured leaf from the modified tobacco plant of any one of embodiments 29 to 85.

Embodiment 103. The tobacco product of embodiment 102, wherein said tobacco product is selected from the group consisting of a cigarette, a kretek, a bidi cigarette, a cigar, a cigarillo, a non-ventilated cigarette, a vented recess filter cigarette, pipe tobacco, snuff, snus, chewing tobacco, moist smokeless tobacco, fine cut chewing tobacco, long cut chewing tobacco, pouched chewing tobacco product, gum, a tablet, a lozenge, an e-liquid for a vaping device, and a dissolving strip.

Embodiment 104. A seed giving rise to the modified tobacco plant of any one of embodiments 29 to 85.

Embodiment 105. A method comprising:
A. planting the seed of embodiment 104; and
B. growing a tobacco plant from said seed.

Embodiment 106. A method comprising preparing a tobacco product using cured tobacco leaf from the modified tobacco plant of any one of embodiments 29 to 85.

Embodiment 107. A method of reducing the level of one or more TSNAs in cured leaf from a tobacco plant, said method comprising increasing the level of one or more antioxidants in said tobacco plant by expressing a biosynthetic enzyme, a regulatory transcription factor, a transporter, a catabolic enzyme, or a combination thereof, for said one or more antioxidants.

Embodiment 108. The method of embodiment 107, wherein said one or more antioxidants are selected from the group consisting of anthocyanidin, flavanone, flavanol, flavone, flavonol, isoflavone, hydroxybenzoic acid, hydroxycinnamic acid, ellagitannin, stibene, lignan, carotenoids, and glycyrrhzin.

Embodiment 109. The method of any one of embodiments 107 or 108, wherein said one or more antioxidants are selected from the group consisting of Delphnidin, Cyanidin, Procyanidin, Prodelphinidin, Hesperetin, Naringenin, Catechin, Epicatechin, Apigenin, Luteonin, Quercetin, Myricetin, Rutin, Genistein, Daidzein, Gallic acid, Vanillic acid, Protocatechuic acid, Ferunic acid, Cinnamic acid, Coumeric acid, Chlorogenic acid, Coffeic acid, ferulic acid, Sanguiin, Resveratrol, Sesamin, Caretonoids, and Vitamin C.

Embodiment 110. The method of any one of embodiments 107 to 109, wherein said method does not substantially reduce the level of total alkaloids in said cured leaf from a tobacco plant.

Embodiment 111. The method of one of embodiments 107 to 110, wherein said method does not substantially reduce the level of nicotine in said cured leaf from a tobacco plant.

Embodiment 112. A method for producing a tobacco plant comprising:
A. crossing at least one tobacco plant of a first tobacco variety with at least one tobacco plant of a second tobacco variety, wherein said at least one tobacco plant of said first tobacco variety is the modified tobacco plant of any one of embodiments 29 to 93; and
B. selecting for cured leaf from a progeny tobacco plant comprising a reduced level of one or more tobacco-specific nitrosamines (TSNAs) and further comprising one or more traits selected from the group consisting of
i. a reduced level of nitrite,
ii. an increased level of oxygen radical absorbance capacity (ORAC), and
iii. an increased level of one or more antioxidants;
iv. wherein said reduced or increased level is compared to cured leaf from a control tobacco plant of the same cross grown and cured under comparable conditions.

EXAMPLES

Example 1. Plant Transformation

Figure 2:
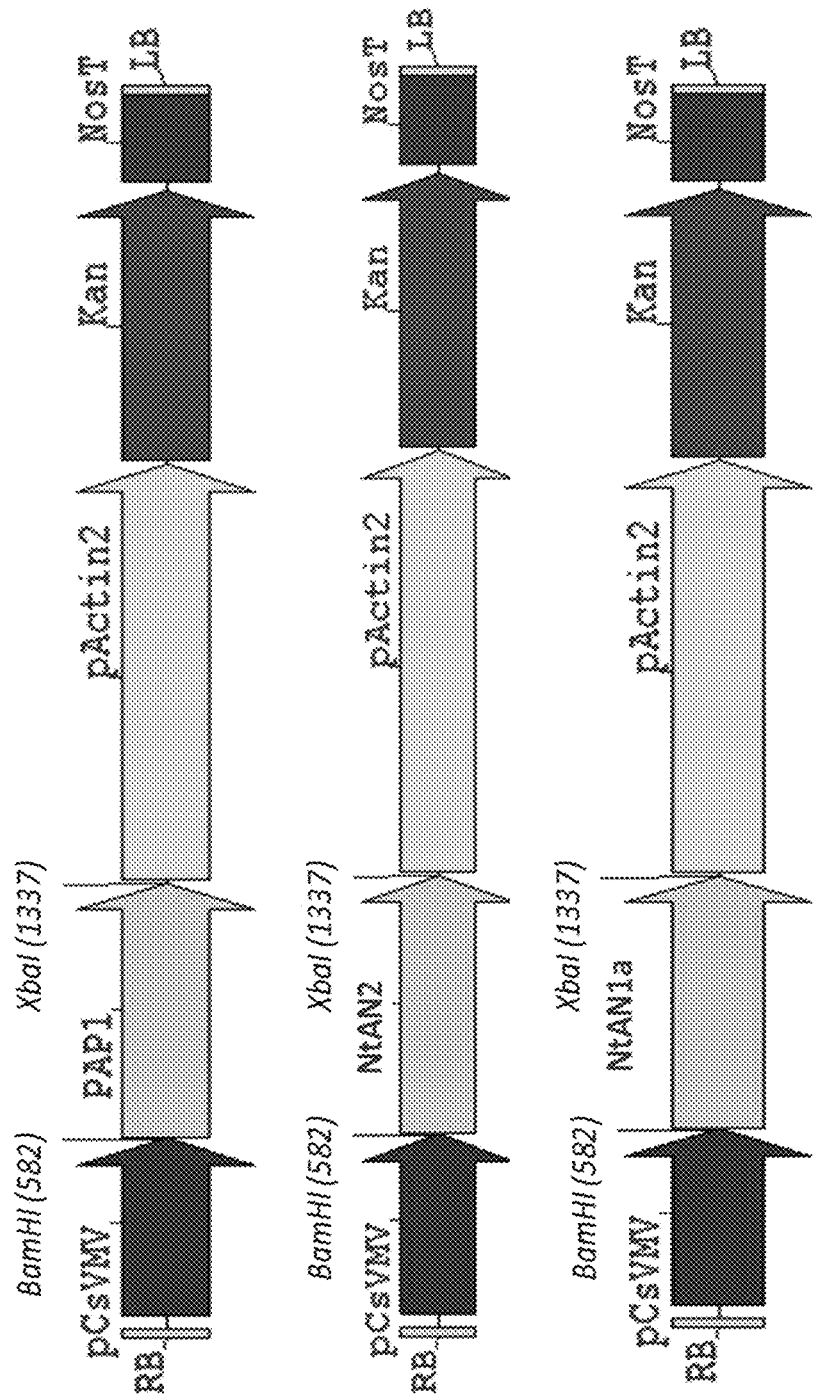
FIG. 2: Cloning of AtPAP1, NtAN2, and NtAN1 into 45-2-7 binary vector.

Tobacco plants overexpressing a gene of interest are generated via *Agrobacterium*-mediated transformation. An expression vector, p45-2-7 (FIG. 2), is used as a backbone to generate multiple transformation vectors. p45-2-7 contains a CsVMV promoter, a NOS terminator, and a cassette comprising a kanamycin selection marker (NPT II) operably linked to an Actin2 promoter and a NOS terminator. Nucleic acid vectors comprising transgenes of interest are introduced into tobacco leaf discs via *Agrobacterium* transformation. See, for example, Mayo et al., 2006, *Nat Protoc.* 1:1105-11 and Horsch et al., 1985, *Science* 227:1229-1231.

Narrow Leaf Madole (NLM) tobacco plants are grown in Magenta™ GA-7 boxes and leaf discs are cut and placed into Petri plates. *Agrobacterium tumefaciens* cells comprising a transformation vector are collected by centrifuging a 20 mL cell suspension in a 50 mL centrifuge tube at 3500 RPM for 10 minutes. The supernatant is removed and the *Agrobacterium tumefaciens* cell pellet is re-suspended in 40 mL liquid re-suspension medium. Tobacco leaf, avoiding the midrib, are cut into eight 0.6 cm discs with a #15 razor blade and placed upside down in a Petri plate. A thin layer of Murashige & Skoog with B5 vitamins liquid re-suspension medium is added to the Petri plate and the leaf discs are poked uniformly with a fine point needle. About 25 mL of the *Agrobacterium tumefaciens* suspension is added to the Petri plate and the leaf discs are incubated in the suspension for 10 minutes.

Leaf discs are transferred to co-cultivation Petri plates (1/2 MS medium) and discs are placed upside down in contact with filter paper overlaid on the co-cultivation TOM medium (MS medium with 20 g/L sucrose; 1 mg/L indole-3-acetic acid; and 2.5 mg/L 6-benzyl aminopurine (BAP)). The Petri plate is sealed with parafilm prior to incubation in dim light (60-80 mE/ms) with 18 hours on, 6 hours off photoperiods at 24 degrees Celsius for three days. After incubation, leaf discs are transferred to regeneration/selection TOM K medium Petri plates (TOM medium plus 300 mg/L kanamycin). Leaf discs are sub-cultured bi-weekly to fresh TOM K medium in dim light with 18 hours on, 6 hours off photoperiods at 24 degrees Celsius until shoots become excisable. Shoots from leaf are removed with forceps and inserted in MS basal medium with 100 mg/L kanamycin. Shoots on MS basal medium with 100 mg/L kanamycin are incubated at 24 degrees Celsius with 18 hours on, 6 hours off photoperiods with high intensity lighting (6080 mE/ms) to induce rooting.

When plantlets containing both shoots and roots grow large enough (e.g., reach approximately half the height of a Magenta™ GA-7 box), they are transferred to soil. Established seedlings are transferred to a greenhouse for further analysis and to set seed. Control plants are either NLM plants that have not been transformed or NLM plants that have been transformed with an empty p45-2-7 vector.

Example 2. AtPAP1 Overexpressing Plants Comprise Reduced TSNAs

Figure 3:
FIG. 3: A control plant (left) exhibits a similar growth profile compared AtPAP1 overexpression plants (right). AtPAP1 plants exhibit a purple color due to anthocyanin accumulation.

Tobacco plants overexpressing AtPAP1 are generated via *Agrobacterium*-mediated transformation. AtPAP1, comprising SEQ ID NO:46, is incorporated into an overexpression vector and transformed into tobacco as described in Example 1. After transformation, established seedlings are transferred to a greenhouse for further analysis and to set seed. Transformed plants are developmentally similar to control plants except that they exhibit a purple color due to anthocyanin accumulation as shown in FIG. 3.

The effect of AtPAP1 overexpression on TSNA levels is determined for five T1 AtPAP1 overexpression lines (six plants each) after cultivation in the greenhouse. At flowering, the plants are topped. After four to six weeks, plants are harvested and leaf is cured in PGC chambers. Cured leaf samples are freeze dried and crushed to 1 mm.

Figure 4B:
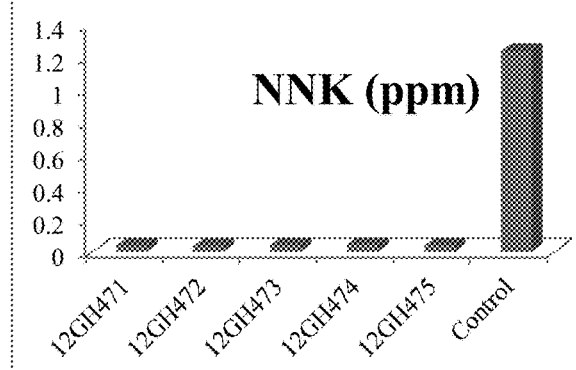
Figure 4C:
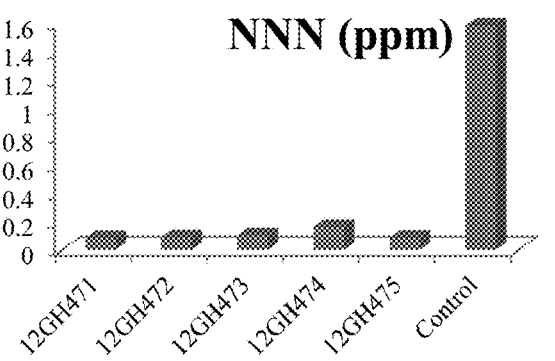
Figure 4D:
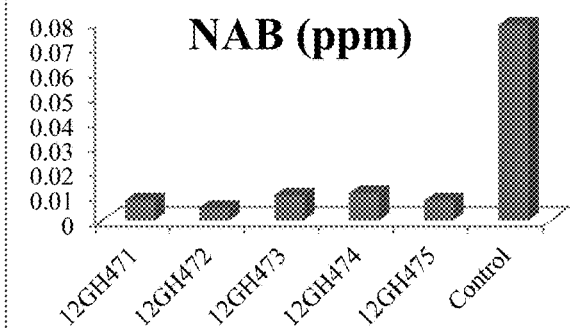
Figure 4E:
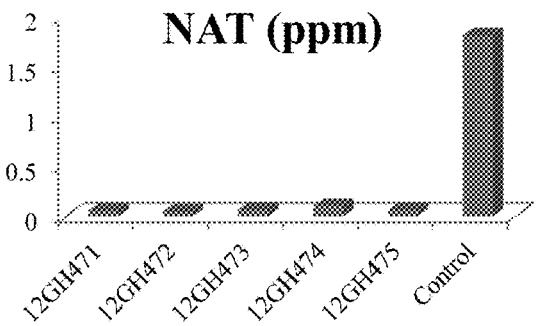

The amounts of four TSNAs are measured: N'-nitrosonornicotine (NNN), 4-methylnitrosoamino-1-(3-pyridyl)-1-butanone (NNK), N'-nitrosoanatabine (NAT) and N'-nitrosoanabasine (NAB) are measured. For TSNA analysis, 750 mg of crushed, freeze-dried leaf is added to 30 mls of 10 mM ammonium acetate. After incubation in a shaker for 30 minutes, approximately 4 mls of sample is transferred into disposable culture tubes containing 0.25 ml of concentrated ammonium hydroxide. The sample is vortexed briefly and 1.5 mls is added to a prewashed and conditioned extraction cartridge with a flow rate of 1 to 2 drops per second. Analytes are eluted from the sample using 1.5 mls of 70:30 methanol with 0.1% acetic acid. Samples are analyzed using liquid chromatography with tandem mass spectrometry (LC/MS/MS). Measurements of NNN, NNK, NAB, and NAT in AtPAP1 overexpressing plants is shown in Table 1. Total TSNA levels are considerably reduced in AtPAP1 plants as shown in FIG. 4A. Considerable reductions in NNK levels (FIG. 4B), NNN levels (FIG. 4C), NAB levels (FIG. 4D), and NAT levels (FIG. 4E) are also observed.

used to determine the ORAC measurement according to manufactures instruction (BioTek, Winooski, VT). Antioxidants are extracted from crushed tissue samples with a methanol/HCL extraction buffer (6/1, v/v). The samples are incubated for 30 minutes at 37° C. in a reaction mixture containing 75 mM phosphate buffer, pH 7.4, and 5 µM PGR. After incubation, 37° C. AAPH solution is added to the reaction mixture to a final concentration of 10 mM. Controls with all the solution components, but without the tissue samples, are used for comparison.

Figure 5:
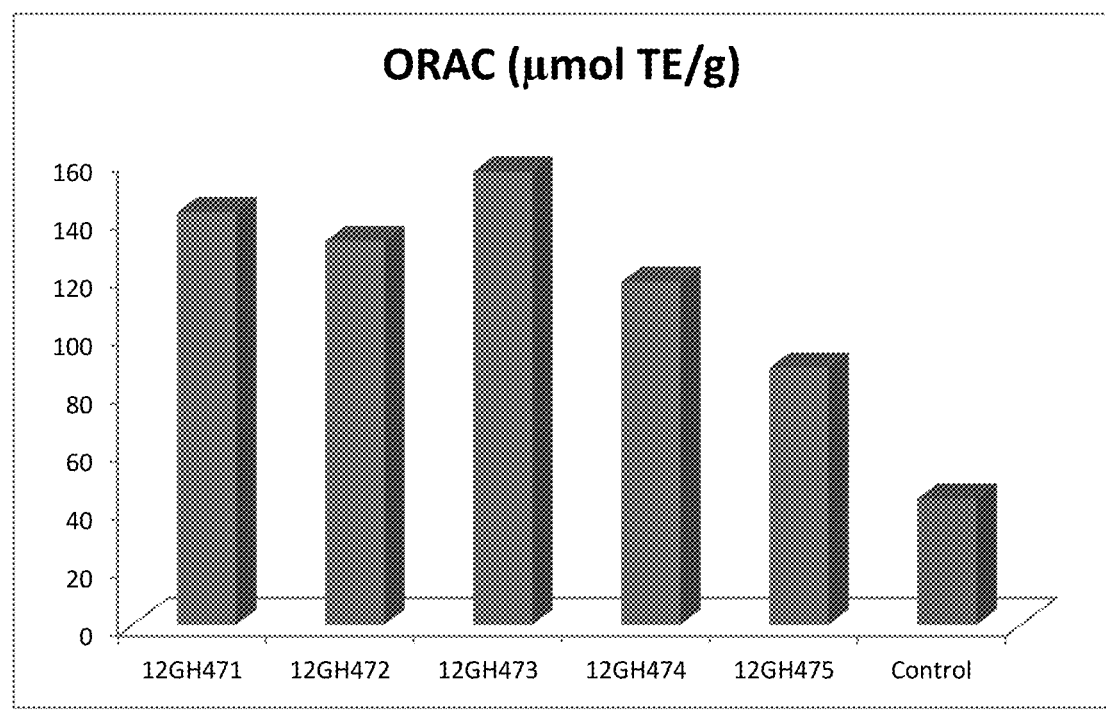
FIG. 5: Oxygen radical absorbance capacity (ORAC) values in AtPAP1 overexpression plants are increased compared to controls.

Reaction and control samples are shaken and the absorption (A) is recorded every 30 seconds for 180 minutes. The kinetic values are recorded as $A/A_{time0}$. ORAC scores are determined based on the Area Under Curve (AUC) values determined scores from the sample and blank. ORAC scores are assessed for all time-points until the $A/A_{time0}$ reaches a value of 0.2 using MicroCal Origin (R17.0, Boston, MA). ORAC values are recorded in FIG. 5 demonstrating increased ORAC values in AtPAP1 overexpression lines.

Example 4. Alkaloid Levels in Tobacco Plants Expressing AtPAP1

The effect of AtPAP1 overexpression on total alkaloid levels is determined for five T1 AtPAP1 overexpression lines (six plants each) after cultivation in the greenhouse. The levels of the alkaloids nicotine, nornicotine, anatabine, and anabasine are determined with Gas Chromatography followed by Mass Spectrometry (GC-MS). For example, measurement of anatabine is performed by mixing one gram of

TABLE 1

TSNA levels in AtPAP1 overexpression plants are reduced compared to controls.

| Plant ID | Variety | NNN (ppm) | NNK (ppm) | NAB (ppm) | NAT (ppm) | Total TSNA (ppm) | % TSNA Reduction |
|---|---|---|---|---|---|---|---|
| 12GH471 | t-NL Madole LC T821 (PAP1 OEX) | 0.087 | 0.035 | 0.008 | 0.059 | 0.189 | 95.98 |
| 12GH472 | t-NL Madole LC T824 (PAP1 OEX) | 0.091 | 0.031 | 0.005 | 0.048 | 0.175 | 96.28 |
| 12GH473 | t-NL Madole LC T827 (PAP1 OEX) | 0.105 | 0.037 | 0.01 | 0.069 | 0.221 | 95.30 |
| 12GH474 | t-NL Madole LC T827 (PAP1 OEX) | 0.164 | 0.043 | 0.011 | 0.103 | 0.321 | 93.18 |
| 12GH475 | t-NL Madole LC T836 (PAP1 OEX) | 0.089 | 0.036 | 0.008 | 0.067 | 0.2 | 95.75 |
| Control | NL Madole | 1.581 | 1.232 | 0.079 | 1.812 | 4.704 | — |

Example 3. AtPAP1 Overexpressing Plants Exhibit Increased Oxygen Radical Absorbance Capacity The effect of AtPAP1 overexpression on oxidative capacity is determined for five T1 AtPAP1 overexpression lines (six plants each) after cultivation in the greenhouse. Oxygen Radical Absorbance Capacity (ORAC) is measured to determine antioxidant activity in AtPAP1 overexpressing plants. Quenching of a Progallol Red (PGR) florescent probe is cured leaf tissue with 10 mls of 2N NaOH, followed by incubation at room temperature for fifteen minutes. Anatabine is then extracted by addition of 50 mls of 0.04% quinolone (w/v) dissolved in methyl-tert-butyl ether followed by rotation on a linear shaker for three hours. After phase separation, alkaloid levels are determined using an Agilent 6890 Gas Chromatograph and an Agilent 5973N Mass Spectrometer. The results of measurements for the alkaloids nicotine, nornicotine, anatabine, and anabasine are recorded in Table 2.

TABLE 2

| | | Nicotine | Nornicotine | Anabasine | Anatabine |
|---|---|---|---|---|---|
| Plant ID | Variety | (% by wt) | (% by wt) | (% by wt) | (% by wt) |
| 12GH471 | t-NL Madole LC T821 (PAP1 OEX) | 3.679 | 0.046 | 0.009 | 0.038 |
| 12GH472 | t-NL Madole LC T824 (PAP1 OEX) | 3.009 | 0.089 | 0.008 | 0.034 |
| 12GH473 | t-NL Madole LC T827 (PAP1 OEX) | 4.323 | 0.073 | 0.011 | 0.048 |
| 12GH474 | t-NL Madole LC T827 (PAP1 OEX) | 4.609 | 0.052 | 0.009 | 0.037 |
| 12GH475 | t-NL Madole LC T836 (PAP1 OEX) | 3.329 | 0.036 | 0.008 | 0.034 |
| Control | NL Madole | 5.921 | 0.09 | 0.014 | 0.074 |

Alkaloid levels in AtPAP1 overexpressing plants are mildly reduced compared to controls.

Example 5. AtPAP1 Overexpressing Plants Comprise Reduced Nitrite

The effect of AtPAP1 overexpression on nitrite and nitrate levels is determined for five T1 AtPAP1 overexpression lines (six plants each) after cultivation in the greenhouse. Cured leaf Samples are prepared as in Example 2 for LC/MS/MS and tested. Nitrite and nitrate levels as shown in FIG. 6A and FIG. 6B. The overexpression of AtPAP1 reduces the level of nitrite but not nitrate.

Figure 7:
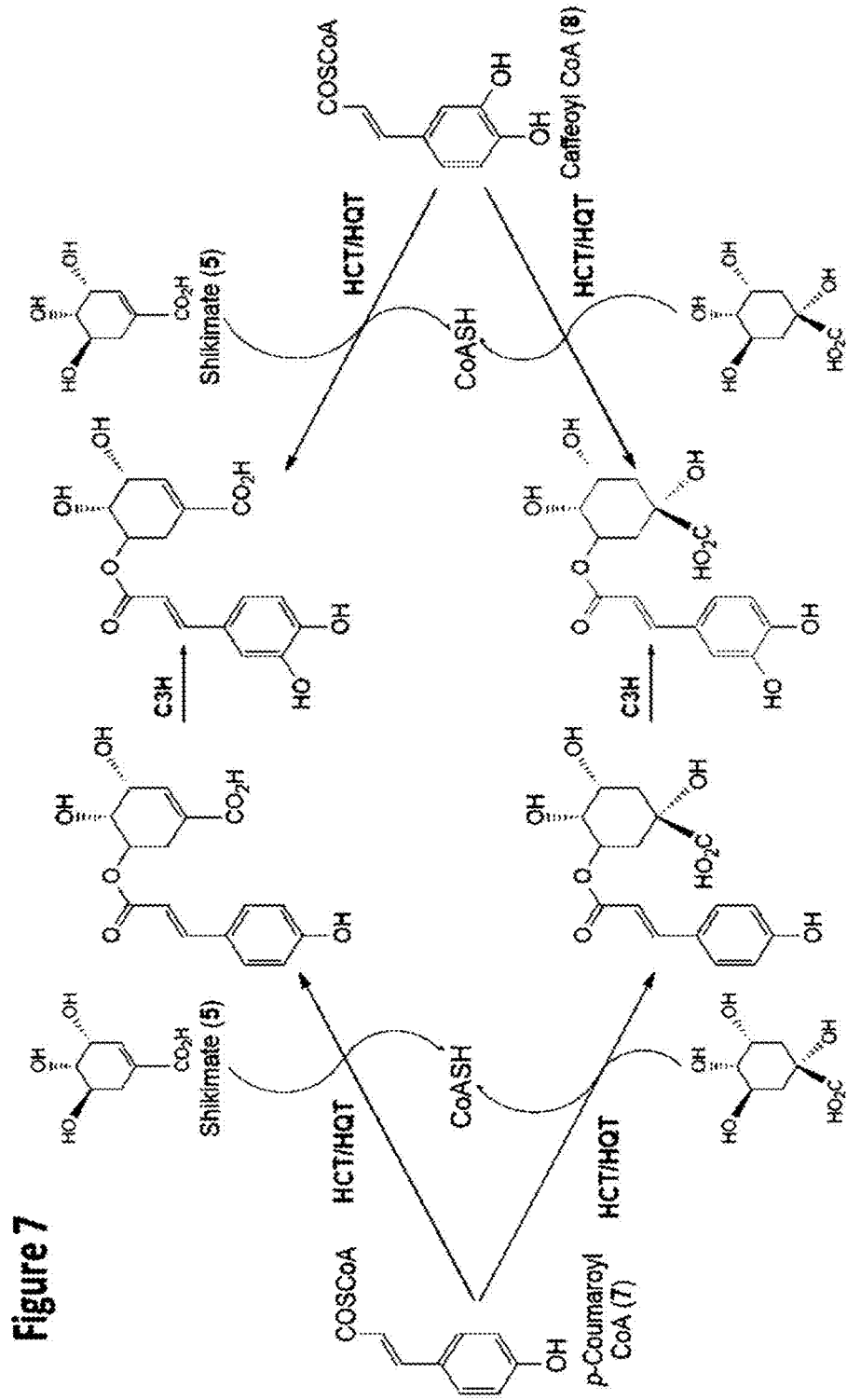
FIG. 7: HCT and HQT function in the biosynthetic pathway of Chlorogenic Acid.
Figure 8:
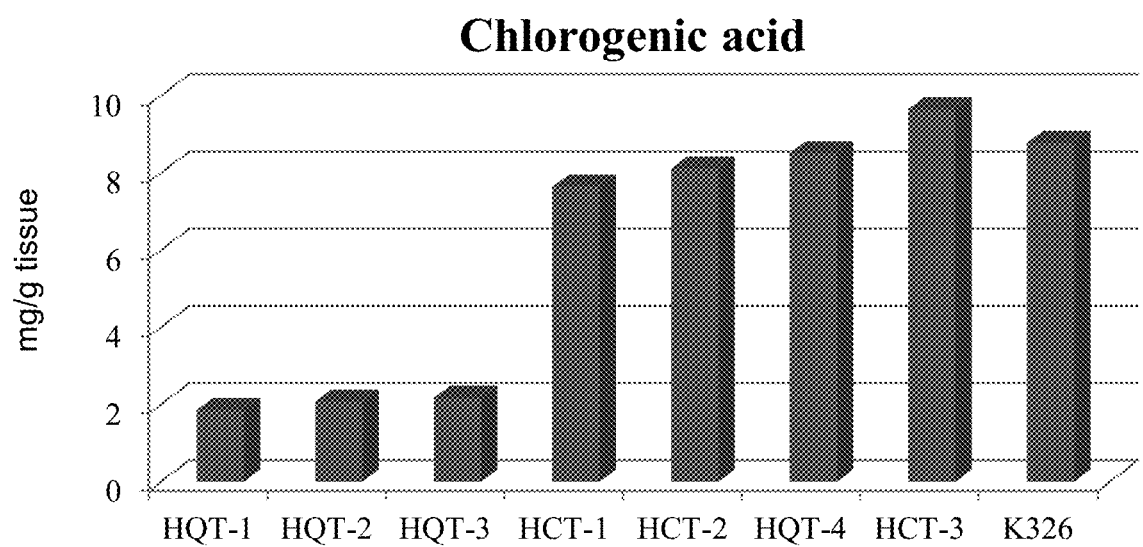
FIG. 8: Chlorogenic Acid levels are reduced in 3 of 4 HQT RNAi lines but not in HCT RNAi lines.
Figure 9:
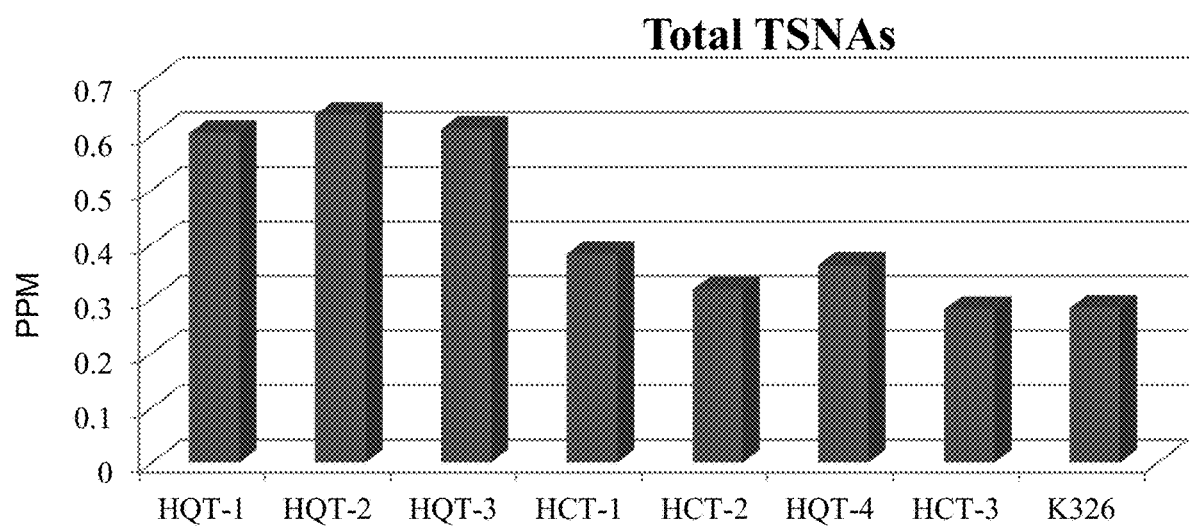
FIG. 9: Total TSNAs are increased in the 3 HQT RNAi lines with decreased Chlorogenic Acid levels.
Figure 11:
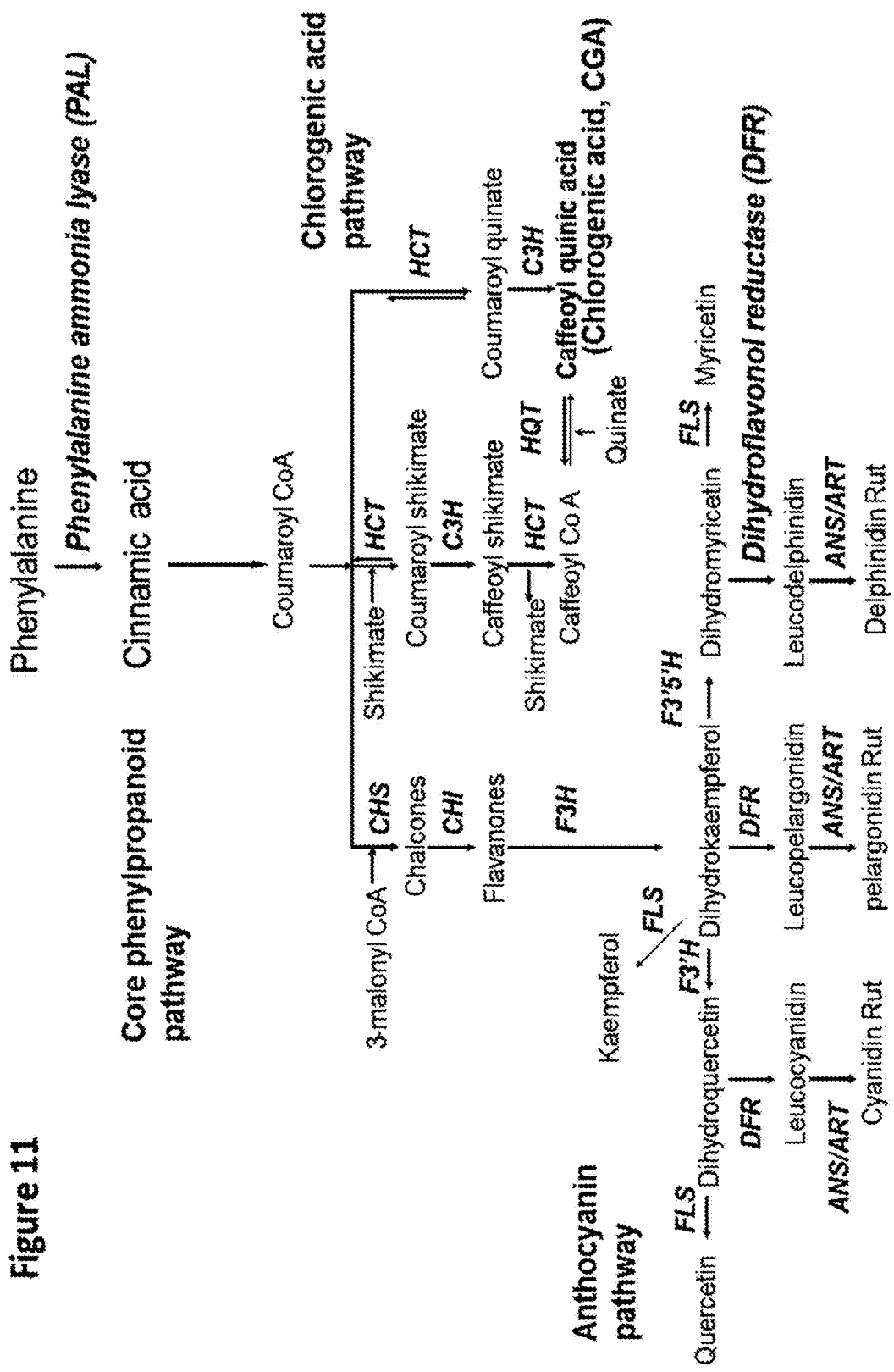
FIG. 11: The phenylpropanoid pathway can be targeted to reduce TSNA levels in tobacco by increasing antioxidant levels.
Figure 12:
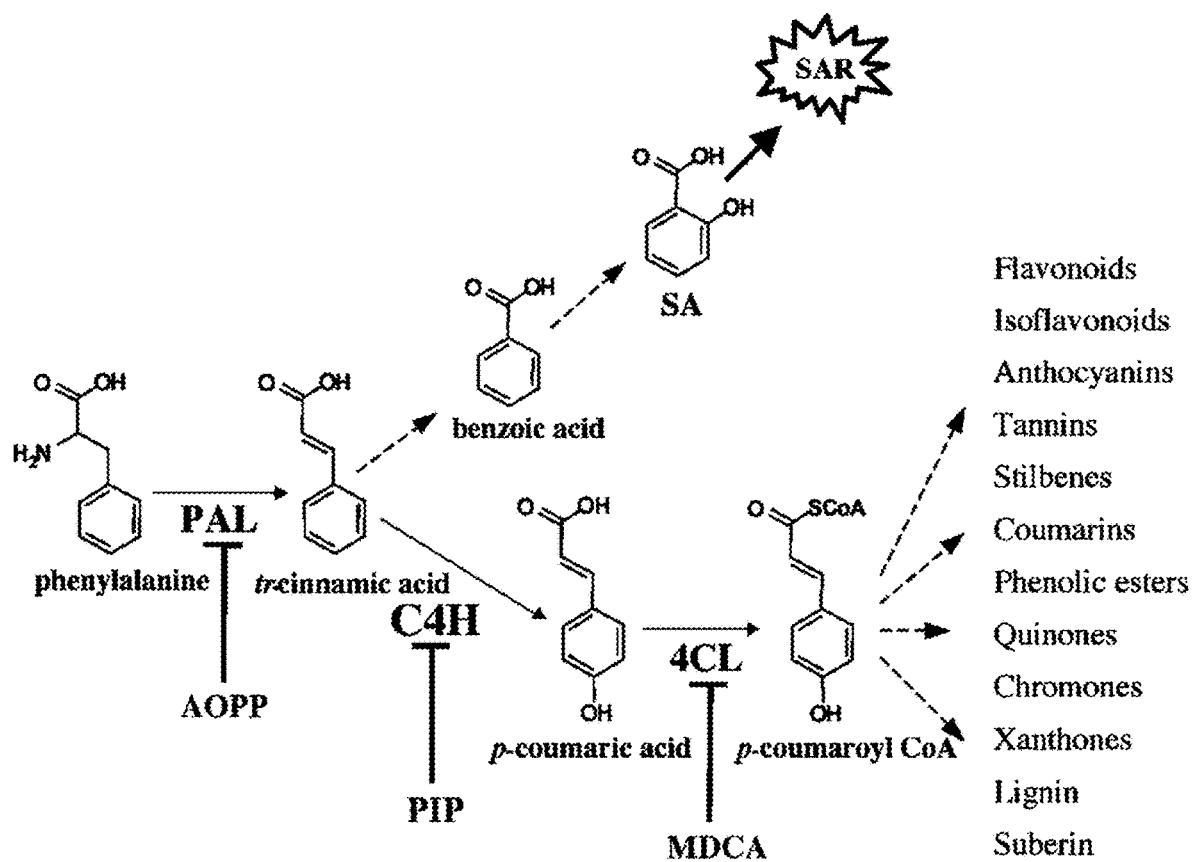
FIG. 12: The phenylpropanoid pathway leads to the biosynthesis of many antioxidants.

Example 6. Reduced Chlorogenic Acid in Tobacco Leaf Correlates with Elevated TSNA Levels The level of additional antioxidants are modulated to further demonstrate a negative correlation between antioxidants and TSNAs. Reduction of Chlorogenic acid (CGA) levels results in an increase in total TSNAs and total alkaloids. CGA or Caffeoyl quinate is generated from Caffeoyl CoA or p-Coumaroyl CoA through the activity of hydroxycinnamoyl-CoA quinate hydroxycinnamoyl transferase (HQT) and hydroxycinnamoyl-CoA shikimate/quinate hydroxycinnamoyl transferase (HCT) (Payyavula et al., 2015, Plant Biotechnology Journal, Hoffmann et al., 2004, The Plant Cell, FIG. 7). The activity of these enzymes is reduced in tobacco by silencing HCT and HQT with RNAi. Silencing HQT and HCT results in a reduction of CGA as shown in FIG. 8 and an increase in total TSNAs as shown in FIG. 9.

Transformation vectors comprising RNAi constructs are designed to inhibit the expression of tobacco genes that promote the conversion of Caffeoyl CoA or p-Coumaroyl CoA to CGA. Modified tobacco plants and control tobacco plants are created and grown as described in Example 1. Cured leaf samples from the modified tobacco plants are prepared for evaluation of TSNAs, alkaloids, and nitrite/nitrate as described in Examples 2, 4 and 5. Alkaloid levels show mild modulations as shown in Table 3. A negative correlation is observed between CGA levels and TSNA levels, as well as the levels of individual TSNAs (NNN, NNK, NAB, and NNA) as shown in FIG. 10A-E and Table 4. Nitrite levels are unchanged and nitrate levels show reductions compared to controls (Table 4).

TABLE 3

Alkaloid and CGA levels in HCT and HQT RNAi lines.

| | | Nicotine (% by wt) | Nornicotine (% by wt) | Myosmine (% by wt) | Anabasine (% by wt) | Anatabine (% by wt) | CGA(mg/g) |
|---|---|---|---|---|---|---|---|
| K326 | HQT-1 | 3.90 | 0.10775 | 0.007918 | 0.0217 | 0.109775 | 1.8525 |
| K326 | HQT-2 | 4.10 | 0.112275 | 0.006815 | 0.022825 | 0.106125 | 2.07 |
| K326 | HQT-3 | 4.04 | 0.115 | 0.006995 | 0.021025 | 0.103175 | 2.17 |
| K326 | HCT-1 | 3.59 | 0.095625 | 0.006978 | 0.018425 | 0.091025 | 7.6375 |
| K326 | HCT-2 | 3.45 | 0.083525 | 0.005678 | 0.0178 | 0.085525 | 8.1075 |
| K326 | HQT-4 | 3.93 | 0.0972 | 0.00643 | 0.01985 | 0.10085 | 8.5025 |
| K326 | HCT-3 | 3.28 | 0.07795 | 0.006198 | 0.0154 | 0.074925 | 9.65 |
| K326 | Control | 3.45 | 0.09165 | 0.007213 | 0.018575 | 0.094975 | 8.775 |

TABLE 4

TSNA, CGA, Nitrite and Nitrate levels in HQT and HCT RNAi plants.

| | | LL NNN (ppm) | LL NNK (ppm) | LL NAB (ppm) | LL NAT (ppm) | LL TSNA (ppm) | LL Nitrite (ppm) | LL Nitrate (ppm) | CGA(mg/g) |
|---|---|---|---|---|---|---|---|---|---|
| K326 | HQT-1 | 0.205 | 0.08425 | 0.02675 | 0.2875 | 0.6035 | 0.245 | 3192.5 | 1.8525 |
| K326 | HQT-2 | 0.2175 | 0.09825 | 0.0285 | 0.2925 | 0.63675 | 0.2 | 3257.5 | 2.07 |
| K326 | HQT-3 | 0.195 | 0.1265 | 0.02475 | 0.265 | 0.61125 | 0.22 | 2685 | 2.17 |
| K326 | HCT-1 | 0.13325 | 0.0635 | 0.02 | 0.165 | 0.38175 | 0.2 | 3285 | 7.6375 |
| K326 | HCT-2 | 0.0955 | 0.07025 | 0.02 | 0.13075 | 0.3165 | 0.2225 | 3202.5 | 8.1075 |

TABLE 4-continued

TSNA, CGA, Nitrite and Nitrate levels in HQT and HCT RNAi plants.

| | | LL NNN (ppm) | LL NNK (ppm) | LL NAB (ppm) | LL NAT (ppm) | LL TSNA (ppm) | LL Nitrite (ppm) | LL Nitrate (ppm) | CGA(mg/g) |
|---|---|---|---|---|---|---|---|---|---|
| K326 | HQT-4 | 0.11475 | 0.07 | 0.0215 | 0.155 | 0.36125 | 0.215 | 2655 | 8.5025 |
| K326 | HCT-3 | 0.088 | 0.0635 | 0.02 | 0.1085 | 0.28 | 0.2525 | 2945.5 | 9.65 |
| K326 | Control | 0.0885 | 0.0575 | 0.02 | 0.1165 | 0.2825 | 0.2 | 1862.5 | 8.775 |

Example 7: Increased Antioxidant Capacity in Field Grown AtPAP1 Overexpressing Plants A Ferric Reducing Antioxidant Power (FRAP) analysis is conducted on field grown tobacco plants overexpressing AtPAP1. AtPAP1 overexpression constructs are transformed into TN90 and Narrow Leaf Madole (NLM) tobacco plants as described in Example 1. Modified and unmodified control plants are grown in a field under standard field conditions. Plants are topped at flowering and leaves for analysis are collected harvest stage (4 weeks) later. At least five plants from two independent transgenic events in both the TN90 background and the NLM background and at least five plants from unmodified TN90 and NLM plants are sampled and tested. 10 mg of freeze dried leaf is taken into an Eppendorf tube and 15000 of 80% ethanol is added and sonicated for 10 minutes. After centrifuge, 5-10 µl of supernatant is used to measure antioxidant capacity.

The Ferric Reducing Antioxidant Power (FRAP) method is based on the reduction of complexes of 2,4,6-tripyridyl-s-triazine (TPTZ) with ferric chloride hexahydrate ($FeCl3 \cdot 6H2O$) which forms blue ferrous complexes after its reduction (Benzie & Strain, 1996, Analytical Biochemistry, 239, 70-76). Three solutions are used for the assay: Solution 1) 10 mmol·L-1 solution of TPTZ (0.07802 g/25 mL), in 40 mM of hydrochloric acid; Solution 2) 20 mM solution of ferric chloride hexahydrate (0.13513 g/25 mL) in ACS water; Solution 3) 20 mM acetate buffer, pH 3.6 (weight of sodium acetate trihydrate is 0.27216 g in 100 mL ACS water, adjusted to the desired pH using HCl). These three solutions (TPTZ, FeCl3, acetate buffer) are mixed in a 1:1:10 ratio. A 245 µL volume of the mixed solution is pipetted into a plastic cuvette with subsequent addition of a 5 µL sample (gallic acid, Trolox®). Absorbance is measured at primary $\lambda$ 593 nm wavelength. Different concentrations of Trolox® was used to make a standard curve and samples are compared to standard curve. Total antioxidants are calculated using the following equation $$\text{Antioxidants (nmol/mg)} = \frac{\text{nmoles present in the sample } X \text{ total sample extraction volume}}{\text{total } wt \text{ of the sample } X \text{ volume used measurement}}$$

Figure 13:
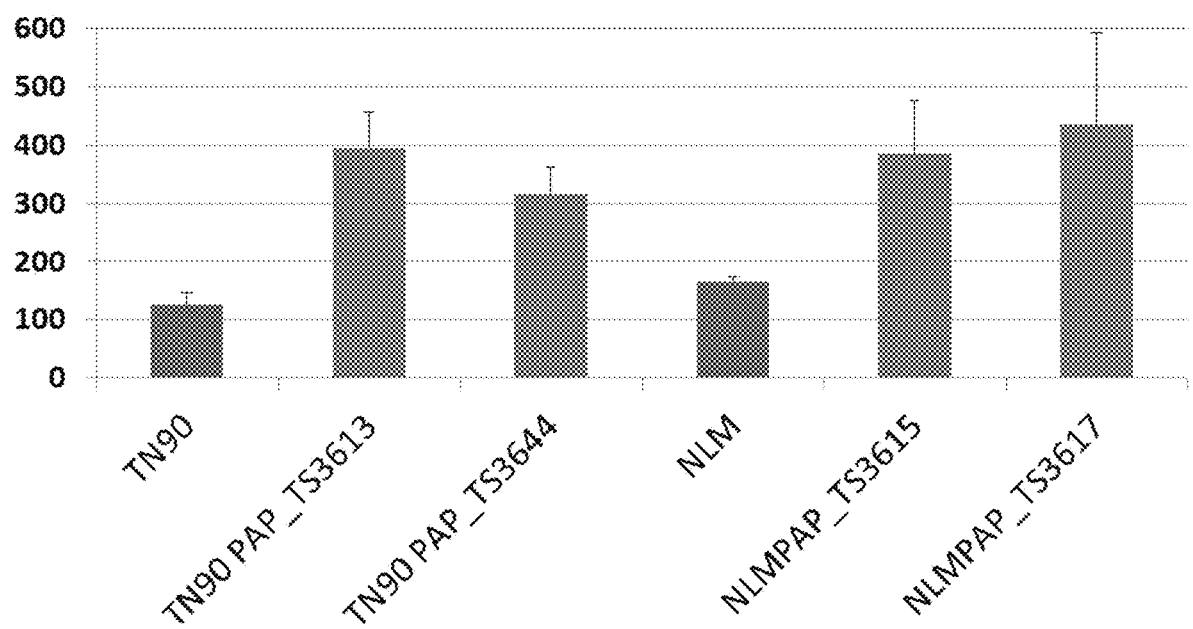
FIG. 13: Overexpression of AtPAP1 in TN90 and Narrow Leaf Madole (NLM) results in increased antioxidant capacity as measured using a FRAP assay. Measurements from leaves from at least five plants are averaged together for unmodified TN90 and NLM, two independent lines overexpressing AtPAP1 in TN90, and two independent lines overexpressing AtPAP1 in NLM are tested using a FRAP assay. Both independent lines overexpressing AtPAP1 in TN90 exhibit a highly significant increase in average antioxidant capacity (P<0.01) compared to unmodified TN90 plants. Both independent lines overexpressing AtPAP1 in NLM exhibit a highly significant increase in average antioxidant capacity (P<0.01) compared to unmodified NLM plants.

Modified tobacco plants overexpressing AtPAP1 show a significantly increased antioxidant capacity as measured by FRAP analysis compared to the unmodified controls ($P<0.01$) (FIG. 13).

Example 8. Secondary Metabolite Accumulation in Field Grown AtPAP1 Overexpressing Plants A secondary metabolite accumulation analysis is conducted on greenhouse grown AtPAP1 overexpressing plants. AtPAP1 overexpression constructs are transformed into Narrow Leaf Madole (NLM) tobacco plants as described in Example 1. Modified and unmodified control plants are grown in a greenhouse under standard conditions. Plants are topped at flowering and leaves for analysis are collected two weeks later from two independently modified NLM plants (D1 and D2) and one unmodified NLM plant. A set of Benzenoids, Flavonoids, and Phenylpropanoids show significantly increased levels in modified plants compared to unmodified plants ($P<0.01$) (See Table 5).

TABLE 5

Secondary metabolite accumulation in 35:AtPAP1 overexpressing Narrow Leaf Madole tobacco plants.

| Pathway | Biochemical Name | D1/DC | D2/DC | D1 | D2 | DC |
|---|---|---|---|---|---|---|
| Benzenoids | protocatechuic acid-3-glucoside | 109.21* | 101.57* | 5.56 | 5.17 | 0.05 |
| | 4-hydroxybenzoate | 12.26* | 11.42* | 1.37 | 1.27 | 0.11 |
| | gentisic acid-5-glucoside | 5.98* | 6.23* | 2.16 | 2.25 | 0.36 |
| | salicylate-glucoside | 5.09** | 5.85* | 0.95 | 1.10 | 0.19 |
| | benzoyl-O-glucose | 4.62* | 4.6* | 0.27 | 0.27 | 0.06 |
| | salicylate | 2.22* | 2.81* | 0.63 | 0.80 | 0.28 |
| | benzoate | 1.49 | 2.07* | 0.52 | 0.72 | 0.35 |
| Flavonoids | rutinose | 99.63* | 93.99* | 41.90 | 39.52 | 0.42 |
| | naringenin | 5.26* | 3.79* | 1.19 | 0.86 | 0.23 |
| | quercetin 3-galactoside | 2.54 | 3.11 | 0.14 | 0.17 | 0.05 |
| Phenylpropanoids | coumaroylquinate (4) | 92.06* | 45.21* | 21.81 | 10.71 | 0.24 |
| | coumaroylquinate (2) | 16.17* | 12.87* | 10.70 | 8.52 | 0.66 |
| | chlorogenate | 9.15* | 6.59* | 7.55 | 5.44 | 0.83 |
| | vanillate | 5.95* | 7.25* | 0.39 | 0.47 | 0.06 |

TABLE 5-continued

Secondary metabolite accumulation in 35:AtPAP1 overexpressing Narrow Leaf Madole tobacco plants.

| Pathway | Biochemical Name | D1/DC | D2/DC | D1 | D2 | DC |
|---------|------------------|-------|-------|-----|-----|-----|
| | cryptochlorogenic acid | 4.74* | 3.93* | 2.18 | 1.80 | 0.46 |
| | coumaroylquinate (5) | 5.74* | 5.86* | 5.44 | 5.55 | 0.95 |
| | coumaroylquinate (3) | 3.2* | 2.99* | 2.32 | 2.17 | 0.72 |
| | dihydroferulic acid | 2.45** | 2.57* | 0.74 | 0.78 | 0.30 |
| | vanillin | 2.37* | 1.82** | 0.77 | 0.60 | 0.33 |

D1 and D2 represent individual plants from independently transformed lines and DC represents an unmodified control plant.
Highly significant differences as compared to the unmodified control plant (P < 0.01) are indicated with*.
Significant differences as compared to the unmodified control plant (P < 0.05) are indicated with**.

Example 9. Expression of Additional Genes to Modulate TSNA Levels

Transformation vectors and modified tobacco plants are generated to overexpress full-length coding sequences from tobacco genes (e.g., SEQ ID NOs: 24-42, 44, 45, and 53 to 58) or non-tobacco origin genes (e.g., SEQ ID NOs: 43 and 46) that promote or are involved in the production or accumulation of one or more antioxidants (see Table 6). The overexpression of transcription factors that promote or are involved in the production or accumulation of one or more antioxidants is described below. Nucleotide (Table 7) and protein (Table 8) identity scores are shown comparing the transcription factors used in this study. Exemplary genes and their sequences are listed in the sequence listing and Table 9.

Figure 14:
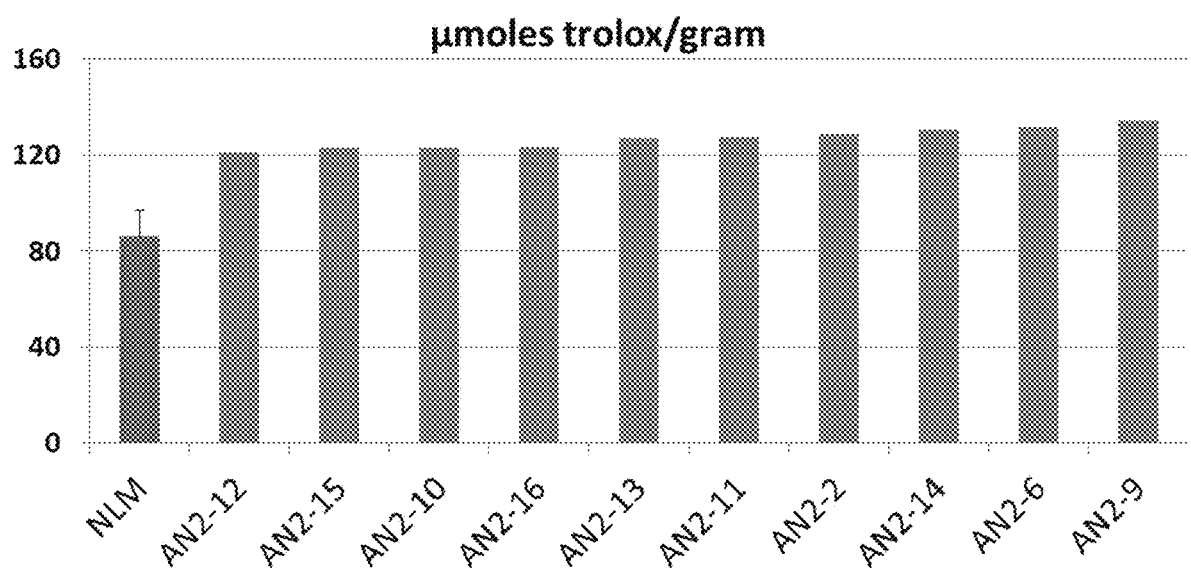
FIG. 14: Overexpression of NtAN2 (SEQ ID NO: 30) in NLM results in increased antioxidant capacity as measured using a FRAP assay. Greenhouse grown, individually tested TO plants overexpressing NtAN2 show increased antioxidant capacity compared to the average antioxidant capacity determined for at least five unmodified NLM plants.

NtAN2, SEQ ID NO: 30, is incorporated into a p45-2-7 transformation vector, and modified tobacco plants are generated, according to Example 1. Modified NLM tobacco plants (T0 and T1 generation) and control tobacco plants are grown for 4-6 weeks after transplantation to soil, harvested, and cured in PGC chambers. Cured leaf samples are prepared for evaluation of TSNAs, oxidative degradation potential, alkaloids, and nitrites/nitrates as described in Examples 2 to 5. A FRAP assay is used to determine antioxidant capacity in T0 plants as described in Example 7. Increased antioxidant capacity is detected in individual field grown T0 plants compared to the average antioxidant capacity determined for at least five unmodified Narrow leaf Madole plants (FIG. 14).

Figure 15:
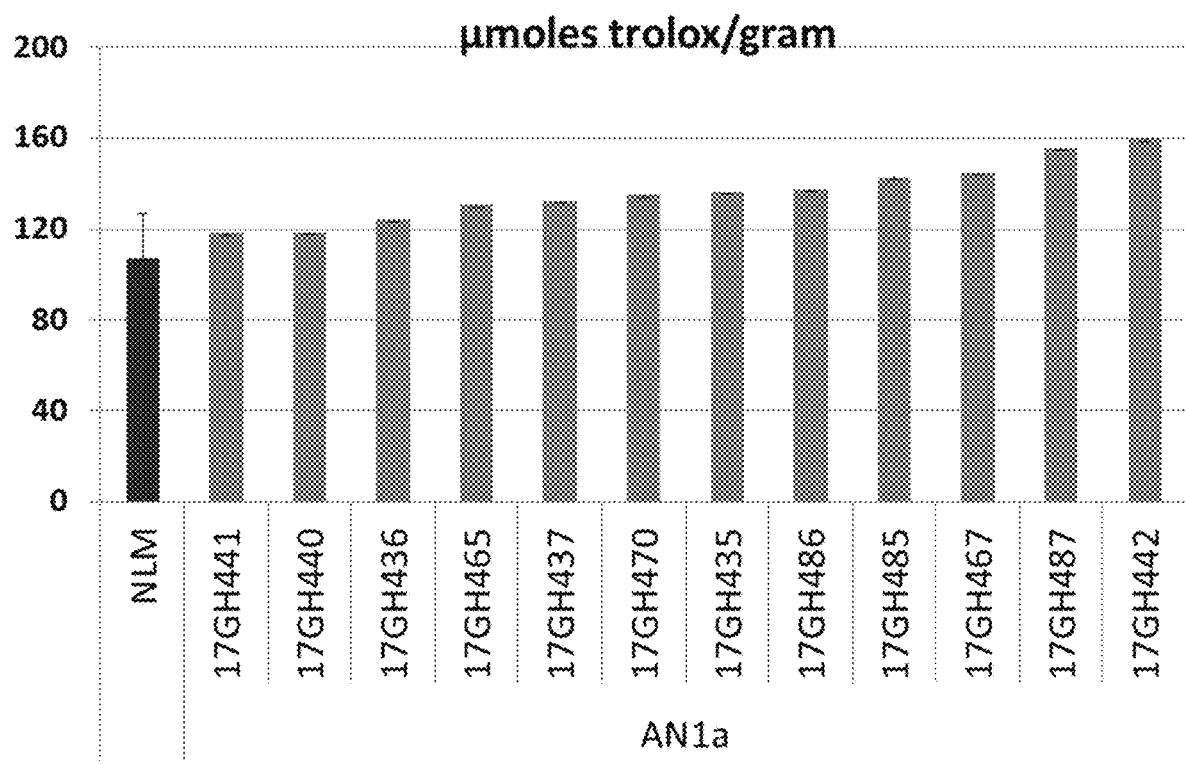
FIG. 15: Overexpression of NtAN1a (SEQ ID NO: 28) in NLM results in increased antioxidant capacity as measured using a FRAP assay. Greenhouse grown, individually tested TO plants overexpressing NtAN1a show increased antioxidant capacity compared to the average antioxidant capacity determined for at least five unmodified NLM plants.

NtAN1a, SEQ ID NO: 28, is incorporated into a p45-2-7 transformation vector, and modified tobacco plants are generated, according to Example 1. Modified NLM tobacco plants (T0 and T1 generation) and control tobacco plants are grown for 4-6 weeks after transplantation to soil, harvested, and cured in PGC chambers. Cured leaf samples are prepared for evaluation of TSNAs, oxidative degradation potential, alkaloids, and nitrites/nitrates as described in Examples 2 to 5. A FRAP assay is used to determine antioxidant capacity in T0 plants as described in Example 7. Increased antioxidant capacity is detected in individual greenhouse grown T0 plants compared to the average antioxidant capacity determined for at least five unmodified Narrow leaf Madole plants (FIG. 15).

Figure 16:
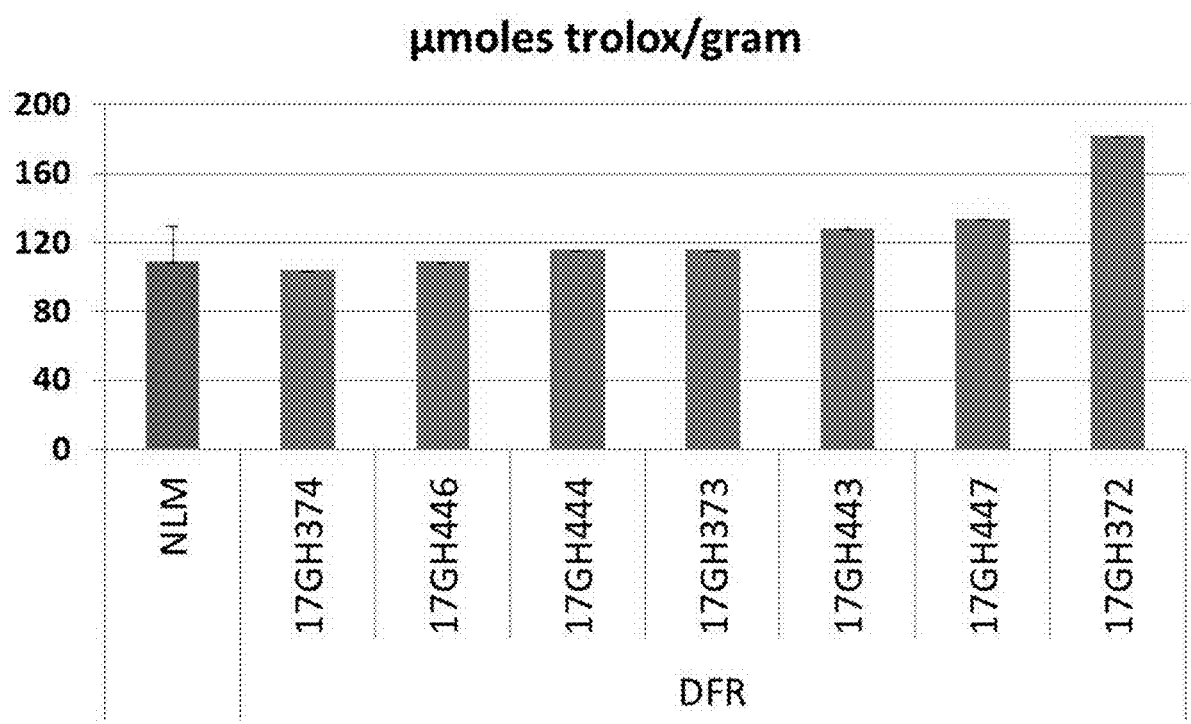
FIG. 16: Overexpression of NtDFR (SEQ ID NO: 37) in NLM results in increased antioxidant capacity as measured using a FRAP assay. Greenhouse grown, individually tested TO plants overexpressing NtDFR show increased antioxidant capacity compared to the average antioxidant capacity determined for at least five unmodified NLM plants.

NtDFR, SEQ ID NO: 37, is incorporated into a p45-2-7 transformation vector, and modified tobacco plants are generated, according to Example 1. Modified NLM tobacco plants (T0 and T1 generation) and control tobacco plants are grown for 4-6 weeks after transplantation to soil, harvested, and cured in PGC chambers. Cured leaf samples are prepared for evaluation of TSNAs, oxidative degradation potential, alkaloids, and nitrites/nitrates as described in Examples 2 to 5. A FRAP assay is used to determine antioxidant capacity in T0 plants as described in Example 7. Increased antioxidant capacity is detected in individual greenhouse grown T0 plants compared to the average antioxidant capacity determined for at least five unmodified Narrow leaf Madole plants (FIG. 16).

Figure 17:
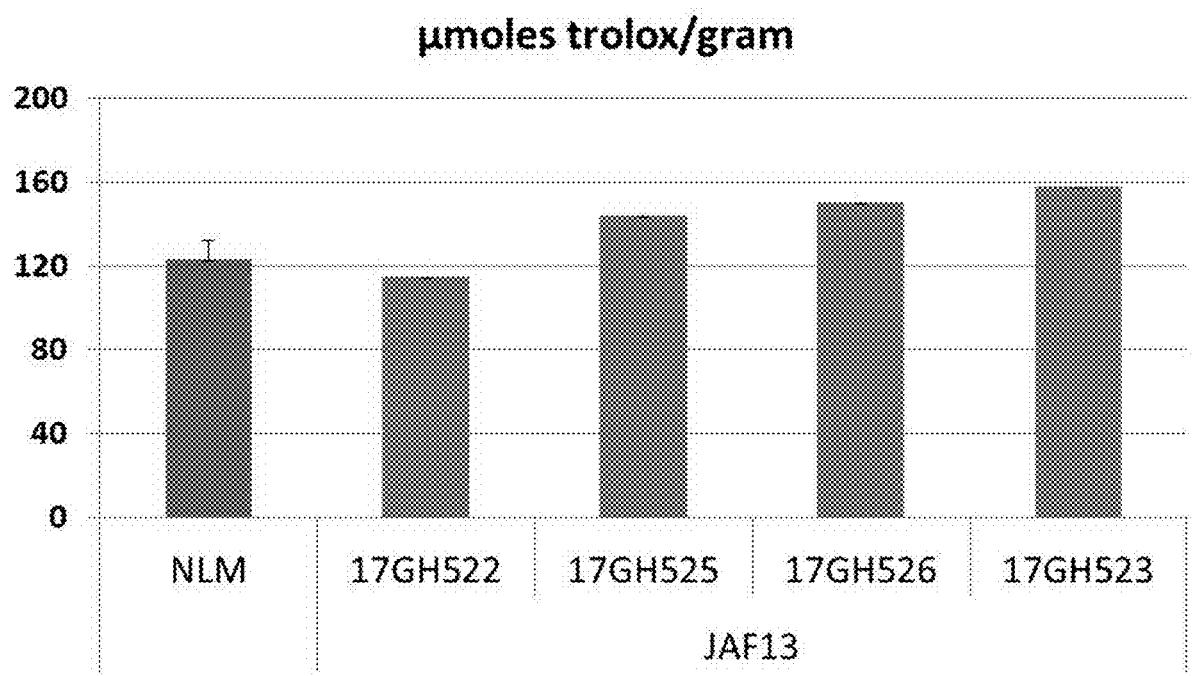
FIG. 17: Overexpression of NtJAF13 (SEQ ID NO: 33) in NLM results in increased antioxidant capacity as measured using a FRAP assay. Greenhouse grown, individually tested TO plants overexpressing NtJAF13 show increased antioxidant capacity compared to the average antioxidant capacity determined for at least five unmodified NLM plants.

NtJAF13, SEQ ID NO: 33, is incorporated into a p45-2-7 transformation vector, and modified tobacco plants are generated, according to Example 1. Modified NLM tobacco plants (T0 and T1 generation) and control tobacco plants are grown for 4-6 weeks after transplantation to soil, harvested, and cured in PGC chambers. Cured leaf samples are prepared for evaluation of TSNAs, oxidative degradation potential, alkaloids, and nitrites/nitrates as described in Examples 2 to 5. A FRAP assay is used to determine antioxidant capacity in T0 plants as described in Example 7. Increased antioxidant capacity is detected in individual greenhouse grown T0 plants compared to the average antioxidant capacity determined for at least five unmodified Narrow leaf Madole plants (FIG. 17).

Figure 18:
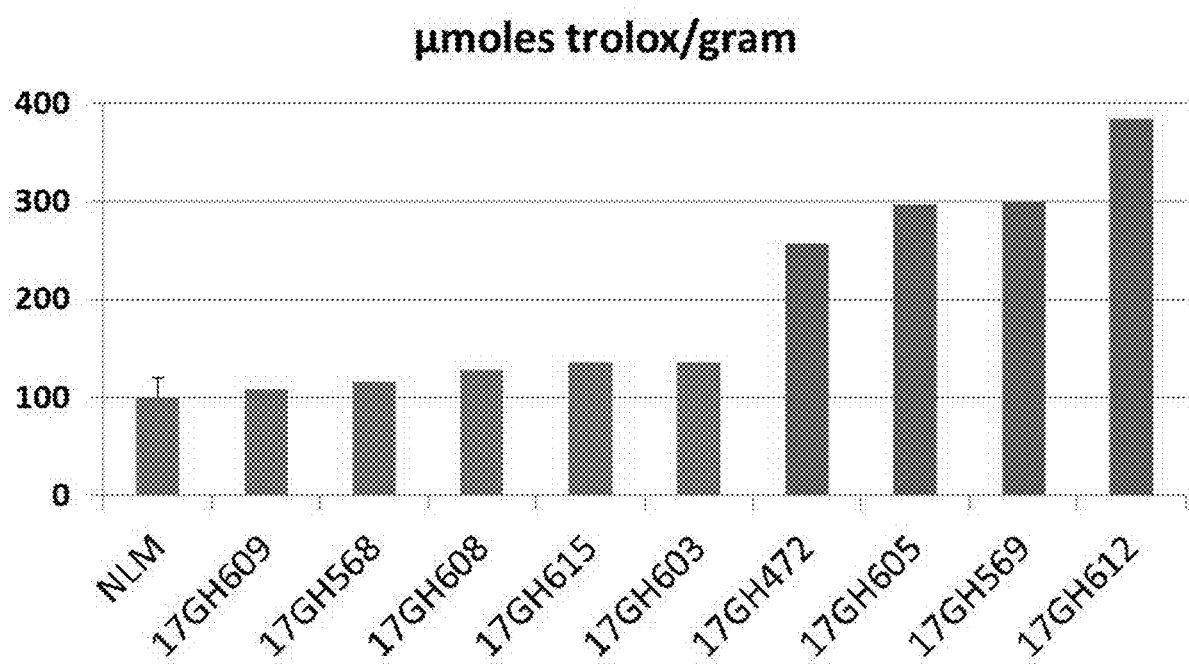
FIG. 18: Overexpression of NtMYB3 (SEQ ID NO: 36) in NLM results in increased antioxidant capacity as measured using a FRAP assay. Greenhouse grown, individually tested TO plants overexpressing NtMYB3 show increased antioxidant capacity compared to the average antioxidant capacity determined for at least five unmodified NLM plants.
Figure 19:
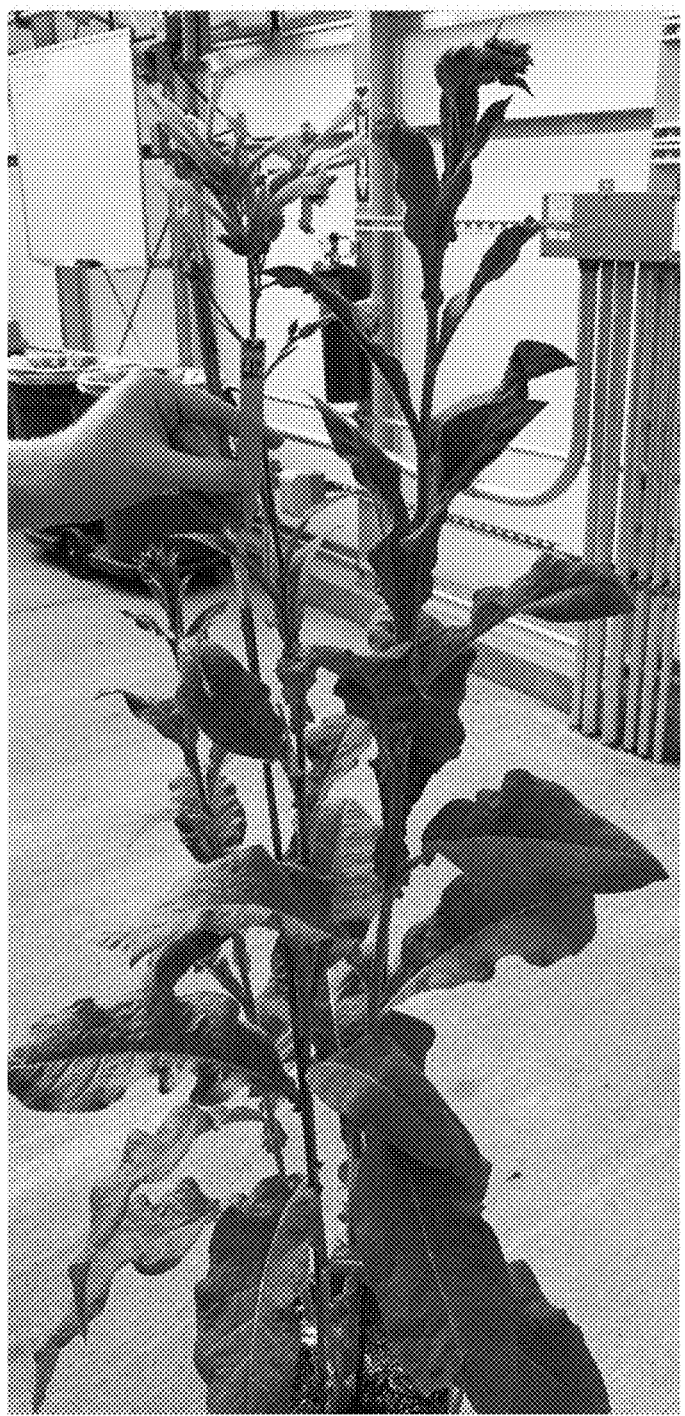
FIG. 19: Overexpression of NtMYB3 (SEQ ID NO: 36) in NLM results in tobacco plants with normal leaf color in TO plants grown in the greenhouse.

NtMYB3, SEQ ID NO: 36, is incorporated into a p45-2-7 transformation vector, and modified tobacco plants are generated, according to Example 1. Modified tobacco plants (T0 and T1 generation) and control tobacco plants are grown for 4-6 weeks after transplantation to soil, harvested, and cured in PGC chambers. Cured leaf samples are prepared for evaluation of TSNAs, oxidative degradation potential, alkaloids, and nitrites/nitrates as described in Examples 2 to 5. A FRAP assay is used to determine antioxidant capacity in T0 plants as described in Example 7. Increased antioxidant capacity is detected in individual greenhouse grown T0 plants compared to the average antioxidant capacity determined for at least five unmodified Narrow leaf Madole plants (FIG. 18). Plants overexpressing NtMYB3 show a normal leaf color in the T0 generation (FIG. 19).

TABLE 6

A list of plant-origin antioxidants that can be used to reduce TSNAs.

| Chemical Classes | Compounds | Source of the Species |
|------------------|-----------|----------------------|
| Anthocyanidin | Delphnidin | Tobacco, *Arabidopsis*. Cabbage, potato or petunia |
| | Cyanidin | Tobacco, *Arabidopsis*. Cabbage, potato or petunia |

TABLE 6-continued

A list of plant-origin antioxidants that can be used to reduce TSNAs.

| Chemical Classes | Compounds | Source of the Species |
|---|---|---|
| | Procyanidin | Tobacco, *Arabidopsis*. Cabbage, potato or petunia |
| | Prodelphinidin | Tobacco, *Arabidopsis*. Cabbage, potato or petunia |
| Flavanone | Hesperetin | Citrus or related species |
| | Naringenin | Citrus or related species |
| Flavanol | Catechin | Tobacco or other related species |
| | Epicatechin | Tobacco or other related species |
| Flavone | Apigenin | Parsley, tobacco or other related species |
| | Luteonin | Parsley, tobacco or other related species |
| Flavonol | Quercetin | Red kidney bean or other related species |
| | Myricetin | Red kidney bean or other related species |
| | Rutin | Tobacco, Red kidney bean or other related species |
| Isoflavone | Genistein | Soybean or other related species |
| | Daidzein | Soybean or other related species |
| HydroxybenzoicAcid | Gallic acid | Tobacco, oak or other related species |
| | Vanillic acid | Tobacco, Acai or other related species |
| | Protocatechuic acid | Tobacco, Hibiscus or other related species |
| Hydroxycinnamic acid | Ferunic acid | Tobacco or other related species |
| | Cinnamic acid | Tobacco or other related species |
| | Coumeric acid | Tobacco or other related species |
| | Chlorogenic acid | Tobacco or other related species |
| | Coffeic acid | Tobacco or other related species |
| | Ferulic acid | Tobacco or other related species |
| Ellagitannin | Sanguiin | Raspberry or other related species |
| Stibene | Resveratrol | Grape or other related species |
| Lignan | Sesamin | Sesame or other related species |
| carotenoids | Caretonoids | Tobacco or carrots |
| | Vitamin C | Tobacco or carrots |
| Glycyrrhzin | | Licorice |

TABLE 7

Nucleotide sequence comparison between selected transcription factors. Percent identity is shown.
Nucleotide identity

| | AtPAP1 | NtAN1 | NtAN2 | NtMYB3 | NtJAF13 |
|---|---|---|---|---|---|
| AtPAP1 | | 15.12 | 49.35 | 46.99 | 17.72 |
| NtAN1 | 15.12 | | 13.29 | 17.4 | 46.75 |
| NtAN2 | 49.35 | 13.29 | | 39.98 | 14.24 |
| NtMYB3 | 46.99 | 17.4 | 39.98 | | 19.4 |
| NtJAF13 | 17.72 | 46.75 | 14.24 | 19.4 | |

TABLE 8

Amino acid sequence comparison between selected transcription factors. Percent identity is shown.
Amino Acid identity

| | AtPAP1 | NtAN1 | NtAN2 | NtMYB3 | NtJAF13 |
|---|---|---|---|---|---|
| AtPAP1 | | 6.8 | 46.3 | 33.67 | 7.5 |
| NtAN1 | 6.8 | | 5.77 | 7.4 | 30.64 |
| NtAN2 | 46.3 | 5.77 | | 32.78 | 7.19 |
| NtMYB3 | 33.67 | 7.4 | 32.78 | | 9.25 |
| NtJAF13 | 7.5 | 30.64 | 7.19 | 9.25 | |

TABLE 9

Nucleotide and protein sequences.

| Target Antioxidant | Gene Function annotation | Source | Protein SEQ ID No. | Coding SEQ ID No. |
|---|---|---|---|---|
| Anthocyanin | Putative alcohol dehydrogenase; [*Solanum lycopersicum* (Tomato) (*Lycopersicon esculentum*).] | tobacco | 1 | 24 |
| Anthocyanin | 1-O-acylglucose:anthocyanin-O-acyltransferase; [*Clitoria ternatea* (Butterfly pea).] | tobacco | 2 | 25 |
| Chlorogenic acid | 4-coumarate:CoA ligase; [*Ipomoea batatas* (Sweet potato) (*Convolvulus batatas*).]. Also called 4CL | tobacco | 3 | 26 |
| Chlorogenic acid | 4-coumarate:CoA ligase-like; [*Nicotiana sylvestris* (Wood tobacco) (South American tobacco).]. Also called 4CL. | tobacco | 4 | 27 |
| Anthocyanin | Anthocyanin 1a; [*Nicotiana tabacum* (Common tobacco).]. Also called AN1a. | tobacco | 5 | 28 |
| Anthocyanin | Anthocyanin 1b; [*Nicotiana tabacum* (Common tobacco).]. Also called AN1b. | tobacco | 6 | 29 |
| Anthocyanin | Anthocyanin 2; [*Nicotiana tomentosiformis* (Tobacco).] | tobacco | 7 | 30 |
| Anthocyanin | anthocyanidin synthase 2 [*Nicotiana tabacum*]. Also called ANS2. | tobacco | 8 | 31 |
| Anthocyanin | leucoanthocyanidin dioxygenase [*Nicotiana tabacum*] | tobacco | 9 | 32 |

TABLE 9-continued

Nucleotide and protein sequences.

| Target Antioxidant | Gene Function annotation | Source | Protein SEQ ID No. | Coding SEQ ID No. |
|---|---|---|---|---|
| Anthocyanin | BHLH transcription factor JAF13; [*Petunia hybrida* (Petunia).] | tobacco | 10 | 33 |
| Ferulic acid | *Nicotiana tabacum* caffeic acid O-methyltransferase II gene | tobacco | 11 | 34 |
| chlorogenic acid | trans-cinnamate 4-monooxygenase-like [*Nicotiana tomentosiformis*], Also called C4H. | tobacco | 12 | 35 |
| Anthocyanin | transcription factor MYB3-like [*Nicotiana tabacum*]; tobacco homolog of AtPAP1 | tobacco | 13 | 36 |
| Anthocyanin | *Nicotiana tabacum* dihydroflavonol-4-reductase (LOC107797232) | tobacco | 14 | 37 |
| Anthocyanin | *Nicotiana tabacum* NtDFR2 gene for dihydroflavonol-4-reductase | tobacco | 15 | 38 |
| Anthocyanin | *Nicotiana tabacum* myb-related protein 308-like (LOC107782378), mRNA-XM_016603259. | tobacco | 16 | 39 |
| Chlorogenic acid | *Nicotiana tabacum* shikimate O-hydroxycinnamoyltransferase-like; also called HCT. | tobacco | 17 | 40 |
| Chlorogenic acid | *Nicotiana tabacum* mRNA for hydroxycinnamoyl CoA quinate transferase (hqt gene); also called HQT. | tobacco | 18 | 41 |
| Anthocyanin, CGA, ferulic acid, cinnamate, coumarate caffeic acid | *Nicotiana tabacum* phenylalanine ammonia lyase (tpa1) gene; also called PAL. | tobacco | 19 | 42 |
| Anthocyanin | *Arabidopsis thaliana* ttg1 gene; WD40. | *Arabidopsis* | 20 | 43 |
| carotenoids | phytoene synthase 1 [*Nicotiana tabacum*] | tobacco | 21 | 44 |
| carotenoids | phytoene synthase 2, chloroplastic [*Nicotiana sylvestris*] | tobacco | 22 | 45 |
| Anthocyanin | Production of anthocyanin pigment 1; PAP1. | *Arabidopsis* | 23 | 46 |
| Flavonoids and anthocyanins | Phenylalanine ammonia-lyase 4 (NtPAL4) | tobacco | 47 | 53 |
| Flavonoids and anthocyanins | Phenylalanine ammonia-lyase 2 (NtPAL2) | tobacco | 48 | 54 |
| Flavonoids and anthocyanins | Chalcone synthase (NtCHS) | tobacco | 49 | 55 |
| Flavonoids and anthocyanins | Flavonol 3-hydratase (NtF3H) | tobacco | 50 | 56 |
|  | Arogenate dehydrogenase 1 (NtADT1) | tobacco | 51 | 57 |
| Chlorogenic acid, Flavonoids and anthocyanins | Arogenate dehydrogenase 2 (NtADT2) | tobacco | 52 | 58 |

Example 10: Creation of Cisgenic Constructs to Modulate TSNA Levels

Cisgenic constructs are created to constitutively express AtPAP1, NtAN2, and NtAN1a. Tobacco native Ubiquitin (Ubi-4) or Tubulin (Tub) promoters are used in conjunction with a tobacco native heat shock protein (HSP) terminator. Sequences are incorporated into a p45-2-7 transformation vector, and modified tobacco plants are generated, according to Example 1. Constructs encoding Ubi4-P:PAP1-HSP-T (SEQ ID NO:59), Ubi4-P:NtAN2-HSP-T (SEQ ID NO:60), Tub-P:NtAN2-HSP-T (SEQ ID NO:61), Ubi4-P:NtAN2-HSP-T:Tub-P:NtAN2-HSP-T (SEQ ID NO:62), and Ubi4-P:NtAN1a-HSP-T:Tub-P:NtAN2-HSP-T (SEQ ID NO:63) are transformed into tobacco plants. The presence of the cisgenic construct in a transformed plant is confirmed using amplicon sequencing. Modified tobacco plants (T0 and T1 generation) and control tobacco plants are grown for 4-6 weeks after transplantation to soil, harvested, and cured in PGC chambers. Cured leaf samples are prepared for evaluation of TSNAs, oxidative degradation potential, alkaloids, and nitrites/nitrates as described in Examples 2 to 7.

Example 11: A Combination Approach for Further Reduction of TSNAs

Three nicotine demethylase genes, known as CYP82E4, CYP82E5, and CYP82E10, mediate nornicotine biosynthesis in *Nicotiana tabacum*. Triple knockout mutants (cyp82e4, cyp82e5, cyp82e10) exhibit a dramatic reduction of nornicotine and consequently a reduction of NNN. A combination strategy is taken to combine nicotine demethylase mutants and the approach provided in Examples 2 to 7 to achieve a further TSNA reduction. A cyp82e4, cyp82e5, cyp82e10 triple mutant is transformed with one or more constructs described in Example 9 to increase antioxidant levels. Alternatively, cyp82e4, cyp82e5, cyp82e10 triple mutants are crossed with mutant or transgenic tobacco having elevated antioxidant levels described in Example 2.

What is claimed is:

1. Cured leaf of a modified tobacco plant comprising a nucleic acid molecule comprising a nucleotide sequence selected from the group consisting of SEQ ID NOs: 60 to 63, and further comprising an increased level of one or more antioxidants, wherein said reduced and increased levels are compared to a control cured leaf of an unmodified tobacco plant of the same variety when grown and cured under comparable conditions.

2. A tobacco product comprising the cured leaf of claim 1.

3. The cured leaf of claim 1, wherein said cured leaf comprises an increased level of oxygen radical absorbance capacity (ORAC) compared to said control cured leaf.

4. The cured leaf of claim 1, wherein said cured tobacco leaf comprises less than 2 ppm total tobacco-specific nitrosamines (TSNAs).

5. The cured leaf of claim 1, wherein said cured tobacco leaf comprises less than 0.08 ppm 4-methylnitrosoamino-1-(3-pyridyl)-1-butanone (NNK), wherein the level of said total TSNAs is measured based on a freeze-dried cured leaf sample using liquid chromatograph with tandem mass spectrometry (LC/MS/MS).

6. The cured leaf of claim 1, wherein said one or more antioxidants are selected from the group consisting of anthocyanidin, flavanone, flavanol, flavone, flavonol, isoflavone, hydroxybenzoic acid, hydroxycinnamic acid, ellagitannin, stibene, lignan, carotenoids, and glycyrrhizin.

7. The cured leaf of claim 1, wherein said one or more TSNAs are selected from the group consisting of N'-nitrosonornicotine (NNN), 4-methylnitrosoamino-1-(3-pyridyl)-1-butanone (NNK), N'-nitrosoanatabine (NAT), and any combination thereof.

8. The cured leaf of claim 1, wherein said modified tobacco plant is selected from the group consisting of a flue-cured variety, a Burley variety, a Maryland variety, a dark variety, and an Oriental variety.

9. The cured leaf of claim 1, wherein a genetic modification in said modified tobacco plant comprises a tobacco genome mutation or a transgene.

10. The cured leaf of claim 9, wherein the level of said one or more TSNAs is reduced by at least 50% compared to cured tobacco leaf or a tobacco product from a control tobacco plant not comprising said genetic modification.

11. Cured leaf of a modified tobacco plant comprising nucleic acid molecule comprising a nucleotide sequence selected from the group consisting of SEQ ID NOs: 60 to 63, wherein said cured leaf comprises a reduced level of one or more tobacco-specific nitrosamines (TSNAs), and further comprising an increased level of one or more antioxidants, wherein said reduced and increased levels are compared to a control cured leaf of an unmodified tobacco plant of the same variety when grown and cured under comparable conditions.

12. A tobacco product comprising the cured leaf of claim 11.

13. The cured leaf of claim 11, wherein said cured leaf comprises an increased level of oxygen radical absorbance capacity (ORAC) compared to said control cured leaf.

14. The cured leaf of claim 11, wherein said cured tobacco leaf comprises less than 2 ppm total TSNAs.

15. The cured leaf of claim 14, wherein said cured tobacco leaf comprises less than 0.08 ppm 4-methylnitrosoamino-1-(3-pyridyl)-1-butanone (NNK), wherein the level of said total TSNAs is measured based on a freeze-dried cured leaf sample using liquid chromatograph with tandem mass spectrometry (LC/MS/MS).

16. The cured leaf of claim 11, wherein said cured leaf comprises a reduced level of one or more TSNAs selected from the group consisting of N'-nitrosonornicotine (NNN), 4-methylnitrosoamino-1-(3-pyridyl)-1-butanone (NNK), N'-nitrosoanatabine (NAT), and any combination thereof.

17. The cured leaf of claim 11, wherein said modified tobacco plant is selected from the group consisting of a flue-cured variety, a Burley variety, a Maryland variety, a dark variety, and an Oriental variety.

18. The cured leaf of claim 11, wherein a modification in said modified tobacco plant comprises a tobacco genome mutation or a transgene.

19. The cured leaf of claim 18, wherein the level of nitrite is reduced by at least 50% compared to cured tobacco leaf or a tobacco product from a control tobacco plant not comprising said genetic modification.

* * * * *